US007420038B2

(12) United States Patent
Sun et al.

(10) Patent No.: US 7,420,038 B2

(45) Date of Patent: Sep. 2, 2008

(54) COMPOSITIONS FOR CONTROLLING HAIR GROWTH

(75) Inventors: Tung-Tien Sun, Dobbs Ferry, NY (US); Qiong Cao, Boston, MA (US)

(73) Assignee: New York University, New York, NY (US)

(*) Notice: Subject to any disclaimer, the term of this patent is extended or adjusted under 35 U.S.C. 154(b) by 3 days.

(21) Appl. No.: 11/709,074

(22) Filed: Feb. 21, 2007

(65) Prior Publication Data

US 2008/0076151 A1 Mar. 27, 2008

Related U.S. Application Data

(62) Division of application No. 11/096,070, filed on Mar. 31, 2005, now Pat. No. 7,223,562.

(60) Provisional application No. 60/558,341, filed on Mar. 31, 2004.

(51) Int. Cl.
*C07K 1/00* (2006.01)

(52) U.S. Cl. ............... 530/350; 435/252.3; 435/254.11; 435/419; 435/325; 435/320.1; 536/23.5

(58) Field of Classification Search ....................... None
See application file for complete search history.

(56) References Cited

U.S. PATENT DOCUMENTS

| | | | |
|---|---|---|---|
| 4,139,619 | A | 2/1979 | Chidsey, III |
| 5,643,898 | A | 7/1997 | Grollier et al. |
| 5,656,300 | A | 8/1997 | Levin |
| 5,663,160 | A | 9/1997 | Meybeck et al. |
| 5,674,497 | A | 10/1997 | Kuwana et al. |
| 5,679,378 | A | 10/1997 | Fischer |
| 5,723,149 | A | 3/1998 | Bonte et al. |
| 5,739,111 | A | 4/1998 | Mahe |
| 5,741,816 | A | 4/1998 | Tsujihara et al. |
| 5,750,107 | A | 5/1998 | Nomura |
| 5,753,713 | A | 5/1998 | Bass |
| 5,767,152 | A | 6/1998 | Nielsen et al. |
| 5,798,341 | A | 8/1998 | Klingelholler |
| 5,800,477 | A | 9/1998 | Groux |
| 6,093,748 | A | 7/2000 | Ahluwalia et al. |
| 6,291,740 | B1 | 9/2001 | Bremel et al. |

FOREIGN PATENT DOCUMENTS

| | | | |
|---|---|---|---|
| WO | WO-9513796 | | 5/1995 |
| WO | WO 0261076 | * | 8/2002 |

OTHER PUBLICATIONS

GenBank Accession No. BX538105. *Homo sapiens* mRNA, cDNA DKFZp686J18145. (2003).*

Bal et al., *Biochemistry*, 32(4):1047-53, 1993.

Betolino et al., "Differentiation of the hair shaft" in *Differentiation of the Hair Shaft*, pp. 21-37, Olsen EA (ed.), McGraw Hill, Inc. New York, 1994.

Bertolino et al. Disorders of epidermal appendages and related disorders. *Dermatology in General Medicine*, 1993, 4th ed., pp. 671-695, Fitzpatrick et al. eds., McGraw-Hill.

Botchkarev et al., *J. Exp. Zool. Mol. Dev. Evol.*, 298(1):164-180, 2003.

Cao et al. Expression of an Olfactomedin-related Gene in Rat Hair Follicular Papilla Cells, *J. Invest. Dermatol.*, 2005, pp. 24-33, vol. 125, No. 1.

Cotsarelis et al., Existence of Slow-Cycling Limbal Epithelial Basal Cells That Can be Preferentially Stimulated to Proliferate: Implications on Epithelial Stem Cells, *Cell*, 1989, pp. 201-209, vol. 57.

Cotsarelis et al., Trends Mol. Med., 7(7):293-301, 2001.

Elliott et al., *J. Invest. Dermatol.*, 113:873-877, 1999.

Fields et al., *Trends Genet.*, 10(8):286-92, 1994.

Garces et al., *Methods Mol. Biol.*, 161:3-8, 2001.

Green et al., *Mol. Cell. Prot.*, 1.5:394-403, 2002.

Hardy, *Trends Genet.*, 8:55-61, 1992.

Hutchinson et al., *J. Biol. Chem.*, 253:6551, 1978.

Jahoda, C. A., *Development*, 115:1103-1109, 1992.

Jahoda et al., *Nature*, 311:560-562, 1984.

Jahoda et al., *Exp. Dermatol.*, 10(4):229-37, 2001.

Kamimura et al., *J. Invest. Dermatol.*, 109(4):534-40, 1997.

Kim et al., *Dermatol. Surg.*, 21(4):312-313, 1995.

Klein et al., *Mol. Cell. Prot.*, 1.5:394-403, 2002.

Lachgar et al., *Br. J. Dermatol.*, 138:407-411, 1998.

Lehrer et al. Strategies of epithelial repair: modulation of stem cell and transit amplifying cell proliferation, *Journal of Cell Science*, 1998, pp. 2867-2975, vol. 111.

Muller-Rover et al., *J. Invest. Dermatol.*, 117:3-15, 2001.

Oshima et al., *Cell*, 104:233-245, 2001.

Oliver, *J. Embryol. Exp. Morphol.*, 15:331-347, 1966.

Philpott et al. Whole Hair Follicle Culture, *Dermatologic Clinics*, 1996, pp. 595-607, vol. 14, No. 4.

Porter, *J. Anat.*, 202:125-131, 2003.

Reynolds, A. J. et al., *Nature*, 402:33-34, 1999.

"siRNA Selection Program," Whitehead Institute for Biomedical Research, 2003.

Snyder et al., *Biochem.*, 30(38):9143-153, 1991.

Stenn et al., *Physiol. Rev.*, 81:449-494, 2001.

Trimble and Maley, *Anal. Biochem.*, 141(2):515-22, 1984.

Yokoe et al., *Proc. Natl. Acad. Sci. USA* 90:4655-4659, 1993.

* cited by examiner

*Primary Examiner*—Kathleen Kerr Bragdon
*Assistant Examiner*—Agnes B. Rooke
(74) *Attorney, Agent, or Firm*—Wilmer Cutler Pickering Hale & Dorr LLP

(57) ABSTRACT

FP-1 is a protein that is specifically expressed in the follicular papilla of the hair follicle. The nucleic acid and amino acid sequences of FP-1, as well as antibodies that specifically bind FP-1 are provided. In addition, methods of isolating follicular papilla cells and methods of modulating hair growth are also disclosed.

25 Claims, 49 Drawing Sheets

FIG. 2A

```
1                                        M  T  R  A  A  E  R  G  Q  G  A  T  G  W  G
1    ACGCGGGGAGTGCTGCCCTGAGTCGTTCGGCCTGAGCACAGAGACATGACCCGAGCCGCAGAGCGAGGCCAAGGGGCTACAGGCTGGGGA

16    L  R  G  A  L  M  A  V  A  L  L  S  V  L  N  A  V  G  T  V  F  V  L  Y  Q  W  R  E  L  S
91   CTGCGAGGCGCCCTGATGGCCGTGGCGCTGCTGTCAGTGCTGAACGCCGTGGGCACCGTGTTCGTGCTGTACCAGTGGCGCGAGCTGAGC

46    A  A  L  R  A  L  E  A  Q  H  G  Q  E  Q  R  E  D  S  A  L  R  A  F  L  A  E  L  S  R  A
181  GCGGCGCTGCGGGCACTGGAGGCGCAACACGGCCAGGAGCAGCGCGAGGACAGCGCCCTACGCGCCTTTCTAGCTGAATTAAGTCGTGCG

76    P  A  R  V  P  E  P  P  Q  D  P  M  S  A  A  R  N  K  R  S  H  G  G  E  P  A  S  H  I  R
271  CCAGCCCGAGTCCCCGAACCACCCCAGGACCCCATGAGTGCAGCGCGCAATAAGCGCAGCCACGGCGGCGAGCCTGCGTCACACATCCGC

106   A  E  S  Q  D  M  M  M  M  M  T  Y  S  M  V  P  I  R  V  M  I  D  L  C  N  S  T  Q  G  I
361  GCGGAGAGCCAGGACATGATGATGATGATGACCTACAGCATGGTGCCGATCCGGGTGATGATAGACCTGTGCAACAGCACCCAGGGCATC

136   C  L  T  G  P  P  G  P  P  G  P  P  G  A  G  G  L  P  G  H  N  G  S  D  G  Q  P  G  L  Q
451  TGCCTTACAGGACCACCGGGCCCACCAGGACCTCCAGGAGCTGGTGGGTTACCAGGCCACAATGGATCAGATGGACAGCCTGGTCTCCAG

166   G  P  K  G  E  K  G  A  V  G  K  R  G  K  M  G  L  P  G  A  T  G  N  P  G  E  K  G  E  K
541  GGCCCAAAAGGAGAAAAAGGAGCAGTTGGGAAGAGAGGAAAAATGGGGTTACCCGGAGCCACAGGAAATCCAGGGGAAAAGGGAGAGAAG

196   G  D  A  G  E  L  G  L  P  G  N  E  G  P  P  G  Q  K  G  D  K  G  D  K  G  D  V  S  N  D
631  GGAGATGCTGGTGAACTGGGCCTACCTGGAAATGAGGGACCACCAGGACAGAAAGGAGACAAAGGAGACAAAGGAGATGTGTCCAATGAC
```

```
226  V  L  L  T  G  A  K  G  D  Q  G  P  P  G  P  P  G  P  P  G  P  P  G  P  S  G  S  R  R  A
721  GTGCTTTTGACAGGTGCCAAAGGTGACCAAGGGCCCCCTGGCCCACCTGGACCCCCAGGGCCTCCAGGCCCTTCTGGAAGCAGAAGAGCC

256  K  G  P  R  Q  P  N  S  F  T  N  Q  C  P  G  E  T  C  V  I  P  N  D  D  T  L  V  G  R  A
811  AAAGGCCCTCGGCAGCCAAATTCGTTCACCAACCAGTGTCCAGGGGAGACGTGTGTCATACCCAATGATGATACCTTGGTGGGGAGAGCT

286  D  E  K  V  N  E  R  H  S  P  Q  T  E  P  M  I  T  S  I  G  N  P  A  Q  V  L  K  V  K  E
901  GATGAGAAAGTCAATGAGCGCCATTCTCCACAAACAGAACCCATGATCACGTCCATTGGTAACCCGGCCCAAGTCCTCAAAGTGAAAGAG

316  T  F  G  T  W  L  R  E  S  A  N  R  S  D  D  R  I  W  V  T  E  H  F  S  G  I  M  V  K  E
991  ACTTTTGGGACCTGGCTAAGAGAGTCTGCTAACAGGAGTGATGACCGCATTTGGGTGACTGAACATTTTTCAGGCATCATGGTGAAGGAG

346  F  E  D  L  P  A  L  L  N  S  S  F  T  L  L  H  L  P  H  Y  F  H  G  C  G  H  A  V  Y  N
1081 TTTGAAGACCTGCCCGCCCTCCTGAATAGCAGCTTCACCCTCCTCCACCTCCCACATTACTTCCATGGCTGCGGGCACGCTGTTTACAAC

376  N  S  L  Y  Y  H  K  G  G  S  N  T  I  V  R  F  E  F  G  K  E  T  P  Q  T  L  K  L  E  D
1171 AACTCTCTCTACTACCACAAAGGAGGCTCCAACACCATAGTGAGATTTGAATTTGGGAAAGAGACACCTCAAACTCTGAAGCTTGAAGAT

406  A  L  Y  F  D  R  K  Y  L  F  A  N  S  K  T  Y  F  N  I  A  V  D  E  K  G  L  W  I  I  Y
1261 GCTTTGTATTTTGATCGAAAATACCTCTTTGCGAATTCCAAGACTTACTTCAACATAGCAGTGGATGAGAAGGGCCTCTGGATTATCTAC

436  A  S  S  V  D  G  S  S  I  L  V  A  Q  L  D  E  R  T  F  S  V  L  Q  H  I  N  T  T  Y  P
1351 GCCTCGAGTGTGGATGGCTCAAGCATCCTTGTGGCACAGCTGGACGAGAGGACATTCTCTGTGCTGCAGCACATCAATACCACATACCCC
```

FIG. 2B

```
466   K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAAGATACAAGGGTCACGTTTGCCTTTGATTTG

496   L  R  G  K  Q  I  N  A  N  F  G  L  R  M  S  Q  S  V  L  A  M  L  S  Y  N  M  R  D  Q  H
1531  TTACGAGGGAAGCAGATCAATGCAAACTTCGGTCTCAGAATGTCACAGTCTGTTCTTGCCATGTTGTCGTACAATATGAGAGACCAGCAT

526   L  Y  S  W  E  D  G  H  L  M  L  Y  P  V  H  F  S  S  T  A  P  S  Q  R (SEQ ID NO:2)
1621  TTGTACTCGTGGGAAGACGGCCACCTGATGCTCTATCCTGTGCACTTTTCGTCAACAGCACCCAGCCAGCGATAGGCCTGCAGTCGGCTC

1711  CCTCATTATGCACCACACATTTTCTGGGGTTTGACCAAGCCCAACGGAAAGAAGGCCTGTAAAGGATATCCAGATACTCAGAGCATACGC

1801  CCGTGTTACGGGCTTTTGTGCATGTGGCAAGTCCCCCTGTAAGCCAGGTTAACTAAAGGCTGGAAAGTTGAAATGGATAACATTTGGTGA

1891  CCCTTGGTCCCTCTTCAAACTTAGCAAGTTAGTGCTCCCCCCTGACCTTAGTGTCCCCATCAGTAATATGAAACATCTGTGTGATTGCAG

1981  CATTTCCTATACCTATATGAAGTTCTGTGATTCTTGCCTGGTTATATATTAGATTGCTTTCAGGTTTCTTTTTTTTTTCTCCACATGTAA

2071  ATGAGTTTACCTGCAGCTTGAGGGGTGTGCCTATCAGTGATGACGGACATTTGTTTGGTGTTTAGGGAAAAAGCATTGTTTCTTATGGCT

2161  TTTAAAGTATTATATTATCCATAATTTGATATTTTTTTTTGAATACGCCCCTGCCACTACAGAATGATTATTGTTTTCAGCTCCTAAGTA

2251  CAAATCCAAGATTAATAAAAAAAAAACATGAATAGAAAAAAAAAAAAAAAAAAACTCGAGAGTATTAGTCGATGTAGGAAAAC(SEQ ID NO:1)
```

FIG. 2C

```
  1                                                 M  T  R  A  A  E  R  G  Q  G  A  T  G  W  G
  1  ACGCGGGGAGTGCTGCCCTGAGTCGTTCGGCCTGAGCACAGAGACATGACCCGAGCCGCAGAGCGAGGCCAAGGGGCTACAGGCTGGGGA

 16   L  R  G  A  L  M  A  V  A  L  L  S  V  L  N  A  V  G  T  V  F  V  L  Y  Q  Q  R  E  D  S
 91  CTGCGAGGCGCCCTGATGGCCGTGGCGCTGCTGTCAGTGCTGAACGCCGTGGGCACCGTGTTCGTGCTGTACCAGCAGCGCGAGGACAGC

 46   A  L  R  A  F  L  A  E  L  S  R  A  P  A  R  V  P  E  P  P  Q  D  P  M  S  A  A  R  N  K
181  GCCCTACGCGCCTTTCTAGCTGAATTAAGTCGTGCGCCAGCCCGAGTCCCCGAACCACCCCAGGACCCCATGAGTGCAGCGCGCAATAAG

 76   R  S  H  G  G  E  P  A  S  H  I  R  A  E  S  Q  D  M  M  M  M  M  T  Y  S  M  V  P  I  R
271  CGCAGCCACGGCGGCGAGCCTGCGTCACACATCCGCGCGGAGAGCCAGGACATGATGATGATGATGACCTACAGCATGGTGCCGATCCGG

106   V  M  I  D  L  C  N  S  T  Q  G  I  C  L  T  G  P  P  G  P  P  G  P  P  G  A  G  G  L  P
361  GTGATGATAGACCTGTGCAACAGCACCCAGGGCATCTGCCTTACAGGACCACCGGGCCCACCAGGACCTCCAGGAGCTGGTGGGTTACCA

136   G  H  N  G  S  D  G  Q  P  G  L  Q  G  P  K  G  E  K  G  A  V  G  K  R  G  K  M  G  L  P
451  GGCCACAATGGATCAGATGGACAGCCTGGTCTCCAGGGCCCAAAAGGAGAAAAAGGAGCAGTTGGGAAGAGAGGAAAAATGGGGTTACCC

166   G  A  T  G  N  P  G  E  K  G  E  K  G  D  A  G  E  L  G  L  P  G  N  E  G  P  P  G  Q  K
541  GGAGCCACAGGAAATCCAGGGGAAAAGGGAGAGAAGGGAGATGCTGGTGAACTGGGCCTACCTGGAAATGAGGGACCACCAGGACAGAAA
```

FIG. 3A

```
196   G  D  K  G  D  K  G  D  V  S  N  D  V  L  L  T  G  A  K  G  D  Q  G  P  P  G  P  P  G  P
631   GGAGACAAAGGAGACAAAGGAGATGTGTCCAATGACGTGCTTTTGACAGGTGCCAAAGGTGACCAAGGGCCCCCTGGCCCACCTGGACCC

226   P  G  P  P  G  P  S  G  S  R  R  A  K  G  P  R  Q  P  N  S  F  T  N  Q  C  P  G  E  T  C
721   CCAGGGCCTCCAGGCCCTTCTGGAAGCAGAAGAGCCAAAGGCCCTCGGCAGCCAAATTCGTTCACCAACCAGTGTCCAGGGGAGACGTGT

256   V  I  P  N  D  D  T  L  V  G  R  A  D  E  K  V  N  E  R  H  S  P  Q  T  E  P  M  I  T  S
811   GTCATACCCAATGATGATACCTTGGTGGGGAGAGCTGATGAGAAAGTCAATGAGCGCCATTCTCCACAAACAGAACCCATGATCACGTCC

286   I  G  N  P  A  Q  V  L  K  V  K  E  T  F  G  T  W  L  R  E  S  A  N  R  S  D  D  R  I  W
901   ATTGGTAACCCGGCCCAAGTCCTCAAAGTGAAAGAGACTTTTGGGACCTGGCTAAGAGAGTCTGCTAACAGGAGTGATGACCGCATTTGG

316   V  T  E  H  F  S  G  I  M  V  K  E  F  E  D  L  P  A  L  L  N  S  S  F  T  L  L  H  L  P
991   GTGACTGAACATTTTTCAGGCATCATGGTGAAGGAGTTTGAAGACCTGCCCGCCCTCCTGAATAGCAGCTTCACCCTCCTCCACCTCCCA

346   H  Y  F  H  G  C  G  H  A  V  Y  N  N  S  L  Y  Y  H  K  G  G  S  N  T  I  V  R  F  E  F
1081  CATTACTTCCATGGCTGCGGGCACGCTGTTTACAACAACTCTCTCTACTACCACAAAGGAGGCTCCAACACCATAGTGAGATTTGAATTT

376   G  K  E  T  P  Q  T  L  K  L  E  D  A  L  Y  F  D  R  K  Y  L  F  A  N  S  K  T  Y  F  N
1171  GGGAAAGAGACACCTCAAACTCTGAAGCTTGAAGATGCTTTGTATTTTGATCGAAAATACCTCTTTGCGAATTCCAAGACTTACTTCAAC

406   I  A  V  D  E  K  G  L  W  I  I  Y  A  S  S  V  D  G  S  S  I  L  V  A  Q  L  D  E  R  T
1261  ATAGCAGTGGATGAGAAGGGCCTCTGGATTATCTACGCCTCGAGTGTGGATGGCTCAAGCATCCTTGTGGCACAGCTGGACGAGAGGACA
```

FIG. 3B

```
436   F  S  V  L  Q  H  I  N  T  T  Y  P  K  S  K  A  G  N  A  F  I  A  Q  G  I  L  Y  V  T  D
1351  TTCTCTGTGCTGCAGCACATCAATACCACATACCCCAAGTCCAAGGCTGGCAATGCCTTCATAGCTCAAGGGATCCTCTATGTCACGGAC

466   T  K  D  T  R  V  T  F  A  F  D  L  L  R  G  K  Q  I  N  A  N  F  G  L  R  M  S  Q  S  V
1441  ACAAAAGATACAAGGGTCACGTTTGCCTTTGATTTGTTACGAGGGAAGCAGATCAATGCAAACTTCGGTCTCAGAATGTCACAGTCTGTT

496   L  A  M  L  S  Y  N  M  R  D  Q  H  L  Y  S  W  E  D  G  H  L  M  L  Y  P  V  H  F  S  S
1531  CTTGCCATGTTGTCGTACAATATGAGAGACCAGCATTTGTACTCGTGGGAAGACGGCCACCTGATGCTCTATCCTGTGCACTTTTCGTCA

526   T  A  P  S  Q  R   (SEQ ID NO:4)
1621  ACAGCACCCAGCCAGCGATAGGCCTGCAGTCGGCTCCCTCATTATGCACCACACATTTTCTGGGGTTTGACCAAGCCCAACGGAAAGAAG

1711  GCCTGTAAAGGATATCCAGATACTCAGAGCATACGCCCGTGTTACGGGCTTTTGTGCATGTGGCAAGTCCCCCTGTAAGCCAGGTTAACT

1801  AAAGGCTGGAAAGTTGAAATGGATAACATTTGGTGACCCTTGGTCCCTCTTCAAACTTAGCAAGTTAGTGCTCCCCCCTGACCTTAGTGT

1891  CCCCATCAGTAATATGAAACATCTGTGTGATTGCAGCATTTCCTATACCTATATGAAGTTCTGTGATTCTTGCCTGGTTATATATTAGAT

1981  TGCTTTCAGGTTTCTTTTTTTTTTCTCCACATGTAAATGAGTTTACCTGCAGCTTGAGGGGTGTGCCTATCAGTGATGACGGACATTTGT

2071  TTGGTGTTTAGGGAAAAAGCATTGTTTCTTATGGCTTTTAAAGTATTATATTATCCATAATTTGATATTTTTTTTTGAATACGCCCCTGC

2161  CACTACAGAATGATTATTGTTTTCAGCTCCTAAGTACAAATCCAAGATTAATAAAAAAAAAACATGAATAGAAAAAAAAAAAAAAAAAC

2251  TCGAGAGTATTAGTCGATGTAGGAAAAC (SEQ ID NO:3)
```

FIG. 3C

```
1   GAATTCGGCACGAGGGGGGCTTCTGGGGCGCCACGATTACTGTCCCCAACCCGCCTCGCCAGACGGGTCTAAAGGCAGCTTGACTCACGACT

93  CTGCCACCAGCCCACCACTCGCGCGAGGGTATAAAACCTGCCACTGCGGGAGGAGGCCCAGTGCTGCCCTGAGTCGTTCGGCCTGAGCAC

1          M  T  R  A  A  E  R  G  Q  G  A  T  G  W  G  L  R  G  A  L  M  A  V  A  L  L  S  V
183 AGAGACATGACCCGAGCCGCAGAGCGAGGCCAAGGGGCTACAGGCTGGGGACTGCGAGGCGCCCTGATGGCCGTGGCGCTGCTGTCAGTG

29   L  N  A  V  G  T  V  F  V  L  Y  Q  W  R  E  L  S  A  A  L  R  A  L  E  A  Q  H  G  Q  E
273 CTGAACGCCGTGGGCACCGTGTTCGTGCTGTACCAGTGGCGCGAGCTGAGCGCGGCGCTGCGGGCACTGGAGGCGCAACACGGCCAGGAG

59   Q  R  E  D  S  A  L  R  A  F  L  A  E  L  S  R  A  P  A  R  V  P  E  P  P  Q  D  P  M  S
363 CAGCGCGAGGACAGCGCCCTACGCGCCTTTCTAGCTGAATTAAGTCGTGCGCCAGCCCGAGTCCCCGAACCACCCCAGGACCCCATGAGT

89   A  A  R  N  K  R  S  H  G  G  E  P  A  S  H  I  R  A  E  S  Q  D  M  M  M  M  M  T  Y  S
453 GCAGCGCGCAATAAGCGCAGCCACGGCGGCGAGCCTGCGTCACACATCCGCGCGGAGAGCCAGGACATGATGATGATGATGACCTACAGC

119  M  V  P  I  R  V  M  I  D  L  C  N  S  T  Q  G  I  C  L  T  G  P  P  G  P  P  G  P  P  G
543 ATGGTGCCGATCCGGGTGATGATAGACCTGTGCAACAGCACCCAGGGCATCTGCCTTACAGGACCACCGGGCCCACCAGGACCTCCAGGA

149  A  G  G  L  P  G  H  N  G  S  D  G  Q  P  G  L  Q  G  P  K  G  E  K  G  A  V  G  K  R  G
633 GCTGGTGGGTTACCAGGCCACAATGGATCAGATGGACAGCCTGGTCTCCAGGGCCCAAAAGGAGAAAAAGGAGCAGTTGGGAAGAGAGGA

179  K  M  G  L  P  G  A  T  G  N  P  G  E  K  G  E  K  G  D  A  G  E  L  G  L  P  G  N  E  G
723 AAAATGGGGTTACCCGGAGCCACAGGAAATCCAGGGGAAAAGGGAGAGAAGGGAGATGCTGGTGAACTGGGCCTACCTGGAAATGAGGGA
```

FIG. 4A

```
209   P  P  G  Q  K  G  D  K  G  D  K  G  D  V  S  N  D  V  L  L  T  G  A  K  G  D  Q  G  P  P
813  CCACCAGGACAGAAAGGAGACAAAGGAGACAAAGGAGATGTGTCCAATGACGTGCTTTTGACAGGTGCCAAAGGTGACCAAGGGCCCCCT

239   G  P  P  G  P  P  G  P  P  G  P  P  G  S  R  R  A  K  G  P  R  Q  P  N  S  F  T  N  Q  C
903  GGCCCACCTGGACCCCCAGGGCCTCCAGGCCCTCCTGGAAGCAGAAGAGCCAAAGGCCCTCGGCAGCCAAATTCGTTCACCAACCAGTGT

269   P  G  E  T  C  V  I  P  N  D  D  T  L  V  G  R  A  D  E  K  V  N  E  R  H  S  P  Q  T  E
993  CCAGGGGAGACGTGTGTCATACCCAATGATGATACCTTGGTGGGGAGAGCTGATGAGAAAGTCAATGAGCGCCATTCTCCACAAACAGAA

299   P  M  I  T  S  I  G  N  P  A  Q  V  L  K  V  K  E  T  F  G  T  W  L  R  E  S  A  N  R  S
1083 CCCATGATCACGTCCATTGGTAACCCGGCCCAAGTCCTCAAGGTGAAAGAGACTTTTGGGACCTGGCTAAGAGAGTCTGCTAACAGGAGT

329   D  D  R  I  W  V  T  E  H  F  S  G  I  M  V  K  E  F  E  D  L  P  A  L  L  N  S  S  F  T
1173 GACGACCGCATTTGGGTGACTGAACATTTTTCAGGCATCATGGTGAAGGAGTTTGAAGACCTGCCCGCCCTCCTGAATAGCAGCTTCACC

359   L  L  H  L  P  H  Y  F  H  G  C  G  H  A  V  Y  N  N  S  L  Y  Y  H  K  G  G  S  N  T  I
1263 CTCCTCCACCTCCCACATTACTTCCATGGCTGCGGGCACGCTGTTTACAACAACTCTCTCTACTACCACAAAGGAGGCTCCAACACCATA

389   V  R  F  E  F  G  K  E  T  P  Q  T  L  K  L  E  D  A  L  Y  F  D  R  K  Y  L  F  A  N  S
1353 GTGAGATTTGAATTTGGGAAAGAGACACCTCAAACTCTGAAGCTTGAAGATGCTTTGTATTTTGATCGAAAATACCTCTTTGCGAATTCC

419   K  T  Y  F  N  I  A  V  D  E  K  G  L  W  I  I  Y  A  S  S  V  D  G  S  S  I  L  V  A  Q
1443 AAGACTTACTTCAACATAGCAGTGGATGAGAAGGGCCTCTGGATTATCTACGCCTCGAGTGTGGATGGCTCAAGCATCCTTGTGGCACAG
```

FIG. 4B

```
449  L  D  E  R  T  F  S  V  L  R  H  I  N  T  T  Y  P  K  S  K  A  G  N  A  F  I  A  Q  G  I
1533 CTGGACGAGAGGACATTCTCTGTGCTGCGGCACATCAATACCACATACCCCAAGTCCAAGGCTGGCAATGCCTTCATAGCTCAAGGGATC

479  L  Y  V  T  D  T  K  D  T  R  V  T  F  A  F  D  L  L  R  G  K  Q  I  N  A  N  F  G  L  R
1623 CTCTATGTCACGGACACCAAAGATACAAGGGTCACGTTTGCCTTTGATTTGTTACGAGGGAAGCAGATCAATGCAAACTTCGGTCTCAGA

509  M  S  Q  S  V  L  A  M  L  S  Y  N  M  R  D  Q  H  L  Y  S  W  E  D  G  H  L  M  L  Y  P
1713 ATGTCACAGTCTGTTCTTGCCATGTTGTCGTACAATATGAGAGACCAGCATTTGTACTCGTGGGAAGACGGCCACCTGATGCTCTATCCT

539  V  H  F  S  S  T  A  P  S  Q  R  (SEQ ID NO:6)
1803 GTGCACTTTTCGTCAACAGCACCCAGCCAGCGATAGGCCTGCAGTCGGCTCCCTCATTATGCACCACACATTTTCTGGGGTTTGACCAAG

1893 CCCAACGGAAAGAAGGCCTGTAAAGGATATCCAGATACTCAGAGCATACGCCCGTGCTACGGGCTCTTGTGCATGTGGCAAGTCCCCCTG

1983 TAAGCCAGGTTAGCTAGAGGCTGGAAGTTGAAATGGATAACATCTGGTGACCCTTGGTCCCTCTTCAAACTTAGCAAGTTAGTGCTCCCC

2073 CCTGACCTTAGTGTCCCCATCAGTAATATGAAACATCTGTGTGATTGACAGCATTTCCTCTACCTATATGAAGTTCTGTGATTCTTGCCT

2163 GGTTATATATTAGATTGCTTTCTGGTTTCTTTTTTTTTCTCCACATGTAAATGAGTTTACCTGCAGCTTGAGGGGTGTGCCTATCAGTG

2253 ATGACGGACATTTGTTTGGTGTTTAGGGAAGATGCATTGTCTCTTATGGCTTCTAAAGTATTATATTATCCATAATTTGATATTTTTCTC

2343 TGAATACGCACCTGCCACTACAGAATGATTATTGTTTCAGCTCCTAAGTACAAATCCAAAAAAAAAAAAAAAAA (SEQ ID NO: 5)
```

FIG. 4C

```
1                                          M  T  R  A  A  E  R  G  Q  G  A  T  G  W  G  L  R
1    TCAGTGCTGCCCTGAGCCGCCCGGCCTGAGCACGCAGACATGACCCGAGCCGCAGAGCGAGGCCAAGGGGCTACAGGCTGGGGGCTGCGC

18    G  A  L  V  A  I  A  L  L  S  A  L  N  A  A  G  T  V  F  V  L  C  Q  W  R  G  L  S  A  A
91   GGCGCCCTGGTGGCCATAGCGCTGCTGTCCGCACTGAACGCCGCGGGCACCGTGTTCGTGCTGTGCCAGTGGCGGGGGTTAAGCGCGGCG

48    L  R  A  L  E  A  Q  R  G  R  E  Q  R  E  D  S  A  L  R  A  F  L  A  E  L  S  R  A  P  G
181  CTACGGGCGCTGGAGGCTCAACGCGGCCGAGAGCAGCGCGAGGACAGCGCCCTACGCGCCTTTCTGGCCGAATTGAGTCGTGCGCCGGGC

78    R  V  P  E  P  S  Q  D  P  M  S  A  A  R  N  K  R  S  H  N  G  E  P  A  S  H  I  R  A  E
271  CGGGTCCCCGAACCATCCCAGGACCCCATGAGCGCAGCGCGCAACAAGCGCAGCCACAACGGCGAGCCTGCGTCACACATCCGTGCGGAG

108   S  Q  D  M  M  M  M  M  T  Y  S  M  V  P  I  R  V  M  I  D  L  C  N  S  T  Q  G  I  C  L
361  AGCCAGGACATGATGATGATGATGACCTACTCCATGGTGCCGATTCGAGTGATGATAGACCTGTGCAACAGTACCCAGGGCATCTGCCTC

138   T  G  P  P  G  P  P  G  P  P  G  A  G  G  L  P  G  H  N  G  S  D  G  Q  P  G  L  Q  G  P
451  ACAGGACCACCGGGCCCACCAGGACCTCCAGGAGCCGGCGGGTTACCAGGCCACAATGGATCAGATGGACAGCCTGGTCTCCAGGGCCCA

168   K  G  E  K  G  A  I  G  K  R  G  K  M  G  L  P  G  A  T  G  N  P  G  E  K  G  E  K  G  D
541  AAAGGAGAAAAAGGAGCAATTGGCAAGAGAGGAAAAATGGGGTTACCTGGAGCCACCGGAAATCCAGGGGAAAAGGGAGAAAAGGGAGAT
```

FIG. 5A

```
198  A  G  E  L  G  L  P  G  N  E  G  P  P  G  Q  K  G  D  K  G  D  K  G  D  V  S  N  D  V  L
631  GCTGGTGAACTGGGTCTACCTGGAAATGAGGGCCCACCAGGGCAGAAAGGTGACAAGGGAGACAAAGGAGACGTGTCCAATGACGTGCTT

228  L  T  G  A  K  G  D  Q  G  P  P  G  P  P  G  P  P  G  P  P  G  P  P  G  S  R  R  S  K  G
721  TTGACAGGTGCCAAAGGTGACCAAGGTCCCCCTGGCCCCCCTGGACCTCCAGGGCCTCCAGGCCCTCCTGGAAGCAGAAGATCCAAAGGC

258  P  R  P  P  N  V  F  N  S  Q  C  P  G  E  T  C  V  I  P  N  D  D  T  L  V  G  R  A  D  E
811  CCTCGGCCACCAAACGTGTTCAACAGCCAGTGTCCAGGGGAGACGTGTGTCATACCCAATGATGATACCTTGGTGGGAAGAGCTGATGAG

288  K  A  N  E  R  H  S  P  Q  T  E  S  M  I  T  S  I  G  N  P  A  Q  V  L  K  V  R  E  T  F
901  AAAGCAAATGAACGCCATTCACCACAAACAGAATCTATGATCACTTCCATTGGCAACCCAGCCCAAGTCCTAAAAGTGAGAGAGACTTTT

318  G  T  W  M  R  E  S  A  N  K  S  D  D  R  I  W  V  T  E  H  F  S  G  I  M  V  K  E  F  K
991  GGGACTTGGATGAGAGAGTCTGCTAACAAAAGTGACGACCGCATTTGGGTGACTGAACATTTTTCAGGCATCATGGTGAAGGAGTTCAAA

348  D  L  P  A  L  L  N  S  S  F  T  L  L  H  L  P  H  Y  F  H  G  C  G  H  A  V  Y  N  N  S
1081 GACCTGCCGGCGCTCCTCAATAGCAGCTTCACACTCCTCCACCTCCCACATTATTTCCACGGCTGTGGGCACGCTGTTTACAACAACTCT

378  L  Y  Y  H  K  G  G  S  N  T  I  V  R  F  E  F  G  K  E  T  P  Q  T  L  K  L  E  N  A  L
1171 CTCTACTACCACAAAGGAGGCTCCAACACCATAGTGAGATTTGAATTTGGGAAAGAGACACCTCAGACTCTGAAGCTGGAAAATGCTTTG

408  Y  F  D  R  K  Y  L  F  A  N  S  K  T  Y  F  N  I  A  V  D  E  K  G  I  W  I  I  Y  A  S
1261 TATTTTGATCGAAAATACCTCTTTGCAAATTCCAAGACTTACTTCAACATAGCAGTGGATGAGAAGGGCATCTGGATTATCTACGCTTCA
```

FIG. 5B

```
 438  S  V  D  G  S  S  I  L  V  A  Q  L  D  E  R  T  F  S  V  T  Q  H  I  N  T  T  Y  P  K  S
1351  AGTGTGGATGGCTCAAGCATCCTTGTAGCACAGCTGGATGAGAGGACATTCTCCGTGACACAGCACATCAACACCACATACCCCAAATCC

 468  K  A  G  N  A  F  I  A  R  G  I  L  Y  V  T  D  T  K  D  T  R  V  T  F  A  F  D  L  L  G
1441  AAGGCTGGCAATGCCTTCATAGCCCGAGGGATCCTCTATGTCACAGACACCAAAGATACGAGGGTCACGTTTGCCTTTGATTTGTTAGGA

 498  G  K  Q  I  N  A  N  F  D  F  R  M  S  Q  S  V  L  A  M  L  S  Y  N  M  R  D  Q  H  L  Y
1531  GGAAAGCAAATCAATGCAAACTTTGATTTCAGAATGTCCCAGTCTGTTCTTGCCATGCTGTCATACAACATGAGAGATCAGCATTTATAC

 528  S  W  E  D  G  H  L  M  L  Y  P  V  Q  F  L  S  A  A  S  S  Q  R  (SEQ ID NO:8)
1621  TCGTGGGAAGATGGCCATCTGATGCTCTATCCTGTGCAGTTTCTGTCAGCGGCATCAAGTCAGCGGTAGGGTTCCCTCGGCTGTCTGCTC

1711  CCTCTCTATACTCCACATTGTCTAGGGTTTGGTCAAGCCCAACAGAAAGCTAGCCGGTAAAGGATACCCAGGCACTCGGAGCGTAAGCCC

1801  ATGCCACGGGCTCTTGCACAAGCGGCGAGTCCGCTCTAAGCCAGGTTGTTGAAATAGCTACAGATTAGAAATGGATGTGGAAGAGATCTG

1891  GTGACCCAGTATCCCTCCTCAAACTCAGCAAGTTAGCTCTCCCCCGACCGTAGCGTCCCCATAGGTAATACGAAACATCTGGGTATGACT

1981  GACATTTCCTCTTCCTAGATGAAATTCTGTGATTCTTGCCTGATTATATATTAGAATGCTTTCTGGATTCTTTTTTTTTTTCTCCACAT

2071  GTAAGTGAGCTTACTTGCAGCTTGAGGGGTGGGCCTTTCAGTGATGACTTATTTGGTATTTAGGGAAGGTGCACTGGCTCTTATGGCTTC

2161  TAAGGTTTTATTTTATTCATAATTTGTTATTTTCTCTGAATATTCACCTACCACTACAGAATGATCATTGTTTTCAGCTCCTAAACACAA

2251  ATCCAAGATTAATAAACAAACAAACAAACCATGAATAGATACAGGCTCAGAACTCTAAATGGAGCTGCATCAGGCCCATAGGCCATCTAG
```

FIG. 5C

```
2341  ATGCTGTCAATTTCTGATCATATTGTTTGCTGCTGGGAAAGTAAACAGGATATCTTCAGTTCGTGGTCCCTTTTGCCAAGGCCATGGGAT
2431  TGTTATCAGAGTGTCAAACACTAAGTGGCCAATAATCTGGTTAGAAGCATGGAAACATGATGGTTTTTCAGAAAACAGGCACCATTTAT
2521  ACTTACTGTTTAGAATGAGGGAAGGCAATTGGCTCAAAGGCCAAAGTCAGCTTAGCTCTTTTTCCTGTACCATCGCATCCCTGCACCTAA
2611  GAATCTCGCCTCAGAGTGTGTCAGCAGTGAAGCAGAGCCGCTCTGTAAATCCTGAACCATTACTGCCTGGCCTTTACAGAAAGAAAGAAA
2701  AAAAAATGTTGACCTTTCATCTAAGGACAGGGAACGAGCCAGGTTCTCAGAAGGGCTCACTCCCTGAGTCTGGTTAGGCTTTTTACGGAC
2791  TGACAGGCAGCATTTTATGTGGCTTGGGCTTTGGCAGAGGGAACAGGTAAGGACAGCATCAGATGGAGTAAGAGAACCTCCAGCCGTGGA
2881  GATGTTCACTCCCACGTGGTCCTCAAAGTTGGGTCTGTCCTCTTGGATAGCAAGGATCTAGTTTAATTGGTTCCTACAAGACCTTAAATA
2971  ACCACGTTCTCTGTCAACTCATTGAGTTCCAGGCAGGCCTGTGGAGCTTCAAAGAGGAAGCTGTGGATTTCATCGCCCCCCCCCCCCCGG
3061  AATATAGAAAAAGACACTACAGAAACTGTCCAGGAAAGACTGGCCAGCTGTTCCAAACCCACTCTCAGTGGGCCTGTGACCTGGTTTAGT
3151  TTTTTTAATAGAAGCATCTTGAGGCTTGGGGTATGCATTTTAACTATTTAACTTTCCCTGCCCTCTGAAAGCACCCAGGCAGCTGTTACT
3241  GGTGAACCTGTTGAGTTCTCAAGGTCATGGGTCCCAAAGCTTCCCCACTTCTTGATTAGATGGTTTTGCAGTTGGTCATCACAGCTTTTA
3331  AAGATATTCTCTCAGATTCATTTGTTGCAATGTAGAGTTCTAATGTTTCATCAGTGTATCTAATGAATGGTATTGTTCTTTTAAAGTATT
3421  CAAATATGAGATACTGTTTCTGAGTGCGGTAGACCTGGATATACATATAATTCCATTTTTTATTACTTAGTAGCATTGCTGAGAATAGA
```

FIG. 5D

3511 TACAATACTAATTGTACATACAAGCAAAATAGTTTAGTTATTGAATTAGCTCATTTTTAATATCTGAACTAGCAAATGTCTTAGCTTTCC

3601 TTTACTTTTTTCTTTCTTTTCCTTTCTTTTCTCTTCTTTTCCTTTCTTTCCTTTCCTTTTCTTTTCTTTTTTTTAAAGCAATGTCTTTGT

3691 GTTCGCCCAGACTTATCACAAACTCCTGCTTCAGATTCCTGGGTGCTGGGACCACAGGCACAGTGGCTCTTTGACTCTCTTAATTGTGTG

3781 TAAGGAATCATACATATACTCACGATTAGAGAAACTCGTCTGAAGATTTTGTTTCTTTTCATGGTTGTTTCTTTCTTTCTTTCTTTCTTT

3871 CTTTCTTTCGTTATAGTGTAGTGGGATTAGAACAAGTAAGGTTGACTGGTGTTTAATGAATTTATCTTTGCAGAAGGAAAGGAATTAAGG

3961 TTTTATTCCTTTTCTTGCAAACAGGACTTCATTCTATATCACTCAACACAGTGTTTCAGGCTCACTGCTAAAATAGTGTGCACATCTTAT

4051 ATTTTTAAATGAAGATAGTAATCAACCCTGCTGTCACTTGTAGCCAAGCTGTTCTAAAAGCACTTCATTTATGTCTGTATGAAATCAAGT

4141 GATTCTCCAATTCCTCTGAAATCTAAAGTAGATACCATTATACTAGAAACCACACCTTCCAGCTTCAAAGGTAGGCCAGACTCAACATTT

4231 ACAAAGCATTTCTATTAACTAATATAGAGTCCAACTAAGGTTGCAGAGTTGGCTCTGGCCTCAATGTATCATGTATCAATGTATCAGAGA

4321 ACGTGGTCCGGGCTGAATATTTCAGATCAATTCTGGTGCTGGGCTCATTCGAAGTCTTTTTACCCTCATAATCAAATGACAAGGTGAGAT

4411 GACAAATGAGGAAGCACAGTCCTTGAAAAGTCACTCGTCATCCTCCAAGCATAGCAAGTACCTTACTCAGGCATTGCCTGTCTGGTGTTG

4501 AGCTACCTGAAGGAAAAGTGGGGGGTGGAGCTCTTCAGTTTTCATCAGTGCTGTGGCCTTATTTATCTCATAATCTCCCATCAGTAACCA

4591 CAGATTCTAAACGACCAGCAAGTAACAGTTGTAAGTAGTAAAATAAAATTATCCTGAAT (SEQ ID NO:7)

FIG. 5E

```
1                                                    M  V  D  L  C  N  S  T  K  G  I  C  L  T
1 GACCATTGTGTATGATTCGTTGTTGACTGCAGCATCACTAGATCCGAGTGATGGTGGACCTGTGCAACAGCACCAAGGGCATCTGCCTCACA

15   G  P  S  G  P  P  G  P  P  G  A  G  G  L  P  G  H  N  G  L  D  G  Q  P  G  P  Q  G  P  K
93   GGACCTTCTGGACCACCAGGACCTCCGGGAGCCGGCGGGTTGCCAGGACACAACGGATTGGATGGACAGCCTGGTCCTCAGGGCCCAAAA

45   G  E  K  G  A  N  G  K  R  G  K  M  G  I  P  G  A  A  G  N  P  G  E  R  G  E  K  G  D  H
183  GGAGAAAAAGGAGCAAATGGAAAAAGAGGAAAAATGGGGATACCTGGAGCTGCAGGAAATCCAGGGGAAAGGGGAGAAAAGGGAGACCAT

75   G  E  L  G  L  Q  G  N  E  G  P  P  G  Q  K  G  E  K  G  D  K  G  D  V  S  N  D  V  L  L
273  GGTGAACTGGGCCTGCAGGGAAATGAGGGCCCACCAGGGCAGAAGGGAGAAAAGGGTGACAAAGGAGATGTGTCCAACGACGTGCTCCTG

105  A  G  A  K  G  D  Q  G  P  P  G  P  P  G  P  P  G  P  P  G  P  P  G  P  P  G  S  R  R  A
363  GCAGGTGCCAAAGGTGACCAAGGCCCACCCGGTCCACCTGGCCCCCAGGCCCTCCAGGTCCTCCAGGGCCCCCTGGAAGCAGAAGAGCC

135  K  G  P  R  Q  P  S  M  F  N  G  Q  C  P  G  E  T  C  A  I  P  N  D  D  T  L  V  G  K  A
453  AAAGGCCCTCGGCAGCCAAGCATGTTCAACGGCCAGTGCCCAGGTGAGACTTGTGCCATACCAAATGATGATACCTTGGTTGGAAAAGCT

165  D  E  K  A  S  E  H  H  S  P  Q  A  E  S  M  I  T  S  I  G  N  P  V  Q  V  L  K  V  T  E
543  GATGAGAAAGCCAGTGAACACCATTCCCCACAAGCAGAATCCATGATCACTTCCATTGGAAACCCAGTGCAAGTACTGAAAGTGACAGAG
```

FIG. 6A

```
195   T  F  G  T  W  I  R  E  S  A  N  K  S  D  D  R  I  W  V  T  E  H  F  S  G  I  M  V  K  E
633  ACATTTGGGACTTGGATAAGAGAGTCTGCTAACAAGAGTGATGACCGGATTTGGGTGACAGAGCATTTTTCAGGCATCATGGTTAAGGAA

225   F  K  D  Q  P  S  L  L  N  G  S  Y  T  F  I  H  L  P  Y  Y  F  H  G  C  G  H  V  A  Y  N
723  TTCAAGGATCAGCCCTCACTTCTGAATGGCAGTTACACGTTCATCCACCTTCCATACTATTTCCATGGCTGTGGGCACGTTGCTTACAAC

255   N  S  L  Y  Y  H  K  G  G  S  N  T  L  V  R  F  E  F  G  Q  E  T  S  Q  T  L  K  L  E  N
813  AACTCTCTCTACTACCACAAAGGGGGTTCTAATACCCTAGTGAGATTTGAATTTGGCCAGGAAACATCCCAAACTCTGAAGCTTGAAAAT

285   A  L  Y  F  D  R  K  Y  L  F  A  N  S  K  T  Y  F  N  L  A  V  D  E  K  G  L  W  I  I  Y
903  GCCTTGTATTTTGATCGAAAATACCTTTTTGCAAATTCCAAAACTTACTTCAATCTAGCTGTAGATGAAAAGGGCCTTTGGATTATCTAT

315   A  S  S  V  D  G  S  S  I  L  V  A  Q  L  D  E  R  T  F  S  V  V  Q  H  V  N  T  T  Y  P
993  GCGTCAAGTGTGGACGGCTCGAGCATTCTTGTAGCACAACTGGATGAGAGGACATTCTCAGTGGTGCAACACGTCAATACCACGTACCCT

345   K  S  K  A  G  N  A  F  I  A  R  G  I  L  Y  V  T  D  T  K  D  M  R  V  T  F  A  F  D  L
1083 AAATCCAAGGCTGGCAACGCCTTCATTGCCCGAGGAATCCTCTATGTCACAGACACCAAAGATATGAGGGTCACATTTGCCTTTGATTTG

375   L  G  G  K  Q  I  N  A  N  F  D  L  R  T  S  Q  S  V  L  A  M  L  A  Y  N  M  R  D  Q  H
1173 TTAGGAGGGAAACAGATCAATGCAAACTTTGATTTAAGAACTTCCCAGTCTGTTCTTGCCATGTTAGCATACAACATGAGAGATCAGCAT

405   L  Y  S  W  E  D  G  H  L  M  L  Y  P  V  Q  F  L  S  T  T  L  N  Q  (SEQ ID NO:10)
1263 TTATATTCATGGGAAGATGGCCATTTAATGCTTTATCCTGTGCAGTTTTTGTCAACTACCTTAAATCAGTGATGTGCTGCATTCGGCTCC
```

FIG. 6B

1353 CTTCAGCAAATTTCAGGGGTTTTCTGGGACCAGTTCTCCCCCAACAGGAAACTTGTTTTTTAACGTCAGCCAGATATTTAGAAAATAAC

1443 CTCAAAAGTGTTTATATGGTCAGTGAGCCCCGCTTAGTGAAATAGCAACAGATTGGAAGTTGAAATGGCTGAGATTTGGTGATCTCCCCA

1533 CAGCTGGCTCTGCAAGTTACCTCTTTCTCCTTGGGCCTTAGTTTCCCCATTGGTAATCTGAATTGGCTAAGATGATTGGGGAGATTTTCT

1623 GTACCTGTAGGTAATTTGGTGATTCTTGGTGGCTGCTCTTCTCACAACTTTTATGTATCTGCTTCTGTCGTTTAGCTTTTTTAGCCACAT

1713 GCTGACCAAATTTACCTTTGAGTTGATAAGTCCAGTGGCTTGAGTAGTGAATCCCTCAGTGCTGACTTATATCTTGTTCTTTGAAAAAAT

1803 GCATTGACTCTTTAAGACATCTAAAGTATCACATTATCCATAATTTATTGCTTTTCTTTGCATCTGCACCTGCCACCACAGAATAACCAT

1893 TACCCTCAGCTGCTGATTGGGCAGCTCTGAGATTAGCAAAAGCCAGGGACAGCTACATGTTCAGGTTTTTTTTTTTTTTTTTTCAATAG

1983 GCTATTTTTTTCTTTTCTTATTTTAAATAGAGAGAGAGTCTTGCTATGTTTCCCAGGCTGGTCTTGAACTCCTGGGGCTCAAGTGATCC

2073 TCCTGCCTTGGCCTCCCAAAATGCTGGATTACAGGCATGTGTGCCTGGCCCAGGTTTCTTAATAAAACAGAATCATGATCTTCCAGGTTC

2163 CCCCCAGTTTCTGATCATGTTGATTTGTAGCTGTGGATCATGAACACTGAATCCCCAGATCACTCTGACTTCTTATGCTTCTCCTGTGGA

2253 TCCACTATCAAAGTACTAAATGCTGTGTAAGTAGACGTTAATCTGGCTGGAACCATGGGAAGCACTTTGCAGTGTTCAGAAGAGAGGCTC

2343 CATTTGTGGCTATTATGTAGAACTGGGCCAGAGCCAGTCCATTGCCTGTTTTTTTAAATAAGGTTTACTGAGCACAGCCACACTCATTT

2433 GTTTATGCAGTACGGCCTGACATTGCTTTTGCTCTGCAACAGCAGAGTCGAGTCATTGCAACAAAGAGCATATGGCCCCACAGTGCCTAA

FIG. 6C

2523 AATATTGACCAGCTACCCCTTTATGGAAAAAGATTGCTGACTCCTGATAAAGAATATAAAGTGAGCCTGATTCTTGAAAAAATCAGAACC

2613 AGAGCCTGTTTTGTTTTGTTCTAAACTAAGAAGCCGCATAGGATGTGACTTGCGTTTTGAGTAGAGGGGAAGGCTGATAACGGCGTAAGA

2703 TGAAGTGGCCCTCCACAAAGGCTGGTTAGGGGACAGTTCTTTCTCTAACATAGTTTTAAAGGATGTGATCTGGTCCCCTTGGATGCCAGG

2793 AGAGAATCCAGTTGAACTTGCTCCTAAATGCTCTTAAATATGCATATTTTCTGCCAACTCACTTCTTTAAACATCTTTCAGCCCAGCGCT

2883 GCGGCCCCGGGAAGGGCCACTGCGAATAGAGAGGAAGCTGGAAAAGTTCCTGGGGCTCTGCAGCCAGGAAGGGGAACCAGGGCAAATCTT

2973 ATGTAAAGATTTTTCAGCAACTTGTCCCAATTTGTGTGTATTCTGAAACTTTCTCTTTGGGACCAAATTCATTCTCAATGGCCCTGAGTT

3063 CAATATATTATTAACAGCAGTATTTTAAAACTTAGGGTTGAACTGGGCATGGTGGCACATAACTGCAATCCCAGCTACTTTGGAGGCAGG

3153 GATGGGAGGATCACTTGAGGCCAGGATCTCAGGACCAGCCTAGAGAGATCCCATCTCTAAAAAATAAAATATAAGAAAATAAAACTTAGG

3243 GGATATACAGATTTAAATATTCAAATCTCCCTGCTCCCCTGAAAGTCCCCAGGCAGCTGTTAATGACTTGTTTGTTGTGTTCTCAATATG

3333 ATGGCTATTTGAAACTTCACCTACTTTTCATTAGATTGGTTGTACCATGTCACCTTAGCTTTTAAAAATACTCTTTTCAGATTCACGTTC

3423 TCTAACAAAGAGTCTCATGTTCAAGATCAATATGTCTAATAAGCGCTGGTGTCCTTTTAAAGTATTTAAATATATATGTTGCTGTTGCTG

3513 AATACAGGAGACCAGGTTAGGAATATAGTTTCATAATAATAGTACATACAATACTAATTGTATATAAGGTAGCAACCAAAAGAGGTTGTT

3603 AATTAGCACATATTCCTTTTAGAAAAATGTTTCAGAAACCTCAGTCTTGATATCTGAGCTATCTGGGCTCCCTTACTTGTGAGTAAGGGA

FIG. 6D

3693 TCATGCTCACCACTGGAGAAGCTTACACCGGGACTTTTTTTCTTTTTTCTTTTTTTTTTGCTATGACAGAGTAATGCTAACGTAAGGACA

3783 ACTGAGTTTGATCAGTGTTTAATCGCAGTGGGTAATCTTATCTGATTGTCTTTAAAAGTGAAAAGGATTAAGATTTTATTCTTTCTTGTA

3873 AACATTACTTGATTTTTTAAAGAAGTTTTGGGCTCACTGCTAAAATAGAGTATACAACTGAATGTTTTTAAGTCAAGATACTGTTTTAGG

3963 AGTTTACCCTCTCATTTATAACCAAAGTTGCTCTAAAACACTTTCCAAATATCTGCACTTCTGATGTCAGAATCAAACCAGATAATTCTC

4053 TAATTCTTCTTTAATCTAAAGTAGATAGCTTCCCACTGGAAAGTAAACAAAACCATCCCTCCCAACCTCAAAGCTAGGCCACACTCTATT

4143 TCAAGGCATTTTCTTTCAGCTGATAAGGTGTCCTCCTGAAGCCAAGTAGGTGGTTCTGGTCTCCAAGTATCGTTAAGCACAGGTGCTATG

4233 ACAGAAAAAGTTCTGGGGTGGAAGTTTTAAGATGAGGAGTTCTGATCTTAGGCATCTTAACAGTCACAAGGTGAAAAGTCAAATGAAACA

4323 GTACAATTCTTGATGAGTGAGGTGTCATCTTCCAACCACACAGAGGACGTTTTGGCTATGATCATCTGATGGCAAGTGAAGGAGAAATGA

4413 GTGATAGGGCTTTGCGTTTTCATCCAGATGCTGTGGCCCTGTGTTTCACAGCATTAAGAGCCATAATTTCCAACCTGCACAGATCCTGAA

4503 CAACAAATGAATAACGATGAATGTCTTTTTGGTTGTAATTTAACAAGTCAAATAAATAATCATTGCTGAGCACAATCACCAAAAAAAAAA

4593 AAAAAAAAAAAAAAAAAAAAAAAAAAAAAAAAAAAAAGAAAAAAAAAAAAAAAAAACA (SEQ ID NO:9)

FIG. 6E

```
1   M  A  R  G  A  E  G  G  R  G  D  A  G  W  G  L  R  G  A  L  A  A  V  A  L  L  S  A  L  N
1   ATGGCCCGAGGCGCTGAGGGAGGCCGTGGGGACGCGGGTTGGGGCCTGCGTGGCGCCCTGGCGGCCGTGGCGCTGCTCTCGGCGCTCAAC

31  A  A  G  T  V  F  A  L  C  Q  W  R  G  L  S  S  A  L  R  A  L  E  A  Q  R  G  R  E  Q  R
91  GCTGCGGGCACGGTGTTCGCGCTGTGCCAGTGGCGCGGGCTGAGCTCGGCGCTGCGGGCTTTGGAGGCGCAGCGGGGCCGGGAGCAGCGC
```

FIG. 7A

```
 61  E  D  S  A  L  R  S  F  L  A  E  L  S  R  A  P  R  G  A  S  A  P  P  Q  D  P  A  S  S  A
181  GAGGACAGTGCCCTGCGCTCCTTCCTGGCCGAGTTGAGCCGCGCGCCGCGCGGGGCGTCCGCACCACCCCAAGACCCGGCCAGCTCAGCT

 91  R  N  K  R  S  H  S  G  E  P  A  P  H  I  R  A  E  S  H  D  M  L  M  M  M  T  Y  S  M  V
271  CGCAACAAGCGCAGCCACAGCGGCGAGCCCGCGCCGCATATCCGCGCCGAGAGCCATGACATGCTGATGATGATGACCTACTCCATGGTG

121  P  I  R  V  M  V  D  L  C  N  S  T  K  G  I  C  L  T  G  P  S  G  P  P  G  P  P  G  A  G
361  CCGATCCGAGTGATGGTGGACCTGTGCAACAGCACCAAGGGCATCTGCCTCACAGGACCTTCTGGACCACCAGGACCTCCGGGAGCCGGC

151  G  L  P  G  H  N  G  L  D  G  Q  P  G  P  Q  G  P  K  G  E  K  G  A  N  G  K  R  G  K  M
451  GGGTTGCCAGGACACAACGGATTGGATGGACAGCCTGGTCCTCAGGGCCCAAAAGGAGAAAAAGGAGCAAATGGAAAAAGAGGAAAAATG

181  G  I  P  G  A  A  G  N  P  G  E  R  G  E  K  G  D  H  G  E  L  G  L  Q  G  N  E  G  P  P
541  GGGATACCTGGAGCTGCAGGAAATCCAGGGGAAAGGGGAGAAAAGGGAGACCATGGTGAACTGGGCCTGCAGGGAAATGAGGGCCCACCA

211  G  Q  K  G  E  K  G  D  K  G  D  V  S  N  D  V  L  L  A  G  A  K  G  D  Q  G  P  P  G  P
631  GGGCAGAAGGGAGAAAAGGGTGACAAAGGAGATGTGTCCAACGACGTGCTCCTGGCAGGTGCCAAAGGTGACCAAGGCCCACCCGGTCCA

241  P  G  P  P  G  P  P  G  P  P  G  P  P  G  S  R  R  A  K  G  P  R  Q  P  S  M  F  N  G  Q
721  CCTGGGCCCCCAGGCCCTCCAGGTCCTCCAGGGCCCCCTGGAAGCAGAAGAGCCAAAGGCCCTCGGCAGCCAAGCATGTTCAACGGCCAG

271  C  P  G  E  T  C  A  I  P  N  D  D  T  L  V  G  K  A  D  E  K  A  S  E  H  H  S  P  Q  A
811  TGCCCAGGTGAGACTTGTGCCATACCAAATGATGATACCTTGGTTGGAAAAGCTGATGAGAAAGCCAGTGAACACCATTCCCCACAAGCA
```

FIG. 7B

```
301   E  S  M  I  T  S  I  G  N  P  V  Q  V  L  K  V  T  E  T  F  G  T  W  I  R  E  S  A  N  K
901   GAATCCATGATCACTTCCATTGGAAACCCAGTGCAAGTACTGAAAGTGACAGAGACATTTGGGACTTGGATAAGAGAGTCTGCTAACAAG

331   S  D  D  R  I  W  V  T  E  H  F  S  G  I  M  V  K  E  F  K  D  Q  P  S  L  L  N  G  S  Y
991   AGTGATGACCGGATTTGGGTGACAGAGCATTTTTCAGGCATCATGGTTAAGGAATTCAAGGATCAGCCCTCACTTCTGAATGGCAGTTAC

361   T  F  I  H  L  P  Y  Y  F  H  G  C  G  H  V  A  Y  N  N  S  L  Y  Y  H  K  G  G  S  N  T
1081  ACGTTCATCCACCTTCCATACTATTTCCATGGCTGTGGGCACGTTGCTTACAACAACTCTCTCTACTACCACAAAGGGGGTTCTAATACC

391   L  V  R  F  E  F  G  Q  E  T  S  Q  T  L  K  L  E  N  A  L  Y  F  D  R  K  Y  L  F  A  N
1171  CTAGTGAGATTTGAATTTGGCCAGGAAACATCCCAAACTCTGAAGCTTGAAAATGCCTTGTATTTTGATCGAAAATACCTTTTTGCAAAT

421   S  K  T  Y  F  N  L  A  V  D  E  K  G  L  W  I  I  Y  A  S  S  V  D  G  S  S  I  L  V  A
1261  TCCAAAACTTACTTCAATCTAGCTGTAGATGAAAAGGGCCTTTGGATTATCTATGCGTCAAGTGTGGACGGCTCGAGCATTCTTGTAGCA

451   Q  L  D  E  R  T  F  S  V  V  Q  H  V  N  T  T  Y  P  K  S  K  A  G  N  A  F  I  A  R  G
1351  CAACTGGATGAGAGGACATTCTCAGTGGTGCAACACGTCAATACCACGTACCCTAAATCCAAGGCTGGCAACGCCTTCATTGCCCGAGGA

481   I  L  Y  V  T  D  T  K  D  M  R  V  T  F  A  F  D  L  L  G  G  K  Q  I  N  A  N  F  D  L
1441  ATCCTCTATGTCACAGACACCAAAGATATGAGGGTCACATTTGCCTTTGATTTGTTAGGAGGGAAACAGATCAATGCAAACTTTGATTTA

511   R  T  S  Q  S  V  L  A  M  L  A  Y  N  M  R  D  Q  H  L  Y  S  W  E  D  G  H  L  M  L  Y
1531  AGAACTTCCCAGTCTGTTCTTGCCATGTTAGCATACAACATGAGAGATCAGCATTTATATTCATGGGAAGATGGCCATTTAATGCTTTAT
```

FIG. 7C

541 P V Q F L S T T L N Q (SEQ ID NO:12)
1621 CCTGTGCAGTTTTTGTCAACTACCTTAAATCAGTGATGTGCTGCATTCGGCTCCCTTCAGCAAATTTCAGGGGTTTTCTGGACCAGTTC

1711 TCCCCCAACAGGAAACTTGTTTTTTTAACGTCAGCCAGATATTTAGAAAATAACCTCAAAAGTGTTTATATGGTCAGTGAGCCCCGCTTA

1801 GTGAAATAGCAACAGATTGGAAGTTGAAATGGCTGAGATTTGGTGATCTCCCCACAGCTGGCTCTGCAAGTTACCTCTTTCTCCTTGGGC

1891 CTTAGTTTCCCCATTGGTAATCTGAATTGGCTAAGATGATTGGGGAGATTTTCTGTACCTGTAGGTAATTTGGTGATTCTTGGTGGCTGC

1981 TCTTCTCACAACTTTTATGTATCTGCTTCTGTCGTTTAGCTTTTTAGCCACATGCTGACCAAATTTACCTTTGAGTTGATAAGTCCAGT

2071 GGCTTGAGTAGTGAATCCCTCAGTGCTGACTTATATCTTGTTCTTTGAAAAAATGCATTGACTCTTTAAGACATCTAAAGTATCACATTA

2161 TCCATAATTTATTGCTTTTCTTTGCATCTGCACCTGCCACCACAGAATAACCATTACCCTCAGCTGCTGATTGGGCAGCTCTGAGATTAG

2251 CAAAAGCCAGGGACAGCTACATGTTCAGGTTTTTTTTTTTTTTTTTTTTCAATAGGCTATTTTTTTTCTTTTCTTATTTAAATAGAGAGA

2341 GAGTCTTGCTATGTTTCCCAGGCTGGTCTTGAACTCCTGGGGCTCAAGTGATCCTCCTGCCTTGGCCTCCCAAAATGCTGGATTACAGGC

2431 ATGTGTGCCTGGCCCAGGTTTCTTAATAAAACAGAATCATGATCTTCCAGGTTCCCCCCAGTTTCTGATCATGTTGATTTGTAGCTGTGG

2521 ATCATGAACACTGAATCCCCAGATCACTCTGACTTCTTATGCTTCTCCTGTGGATCCACTATCAAAGTACTAAATGCTGTGTAAGTAGAC

2611 GTTAATCTGGCTGGAACCATGGGAAGCACTTTGCAGTGTTCAGAAGAGAGGCTCCATTTGTGGCTATTATGTAGAACTGGGCCAGAGCCA

FIG. 7D

2701 GTCCATTGCCTGTTTTTTTAAATAAGGTTTTACTGAGCACAGCCACACTCATTTGTTTATGCAGTACGGCCTGACATTGCTTTTGCTCTG

2791 CAACAGCAGAGTCGAGTCATTGCAACAAAGAGCATATGGCCCCACAGTGCCTAAAATATTGACCAGCTACCCCTTTATGGAAAAAGATTG

2881 CTGACTCCTGATAAAGAATATAAAGTGAGCCTGATTCTTGAAAAAATCAGAACCAGAGCCTGTTTTGTTTTGTTCTAAACTAAGAAGCCG

2971 CATAGGATGTGACTTGCGTTTTGAGTAGAGGGGAAGGCTGATAACGGCGTAAGATGAAGTGGCCCTCCACAAAGGCTGGTTAGGGGACAG

3061 TTCTTTCTCTAACATAGTTTTAAAGGATGTGATCTGGTCCCCTTGGATGCCAGGAGAGAATCCAGTTGAACTTGCTCCTAAATGCTCTTA

3151 AATATGCATATTTTCTGCCAACTCACTTCTTTAAACATCTTTCAGCCCAGCGCTGCGGCCCCGGGAAGGGCCACTGCGAATAGAGAGGAA

3241 GCTGGAAAAGTTCCTGGGGCTCTGCAGCCAGGAAGGGGAACCAGGGCAAATCTTATGTAAAGATTTTTCAGCAACTTGTCCCAATTTGTG

3331 TGTATTCTGAAACTTTCTCTTTGGGACCAAATTCATTCTCAATGGCCCTGAGTTCAATATATTATTAACAGCAGTATTTTAAAACTTAGG

3421 GTTGAACTGGGCATGGTGGCACATAACTGCAATCCCAGCTACTTTGGAGGCAGGGATGGGAGGATCACTTGAGGCCAGGATCTCAGGACC

3511 AGCCTAGAGAGATCCCATCTCTAAAAAATAAAATATAAGAAAATAAAACTTAGGGGATATACAGATTTAAATATTCAAATCTCCCTGCTC

3601 CCCTGAAAGTCCCCAGGCAGCTGTTAATGACTTGTTTGTTGTGTTCTCAATATGATGGCTATTTGAAACTTCACCTACTTTTCATTAGAT

3691 TGGTTGTACCATGTCACCTTAGCTTTTAAAAATACTCTTTTCAGATTCACGTTCTCTAACAAAGAGTCTCATGTTCAAGATCAATATGTC

3781 TAATAAGCGCTGGTGTCCTTTTAAAGTATTTAAATATATATGTTGCTGTTGCTGAATACAGGAGACCAGGTTAGGAATATAGTTTCATAA

FIG. 7E

```
3871  TAATAGTACATACAATACTAATTGTATATAAGGTAGCAACCAAAAGAGGTTGTTAATTAGCACATATTCCTTTTAGAAAAATGTTTCAGA
3961  AACCTCAGTCTTGATATCTGAGCTATCTGGGCTCCCTTACTTGTGAGTAAGGGATCATGCTCACCACTGGAGAAGCTTACACCGGGACTT
4051  TTTTTCTTTTTTCTTTTTTTTTTGCTATGACAGAGTAATGCTAACGTAAGGACAACTGAGTTTGATCAGTGTTTAATCGCAGTGGGTAAT
4141  CTTATCTGATTGTCTTTAAAAGTGAAAAGGATTAAGATTTTATTCTTTCTTGTAAACATTACTTGATTTTTTAAAGAAGTTTTGGGCTCA
4231  CTGCTAAAATAGAGTATACAACTGAATGTTTTTAAGTCAAGATACTGTTTTAGGAGTTTACCCTCTCATTTATAACCAAAGTTGCTCTAA
4321  AACACTTTCCAAATATCTGCACTTCTGATGTCAGAATCAAACCAGATAATTCTCTAATTCTTCTTTAATCTAAAGTAGATAGCTTCCCAC
4411  TGGAAAGTAAACAAAACCATCCCTCCCAACCTCAAAGCTAGGCCACACTCTATTTCAAGGCATTTTCTTTCAGCTGATAAGGTGTCCTCC
4501  TGAAGCCAAGTAGGTGGTTCTGGTCTCCAAGTATCGTTAAGCACAGGTGCTATGACAGAAAAAGTTCTGGGGTGGAAGTTTTAAGATGAG
4591  GAGTTCTGATCTTAGGCATCTTAACAGTCACAAGGTGAAAAGTCAAATGAAACAGTACAATTCTTGATGAGTGAGGTGTCATCTTCCAAC
4681  CACACAGAGGACGTTTTGGCTATGATCATCTGATGGCAAGTGAAGGAGAAATGAGTGATAGGGCTTTGCGTTTTCATCCAGATGCTGTGG
4771  CCCTGTGTTTCACAGCATTAAGAGCCATAATTTCCAACCTGCACAGATCCTGAACAACAAATGAATAACGATGAATGTCTTTTTGGTTGT
4861  AATTTAACAAGTCAAATAAATAATCATTGCTGAGCACAATCACCAAAAAAAAAAAAAAAAAAAAAAAAAAAAAAAAAAAAAAAAAAAAAA
4951  AAAAAAGAAAAAAAAAAAAAAAAACA (SEQ ID NO:11)
```

FIG. 7F

```
               1            15 16           30 31           45 46           60 61           75 76           90
1 rFP-1a       MTRAAERGQGATGWG LRGALMAVALLSVLN AVGTVFVLYQWRELS AALRALEAQHGQEQR EDSALRAFLAELSRA PARVPEPPQDPMSAA   90
2 rGliomedin   MTRAAERGQGATGWG LRGALMAVALLSVLN AVGTVFVLYQWRELS AALRALEAQHGQEQR EDSALRAFLAELSRA PARVPEPPQDPMSAA   90
3 rFP-1b       MTRAAERGQGATGWG LRGALMAVALLSVLN AVGTVFVLYQQ---- --------------R EDSALRAFLAELSRA PARVPEPPQDPMSAA   72
4 mCRG-L2      MTRAAERGQGATGWG LRGALVAIALLSALN AAGTVFVLCQWRGLS AALRALEAQRGREQR EDSALRAFLAELSRA PGRVPEPSQDPMSAA   90
5 hCRG-L2      --------------- --------------- --------------- --------------- --------------- ---------------    0
6 hFP-1        MARGAEGGRGDAGWG LRGALAAVALLSALN AAGTVFALCQWRGLS SALRALEAQRGREQR EDSALRSFLAELSRA PRGASAPPQDPASSA   90

               91          105 106         120 121         135 136         150 151         165 166         180
1 rFP-1a       RNKRSHGGEPASHIR AESQDMMMMMTYSMV PIRVMIDLCNSTQGI CLTGPPGPPGPPGAG GLPGHNGSDGQPGLQ GPKGEKGAVGKRGKM  180
2 rGliomedin   RNKRSHGGEPASHIR AESQDMMMMMTYSMV PIRVMIDLCNSTQGI CLTGPPGPPGPPGAG GLPGHNGSDGQPGLQ GPKGEKGAVGKRGKM  180
3 rFP-1b       RNKRSHGGEPASHIR AESQDMMMMMTYSMV PIRVMIDLCNSTQGI CLTGPPGPPGPPGAG GLPGHNGSDGQPGLQ GPKGEKGAVGKRGKM  162
4 mCRG-L2      RNKRSHNGEPASHIR AESQDMMMMMTYSMV PIRVMIDLCNSTQGI CLTGPPGPPGPPGAG GLPGHNGSDGQPGLQ GPKGEKGAIGKRGKM  180
5 hCRG-L2      --------------- --------------- ----MVDLCNSTKGI CLTGPSGPPGPPGAG GLPGHNGLDGQPGPQ GPKGEKGANGKRGKM   56
6 hFP-1        RNKRSHSGEPAPHIR AESHDMLMMMTYSMV PIRVMVDLCNSTKGI CLTGPSGPPGPPGAG GLPGHNGLDGQPGPQ GPKGEKGANGKRGKM  180

               181         195 196         210 211         225 226         240 241         255 256         270
1 rFP-1a       GLPGATGNPGEKGEK GDAGELGLPGNEGPP GQKGDKGDKGDVSND VLLTGAKGDQGPPGP PGPPGPPGPPG---S RRAKGPRQPNSFTNQ  267
2 rGliomedin   GLPGATGNPGEKGEK GDAGELGLPGNEGPP GQKGDKGDKGDVSND VLLTGAKGDQGPPGP PGPPGPPGPPG---S RRAKGPRQPNSFTNQ  267
3 rFP-1b       GLPGATGNPGEKGEK GDAGELGLPGNEGPP GQKGDKGDKGDVSND VLLTGAKGDQGPPGP PGPPGPPGPPG---S RRAKGPRQPNSFTNQ  249
4 mCRG-L2      GLPGATGNPGEKGEK GDAGELGLPGNEGPP GQKGDKGDKGDVSND VLLTGAKGDQGPPGP PGPPGPPGPPG---S RRSKGPRPPNVFNSQ  267
5 hCRG-L2      GIPGAAGNPGERGEK GDHGELGLQGNEGPP GQKGEKGDKGDVSND VLLAGAKGDQGPPGP PGPPGPPGPPGPPGS RRAKGPRQPSMFNGQ  146
6 hFP-1        GIPGAAGNPGERGEK GDHGELGLQGNEGPP GQKGEKGDKGDVSND VLLAGAKGDQGPPGP PGPPGPPGPPGPPGS RRAKGPRQPSMFNGQ  270
```

FIG. 8A

```
             271           285 286           300 301           315 316           330 331           345 346           360
1 rFP-1a     CPGETCVIPNDDTLV GRADEKVNERHSPQT EPMITSIGNPAQVLK VKETFGTWLRESANR SDDRIWVTEHFSGIM VKEFEDLPALLNSSF    357
2 rGliomedin CPGETCVIPNDDTLV GRADEKVNERHSPQT EPMITSIGNPAQVLK VKETFGTWLRESANR SDDRIWVTEHFSGIM VKEFEDLPALLNSSF    357
3 rFP-1b     CPGETCVIPNDDTLV GRADEKVNERHSPQT EPMITSIGNPAQVLK VKETFGTWLRESANR SDDRIWVTEHFSGIM VKEFEDLPALLNSSF    339
4 mCRG-L2    CPGETCVIPNDDTLV GRADEKANERHSPQT ESMITSIGNPAQVLK VRETFGTWMRESANK SDDRIWVTEHFSGIM VKEFKDLPALLNSSF    357
5 hCRG-L2    CPGETCAIPNDDTLV GKADEKASEHHSPQA ESMITSIGNPVQVLK VTETFGTWIRESANK SDDRIWVTEHFSGIM VKEFKDQPSLLNGSY    236
6 hFP-1      CPGETCAIPNDDTLV GKADEKASEHHSPQA ESMITSIGNPVQVLK VTETFGTWIRESANK SDDRIWVTEHFSGIM VKEFKDQPSLLNGSY    360

             361           375 376           390 391           405 406           420 421           435 436           450
1 rFP-1a     TLLHLPHYFHGCGHA VYNNSLYYHKGGSNT IVRFEFGKETPQTLK LEDALYFDRKYLFAN SKTYFNIAVDEKGLW IIYASSVDGSSILVA    447
2 rGliomedin TLLHLPHYFHGCGHA VYNNSLYYHKGGSNT IVRFEFGKETPQTLK LEDALYFDRKYLFAN SKTYFNIAVDEKGLW IIYASSVDGSSILVA    447
3 rFP-1b     TLLHLPHYFHGCGHA VYNNSLYYHKGGSNT IVRFEFGKETPQTLK LEDALYFDRKYLFAN SKTYFNIAVDEKGLW IIYASSVDGSSILVA    429
4 mCRG-L2    TLLHLPHYFHGCGHA VYNNSLYYHKGGSNT IVRFEFGKETPQTLK LENALYFDRKYLFAN SKTYFNIAVDEKGIW IIYASSVDGSSILVA    447
5 hCRG-L2    TFIHLPYYFHGCGHV AYNNSLYYHKGGSNT LVRFEFGQETSQTLK LENALYFDRKYLFAN SKTYFNLAVDEKGLW IIYASSVDGSSILVA    326
6 hFP-1      TFIHLPYYFHGCGHV AYNNSLYYHKGGSNT LVRFEFGQETSQTLK LENALYFDRKYLFAN SKTYFNLAVDEKGLW IIYASSVDGSSILVA    450

             451           465 466           480 481           495 496           510 511           525 526           540
1 rFP-1a     QLDERTFSVLQHINT TYPKSKAGNAFIAQG ILYVTDTKDTRVTFA FDLLRGKQINANFGL RMSQSVLAMLSYNMR DQHLYSWEDGHLMLY    537
2 rGliomedin QLDERTFSVLRHINT TYPKSKAGNAFIAQG ILYVTDTKDTRVTFA FDLLRGKQINANFGL RMSQSVLAMLSYNMR DQHLYSWEDGHLMLY    537
3 rFP-1b     QLDERTFSVLQHINT TYPKSKAGNAFIAQG ILYVTDTKDTRVTFA FDLLRGKQINANFGL RMSQSVLAMLSYNMR DQHLYSWEDGHLMLY    519
4 mCRG-L2    QLDERTFSVTQHINT TYPKSKAGNAFIARG ILYVTDTKDTRVTFA FDLLGGKQINANFDF RMSQSVLAMLSYNMR DQHLYSWEDGHLMLY    537
5 hCRG-L2    QLDERTFSVVQHVNT TYPKSKAGNAFIARG ILYVTDTKDMRVTFA FDLLGGKQINANFDL RTSQSVLAMLAYNMR DQHLYSWEDGHLMLY    416
6 hFP-1      QLDERTFSVVQHVNT TYPKSKAGNAFIARG ILYVTDTKDMRVTFA FDLLGGKQINANFDL RTSQSVLAMLAYNMR DQHLYSWEDGHLMLY    540
```

FIG. 8B

| | | | |
|---|---|---|---|
| | 541 | | |
| 1 rFP-1a | PVHFSSTAPSQR | 549 | - SEQ ID NO: 2 |
| 2 rGliomedin | PVHFSSTAPSQR | 549 | - SEQ ID NO: 4 |
| 3 rFP-1b | PVHFSSTAPSQR | 531 | - SEQ ID NO: 6 |
| 4 mCRG-L2 | PVQFLSAASSQR | 549 | - SEQ ID NO: 8 |
| 5 hCRG-L2 | PVQFLSTTLNQ- | 427 | - SEQ ID NO: 10 |
| 6 hFP-1 | PVQFLSTTLNQ- | 551 | - SEQ ID NO: 12 |

1. rat FP-1a
2. rat gliomedin (AAP22419)
3. rat FP-1b
4. mouse CRG-L2 (NP_796324)
5. human likely ortholog of mouse cancer related gene - liver 2 (CRG-L2): (NP_861454)
6. hypothetical human FP-1 full length

FIG. 8C

| | 1 15 | 16 30 | 31 45 | 46 60 | 61 75 | 76 90 | |
|---|---|---|---|---|---|---|---|
| 1 FP-1a | ATGACCCGAGCCGCA | GAGCGAGGCCAAGGG | GCTACAGGCTGGGGA | CTGCGAGGCGCCCTG | ATGGCCGTGGCGCTG | CTGTCAGTGCTGAAC | 90 |
| 2 rGliomedin | ATGACCCGAGCCGCA | GAGCGAGGCCAAGGG | GCTACAGGCTGGGGA | CTGCGAGGCGCCCTG | ATGGCCGTGGCGCTG | CTGTCAGTGCTGAAC | 90 |
| 3 hFP-1 | ATGGCCCGAGGCGCT | GAGGGAGGCCGTGGG | GACGCGGGTTGGGGC | CTGCGTGGCGCCCTG | GCGGCCGTGGCGCTG | CTCTCGGCGCTCAAC | 90 |
| 4 hCrgl2 | --------------- | --------------- | --------------- | --------------- | --------------- | --------------- | 0 |
| 5 FP-1b | ATGACCCGAGCCGCA | GAGCGAGGCCAAGGG | GCTACAGGCTGGGGA | CTGCGAGGCGCCCTG | ATGGCCGTGGCGCTG | CTGTCAGTGCTGAAC | 90 |
| 6 mCRG-L2 | ATGACCCGAGCCGCA | GAGCGAGGCCAAGGG | GCTACAGGCTGGGGG | CTGCGCGGCGCCCTG | GTGGCCATAGCGCTG | CTGTCCGCACTGAAC | 90 |

FIG. 9A

```
1 FP-1a      GCCGTGGGCACCGTG TTCGTGCTGTACCAG TGGCGCGAGCTGAGC GCGGCGCTGCGGGCA CTGGAGGCGCAACAC GGCCAGGAGCAGCGC    180
2 rGliomedin GCCGTGGGCACCGTG TTCGTGCTGTACCAG TGGCGCGAGCTGAGC GCGGCGCTGCGGGCA CTGGAGGCGCAACAC GGCCAGGAGCAGCGC    180
3 hFP-1      GCTGCGGGCACGGTG TTCGCGCTGTGCCAG TGGCGCGGGCTGAGC TCGGCGCTGCGGGCT TTGGAGGCGCAGCGG GGCCGGGAGCAGCGC    180
4 hCrgl2     --------------- --------------- --------------- --------------- --------------- ---------------      0
5 FP-1b      GCCGTGGGCACCGTG TTCGTGCTGTACCAG --------------- --------------- --------------- ---------CAGCGC    126
6 mCRG-L2    GCCGCGGGCACCGTG TTCGTGCTGTGCCAG TGGCGGGGGTTAAGC GCGGCGCTACGGGCG CTGGAGGCTCAACGC GGCCGAGAGCAGCGC    180

             181         195 196         210 211         225 226         240 241         255 256         270
1 FP-1a      GAGGACAGCGCCCTA CGCGCCTTTCTAGCT GAATTAAGTCGTGCG CCAGCCCGAGTCCCC GAACCACCCCAGGAC CCCATGAGTGCAGCG    270
2 rGliomedin GAGGACAGCGCCCTA CGCGCCTTTCTAGCT GAATTAAGTCGTGCG CCAGCCCGAGTCCCC GAACCACCCCAGGAC CCCATGAGTGCAGCG    270
3 hFP-1      GAGGACAGTGCCCTG CGCTCCTTCCTGGCC GAGTTGAGCCGCGCG CCGCGCGGGGCGTCC GCACCACCCCAAGAC CCGGCCAGCTCAGCT    270
4 hCrgl2     --------------- --------------- --------------- --------------- --------------- ---------------      0
5 FP-1b      GAGGACAGCGCCCTA CGCGCCTTTCTAGCT GAATTAAGTCGTGCG CCAGCCCGAGTCCCC GAACCACCCCAGGAC CCCATGAGTGCAGCG    216
6 mCRG-L2    GAGGACAGCGCCCTA CGCGCCTTTCTGGCC GAATTGAGTCGTGCG CCGGGCCGGGTCCCC GAACCATCCCAGGAC CCCATGAGCGCAGCG    270

             271         285 286         300 301         315 316         330 331         345 346         360
1 FP-1a      CGCAATAAGCGCAGC CACGGCGGCGAGCCT GCGTCACACATCCGC GCGGAGAGCCAGGAC ATGATGATGATGATG ACCTACAGCATGGTG    360
2 rGliomedin CGCAATAAGCGCAGC CACGGCGGCGAGCCT GCGTCACACATCCGC GCGGAGAGCCAGGAC ATGATGATGATGATG ACCTACAGCATGGTG    360
3 hFP-1      CGCAACAAGCGCAGC CACAGCGGCGAGCCC GCGCCGCATATCCGC GCCGAGAGCCATGAC ATGCTGATGATGATG ACCTACTCCATGGTG    360
4 hCrgl2     --------------- --------------- --------------- --------------- --------------- ---------------      0
5 FP-1b      CGCAATAAGCGCAGC CACGGCGGCGAGCCT GCGTCACACATCCGC GCGGAGAGCCAGGAC ATGATGATGATGATG ACCTACAGCATGGTG    306
6 mCRG-L2    CGCAACAAGCGCAGC CACAACGGCGAGCCT GCGTCACACATCCGT GCGGAGAGCCAGGAC ATGATGATGATGATG ACCTACTCCATGGTG    360
```

FIG. 9B

```
              361           375 376           390 391           405 406           420 421           435 436           450
1 FP-1a       CCGATCCGGGTGATG ATAGACCTGTGCAAC AGCACCCAGGGCATC TGCCTTACAGGACCA CCGGGCCCACCAGGA CCTCCAGGAGCTGGT   450
2 rGliomedin  CCGATCCGGGTGATG ATAGACCTGTGCAAC AGCACCCAGGGCATC TGCCTTACAGGACCA CCGGGCCCACCAGGA CCTCCAGGAGCTGGT   450
3 hFP-1       CCGATCCGAGTGATG GTGGACCTGTGCAAC AGCACCAAGGGCATC TGCCTCACAGGACCT TCTGGACCACCAGGA CCTCCGGGAGCCGGC   450
4 hCrgl2      ------------ATG GTGGACCTGTGCAAC AGCACCAAGGGCATC TGCCTCACAGGACCT TCTGGACCACCAGGA CCTCCGGGAGCCGGC    78
5 FP-1b       CCGATCCGGGTGATG ATAGACCTGTGCAAC AGCACCCAGGGCATC TGCCTTACAGGACCA CCGGGCCCACCAGGA CCTCCAGGAGCTGGT   396
6 mCRG-L2     CCGATTCGAGTGATG ATAGACCTGTGCAAC AGTACCCAGGGCATC TGCCTCACAGGACCA CCGGGCCCACCAGGA CCTCCAGGAGCCGGC   450

              451           465 466           480 481           495 496           510 511           525 526           540
1 FP-1a       GGGTTACCAGGCCAC AATGGATCAGATGGA CAGCCTGGTCTCCAG GGCCCAAAAGGAGAA AAAGGAGCAGTTGGG AAGAGAGGAAAAATG   540
2 rGliomedin  GGGTTACCAGGCCAC AATGGATCAGATGGA CAGCCTGGTCTCCAG GGCCCAAAAGGAGAA AAAGGAGCAGTTGGG AAGAGAGGAAAAATG   540
3 hFP-1       GGGTTGCCAGGACAC AACGGATTGGATGGA CAGCCTGGTCCTCAG GGCCCAAAAGGAGAA AAAGGAGCAAATGGA AAAAGAGGAAAAATG   540
4 hCrgl2      GGGTTGCCAGGACAC AACGGATTGGATGGA CAGCCTGGTCCTCAG GGCCCAAAAGGAGAA AAAGGAGCAAATGGA AAAAGAGGAAAAATG   168
5 FP-1b       GGGTTACCAGGCCAC AATGGATCAGATGGA CAGCCTGGTCTCCAG GGCCCAAAAGGAGAA AAAGGAGCAGTTGGG AAGAGAGGAAAAATG   486
6 mCRG-L2     GGGTTACCAGGCCAC AATGGATCAGATGGA CAGCCTGGTCTCCAG GGCCCAAAAGGAGAA AAAGGAGCAATTGGC AAGAGAGGAAAAATG   540

              541           555 556           570 571           585 586           600 601           615 616           630
1 FP-1a       GGGTTACCCGGAGCC ACAGGAAATCCAGGG GAAAAGGGAGAGAAG GGAGATGCTGGTGAA CTGGGCCTACCTGGA AATGAGGGACCACCA   630
2 rGliomedin  GGGTTACCCGGAGCC ACAGGAAATCCAGGG GAAAAGGGAGAGAAG GGAGATGCTGGTGAA CTGGGCCTACCTGGA AATGAGGGACCACCA   630
3 hFP-1       GGGATACCTGGAGCT GCAGGAAATCCAGGG GAAAGGGGAGAAAAG GGAGACCATGGTGAA CTGGGCCTGCAGGGA AATGAGGGCCCACCA   630
4 hCrgl2      GGGATACCTGGAGCT GCAGGAAATCCAGGG GAAAGGGGAGAAAAG GGAGACCATGGTGAA CTGGGCCTGCAGGGA AATGAGGGCCCACCA   258
5 FP-1b       GGGTTACCCGGAGCC ACAGGAAATCCAGGG GAAAAGGGAGAGAAG GGAGATGCTGGTGAA CTGGGCCTACCTGGA AATGAGGGACCACCA   576
6 mCRG-L2     GGGTTACCTGGAGCC ACCGGAAATCCAGGG GAAAAGGGAGAAAAG GGAGATGCTGGTGAA CTGGGTCTACCTGGA AATGAGGGCCCACCA   630
```

FIG. 9C

```
             631         645 646         660 661         675 676         690 691         705 706         720
1 FP-1a      GGACAGAAAGGAGAC AAAGGAGACAAAGGA GATGTGTCCAATGAC GTGCTTTTGACAGGT GCCAAAGGTGACCAA GGGCCCCCTGGCCCA  720
2 rGliomedin GGACAGAAAGGAGAC AAAGGAGACAAAGGA GATGTGTCCAATGAC GTGCTTTTGACAGGT GCCAAAGGTGACCAA GGGCCCCCTGGCCCA  720
3 hFP-1      GGGCAGAAGGGAGAA AAGGGTGACAAAGGA GATGTGTCCAACGAC GTGCTCCTGGCAGGT GCCAAAGGTGACCAA GGCCCACCCGGTCCA  720
4 hCrgl2     GGGCAGAAGGGAGAA AAGGGTGACAAAGGA GATGTGTCCAACGAC GTGCTCCTGGCAGGT GCCAAAGGTGACCAA GGCCCACCCGGTCCA  348
5 FP-1b      GGACAGAAAGGAGAC AAAGGAGACAAAGGA GATGTGTCCAATGAC GTGCTTTTGACAGGT GCCAAAGGTGACCAA GGGCCCCCTGGCCCA  666
6 mCRG-L2    GGGCAGAAAGGTGAC AAGGGAGACAAAGGA GACGTGTCCAATGAC GTGCTTTTGACAGGT GCCAAAGGTGACCAA GGTCCCCCTGGCCCC  720

             721         735 736         750 751         765 766         780 781         795 796         810
1 FP-1a      CCTGGACCCCCAGGG CCTCCAGGCCCTTC- --------TGGAAGC AGAAGAGCCAAAGGC CCTCGGCAGCCAAAT TCGTTCACCAACCAG  801
2 rGliomedin CCTGGACCCCCAGGG CCTCCAGGCCCTCC- --------TGGAAGC AGAAGAGCCAAAGGC CCTCGGCAGCCAAAT TCGTTCACCAACCAG  801
3 hFP-1      CCTGGGCCCCCAGGC CCTCCAGGTCCTCCA GGGCCCCCTGGAAGC AGAAGAGCCAAAGGC CCTCGGCAGCCAAGC ATGTTCAACGGCCAG  810
4 hCrgl2     CCTGGGCCCCCAGGC CCTCCAGGTCCTCCA GGGCCCCCTGGAAGC AGAAGAGCCAAAGGC CCTCGGCAGCCAAGC ATGTTCAACGGCCAG  438
5 FP-1b      CCTGGACCCCCAGGG CCTCCAGGCCCTTC- --------TGGAAGC AGAAGAGCCAAAGGC CCTCGGCAGCCAAAT TCGTTCACCAACCAG  747
6 mCRG-L2    CCTGGACCTCCAGGG CCTCCAGGCCCTCC- --------TGGAAGC AGAAGATCCAAAGGC CCTCGGCCACCAAAC GTGTTCAACAGCCAG  801

             811         825 826         840 841         855 856         870 871         885 886         900
1 FP-1a      TGTCCAGGGGAGACG TGTGTCATACCCAAT GATGATACCTTGGTG GGGAGAGCTGATGAG AAAGTCAATGAGCGC CATTCTCCACAAACA  891
2 rGliomedin TGTCCAGGGGAGACG TGTGTCATACCCAAT GATGATACCTTGGTG GGGAGAGCTGATGAG AAAGTCAATGAGCGC CATTCTCCACAAACA  891
3 hFP-1      TGCCCAGGTGAGACT TGTGCCATACCAAAT GATGATACCTTGGTT GGAAAAGCTGATGAG AAAGCCAGTGAACAC CATTCCCCACAAGCA  900
4 hCrgl2     TGCCCAGGTGAGACT TGTGCCATACCAAAT GATGATACCTTGGTT GGAAAAGCTGATGAG AAAGCCAGTGAACAC CATTCCCCACAAGCA  528
5 FP-1b      TGTCCAGGGGAGACG TGTGTCATACCCAAT GATGATACCTTGGTG GGGAGAGCTGATGAG AAAGTCAATGAGCGC CATTCTCCACAAACA  837
6 mCRG-L2    TGTCCAGGGGAGACG TGTGTCATACCCAAT GATGATACCTTGGTG GGAAGAGCTGATGAG AAAGCAAATGAACGC CATTCACCACAAACA  891
```

FIG. 9D

```
              901         915 916         930 931         945 946         960 961         975 976         990
1 FP-1a       GAACCCATGATCACG TCCATTGGTAACCCG GCCCAAGTCCTCAAA GTGAAAGAGACTTTT GGGACCTGGCTAAGA GAGTCTGCTAACAGG   981
2 rGliomedin  GAACCCATGATCACG TCCATTGGTAACCCG GCCCAAGTCCTCAAG GTGAAAGAGACTTTT GGGACCTGGCTAAGA GAGTCTGCTAACAGG   981
3 hFP-1       GAATCCATGATCACT TCCATTGGAAACCCA GTGCAAGTACTGAAA GTGACAGAGACATTT GGGACTTGGATAAGA GAGTCTGCTAACAAG   990
4 hCrgl2      GAATCCATGATCACT TCCATTGGAAACCCA GTGCAAGTACTGAAA GTGACAGAGACATTT GGGACTTGGATAAGA GAGTCTGCTAACAAG   618
5 FP-1b       GAACCCATGATCACG TCCATTGGTAACCCG GCCCAAGTCCTCAAA GTGAAAGAGACTTTT GGGACCTGGCTAAGA GAGTCTGCTAACAGG   927
6 mCRG-L2     GAATCTATGATCACT TCCATTGGCAACCCA GCCCAAGTCCTAAAA GTGAGAGAGACTTTT GGGACTTGGATGAGA GAGTCTGCTAACAAA   981

              991        1005 1006       1020 1021       1035 1036       1050 1051       1065 1066       1080
1 FP-1a       AGTGATGACCGCATT TGGGTGACTGAACAT TTTTCAGGCATCATG GTGAAGGAGTTTGAA GACCTGCCCGCCCTC CTGAATAGCAGCTTC  1071
2 rGliomedin  AGTGACGACCGCATT TGGGTGACTGAACAT TTTTCAGGCATCATG GTGAAGGAGTTTGAA GACCTGCCCGCCCTC CTGAATAGCAGCTTC  1071
3 hFP-1       AGTGATGACCGGATT TGGGTGACAGAGCAT TTTTCAGGCATCATG GTTAAGGAATTCAAG GATCAGCCCTCACTT CTGAATGGCAGTTAC  1080
4 hCrgl2      AGTGATGACCGGATT TGGGTGACAGAGCAT TTTTCAGGCATCATG GTTAAGGAATTCAAG GATCAGCCCTCACTT CTGAATGGCAGTTAC   708
5 FP-1b       AGTGATGACCGCATT TGGGTGACTGAACAT TTTTCAGGCATCATG GTGAAGGAGTTTGAA GACCTGCCCGCCCTC CTGAATAGCAGCTTC  1017
6 mCRG-L2     AGTGACGACCGCATT TGGGTGACTGAACAT TTTTCAGGCATCATG GTGAAGGAGTTCAAA GACCTGCCGGCGCTC CTCAATAGCAGCTTC  1071

              1081       1095 1096       1110 1111       1125 1126       1140 1141       1155 1156       1170
1 FP-1a       ACCCTCCTCCACCTC CCACATTACTTCCAT GGCTGCGGGCACGCT GTTTACAACAACTCT CTCTACTACCACAAA GGAGGCTCCAACACC  1161
2 rGliomedin  ACCCTCCTCCACCTC CCACATTACTTCCAT GGCTGCGGGCACGCT GTTTACAACAACTCT CTCTACTACCACAAA GGAGGCTCCAACACC  1161
3 hFP-1       ACGTTCATCCACCTT CCATACTATTTCCAT GGCTGTGGGCACGTT GCTTACAACAACTCT CTCTACTACCACAAA GGGGGTTCTAATACC  1170
4 hCrgl2      ACGTTCATCCACCTT CCATACTATTTCCAT GGCTGTGGGCACGTT GCTTACAACAACTCT CTCTACTACCACAAA GGGGGTTCTAATACC   798
5 FP-1b       ACCCTCCTCCACCTC CCACATTACTTCCAT GGCTGCGGGCACGCT GTTTACAACAACTCT CTCTACTACCACAAA GGAGGCTCCAACACC  1107
6 mCRG-L2     ACACTCCTCCACCTC CCACATTATTTCCAC GGCTGTGGGCACGCT GTTTACAACAACTCT CTCTACTACCACAAA GGAGGCTCCAACACC  1161
```

FIG. 9E

```
              1171        1185 1186        1200 1201        1215 1216        1230 1231        1245 1246        1260
1 FP-1a       ATAGTGAGATTTGAA TTTGGGAAAGAGACA CCTCAAACTCTGAAG CTTGAAGATGCTTTG TATTTTGATCGAAAA TACCTCTTTGCGAAT  1251
2 rGliomedin  ATAGTGAGATTTGAA TTTGGGAAAGAGACA CCTCAAACTCTGAAG CTTGAAGATGCTTTG TATTTTGATCGAAAA TACCTCTTTGCGAAT  1251
3 hFP-1       CTAGTGAGATTTGAA TTTGGCCAGGAAACA TCCCAAACTCTGAAG CTTGAAAATGCCTTG TATTTTGATCGAAAA TACCTTTTTGCAAAT  1260
4 hCrgl2      CTAGTGAGATTTGAA TTTGGCCAGGAAACA TCCCAAACTCTGAAG CTTGAAAATGCCTTG TATTTTGATCGAAAA TACCTTTTTGCAAAT   888
5 FP-1b       ATAGTGAGATTTGAA TTTGGGAAAGAGACA CCTCAAACTCTGAAG CTTGAAGATGCTTTG TATTTTGATCGAAAA TACCTCTTTGCGAAT  1197
6 mCRG-L2     ATAGTGAGATTTGAA TTTGGGAAAGAGACA CCTCAGACTCTGAAG CTGGAAAATGCTTTG TATTTTGATCGAAAA TACCTCTTTGCAAAT  1251

              1261        1275 1276        1290 1291        1305 1306        1320 1321        1335 1336        1350
1 FP-1a       TCCAAGACTTACTTC AACATAGCAGTGGAT GAGAAGGGCCTCTGG ATTATCTACGCCTCG AGTGTGGATGGCTCA AGCATCCTTGTGGCA  1341
2 rGliomedin  TCCAAGACTTACTTC AACATAGCAGTGGAT GAGAAGGGCCTCTGG ATTATCTACGCCTCG AGTGTGGATGGCTCA AGCATCCTTGTGGCA  1341
3 hFP-1       TCCAAAACTTACTTC AATCTAGCTGTAGAT GAAAAGGGCCTTTGG ATTATCTATGCGTCA AGTGTGGACGGCTCG AGCATTCTTGTAGCA  1350
4 hCrgl2      TCCAAAACTTACTTC AATCTAGCTGTAGAT GAAAAGGGCCTTTGG ATTATCTATGCGTCA AGTGTGGACGGCTCG AGCATTCTTGTAGCA   978
5 FP-1b       TCCAAGACTTACTTC AACATAGCAGTGGAT GAGAAGGGCCTCTGG ATTATCTACGCCTCG AGTGTGGATGGCTCA AGCATCCTTGTGGCA  1287
6 mCRG-L2     TCCAAGACTTACTTC AACATAGCAGTGGAT GAGAAGGGCATCTGG ATTATCTACGCTTCA AGTGTGGATGGCTCA AGCATCCTTGTAGCA  1341

              1351        1365 1366        1380 1381        1395 1396        1410 1411        1425 1426        1440
1 FP-1a       CAGCTGGACGAGAGG ACATTCTCTGTGCTG CAGCACATCAATACC ACATACCCCAAGTCC AAGGCTGGCAATGCC TTCATAGCTCAAGGG  1431
2 rGliomedin  CAGCTGGACGAGAGG ACATTCTCTGTGCTG CGGCACATCAATACC ACATACCCCAAGTCC AAGGCTGGCAATGCC TTCATAGCTCAAGGG  1431
3 hFP-1       CAACTGGATGAGAGG ACATTCTCAGTGGTG CAACACGTCAATACC ACGTACCCTAAATCC AAGGCTGGCAACGCC TTCATTGCCCGAGGA  1440
4 hCrgl2      CAACTGGATGAGAGG ACATTCTCAGTGGTG CAACACGTCAATACC ACGTACCCTAAATCC AAGGCTGGCAACGCC TTCATTGCCCGAGGA  1068
5 FP-1b       CAGCTGGACGAGAGG ACATTCTCTGTGCTG CAGCACATCAATACC ACATACCCCAAGTCC AAGGCTGGCAATGCC TTCATAGCTCAAGGG  1377
6 mCRG-L2     CAGCTGGATGAGAGG ACATTCTCCGTGACA CAGCACATCAACACC ACATACCCCAAATCC AAGGCTGGCAATGCC TTCATAGCCCGAGGG  1431
```

FIG. 9F

```
             1441          1455 1456          1470 1471          1485 1486          1500 1501          1515 1516          1530
1 FP-1a      ATCCTCTATGTCACG GACACAAAAGATACA AGGGTCACGTTTGCC TTTGATTTGTTACGA GGGAAGCAGATCAAT GCAAACTTCGGTCTC   1521
2 rGliomedin ATCCTCTATGTCACG GACACCAAAGATACA AGGGTCACGTTTGCC TTTGATTTGTTACGA GGGAAGCAGATCAAT GCAAACTTCGGTCTC   1521
3 hFP-1      ATCCTCTATGTCACA GACACCAAAGATATG AGGGTCACATTTGCC TTTGATTTGTTAGGA GGGAAACAGATCAAT GCAAACTTTGATTTA   1530
4 hCrgl2     ATCCTCTATGTCACA GACACCAAAGATATG AGGGTCACATTTGCC TTTGATTTGTTAGGA GGGAAACAGATCAAT GCAAACTTTGATTTA   1158
5 FP-1b      ATCCTCTATGTCACG GACACAAAAGATACA AGGGTCACGTTTGCC TTTGATTTGTTACGA GGGAAGCAGATCAAT GCAAACTTCGGTCTC   1467
6 mCRG-L2    ATCCTCTATGTCACA GACACCAAAGATACG AGGGTCACGTTTGCC TTTGATTTGTTAGGA GGAAAGCAAATCAAT GCAAACTTTGATTTC   1521

             1531          1545 1546          1560 1561          1575 1576          1590 1591          1605 1606          1620
1 FP-1a      AGAATGTCACAGTCT GTTCTTGCCATGTTG TCGTACAATATGAGA GACCAGCATTTGTAC TCGTGGGAAGACGGC CACCTGATGCTCTAT   1611
2 rGliomedin AGAATGTCACAGTCT GTTCTTGCCATGTTG TCGTACAATATGAGA GACCAGCATTTGTAC TCGTGGGAAGACGGC CACCTGATGCTCTAT   1611
3 hFP-1      AGAACTTCCCAGTCT GTTCTTGCCATGTTA GCATACAACATGAGA GATCAGCATTTATAT TCATGGGAAGATGGC CATTTAATGCTTTAT   1620
4 hCrgl2     AGAACTTCCCAGTCT GTTCTTGCCATGTTA GCATACAACATGAGA GATCAGCATTTATAT TCATGGGAAGATGGC CATTTAATGCTTTAT   1248
5 FP-1b      AGAATGTCACAGTCT GTTCTTGCCATGTTG TCGTACAATATGAGA GACCAGCATTTGTAC TCGTGGGAAGACGGC CACCTGATGCTCTAT   1557
6 mCRG-L2    AGAATGTCCCAGTCT GTTCTTGCCATGCTG TCATACAACATGAGA GATCAGCATTTATAC TCGTGGGAAGATGGC CATCTGATGCTCTAT   1611

             1621          1635 1636          1650 1651
1 FP-1a      CCTGTGCACTTTTCG TCAACAGCACCCAGC CAGCGATAG   1650 - SEQ ID NO: 28
2 rGliomedin CCTGTGCACTTTTCG TCAACAGCACCCAGC CAGCGATAG   1650 - SEQ ID NO: 29
3 hFP-1      CCTGTGCAGTTTTTG TCAACTACCTTAAAT CAGTGA---   1656 - SEQ ID NO: 30
4 hCrgl2     CCTGTGCAGTTTTTG TCAACTACCTTAAAT CAGTGA---   1284 - SEQ ID NO: 31
5 FP-1b      CCTGTGCACTTTTCG TCAACAGCACCCAGC CAGCGATAG   1596 - SEQ ID NO: 32
6 mCRG-L2    CCTGTGCAGTTTCTG TCAGCGGCATCAAGT CAGCGGTAG   1650 - SEQ ID NO: 33
```

FIG. 9G

```
1 rFP-1a/b CLTGPPGPPGPPGAG GLPGHNGSDGQPGLQ GPKGEKGAVGKRGKM GLPGATGNPGEKGEK   195/213
2 hFP-1    CLTGPSGPPGPPGAG GLPGHNGLDGQPGPQ GPKGEKGANGKRGKM GIPGAAGNPGERGEK   195

                                                                   SEQ ID NO: 34
1 rFP-1a/b GDAGELGLPGNEGPP GQKGDKGDKGDVSND VLLTGAKGDQGPPGP PGPPGPPGPPG---S   252/270
2 hFP-1    GDHGELGLQGNEGPP GQKGEKGDKGDVSND VLLAGAKGDQGPPGP PGPPGPPGPPGPPGS   255
                                                                   SEQ ID NO: 35
```

```
1 FP-1a/b RRAKGPRQPNSFTNQ CPGETCVIPNDDTLV GRADEKVNERHSPQT EPMITSIGNPAQVLK   312/320
2 hFP-1   RRAKGPRQPSMFNGQ CPGETCAIPNDDTLV GKADEKASEHHSPQA ESMITSIGNPVQVLK   314
3 OLF     GILAGVGIPVLLAES QYGKS---------- --------------- ---------------    20

            Region 1
1 FP-1a/b VKETFGTWLRESAN- -RSDDRIWVTEHFS- -GIMVKEFEDLPALL NSS-FTLLHLPHYFH  367/385
2 hFP-1   VTETFGTWIRESAN- -KSDDRIWVTEHFS- -GIMVKEFKDQPSLL NGS-YTFIHLPYYFH  369
3 OLF     -----GAWMRDPLPN SMKAKRRWVMDGFAD VSRVLREYSSMSDFL DGVNKIKYYLPHAAS   75

          Region 3                                        Region 5
1 FP-1a/b GCGHAVYNNSLYYHK GGSNTIVRFEFGKET PQTLKLEDALYFDRK YLFAN-SKTYFNIAV  426/444
2 hFP-1   GCGHVAYNNSLYYHK GGSNTLVRFEFGQET SQTLKLENALYFDRK YLFAN-SKTYFNLAV  429
3 OLF     GTGNVVYNGSLYFNK FGSHSIVRYELETGV QVKEELLPEAGYNDC FPYAWGGHSDIDLAV  135

                            Region 6                Region 7
1 FP-1a/b DEKGLWIIYASSVDG SSILVAQLDERTFSV LQHINTTYPKSKAGN AFIAQGILYVTDTKD  486/504
2 hFP-1   DEKGLWIIYASSVDG SSILVAQLDERTFSV VQHVNTTYPKSKAGN AFIARGILYVTDTKD  489
3 OLF     DENGLWVIYATEQNA GKIVISKLNPATLFV ENTWNTEYNKRSAAN AFMICGVLYVTKSAN  195

            Region 8                              Region 9
1 FP-1a/b ---TRVTFAFDLLRG KQINANFGLRMSQSV LAMLSYNMRDQHLYS WEDGHLMLYPVHFSS  543/561  SEQ ID NO: 36
2 hFP-1   ---MRVTFAFDLLGG KQINANFDLRTSQSV LAMLAYNMRDQHLYS WEDGHLMLYPVQFLS  546      SEQ ID NO: 37
3 OLF     SLGTKITYAYDTNTG KTIPLDIPFYNPYQY ISMLDYNPLDRKLYA WDNGHLLSYDIRLEE  255      SEQ ID NO: 38
```

FIG. 10C

```
1    M T R A A E R G Q G A T G W G
1    ACGCGGGGAGTGCTGCCCTGAGTCGTTCGGCCTGAGCACAGAGACATGACCCGAGCCGCAGAGCGAGGCCAAGGGGCTACAGGCTGGGGA

16   L R G A L M A V A L L S V L N A V G T V F V L Y Q W R E L S
91   CTGCGAGGCGCCCTGATGGCCGTGGCGCTGCTGTCAGTGCTGAACGCCGTGGGCACCGTGTTCGTGCTGTACCAGTGGCGCGAGCTGAGC

46   A A L R A L E A Q H G Q E Q R E D S A L R A F L A E L S R A
181  GCGGCGCTGCGGGCACTGGAGGCGCAACACGGCCAGGAGCAGCGCGAGGACAGCGCCCTACGCGCCTTTCTAGCTGAATTAAGTCGTGCG

                                 Epitope 1
76   P A R V P E P P Q D P M S A A R N K R S H G G E P A S H I R
271  CCAGCCCGAGTCCCCGAACCACCCCAGGACCCCATGAGTGCAGCGCGCAATAAGCGCAGCCACGGCGGCGAGCCTGCGTCACACATCCGC

106  A E S Q D M M M M M T Y S M V P I R V M I D L C N S T Q G I
361  GCGGAGAGCCAGGACATGATGATGATGATGACCTACAGCATGGTGCCGATCCGGGTGATGATAGACCTGTGCAACAGCACCCAGGGCATC

136  C L T G P P G P P G P P G A G G L P G H N G S D G Q P G L Q
451  TGCCTTACAGGACCACCGGGCCCACCAGGACCTCCAGGAGCTGGTGGGTTACCAGGCCACAATGGATCAGATGGACAGCCTGGTCTCCAG

166  G P K G E K G A V G K R G K M G L P G A T G N P G E K G E K
541  GGCCCAAAAGGAGAAAAAGGAGCAGTTGGGAAGAGAGGAAAAATGGGGTTACCCGGAGCCACAGGAAATCCAGGGGAAAAGGGAGAGAAG
```

FIG. 15A

```
196   G  D  A  G  E  L  G  L  P  G  N  E  G  P  P  G  Q  K  G  D  K  G  D  K  G  D  V  S  N  D
631  GGAGATGCTGGTGAACTGGGCCTACCTGGAAATGAGGGACCACCAGGACAGAAAGGAGACAAAGGAGACAAAGGAGATGTGTCCAATGAC

                                                                         Epitope 2
226   V  L  L  T  G  A  K  G  D  Q  G  P  P  G  P  P  G  P  P  G  P  P  G  P  S  G  S  R  R  A
721  GTGCTTTTGACAGGTGCCAAAGGTGACCAAGGGCCCCCTGGCCCACCTGGACCCCCAGGGCCTCCAGGCCCTTCTGGAAGCAGAAGAGCC

                                                                      Epitope 3
256   K  G  P  R  Q  P  N  S  F  T  N  Q  C  P  G  E  T  C  V  I  P  N  D  D  T  L  V  G  R  A
811  AAAGGCCCTCGGCAGCCAAATTCGTTCACCAACCAGTGTCCAGGGGAGACGTGTGTCATACCCAATGATGATACCTTGGTGGGGAGAGCT

286   D  E  K  V  N  E  R  H  S  P  Q  T  E  P  M  I  T  S  I  G  N  P  A  Q  V  L  K  V  K  E
901  GATGAGAAAGTCAATGAGCGCCATTCTCCACAAACAGAACCCATGATCACGTCCATTGGTAACCCGGCCCAAGTCCTCAAAGTGAAAGAG

                Epitope 4
316   T  F  G  T  W  L  R  E  S  A  N  R  S  D  D  R  I  W  V  T  E  H  F  S  G  I  M  V  K  E
991  ACTTTTGGGACCTGGCTAAGAGAGTCTGCTAACAGGAGTGATGACCGCATTTGGGTGACTGAACATTTTTCAGGCATCATGGTGAAGGAG

346   F  E  D  L  P  A  L  L  N  S  S  F  T  L  L  H  L  P  H  Y  F  H  G  C  G  H  A  V  Y  N
1081 TTTGAAGACCTGCCCGCCCTCCTGAATAGCAGCTTCACCCTCCTCCACCTCCCACATTACTTCCATGGCTGCGGGCACGCTGTTTACAAC

                                                          Epitope 5
376   N  S  L  Y  Y  H  K  G  G  S  N  T  I  V  R  F  E  F  G  K  E  T  P  Q  T  L  K  L  E  D
1171 AACTCTCTCTACTACCACAAAGGAGGCTCCAACACCATAGTGAGATTTGAATTTGGGAAAGAGACACCTCAAACTCTGAAGCTTGAAGAT
```

FIG. 15B

```
406   A  L  Y  F  D  R  K  Y  L  F  A  N  S  K  T  Y  F  N  I  A  V  D  E  K  G  L  W  I  I  Y
1261  GCTTTGTATTTTGATCGAAAATACCTCTTTGCGAATTCCAAGACTTACTTCAACATAGCAGTGGATGAGAAGGGCCTCTGGATTATCTAC

436   A  S  S  V  D  G  S  S  I  L  V  A  Q  L  D  E  R  T  F  S  V  L  Q  H  I  N  T  T  Y  P
1351  GCCTCGAGTGTGGATGGCTCAAGCATCCTTGTGGCACAGCTGGACGAGAGGACATTCTCTGTGCTGCAGCACATCAATACCACATACCCC

466   K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAAGATACAAGGGTCACGTTTGCCTTTGATTTG

496   L  R  G  K  Q  I  N  A  N  F  G  L  R  M  S  Q  S  V  L  A  M  L  S  Y  N  M  R  D  Q  H
1531  TTACGAGGGAAGCAGATCAATGCAAACTTCGGTCTCAGAATGTCACAGTCTGTTCTTGCCATGTTGTCGTACAATATGAGAGACCAGCAT

526   L  Y  S  W  E  D  G  H  L  M  L  Y  P  V  H  F  S  S  T  A  P  S  Q  R  (SEQ ID NO:2)
1621  TTGTACTCGTGGGAAGACGGCCACCTGATGCTCTATCCTGTGCACTTTTCGTCAACAGCACCCAGCCAGCGATAGGCCTGCAGTCGGCTC

1711  CCTCATTATGCACCACACATTTTCTGGGGTTTGACCAAGCCCAACGGAAAGAAGGCCTGTAAAGGATATCCAGATACTCAGAGCATACGC
1801  CCGTGTTACGGGCTTTTGTGCATGTGGCAAGTCCCCCTGTAAGCCAGGTTAACTAAAGGCTGGAAAGTTGAAATGGATAACATTTGGTGA
1891  CCCTTGGTCCCTCTTCAAACTTAGCAAGTTAGTGCTCCCCCCTGACCTTAGTGTCCCCATCAGTAATATGAAACATCTGTGTGATTGCAG
1981  CATTTCCTATACCTATATGAAGTTCTGTGATTCTTGCCTGGTTATATATTAGATTGCTTTCAGGTTTCTTTTTTTTTCTCCACATGTAA
2071  ATGAGTTTACCTGCAGCTTGAGGGGTGTGCCTATCAGTGATGACGGACATTTGTTTGGTGTTTAGGGAAAAAGCATTGTTTCTTATGGCT
2161  TTTAAAGTATTATATTATCCATAATTTGATATTTTTTTTGAATACGCCCCTGCCACTACAGAATGATTATTGTTTTCAGCTCCTAAGTA
2251  CAAATCCAAGATTAATAAAAAAAAAACATGAATAGAAAAAAAAAAAAAAAAAACTCGAGAGTATTAGTCGATGTAGGAAAAC (SEQ ID NO:1)
```

FIG. 15C

SEQUENCE LISTING

```
<160> NUMBER OF SEQ ID NOS: 38

<210> SEQ ID NO 1
<211> LENGTH: 2332
<212> TYPE: DNA
<213> ORGANISM: Rattus sp.
<220> FEATURE:
<221> NAME/KEY: CDS
<222> LOCATION: (46)..(1692)

<400> SEQUENCE: 1

acgcggggag tgctgccctg agtcgttcgg cctgagcaca gagac atg acc cga gcc      57
                                                  Met Thr Arg Ala
                                                   1

gca gag cga ggc caa ggg gct aca ggc tgg gga ctg cga ggc gcc ctg       105
Ala Glu Arg Gly Gln Gly Ala Thr Gly Trp Gly Leu Arg Gly Ala Leu
  5                  10                  15                  20

atg gcc gtg gcg ctg ctg tca gtg ctg aac gcc gtg ggc acc gtg ttc       153
Met Ala Val Ala Leu Leu Ser Val Leu Asn Ala Val Gly Thr Val Phe
                 25                  30                  35

gtg ctg tac cag tgg cgc gag ctg agc gcg gcg ctg cgg gca ctg gag       201
Val Leu Tyr Gln Trp Arg Glu Leu Ser Ala Ala Leu Arg Ala Leu Glu
             40                  45                  50

gcg caa cac ggc cag gag cag cgc gag gac agc gcc cta cgc gcc ttt       249
Ala Gln His Gly Gln Glu Gln Arg Glu Asp Ser Ala Leu Arg Ala Phe
         55                  60                  65

cta gct gaa tta agt cgt gcg cca gcc cga gtc ccc gaa cca ccc cag       297
Leu Ala Glu Leu Ser Arg Ala Pro Ala Arg Val Pro Glu Pro Pro Gln
     70                  75                  80

gac ccc atg agt gca gcg cgc aat aag cgc agc cac ggc ggc gag cct       345
Asp Pro Met Ser Ala Ala Arg Asn Lys Arg Ser His Gly Gly Glu Pro
 85                  90                  95                 100

gcg tca cac atc cgc gcg gag agc cag gac atg atg atg atg atg acc       393
Ala Ser His Ile Arg Ala Glu Ser Gln Asp Met Met Met Met Met Thr
                105                 110                 115

tac agc atg gtg ccg atc cgg gtg atg ata gac ctg tgc aac agc acc       441
Tyr Ser Met Val Pro Ile Arg Val Met Ile Asp Leu Cys Asn Ser Thr
            120                 125                 130

cag ggc atc tgc ctt aca gga cca ccg ggc cca cca gga cct cca gga       489
Gln Gly Ile Cys Leu Thr Gly Pro Pro Gly Pro Pro Gly Pro Pro Gly
        135                 140                 145

gct ggt ggg tta cca ggc cac aat gga tca gat gga cag cct ggt ctc       537
Ala Gly Gly Leu Pro Gly His Asn Gly Ser Asp Gly Gln Pro Gly Leu
    150                 155                 160
```

-continued

```
cag ggc cca aaa gga gaa aaa gga gca gtt ggg aag aga gga aaa atg      585
Gln Gly Pro Lys Gly Glu Lys Gly Ala Val Gly Lys Arg Gly Lys Met
165                 170                 175                 180

ggg tta ccc gga gcc aca gga aat cca ggg gaa aag gga gag aag gga      633
Gly Leu Pro Gly Ala Thr Gly Asn Pro Gly Glu Lys Gly Glu Lys Gly
                185                 190                 195

gat gct ggt gaa ctg ggc cta cct gga aat gag gga cca cca gga cag      681
Asp Ala Gly Glu Leu Gly Leu Pro Gly Asn Glu Gly Pro Pro Gly Gln
            200                 205                 210

aaa gga gac aaa gga gac aaa gga gat gtg tcc aat gac gtg ctt ttg      729
Lys Gly Asp Lys Gly Asp Lys Gly Asp Val Ser Asn Asp Val Leu Leu
        215                 220                 225

aca ggt gcc aaa ggt gac caa ggg ccc cct ggc cca cct gga ccc cca      777
Thr Gly Ala Lys Gly Asp Gln Gly Pro Pro Gly Pro Pro Gly Pro Pro
    230                 235                 240

ggg cct cca ggc cct tct gga agc aga aga gcc aaa ggc cct cgg cag      825
Gly Pro Pro Gly Pro Ser Gly Ser Arg Arg Ala Lys Gly Pro Arg Gln
245                 250                 255                 260

cca aat tcg ttc acc aac cag tgt cca ggg gag acg tgt gtc ata ccc      873
Pro Asn Ser Phe Thr Asn Gln Cys Pro Gly Glu Thr Cys Val Ile Pro
                265                 270                 275

aat gat gat acc ttg gtg ggg aga gct gat gag aaa gtc aat gag cgc      921
Asn Asp Asp Thr Leu Val Gly Arg Ala Asp Glu Lys Val Asn Glu Arg
            280                 285                 290

cat tct cca caa aca gaa ccc atg atc acg tcc att ggt aac ccg gcc      969
His Ser Pro Gln Thr Glu Pro Met Ile Thr Ser Ile Gly Asn Pro Ala
        295                 300                 305

caa gtc ctc aaa gtg aaa gag act ttt ggg acc tgg cta aga gag tct     1017
Gln Val Leu Lys Val Lys Glu Thr Phe Gly Thr Trp Leu Arg Glu Ser
    310                 315                 320

gct aac agg agt gat gac cgc att tgg gtg act gaa cat ttt tca ggc     1065
Ala Asn Arg Ser Asp Asp Arg Ile Trp Val Thr Glu His Phe Ser Gly
325                 330                 335                 340

atc atg gtg aag gag ttt gaa gac ctg ccc gcc ctc ctg aat agc agc     1113
Ile Met Val Lys Glu Phe Glu Asp Leu Pro Ala Leu Leu Asn Ser Ser
                345                 350                 355

ttc acc ctc ctc cac ctc cca cat tac ttc cat ggc tgc ggg cac gct     1161
Phe Thr Leu Leu His Leu Pro His Tyr Phe His Gly Cys Gly His Ala
            360                 365                 370

gtt tac aac aac tct ctc tac tac cac aaa gga ggc tcc aac acc ata     1209
Val Tyr Asn Asn Ser Leu Tyr Tyr His Lys Gly Gly Ser Asn Thr Ile
        375                 380                 385

gtg aga ttt gaa ttt ggg aaa gag aca cct caa act ctg aag ctt gaa     1257
Val Arg Phe Glu Phe Gly Lys Glu Thr Pro Gln Thr Leu Lys Leu Glu
    390                 395                 400

gat gct ttg tat ttt gat cga aaa tac ctc ttt gcg aat tcc aag act     1305
Asp Ala Leu Tyr Phe Asp Arg Lys Tyr Leu Phe Ala Asn Ser Lys Thr
405                 410                 415                 420

tac ttc aac ata gca gtg gat gag aag ggc ctc tgg att atc tac gcc     1353
Tyr Phe Asn Ile Ala Val Asp Glu Lys Gly Leu Trp Ile Ile Tyr Ala
                425                 430                 435

tcg agt gtg gat ggc tca agc atc ctt gtg gca cag ctg gac gag agg     1401
Ser Ser Val Asp Gly Ser Ser Ile Leu Val Ala Gln Leu Asp Glu Arg
            440                 445                 450

aca ttc tct gtg ctg cag cac atc aat acc aca tac ccc aag tcc aag     1449
Thr Phe Ser Val Leu Gln His Ile Asn Thr Thr Tyr Pro Lys Ser Lys
        455                 460                 465

gct ggc aat gcc ttc ata gct caa ggg atc ctc tat gtc acg gac aca     1497
Ala Gly Asn Ala Phe Ile Ala Gln Gly Ile Leu Tyr Val Thr Asp Thr
```

-continued

```
    470                 475                 480

aaa gat aca agg gtc acg ttt gcc ttt gat ttg tta cga ggg aag cag      1545
Lys Asp Thr Arg Val Thr Phe Ala Phe Asp Leu Leu Arg Gly Lys Gln
485                 490                 495                 500

atc aat gca aac ttc ggt ctc aga atg tca cag tct gtt ctt gcc atg      1593
Ile Asn Ala Asn Phe Gly Leu Arg Met Ser Gln Ser Val Leu Ala Met
                505                 510                 515

ttg tcg tac aat atg aga gac cag cat ttg tac tcg tgg gaa gac ggc      1641
Leu Ser Tyr Asn Met Arg Asp Gln His Leu Tyr Ser Trp Glu Asp Gly
            520                 525                 530

cac ctg atg ctc tat cct gtg cac ttt tcg tca aca gca ccc agc cag      1689
His Leu Met Leu Tyr Pro Val His Phe Ser Ser Thr Ala Pro Ser Gln
        535                 540                 545

cga taggcctgca gtcggctccc tcattatgca ccacacattt tctggggttt          1742
Arg

gaccaagccc aacggaaaga aggcctgtaa aggatatcca gatactcaga gcatacgccc   1802

gtgttacggg cttttgtgca tgtggcaagt ccccctgtaa gccaggttaa ctaaaggctg   1862

gaaagttgaa atggataaca tttggtgacc cttggtccct cttcaaactt agcaagttag   1922

tgctcccccc tgaccttagt gtccccatca gtaatatgaa acatctgtgt gattgcagca   1982

tttcctatac ctatatgaag ttctgtgatt cttgcctggt tatatattag attgctttca   2042

ggtttctttt ttttttctcc acatgtaaat gagtttacct gcagcttgag gggtgtgcct   2102

atcagtgatg acggacattt gtttggtgtt tagggaaaaa gcattgtttc ttatggcttt   2162

taaagtatta tattatccat aatttgatat ttttttttga atacgcccct gccactacag   2222

aatgattatt gttttcagct cctaagtaca aatccaagat taataaaaaa aaaacatgaa   2282

tagaaaaaaa aaaaaaaaaa actcgagagt attagtcgat gtaggaaaac              2332


<210> SEQ ID NO 2
<211> LENGTH: 549
<212> TYPE: PRT
<213> ORGANISM: Rattus sp.

<400> SEQUENCE: 2

Met Thr Arg Ala Ala Glu Arg Gly Gln Gly Ala Thr Gly Trp Gly Leu
  1               5                  10                  15

Arg Gly Ala Leu Met Ala Val Ala Leu Leu Ser Val Leu Asn Ala Val
             20                  25                  30

Gly Thr Val Phe Val Leu Tyr Gln Trp Arg Glu Leu Ser Ala Ala Leu
         35                  40                  45

Arg Ala Leu Glu Ala Gln His Gly Gln Glu Gln Arg Glu Asp Ser Ala
     50                  55                  60

Leu Arg Ala Phe Leu Ala Glu Leu Ser Arg Ala Pro Ala Arg Val Pro
 65                  70                  75                  80

Glu Pro Pro Gln Asp Pro Met Ser Ala Ala Arg Asn Lys Arg Ser His
                 85                  90                  95

Gly Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160
```

-continued

```
Gln Pro Gly Leu Gln Gly Pro Lys Gly Glu Lys Gly Ala Val Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Pro Gly Pro Ser Gly Ser Arg Arg Ala Lys
                245                 250                 255

Gly Pro Arg Gln Pro Asn Ser Phe Thr Asn Gln Cys Pro Gly Glu Thr
            260                 265                 270

Cys Val Ile Pro Asn Asp Asp Thr Leu Val Gly Arg Ala Asp Glu Lys
        275                 280                 285

Val Asn Glu Arg His Ser Pro Gln Thr Glu Pro Met Ile Thr Ser Ile
    290                 295                 300

Gly Asn Pro Ala Gln Val Leu Lys Val Lys Glu Thr Phe Gly Thr Trp
305                 310                 315                 320

Leu Arg Glu Ser Ala Asn Arg Ser Asp Asp Arg Ile Trp Val Thr Glu
                325                 330                 335

His Phe Ser Gly Ile Met Val Lys Glu Phe Glu Asp Leu Pro Ala Leu
            340                 345                 350

Leu Asn Ser Ser Phe Thr Leu Leu His Leu Pro His Tyr Phe His Gly
        355                 360                 365

Cys Gly His Ala Val Tyr Asn Asn Ser Leu Tyr Tyr His Lys Gly Gly
    370                 375                 380

Ser Asn Thr Ile Val Arg Phe Glu Phe Gly Lys Glu Thr Pro Gln Thr
385                 390                 395                 400

Leu Lys Leu Glu Asp Ala Leu Tyr Phe Asp Arg Lys Tyr Leu Phe Ala
                405                 410                 415

Asn Ser Lys Thr Tyr Phe Asn Ile Ala Val Asp Glu Lys Gly Leu Trp
            420                 425                 430

Ile Ile Tyr Ala Ser Ser Val Asp Gly Ser Ser Ile Leu Val Ala Gln
        435                 440                 445

Leu Asp Glu Arg Thr Phe Ser Val Leu Gln His Ile Asn Thr Thr Tyr
    450                 455                 460

Pro Lys Ser Lys Ala Gly Asn Ala Phe Ile Ala Gln Gly Ile Leu Tyr
465                 470                 475                 480

Val Thr Asp Thr Lys Asp Thr Arg Val Thr Phe Ala Phe Asp Leu Leu
                485                 490                 495

Arg Gly Lys Gln Ile Asn Ala Asn Phe Gly Leu Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val His Phe Ser Ser Thr
    530                 535                 540

Ala Pro Ser Gln Arg
545
```

<210> SEQ ID NO 3
<211> LENGTH: 2278
<212> TYPE: DNA

-continued

```
<213> ORGANISM: Rattus sp.
<220> FEATURE:
<221> NAME/KEY: CDS
<222> LOCATION: (46)..(1638)

<400> SEQUENCE: 3

acgcggggag tgctgccctg agtcgttcgg cctgagcaca gagac atg acc cga gcc      57
                                                  Met Thr Arg Ala
                                                  1

gca gag cga ggc caa ggg gct aca ggc tgg gga ctg cga ggc gcc ctg       105
Ala Glu Arg Gly Gln Gly Ala Thr Gly Trp Gly Leu Arg Gly Ala Leu
  5                  10                  15                  20

atg gcc gtg gcg ctg ctg tca gtg ctg aac gcc gtg ggc acc gtg ttc       153
Met Ala Val Ala Leu Leu Ser Val Leu Asn Ala Val Gly Thr Val Phe
                 25                  30                  35

gtg ctg tac cag cag cgc gag gac agc gcc cta cgc gcc ttt cta gct       201
Val Leu Tyr Gln Gln Arg Glu Asp Ser Ala Leu Arg Ala Phe Leu Ala
             40                  45                  50

gaa tta agt cgt gcg cca gcc cga gtc ccc gaa cca ccc cag gac ccc       249
Glu Leu Ser Arg Ala Pro Ala Arg Val Pro Glu Pro Pro Gln Asp Pro
         55                  60                  65

atg agt gca gcg cgc aat aag cgc agc cac ggc ggc gag cct gcg tca       297
Met Ser Ala Ala Arg Asn Lys Arg Ser His Gly Gly Glu Pro Ala Ser
     70                  75                  80

cac atc cgc gcg gag agc cag gac atg atg atg atg atg acc tac agc       345
His Ile Arg Ala Glu Ser Gln Asp Met Met Met Met Met Thr Tyr Ser
 85                  90                  95                 100

atg gtg ccg atc cgg gtg atg ata gac ctg tgc aac agc acc cag ggc       393
Met Val Pro Ile Arg Val Met Ile Asp Leu Cys Asn Ser Thr Gln Gly
                105                 110                 115

atc tgc ctt aca gga cca ccg ggc cca cca gga cct cca gga gct ggt       441
Ile Cys Leu Thr Gly Pro Pro Gly Pro Pro Gly Pro Pro Gly Ala Gly
            120                 125                 130

ggg tta cca ggc cac aat gga tca gat gga cag cct ggt ctc cag ggc       489
Gly Leu Pro Gly His Asn Gly Ser Asp Gly Gln Pro Gly Leu Gln Gly
        135                 140                 145

cca aaa gga gaa aaa gga gca gtt ggg aag aga gga aaa atg ggg tta       537
Pro Lys Gly Glu Lys Gly Ala Val Gly Lys Arg Gly Lys Met Gly Leu
    150                 155                 160

ccc gga gcc aca gga aat cca ggg gaa aag gga gag aag gga gat gct       585
Pro Gly Ala Thr Gly Asn Pro Gly Glu Lys Gly Glu Lys Gly Asp Ala
165                 170                 175                 180

ggt gaa ctg ggc cta cct gga aat gag gga cca cca gga cag aaa gga       633
Gly Glu Leu Gly Leu Pro Gly Asn Glu Gly Pro Pro Gly Gln Lys Gly
                185                 190                 195

gac aaa gga gac aaa gga gat gtg tcc aat gac gtg ctt ttg aca ggt       681
Asp Lys Gly Asp Lys Gly Asp Val Ser Asn Asp Val Leu Leu Thr Gly
            200                 205                 210

gcc aaa ggt gac caa ggg ccc cct ggc cca cct gga ccc cca ggg cct       729
Ala Lys Gly Asp Gln Gly Pro Pro Gly Pro Pro Gly Pro Pro Gly Pro
        215                 220                 225

cca ggc cct tct gga agc aga aga gcc aaa ggc cct cgg cag cca aat       777
Pro Gly Pro Ser Gly Ser Arg Arg Ala Lys Gly Pro Arg Gln Pro Asn
    230                 235                 240

tcg ttc acc aac cag tgt cca ggg gag acg tgt gtc ata ccc aat gat       825
Ser Phe Thr Asn Gln Cys Pro Gly Glu Thr Cys Val Ile Pro Asn Asp
245                 250                 255                 260

gat acc ttg gtg ggg aga gct gat gag aaa gtc aat gag cgc cat tct       873
Asp Thr Leu Val Gly Arg Ala Asp Glu Lys Val Asn Glu Arg His Ser
                265                 270                 275
```

-continued

```
cca caa aca gaa ccc atg atc acg tcc att ggt aac ccg gcc caa gtc      921
Pro Gln Thr Glu Pro Met Ile Thr Ser Ile Gly Asn Pro Ala Gln Val
            280                 285                 290

ctc aaa gtg aaa gag act ttt ggg acc tgg cta aga gag tct gct aac      969
Leu Lys Val Lys Glu Thr Phe Gly Thr Trp Leu Arg Glu Ser Ala Asn
        295                 300                 305

agg agt gat gac cgc att tgg gtg act gaa cat ttt tca ggc atc atg     1017
Arg Ser Asp Asp Arg Ile Trp Val Thr Glu His Phe Ser Gly Ile Met
    310                 315                 320

gtg aag gag ttt gaa gac ctg ccc gcc ctc ctg aat agc agc ttc acc     1065
Val Lys Glu Phe Glu Asp Leu Pro Ala Leu Leu Asn Ser Ser Phe Thr
325                 330                 335                 340

ctc ctc cac ctc cca cat tac ttc cat ggc tgc ggg cac gct gtt tac     1113
Leu Leu His Leu Pro His Tyr Phe His Gly Cys Gly His Ala Val Tyr
                345                 350                 355

aac aac tct ctc tac tac cac aaa gga ggc tcc aac acc ata gtg aga     1161
Asn Asn Ser Leu Tyr Tyr His Lys Gly Gly Ser Asn Thr Ile Val Arg
            360                 365                 370

ttt gaa ttt ggg aaa gag aca cct caa act ctg aag ctt gaa gat gct     1209
Phe Glu Phe Gly Lys Glu Thr Pro Gln Thr Leu Lys Leu Glu Asp Ala
        375                 380                 385

ttg tat ttt gat cga aaa tac ctc ttt gcg aat tcc aag act tac ttc     1257
Leu Tyr Phe Asp Arg Lys Tyr Leu Phe Ala Asn Ser Lys Thr Tyr Phe
    390                 395                 400

aac ata gca gtg gat gag aag ggc ctc tgg att atc tac gcc tcg agt     1305
Asn Ile Ala Val Asp Glu Lys Gly Leu Trp Ile Ile Tyr Ala Ser Ser
405                 410                 415                 420

gtg gat ggc tca agc atc ctt gtg gca cag ctg gac gag agg aca ttc     1353
Val Asp Gly Ser Ser Ile Leu Val Ala Gln Leu Asp Glu Arg Thr Phe
                425                 430                 435

tct gtg ctg cag cac atc aat acc aca tac ccc aag tcc aag gct ggc     1401
Ser Val Leu Gln His Ile Asn Thr Thr Tyr Pro Lys Ser Lys Ala Gly
            440                 445                 450

aat gcc ttc ata gct caa ggg atc ctc tat gtc acg gac aca aaa gat     1449
Asn Ala Phe Ile Ala Gln Gly Ile Leu Tyr Val Thr Asp Thr Lys Asp
        455                 460                 465

aca agg gtc acg ttt gcc ttt gat ttg tta cga ggg aag cag atc aat     1497
Thr Arg Val Thr Phe Ala Phe Asp Leu Leu Arg Gly Lys Gln Ile Asn
    470                 475                 480

gca aac ttc ggt ctc aga atg tca cag tct gtt ctt gcc atg ttg tcg     1545
Ala Asn Phe Gly Leu Arg Met Ser Gln Ser Val Leu Ala Met Leu Ser
485                 490                 495                 500

tac aat atg aga gac cag cat ttg tac tcg tgg gaa gac ggc cac ctg     1593
Tyr Asn Met Arg Asp Gln His Leu Tyr Ser Trp Glu Asp Gly His Leu
                505                 510                 515

atg ctc tat cct gtg cac ttt tcg tca aca gca ccc agc cag cga         1638
Met Leu Tyr Pro Val His Phe Ser Ser Thr Ala Pro Ser Gln Arg
            520                 525                 530

taggcctgca gtcggctccc tcattatgca ccacacattt tctggggttt gaccaagccc   1698

aacggaaaga aggcctgtaa aggatatcca gatactcaga gcatacgccc gtgttacggg   1758

cttttgtgca tgtggcaagt ccccctgtaa gccaggttaa ctaaaggctg gaaagttgaa   1818

atggataaca tttggtgacc cttggtccct cttcaaactt agcaagttag tgctcccccc   1878

tgaccttagt gtccccatca gtaatatgaa acatctgtgt gattgcagca tttcctatac   1938

ctatatgaag ttctgtgatt cttgcctggt tatatattag attgctttca ggtttctttt   1998

tttttctcc acatgtaaat gagtttacct gcagcttgag ggtgtgcct atcagtgatg   2058

acggacattt gtttggtgtt tagggaaaaa gcattgtttc ttatggcttt taaagtatta   2118
```

-continued

```
tattatccat aatttgatat ttttttttga atacgcccct gccactacag aatgattatt   2178

gttttcagct cctaagtaca aatccaagat taataaaaaa aaaacatgaa tagaaaaaaa   2238

aaaaaaaaaa actcgagagt attagtcgat gtaggaaaac                         2278


<210> SEQ ID NO 4
<211> LENGTH: 531
<212> TYPE: PRT
<213> ORGANISM: Rattus sp.

<400> SEQUENCE: 4

Met Thr Arg Ala Ala Glu Arg Gly Gln Gly Ala Thr Gly Trp Gly Leu
  1               5                  10                  15

Arg Gly Ala Leu Met Ala Val Ala Leu Leu Ser Val Leu Asn Ala Val
             20                  25                  30

Gly Thr Val Phe Val Leu Tyr Gln Gln Arg Glu Asp Ser Ala Leu Arg
         35                  40                  45

Ala Phe Leu Ala Glu Leu Ser Arg Ala Pro Ala Arg Val Pro Glu Pro
     50                  55                  60

Pro Gln Asp Pro Met Ser Ala Ala Arg Asn Lys Arg Ser His Gly Gly
 65                  70                  75                  80

Glu Pro Ala Ser His Ile Arg Ala Glu Ser Gln Asp Met Met Met Met
                 85                  90                  95

Met Thr Tyr Ser Met Val Pro Ile Arg Val Met Ile Asp Leu Cys Asn
            100                 105                 110

Ser Thr Gln Gly Ile Cys Leu Thr Gly Pro Pro Gly Pro Pro Gly Pro
        115                 120                 125

Pro Gly Ala Gly Gly Leu Pro Gly His Asn Gly Ser Asp Gly Gln Pro
    130                 135                 140

Gly Leu Gln Gly Pro Lys Gly Glu Lys Gly Ala Val Gly Lys Arg Gly
145                 150                 155                 160

Lys Met Gly Leu Pro Gly Ala Thr Gly Asn Pro Gly Glu Lys Gly Glu
                165                 170                 175

Lys Gly Asp Ala Gly Glu Leu Gly Leu Pro Gly Asn Glu Gly Pro Pro
            180                 185                 190

Gly Gln Lys Gly Asp Lys Gly Asp Lys Gly Asp Val Ser Asn Asp Val
        195                 200                 205

Leu Leu Thr Gly Ala Lys Gly Asp Gln Gly Pro Pro Gly Pro Pro Gly
    210                 215                 220

Pro Pro Gly Pro Pro Gly Pro Ser Gly Ser Arg Arg Ala Lys Gly Pro
225                 230                 235                 240

Arg Gln Pro Asn Ser Phe Thr Asn Gln Cys Pro Gly Glu Thr Cys Val
                245                 250                 255

Ile Pro Asn Asp Asp Thr Leu Val Gly Arg Ala Asp Glu Lys Val Asn
            260                 265                 270

Glu Arg His Ser Pro Gln Thr Glu Pro Met Ile Thr Ser Ile Gly Asn
        275                 280                 285

Pro Ala Gln Val Leu Lys Val Lys Glu Thr Phe Gly Thr Trp Leu Arg
    290                 295                 300

Glu Ser Ala Asn Arg Ser Asp Asp Arg Ile Trp Val Thr Glu His Phe
305                 310                 315                 320

Ser Gly Ile Met Val Lys Glu Phe Glu Asp Leu Pro Ala Leu Leu Asn
                325                 330                 335

Ser Ser Phe Thr Leu Leu His Leu Pro His Tyr Phe His Gly Cys Gly
```

-continued

```
            340                 345                 350

His Ala Val Tyr Asn Asn Ser Leu Tyr Tyr His Lys Gly Gly Ser Asn
        355                 360                 365

Thr Ile Val Arg Phe Glu Phe Gly Lys Glu Thr Pro Gln Thr Leu Lys
    370                 375                 380

Leu Glu Asp Ala Leu Tyr Phe Asp Arg Lys Tyr Leu Phe Ala Asn Ser
385                 390                 395                 400

Lys Thr Tyr Phe Asn Ile Ala Val Asp Glu Lys Gly Leu Trp Ile Ile
                405                 410                 415

Tyr Ala Ser Ser Val Asp Gly Ser Ser Ile Leu Val Ala Gln Leu Asp
            420                 425                 430

Glu Arg Thr Phe Ser Val Leu Gln His Ile Asn Thr Thr Tyr Pro Lys
        435                 440                 445

Ser Lys Ala Gly Asn Ala Phe Ile Ala Gln Gly Ile Leu Tyr Val Thr
    450                 455                 460

Asp Thr Lys Asp Thr Arg Val Thr Phe Ala Phe Asp Leu Leu Arg Gly
465                 470                 475                 480

Lys Gln Ile Asn Ala Asn Phe Gly Leu Arg Met Ser Gln Ser Val Leu
                485                 490                 495

Ala Met Leu Ser Tyr Asn Met Arg Asp Gln His Leu Tyr Ser Trp Glu
            500                 505                 510

Asp Gly His Leu Met Leu Tyr Pro Val His Phe Ser Ser Thr Ala Pro
        515                 520                 525

Ser Gln Arg
    530


<210> SEQ ID NO 5
<211> LENGTH: 2416
<212> TYPE: DNA
<213> ORGANISM: Rattus sp.
<220> FEATURE:
<221> NAME/KEY: CDS
<222> LOCATION: (189)..(1835)

<400> SEQUENCE: 5

gaattcggca cgaggggggc ttctggggcg ccacgattac tgtccccaac ccgcctcgcc      60

agacgggtct aaaggcagct tgactcacga ctctgccacc agcccaccac tcgcgcgagg     120

gtataaaacc tgccactgcg ggaggaggcc cagtgctgcc ctgagtcgtt cggcctgagc     180

acagagac atg acc cga gcc gca gag cga ggc caa ggg gct aca ggc tgg      230
         Met Thr Arg Ala Ala Glu Arg Gly Gln Gly Ala Thr Gly Trp
           1               5                  10

gga ctg cga ggc gcc ctg atg gcc gtg gcg ctg ctg tca gtg ctg aac       278
Gly Leu Arg Gly Ala Leu Met Ala Val Ala Leu Leu Ser Val Leu Asn
 15                  20                  25                  30

gcc gtg ggc acc gtg ttc gtg ctg tac cag tgg cgc gag ctg agc gcg       326
Ala Val Gly Thr Val Phe Val Leu Tyr Gln Trp Arg Glu Leu Ser Ala
                 35                  40                  45

gcg ctg cgg gca ctg gag gcg caa cac ggc cag gag cag cgc gag gac       374
Ala Leu Arg Ala Leu Glu Ala Gln His Gly Gln Glu Gln Arg Glu Asp
             50                  55                  60

agc gcc cta cgc gcc ttt cta gct gaa tta agt cgt gcg cca gcc cga       422
Ser Ala Leu Arg Ala Phe Leu Ala Glu Leu Ser Arg Ala Pro Ala Arg
         65                  70                  75

gtc ccc gaa cca ccc cag gac ccc atg agt gca gcg cgc aat aag cgc       470
Val Pro Glu Pro Pro Gln Asp Pro Met Ser Ala Ala Arg Asn Lys Arg
     80                  85                  90
```

-continued

```
agc cac ggc ggc gag cct gcg tca cac atc cgc gcg gag agc cag gac      518
Ser His Gly Gly Glu Pro Ala Ser His Ile Arg Ala Glu Ser Gln Asp
 95                 100                 105                 110

atg atg atg atg atg acc tac agc atg gtg ccg atc cgg gtg atg ata      566
Met Met Met Met Met Thr Tyr Ser Met Val Pro Ile Arg Val Met Ile
                115                 120                 125

gac ctg tgc aac agc acc cag ggc atc tgc ctt aca gga cca ccg ggc      614
Asp Leu Cys Asn Ser Thr Gln Gly Ile Cys Leu Thr Gly Pro Pro Gly
            130                 135                 140

cca cca gga cct cca gga gct ggt ggg tta cca ggc cac aat gga tca      662
Pro Pro Gly Pro Pro Gly Ala Gly Gly Leu Pro Gly His Asn Gly Ser
        145                 150                 155

gat gga cag cct ggt ctc cag ggc cca aaa gga gaa aaa gga gca gtt      710
Asp Gly Gln Pro Gly Leu Gln Gly Pro Lys Gly Glu Lys Gly Ala Val
    160                 165                 170

ggg aag aga gga aaa atg ggg tta ccc gga gcc aca gga aat cca ggg      758
Gly Lys Arg Gly Lys Met Gly Leu Pro Gly Ala Thr Gly Asn Pro Gly
175                 180                 185                 190

gaa aag gga gag aag gga gat gct ggt gaa ctg ggc cta cct gga aat      806
Glu Lys Gly Glu Lys Gly Asp Ala Gly Glu Leu Gly Leu Pro Gly Asn
                195                 200                 205

gag gga cca cca gga cag aaa gga gac aaa gga gac aaa gga gat gtg      854
Glu Gly Pro Pro Gly Gln Lys Gly Asp Lys Gly Asp Lys Gly Asp Val
            210                 215                 220

tcc aat gac gtg ctt ttg aca ggt gcc aaa ggt gac caa ggg ccc cct      902
Ser Asn Asp Val Leu Leu Thr Gly Ala Lys Gly Asp Gln Gly Pro Pro
        225                 230                 235

ggc cca cct gga ccc cca ggg cct cca ggc cct cct gga agc aga aga      950
Gly Pro Pro Gly Pro Pro Gly Pro Pro Gly Pro Pro Gly Ser Arg Arg
    240                 245                 250

gcc aaa ggc cct cgg cag cca aat tcg ttc acc aac cag tgt cca ggg      998
Ala Lys Gly Pro Arg Gln Pro Asn Ser Phe Thr Asn Gln Cys Pro Gly
255                 260                 265                 270

gag acg tgt gtc ata ccc aat gat gat acc ttg gtg ggg aga gct gat     1046
Glu Thr Cys Val Ile Pro Asn Asp Asp Thr Leu Val Gly Arg Ala Asp
                275                 280                 285

gag aaa gtc aat gag cgc cat tct cca caa aca gaa ccc atg atc acg     1094
Glu Lys Val Asn Glu Arg His Ser Pro Gln Thr Glu Pro Met Ile Thr
            290                 295                 300

tcc att ggt aac ccg gcc caa gtc ctc aag gtg aaa gag act ttt ggg     1142
Ser Ile Gly Asn Pro Ala Gln Val Leu Lys Val Lys Glu Thr Phe Gly
        305                 310                 315

acc tgg cta aga gag tct gct aac agg agt gac gac cgc att tgg gtg     1190
Thr Trp Leu Arg Glu Ser Ala Asn Arg Ser Asp Asp Arg Ile Trp Val
    320                 325                 330

act gaa cat ttt tca ggc atc atg gtg aag gag ttt gaa gac ctg ccc     1238
Thr Glu His Phe Ser Gly Ile Met Val Lys Glu Phe Glu Asp Leu Pro
335                 340                 345                 350

gcc ctc ctg aat agc agc ttc acc ctc ctc cac ctc cca cat tac ttc     1286
Ala Leu Leu Asn Ser Ser Phe Thr Leu Leu His Leu Pro His Tyr Phe
                355                 360                 365

cat ggc tgc ggg cac gct gtt tac aac aac tct ctc tac tac cac aaa     1334
His Gly Cys Gly His Ala Val Tyr Asn Asn Ser Leu Tyr Tyr His Lys
            370                 375                 380

gga ggc tcc aac acc ata gtg aga ttt gaa ttt ggg aaa gag aca cct     1382
Gly Gly Ser Asn Thr Ile Val Arg Phe Glu Phe Gly Lys Glu Thr Pro
        385                 390                 395

caa act ctg aag ctt gaa gat gct ttg tat ttt gat cga aaa tac ctc     1430
Gln Thr Leu Lys Leu Glu Asp Ala Leu Tyr Phe Asp Arg Lys Tyr Leu
    400                 405                 410
```

-continued

```
ttt gcg aat tcc aag act tac ttc aac ata gca gtg gat gag aag ggc     1478
Phe Ala Asn Ser Lys Thr Tyr Phe Asn Ile Ala Val Asp Glu Lys Gly
415                 420                 425                 430

ctc tgg att atc tac gcc tcg agt gtg gat ggc tca agc atc ctt gtg     1526
Leu Trp Ile Ile Tyr Ala Ser Ser Val Asp Gly Ser Ser Ile Leu Val
                435                 440                 445

gca cag ctg gac gag agg aca ttc tct gtg ctg cgg cac atc aat acc     1574
Ala Gln Leu Asp Glu Arg Thr Phe Ser Val Leu Arg His Ile Asn Thr
            450                 455                 460

aca tac ccc aag tcc aag gct ggc aat gcc ttc ata gct caa ggg atc     1622
Thr Tyr Pro Lys Ser Lys Ala Gly Asn Ala Phe Ile Ala Gln Gly Ile
        465                 470                 475

ctc tat gtc acg gac acc aaa gat aca agg gtc acg ttt gcc ttt gat     1670
Leu Tyr Val Thr Asp Thr Lys Asp Thr Arg Val Thr Phe Ala Phe Asp
    480                 485                 490

ttg tta cga ggg aag cag atc aat gca aac ttc ggt ctc aga atg tca     1718
Leu Leu Arg Gly Lys Gln Ile Asn Ala Asn Phe Gly Leu Arg Met Ser
495                 500                 505                 510

cag tct gtt ctt gcc atg ttg tcg tac aat atg aga gac cag cat ttg     1766
Gln Ser Val Leu Ala Met Leu Ser Tyr Asn Met Arg Asp Gln His Leu
                515                 520                 525

tac tcg tgg gaa gac ggc cac ctg atg ctc tat cct gtg cac ttt tcg     1814
Tyr Ser Trp Glu Asp Gly His Leu Met Leu Tyr Pro Val His Phe Ser
            530                 535                 540

tca aca gca ccc agc cag cga taggcctgca gtcggctccc tcattatgca       1865
Ser Thr Ala Pro Ser Gln Arg
        545

ccacacattt tctggggttt gaccaagccc aacggaaaga aggcctgtaa aggatatcca   1925

gatactcaga gcatacgccc gtgctacggg ctcttgtgca tgtggcaagt ccccctgtaa   1985

gccaggttag ctagaggctg gaagttgaaa tggataacat ctggtgaccc ttggtccctc   2045

ttcaaactta gcaagttagt gctccccccct gaccttagtg tccccatcag taatatgaaa   2105

catctgtgtg attgacagca tttcctctac ctatatgaag ttctgtgatt cttgcctggt   2165

tatatattag attgctttct ggtttctttt ttttttctcc acatgtaaat gagtttacct   2225

gcagcttgag ggtgtgcct atcagtgatg acggacattt gtttggtgtt tagggaagat    2285

gcattgtctc ttatggcttc taaagtatta tattatccat aatttgatat ttttctctga   2345

atacgcacct gccactacag aatgattatt gtttcagctc ctaagtacaa atccaaaaaa   2405

aaaaaaaaaa a                                                        2416


<210> SEQ ID NO 6
<211> LENGTH: 549
<212> TYPE: PRT
<213> ORGANISM: Rattus sp.

<400> SEQUENCE: 6

Met Thr Arg Ala Ala Glu Arg Gly Gln Gly Ala Thr Gly Trp Gly Leu
  1               5                  10                  15

Arg Gly Ala Leu Met Ala Val Ala Leu Leu Ser Val Leu Asn Ala Val
            20                  25                  30

Gly Thr Val Phe Val Leu Tyr Gln Trp Arg Glu Leu Ser Ala Ala Leu
        35                  40                  45

Arg Ala Leu Glu Ala Gln His Gly Gln Glu Gln Arg Glu Asp Ser Ala
     50                  55                  60

Leu Arg Ala Phe Leu Ala Glu Leu Ser Arg Ala Pro Ala Arg Val Pro
 65                  70                  75                  80
```

-continued

```
Glu Pro Pro Gln Asp Pro Met Ser Ala Ala Arg Asn Lys Arg Ser His
                85                  90                  95

Gly Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Val Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Pro Gly Pro Pro Gly Ser Arg Arg Ala Lys
                245                 250                 255

Gly Pro Arg Gln Pro Asn Ser Phe Thr Asn Gln Cys Pro Gly Glu Thr
            260                 265                 270

Cys Val Ile Pro Asn Asp Asp Thr Leu Val Gly Arg Ala Asp Glu Lys
        275                 280                 285

Val Asn Glu Arg His Ser Pro Gln Thr Glu Pro Met Ile Thr Ser Ile
    290                 295                 300

Gly Asn Pro Ala Gln Val Leu Lys Val Lys Glu Thr Phe Gly Thr Trp
305                 310                 315                 320

Leu Arg Glu Ser Ala Asn Arg Ser Asp Asp Arg Ile Trp Val Thr Glu
                325                 330                 335

His Phe Ser Gly Ile Met Val Lys Glu Phe Glu Asp Leu Pro Ala Leu
            340                 345                 350

Leu Asn Ser Ser Phe Thr Leu Leu His Leu Pro His Tyr Phe His Gly
        355                 360                 365

Cys Gly His Ala Val Tyr Asn Asn Ser Leu Tyr Tyr His Lys Gly Gly
    370                 375                 380

Ser Asn Thr Ile Val Arg Phe Glu Phe Gly Lys Glu Thr Pro Gln Thr
385                 390                 395                 400

Leu Lys Leu Glu Asp Ala Leu Tyr Phe Asp Arg Lys Tyr Leu Phe Ala
                405                 410                 415

Asn Ser Lys Thr Tyr Phe Asn Ile Ala Val Asp Glu Lys Gly Leu Trp
            420                 425                 430

Ile Ile Tyr Ala Ser Ser Val Asp Gly Ser Ser Ile Leu Val Ala Gln
        435                 440                 445

Leu Asp Glu Arg Thr Phe Ser Val Leu Arg His Ile Asn Thr Thr Tyr
    450                 455                 460

Pro Lys Ser Lys Ala Gly Asn Ala Phe Ile Ala Gln Gly Ile Leu Tyr
465                 470                 475                 480

Val Thr Asp Thr Lys Asp Thr Arg Val Thr Phe Ala Phe Asp Leu Leu
                485                 490                 495
```

-continued

```
Arg Gly Lys Gln Ile Asn Ala Asn Phe Gly Leu Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val His Phe Ser Ser Thr
    530                 535                 540

Ala Pro Ser Gln Arg
545


<210> SEQ ID NO 7
<211> LENGTH: 4649
<212> TYPE: DNA
<213> ORGANISM: Mus sp.
<220> FEATURE:
<221> NAME/KEY: CDS
<222> LOCATION: (40)..(1686)

<400> SEQUENCE: 7

tcagtgctgc cctgagccgc ccggcctgag cacgcagac atg acc cga gcc gca        54
                                           Met Thr Arg Ala Ala
                                             1               5

gag cga ggc caa ggg gct aca ggc tgg ggg ctg cgc ggc gcc ctg gtg      102
Glu Arg Gly Gln Gly Ala Thr Gly Trp Gly Leu Arg Gly Ala Leu Val
                 10                  15                  20

gcc ata gcg ctg ctg tcc gca ctg aac gcc gcg ggc acc gtg ttc gtg      150
Ala Ile Ala Leu Leu Ser Ala Leu Asn Ala Ala Gly Thr Val Phe Val
             25                  30                  35

ctg tgc cag tgg cgg ggg tta agc gcg gcg cta cgg gcg ctg gag gct      198
Leu Cys Gln Trp Arg Gly Leu Ser Ala Ala Leu Arg Ala Leu Glu Ala
         40                  45                  50

caa cgc ggc cga gag cag cgc gag gac agc gcc cta cgc gcc ttt ctg      246
Gln Arg Gly Arg Glu Gln Arg Glu Asp Ser Ala Leu Arg Ala Phe Leu
     55                  60                  65

gcc gaa ttg agt cgt gcg ccg ggc cgg gtc ccc gaa cca tcc cag gac      294
Ala Glu Leu Ser Arg Ala Pro Gly Arg Val Pro Glu Pro Ser Gln Asp
 70                  75                  80                  85

ccc atg agc gca gcg cgc aac aag cgc agc cac aac ggc gag cct gcg      342
Pro Met Ser Ala Ala Arg Asn Lys Arg Ser His Asn Gly Glu Pro Ala
                 90                  95                 100

tca cac atc cgt gcg gag agc cag gac atg atg atg atg atg acc tac      390
Ser His Ile Arg Ala Glu Ser Gln Asp Met Met Met Met Met Thr Tyr
            105                 110                 115

tcc atg gtg ccg att cga gtg atg ata gac ctg tgc aac agt acc cag      438
Ser Met Val Pro Ile Arg Val Met Ile Asp Leu Cys Asn Ser Thr Gln
        120                 125                 130

ggc atc tgc ctc aca gga cca ccg ggc cca cca gga cct cca gga gcc      486
Gly Ile Cys Leu Thr Gly Pro Pro Gly Pro Pro Gly Pro Pro Gly Ala
    135                 140                 145

ggc ggg tta cca ggc cac aat gga tca gat gga cag cct ggt ctc cag      534
Gly Gly Leu Pro Gly His Asn Gly Ser Asp Gly Gln Pro Gly Leu Gln
150                 155                 160                 165

ggc cca aaa gga gaa aaa gga gca att ggc aag aga gga aaa atg ggg      582
Gly Pro Lys Gly Glu Lys Gly Ala Ile Gly Lys Arg Gly Lys Met Gly
                170                 175                 180

tta cct gga gcc acc gga aat cca ggg gaa aag gga gaa aag gga gat      630
Leu Pro Gly Ala Thr Gly Asn Pro Gly Glu Lys Gly Glu Lys Gly Asp
            185                 190                 195

gct ggt gaa ctg ggt cta cct gga aat gag ggc cca cca ggg cag aaa      678
Ala Gly Glu Leu Gly Leu Pro Gly Asn Glu Gly Pro Pro Gly Gln Lys
        200                 205                 210
```

-continued

```
ggt gac aag gga gac aaa gga gac gtg tcc aat gac gtg ctt ttg aca      726
Gly Asp Lys Gly Asp Lys Gly Asp Val Ser Asn Asp Val Leu Leu Thr
    215                 220                 225

ggt gcc aaa ggt gac caa ggt ccc cct ggc ccc cct gga cct cca ggg      774
Gly Ala Lys Gly Asp Gln Gly Pro Pro Gly Pro Pro Gly Pro Pro Gly
230                 235                 240                 245

cct cca ggc cct cct gga agc aga aga tcc aaa ggc cct cgg cca cca      822
Pro Pro Gly Pro Pro Gly Ser Arg Arg Ser Lys Gly Pro Arg Pro Pro
                250                 255                 260

aac gtg ttc aac agc cag tgt cca ggg gag acg tgt gtc ata ccc aat      870
Asn Val Phe Asn Ser Gln Cys Pro Gly Glu Thr Cys Val Ile Pro Asn
            265                 270                 275

gat gat acc ttg gtg gga aga gct gat gag aaa gca aat gaa cgc cat      918
Asp Asp Thr Leu Val Gly Arg Ala Asp Glu Lys Ala Asn Glu Arg His
        280                 285                 290

tca cca caa aca gaa tct atg atc act tcc att ggc aac cca gcc caa      966
Ser Pro Gln Thr Glu Ser Met Ile Thr Ser Ile Gly Asn Pro Ala Gln
    295                 300                 305

gtc cta aaa gtg aga gag act ttt ggg act tgg atg aga gag tct gct     1014
Val Leu Lys Val Arg Glu Thr Phe Gly Thr Trp Met Arg Glu Ser Ala
310                 315                 320                 325

aac aaa agt gac gac cgc att tgg gtg act gaa cat ttt tca ggc atc     1062
Asn Lys Ser Asp Asp Arg Ile Trp Val Thr Glu His Phe Ser Gly Ile
                330                 335                 340

atg gtg aag gag ttc aaa gac ctg ccg gcg ctc ctc aat agc agc ttc     1110
Met Val Lys Glu Phe Lys Asp Leu Pro Ala Leu Leu Asn Ser Ser Phe
            345                 350                 355

aca ctc ctc cac ctc cca cat tat ttc cac ggc tgt ggg cac gct gtt     1158
Thr Leu Leu His Leu Pro His Tyr Phe His Gly Cys Gly His Ala Val
        360                 365                 370

tac aac aac tct ctc tac tac cac aaa gga ggc tcc aac acc ata gtg     1206
Tyr Asn Asn Ser Leu Tyr Tyr His Lys Gly Gly Ser Asn Thr Ile Val
    375                 380                 385

aga ttt gaa ttt ggg aaa gag aca cct cag act ctg aag ctg gaa aat     1254
Arg Phe Glu Phe Gly Lys Glu Thr Pro Gln Thr Leu Lys Leu Glu Asn
390                 395                 400                 405

gct ttg tat ttt gat cga aaa tac ctc ttt gca aat tcc aag act tac     1302
Ala Leu Tyr Phe Asp Arg Lys Tyr Leu Phe Ala Asn Ser Lys Thr Tyr
                410                 415                 420

ttc aac ata gca gtg gat gag aag ggc atc tgg att atc tac gct tca     1350
Phe Asn Ile Ala Val Asp Glu Lys Gly Ile Trp Ile Ile Tyr Ala Ser
            425                 430                 435

agt gtg gat ggc tca agc atc ctt gta gca cag ctg gat gag agg aca     1398
Ser Val Asp Gly Ser Ser Ile Leu Val Ala Gln Leu Asp Glu Arg Thr
        440                 445                 450

ttc tcc gtg aca cag cac atc aac acc aca tac ccc aaa tcc aag gct     1446
Phe Ser Val Thr Gln His Ile Asn Thr Thr Tyr Pro Lys Ser Lys Ala
    455                 460                 465

ggc aat gcc ttc ata gcc cga ggg atc ctc tat gtc aca gac acc aaa     1494
Gly Asn Ala Phe Ile Ala Arg Gly Ile Leu Tyr Val Thr Asp Thr Lys
470                 475                 480                 485

gat acg agg gtc acg ttt gcc ttt gat ttg tta gga gga aag caa atc     1542
Asp Thr Arg Val Thr Phe Ala Phe Asp Leu Leu Gly Gly Lys Gln Ile
                490                 495                 500

aat gca aac ttt gat ttc aga atg tcc cag tct gtt ctt gcc atg ctg     1590
Asn Ala Asn Phe Asp Phe Arg Met Ser Gln Ser Val Leu Ala Met Leu
            505                 510                 515

tca tac aac atg aga gat cag cat tta tac tcg tgg gaa gat ggc cat     1638
Ser Tyr Asn Met Arg Asp Gln His Leu Tyr Ser Trp Glu Asp Gly His
        520                 525                 530
```

-continued

```
ctg atg ctc tat cct gtg cag ttt ctg tca gcg gca tca agt cag cgg     1686
Leu Met Leu Tyr Pro Val Gln Phe Leu Ser Ala Ala Ser Ser Gln Arg
    535                 540                 545

tagggttccc tcggctgtct gctccctctc tatactccac attgtctagg gtttggtcaa   1746

gcccaacaga aagctagccg gtaaaggata cccaggcact cggagcgtaa gcccatgcca   1806

cgggctcttg cacaagcggc gagtccgctc taagccaggt tgttgaaata gctacagatt   1866

agaaatggat gtggaagaga tctggtgacc cagtatccct cctcaaactc agcaagttag   1926

ctctccccg accgtagcgt ccccataggt aatacgaaac atctgggtat gactgacatt   1986

tcctcttcct agatgaaatt ctgtgattct tgcctgatta tatattagaa tgctttctgg   2046

attctttttt tttttctcc acatgtaagt gagcttactt gcagcttgag gggtgggcct   2106

ttcagtgatg acttatttgg tatttaggga aggtgcactg gctcttatgg cttctaaggt   2166

tttattttat tcataatttg ttattttctc tgaatattca cctaccacta cagaatgatc   2226

attgttttca gctcctaaac acaaatccaa gattaataaa caaacaaaca aaccatgaat   2286

agatacaggc tcagaactct aaatggagct gcatcaggcc cataggccat ctagatgctg   2346

tcaatttctg atcatattgt ttgctgctgg gaaagtaaac aggatatctt cagttcgtgg   2406

tccctttgc caaggccatg ggattgttat cagagtgtca aacactaagt ggccaataat   2466

ctggttagaa gcatggaaac atgatggttt tttcagaaaa caggcaccat ttatacttac   2526

tgtttagaat gagggaaggc aattggctca aaggccaaag tcagcttagc tctttttcct   2586

gtaccatcgc atccctgcac ctaagaatct cgcctcagag tgtgtcagca gtgaagcaga   2646

gccgctctgt aaatcctgaa ccattactgc ctggccttta cagaaagaaa gaaaaaaaaa   2706

tgttgacctt tcatctaagg acagggaacg agccaggttc tcagaagggc tcactccctg   2766

agtctggtta ggctttttac ggactgacag gcagcatttt atgtggcttg ggctttggca   2826

gagggaacag gtaaggacag catcagatgg agtaagagaa cctccagccg tggagatgtt   2886

cactcccacg tggtcctcaa agttgggtct gtcctcttgg atagcaagga tctagtttaa   2946

ttggttccta caagacctta aataaccacg ttctctgtca actcattgag ttccaggcag   3006

gcctgtggag cttcaaagag gaagctgtgg atttcatcgc cccccccccc ccggaatata   3066

gaaaaagaca ctacagaaac tgtccaggaa agactggcca gctgttccaa acccactctc   3126

agtgggcctg tgacctggtt tagtttttt aatagaagca tcttgaggct tggggtatgc   3186

atttaacta tttaactttc cctgccctct gaaagcaccc aggcagctgt tactggtgaa   3246

cctgttgagt tctcaaggtc atgggtccca aagcttcccc acttcttgat tagatggttt   3306

tgcagttggt catcacagct tttaaagata ttctctcaga ttcatttgtt gcaatgtaga   3366

gttctaatgt ttcatcagtg tatctaatga atggtattgt tcttttaaag tattcaaata   3426

tgagatactg tttctgagtg cggtagacct ggatatacat ataattccat tttttatta   3486

cttagtagca ttgctgagaa tagatacaat actaattgta catacaagca aaatagttta   3546

gttattgaat tagctcattt ttaatatctg aactagcaaa tgtcttagct ttcctttact   3606

tttttctttc ttttcctttc ttttctcttc ttttcctttc tttcctttcc ttttcttttc   3666

tttttttaa agcaatgtct ttgtgttcgc ccagacttat cacaaactcc tgcttcagat   3726

tcctgggtgc tgggaccaca ggcacagtgg ctctttgact ctcttaattg tgtgtaagga   3786

atcatacata tactcacgat tagagaaact cgtctgaaga ttttgtttct tttcatggtt   3846

gtttctttct ttctttcttt ctttctttct ttcgttatag tgtagtggga ttagaacaag   3906
```

-continued

```
taaggttgac tggtgtttaa tgaatttatc tttgcagaag gaaaggaatt aaggttttat   3966

tccttttctt gcaaacagga cttcattcta tatcactcaa cacagtgttt caggctcact   4026

gctaaaatag tgtgcacatc ttatattttt aaatgaagat agtaatcaac cctgctgtca   4086

cttgtagcca agctgttcta aaagcacttc atttatgtct gtatgaaatc aagtgattct   4146

ccaattcctc tgaaatctaa agtagatacc attatactag aaaccacacc ttccagcttc   4206

aaaggtaggc cagactcaac atttacaaag catttctatt aactaatata gagtccaact   4266

aaggttgcag agttggctct ggcctcaatg tatcatgtat caatgtatca gagaacgtgg   4326

tccgggctga atatttcaga tcaattctgg tgctgggctc attcgaagtc tttttaccct   4386

cataatcaaa tgacaaggtg agatgacaaa tgaggaagca cagtccttga aaagtcactc   4446

gtcatcctcc aagcatagca agtaccttac tcaggcattg cctgtctggt gttgagctac   4506

ctgaaggaaa agtgggggt ggagctcttc agttttcatc agtgctgtgg ccttatttat   4566

ctcataatct cccatcagta accacagatt ctaaacgacc agcaagtaac agttgtaagt   4626

agtaaaataa aattatcctg aat                                           4649
```

<210> SEQ ID NO 8
<211> LENGTH: 549
<212> TYPE: PRT
<213> ORGANISM: Mus sp.

<400> SEQUENCE: 8

```
Met Thr Arg Ala Ala Glu Arg Gly Gln Gly Ala Thr Gly Trp Gly Leu
  1               5                  10                  15

Arg Gly Ala Leu Val Ala Ile Ala Leu Leu Ser Ala Leu Asn Ala Ala
             20                  25                  30

Gly Thr Val Phe Val Leu Cys Gln Trp Arg Gly Leu Ser Ala Ala Leu
         35                  40                  45

Arg Ala Leu Glu Ala Gln Arg Gly Arg Glu Gln Arg Glu Asp Ser Ala
     50                  55                  60

Leu Arg Ala Phe Leu Ala Glu Leu Ser Arg Ala Pro Gly Arg Val Pro
 65                  70                  75                  80

Glu Pro Ser Gln Asp Pro Met Ser Ala Ala Arg Asn Lys Arg Ser His
                 85                  90                  95

Asn Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Ile Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240
```

-continued

```
Pro Gly Pro Pro Gly Pro Pro Gly Pro Pro Gly Ser Arg Arg Ser Lys
                245                 250                 255

Gly Pro Arg Pro Pro Asn Val Phe Asn Ser Gln Cys Pro Gly Glu Thr
            260                 265                 270

Cys Val Ile Pro Asn Asp Asp Thr Leu Val Gly Arg Ala Asp Glu Lys
        275                 280                 285

Ala Asn Glu Arg His Ser Pro Gln Thr Glu Ser Met Ile Thr Ser Ile
    290                 295                 300

Gly Asn Pro Ala Gln Val Leu Lys Val Arg Glu Thr Phe Gly Thr Trp
305                 310                 315                 320

Met Arg Glu Ser Ala Asn Lys Ser Asp Asp Arg Ile Trp Val Thr Glu
                325                 330                 335

His Phe Ser Gly Ile Met Val Lys Glu Phe Lys Asp Leu Pro Ala Leu
            340                 345                 350

Leu Asn Ser Ser Phe Thr Leu Leu His Leu Pro His Tyr Phe His Gly
        355                 360                 365

Cys Gly His Ala Val Tyr Asn Asn Ser Leu Tyr Tyr His Lys Gly Gly
    370                 375                 380

Ser Asn Thr Ile Val Arg Phe Glu Phe Gly Lys Glu Thr Pro Gln Thr
385                 390                 395                 400

Leu Lys Leu Glu Asn Ala Leu Tyr Phe Asp Arg Lys Tyr Leu Phe Ala
                405                 410                 415

Asn Ser Lys Thr Tyr Phe Asn Ile Ala Val Asp Glu Lys Gly Ile Trp
            420                 425                 430

Ile Ile Tyr Ala Ser Ser Val Asp Gly Ser Ser Ile Leu Val Ala Gln
        435                 440                 445

Leu Asp Glu Arg Thr Phe Ser Val Thr Gln His Ile Asn Thr Thr Tyr
    450                 455                 460

Pro Lys Ser Lys Ala Gly Asn Ala Phe Ile Ala Arg Gly Ile Leu Tyr
465                 470                 475                 480

Val Thr Asp Thr Lys Asp Thr Arg Val Thr Phe Ala Phe Asp Leu Leu
                485                 490                 495

Gly Gly Lys Gln Ile Asn Ala Asn Phe Asp Phe Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val Gln Phe Leu Ser Ala
    530                 535                 540

Ala Ser Ser Gln Arg
545


<210> SEQ ID NO 9
<211> LENGTH: 4654
<212> TYPE: DNA
<213> ORGANISM: Homo sapiens
<220> FEATURE:
<221> NAME/KEY: CDS
<222> LOCATION: (51)..(1331)

<400> SEQUENCE: 9

gaccattgtg tatgattcgt tgttgactgc agcatcacta gatccgagtg atg gtg        56
                                                      Met Val
                                                        1

gac ctg tgc aac agc acc aag ggc atc tgc ctc aca gga cct tct gga      104
Asp Leu Cys Asn Ser Thr Lys Gly Ile Cys Leu Thr Gly Pro Ser Gly
          5                  10                  15
```

-continued

```
cca cca gga cct ccg gga gcc ggc ggg ttg cca gga cac aac gga ttg      152
Pro Pro Gly Pro Pro Gly Ala Gly Gly Leu Pro Gly His Asn Gly Leu
     20                  25                  30

gat gga cag cct ggt cct cag ggc cca aaa gga gaa aaa gga gca aat      200
Asp Gly Gln Pro Gly Pro Gln Gly Pro Lys Gly Glu Lys Gly Ala Asn
 35                  40                  45                  50

gga aaa aga gga aaa atg ggg ata cct gga gct gca gga aat cca ggg      248
Gly Lys Arg Gly Lys Met Gly Ile Pro Gly Ala Ala Gly Asn Pro Gly
                 55                  60                  65

gaa agg gga gaa aag gga gac cat ggt gaa ctg ggc ctg cag gga aat      296
Glu Arg Gly Glu Lys Gly Asp His Gly Glu Leu Gly Leu Gln Gly Asn
             70                  75                  80

gag ggc cca cca ggg cag aag gga gaa aag ggt gac aaa gga gat gtg      344
Glu Gly Pro Pro Gly Gln Lys Gly Glu Lys Gly Asp Lys Gly Asp Val
         85                  90                  95

tcc aac gac gtg ctc ctg gca ggt gcc aaa ggt gac caa ggc cca ccc      392
Ser Asn Asp Val Leu Leu Ala Gly Ala Lys Gly Asp Gln Gly Pro Pro
    100                 105                 110

ggt cca cct ggg ccc cca ggc cct cca ggt cct cca ggg ccc cct gga      440
Gly Pro Pro Gly Pro Pro Gly Pro Pro Gly Pro Pro Gly Pro Pro Gly
115                 120                 125                 130

agc aga aga gcc aaa ggc cct cgg cag cca agc atg ttc aac ggc cag      488
Ser Arg Arg Ala Lys Gly Pro Arg Gln Pro Ser Met Phe Asn Gly Gln
                135                 140                 145

tgc cca ggt gag act tgt gcc ata cca aat gat gat acc ttg gtt gga      536
Cys Pro Gly Glu Thr Cys Ala Ile Pro Asn Asp Asp Thr Leu Val Gly
            150                 155                 160

aaa gct gat gag aaa gcc agt gaa cac cat tcc cca caa gca gaa tcc      584
Lys Ala Asp Glu Lys Ala Ser Glu His His Ser Pro Gln Ala Glu Ser
        165                 170                 175

atg atc act tcc att gga aac cca gtg caa gta ctg aaa gtg aca gag      632
Met Ile Thr Ser Ile Gly Asn Pro Val Gln Val Leu Lys Val Thr Glu
    180                 185                 190

aca ttt ggg act tgg ata aga gag tct gct aac aag agt gat gac cgg      680
Thr Phe Gly Thr Trp Ile Arg Glu Ser Ala Asn Lys Ser Asp Asp Arg
195                 200                 205                 210

att tgg gtg aca gag cat ttt tca ggc atc atg gtt aag gaa ttc aag      728
Ile Trp Val Thr Glu His Phe Ser Gly Ile Met Val Lys Glu Phe Lys
                215                 220                 225

gat cag ccc tca ctt ctg aat ggc agt tac acg ttc atc cac ctt cca      776
Asp Gln Pro Ser Leu Leu Asn Gly Ser Tyr Thr Phe Ile His Leu Pro
            230                 235                 240

tac tat ttc cat ggc tgt ggg cac gtt gct tac aac aac tct ctc tac      824
Tyr Tyr Phe His Gly Cys Gly His Val Ala Tyr Asn Asn Ser Leu Tyr
        245                 250                 255

tac cac aaa ggg ggt tct aat acc cta gtg aga ttt gaa ttt ggc cag      872
Tyr His Lys Gly Gly Ser Asn Thr Leu Val Arg Phe Glu Phe Gly Gln
    260                 265                 270

gaa aca tcc caa act ctg aag ctt gaa aat gcc ttg tat ttt gat cga      920
Glu Thr Ser Gln Thr Leu Lys Leu Glu Asn Ala Leu Tyr Phe Asp Arg
275                 280                 285                 290

aaa tac ctt ttt gca aat tcc aaa act tac ttc aat cta gct gta gat      968
Lys Tyr Leu Phe Ala Asn Ser Lys Thr Tyr Phe Asn Leu Ala Val Asp
                295                 300                 305

gaa aag ggc ctt tgg att atc tat gcg tca agt gtg gac ggc tcg agc     1016
Glu Lys Gly Leu Trp Ile Ile Tyr Ala Ser Ser Val Asp Gly Ser Ser
            310                 315                 320

att ctt gta gca caa ctg gat gag agg aca ttc tca gtg gtg caa cac     1064
Ile Leu Val Ala Gln Leu Asp Glu Arg Thr Phe Ser Val Val Gln His
        325                 330                 335
```

-continued

```
gtc aat acc acg tac cct aaa tcc aag gct ggc aac gcc ttc att gcc     1112
Val Asn Thr Thr Tyr Pro Lys Ser Lys Ala Gly Asn Ala Phe Ile Ala
    340                 345                 350

cga gga atc ctc tat gtc aca gac acc aaa gat atg agg gtc aca ttt     1160
Arg Gly Ile Leu Tyr Val Thr Asp Thr Lys Asp Met Arg Val Thr Phe
355                 360                 365                 370

gcc ttt gat ttg tta gga ggg aaa cag atc aat gca aac ttt gat tta     1208
Ala Phe Asp Leu Leu Gly Gly Lys Gln Ile Asn Ala Asn Phe Asp Leu
                375                 380                 385

aga act tcc cag tct gtt ctt gcc atg tta gca tac aac atg aga gat     1256
Arg Thr Ser Gln Ser Val Leu Ala Met Leu Ala Tyr Asn Met Arg Asp
            390                 395                 400

cag cat tta tat tca tgg gaa gat ggc cat tta atg ctt tat cct gtg     1304
Gln His Leu Tyr Ser Trp Glu Asp Gly His Leu Met Leu Tyr Pro Val
        405                 410                 415

cag ttt ttg tca act acc tta aat cag tgatgtgctg cattcggctc           1351
Gln Phe Leu Ser Thr Thr Leu Asn Gln
    420                 425

ccttcagcaa atttcagggg ttttctggga ccagttctcc cccaacagga aacttgtttt   1411

tttaacgtca gccagatatt tagaaaataa cctcaaaagt gtttatatgg tcagtgagcc   1471

ccgcttagtg aaatagcaac agattggaag ttgaaatggc tgagatttgg tgatctcccc   1531

acagctggct ctgcaagtta cctctttctc cttgggcctt agtttcccca ttggtaatct   1591

gaattggcta agatgattgg ggagattttc tgtacctgta ggtaatttgg tgattcttgg   1651

tggctgctct tctcacaact tttatgtatc tgcttctgtc gtttagcttt tttagccaca   1711

tgctgaccaa atttaccttt gagttgataa gtccagtggc ttgagtagtg aatccctcag   1771

tgctgactta tatcttgttc tttgaaaaaa tgcattgact ctttaagaca tctaaagtat   1831

cacattatcc ataatttatt gcttttcttt gcatctgcac ctgccaccac agaataacca   1891

ttaccctcag ctgctgattg ggcagctctg agattagcaa aagccaggga cagctacatg   1951

ttcaggtttt tttttttttt tttttcaata ggctattttt tttcttttct tattttaaat   2011

agagagagag tcttgctatg tttcccaggc tggtcttgaa ctcctggggc tcaagtgatc   2071

ctcctgcctt ggcctcccaa aatgctggat tacaggcatg tgtgcctggc ccaggtttct   2131

taataaaaca gaatcatgat cttccaggtt ccccccagtt tctgatcatg ttgatttgta   2191

gctgtggatc atgaacactg aatccccaga tcactctgac ttcttatgct tctcctgtgg   2251

atccactatc aaagtactaa atgctgtgta agtagacgtt aatctggctg gaaccatggg   2311

aagcactttg cagtgttcag aagagaggct ccatttgtgg ctattatgta gaactgggcc   2371

agagccagtc cattgcctgt ttttttaaat aaggttttac tgagcacagc cacactcatt   2431

tgtttatgca gtacggcctg acattgcttt tgctctgcaa cagcagagtc gagtcattgc   2491

aacaaagagc atatggcccc acagtgccta aaatattgac cagctacccc tttatggaaa   2551

aagattgctg actcctgata aagaatataa agtgagcctg attcttgaaa aaatcagaac   2611

cagagcctgt tttgttttgt tctaaactaa gaagccgcat aggatgtgac ttgcgttttg   2671

agtagagggg aaggctgata acggcgtaag atgaagtggc cctccacaaa ggctggttag   2731

gggacagttc tttctctaac atagttttaa aggatgtgat ctggtcccct tggatgccag   2791

gagagaatcc agttgaactt gctcctaaat gctcttaaat atgcatattt tctgccaact   2851

cacttcttta aacatctttc agcccagcgc tgcggccccg ggaagggcca ctgcgaatag   2911

agaggaagct ggaaaagttc ctggggctct gcagccagga aggggaacca gggcaaatct   2971
```

-continued

```
tatgtaaaga tttttcagca acttgtccca atttgtgtgt attctgaaac tttctctttg   3031

ggaccaaatt cattctcaat ggccctgagt tcaatatatt attaacagca gtattttaaa   3091

acttagggtt gaactgggca tggtggcaca taactgcaat cccagctact ttggaggcag   3151

ggatgggagg atcacttgag gccaggatct caggaccagc ctagagagat cccatctcta   3211

aaaaataaaa tataagaaaa taaaacttag ggatatatac gatttaaata ttcaaatctc   3271

cctgctcccc tgaaagtccc caggcagctg ttaatgactt gtttgttgtg ttctcaatat   3331

gatggctatt tgaaacttca cctacttttc attagattgg ttgtaccatg tcaccttagc   3391

ttttaaaaat actcttttca gattcacgtt ctctaacaaa gagtctcatg ttcaagatca   3451

atatgtctaa taagcgctgg tgtcctttta aagtatttaa atatatatgt tgctgttgct   3511

gaatacagga gaccaggtta ggaatatagt ttcataataa tagtacatac aatactaatt   3571

gtatataagg tagcaaccaa aagaggttgt taattagcac atattccttt tagaaaaatg   3631

tttcagaaac ctcagtcttg atatctgagc tatctgggct cccttacttg tgagtaaggg   3691

atcatgctca ccactggaga agcttacacc gggacttttt ttcttttttc ttttttttt   3751

gctatgacag agtaatgcta acgtaaggac aactgagttt gatcagtgtt taatcgcagt   3811

gggtaatctt atctgattgt ctttaaaagt gaaaaggatt aagattttat tctttcttgt   3871

aaacattact tgatttttta aagaagtttt gggctcactg ctaaaataga gtatacaact   3931

gaatgttttt aagtcaagat actgttttag gagtttaccc tctcatttat aaccaaagtt   3991

gctctaaaac actttccaaa tatctgcact tctgatgtca gaatcaaacc agataattct   4051

ctaattcttc tttaatctaa agtagatagc ttcccactgg aaagtaaaca aaaccatccc   4111

tcccaacctc aaagctaggc cacactctat ttcaaggcat tttctttcag ctgataaggt   4171

gtcctcctga agccaagtag gtggttctgg tctccaagta tcgttaagca caggtgctat   4231

gacagaaaaa gttctggggt ggaagtttta agatgaggag ttctgatctt aggcatctta   4291

acagtcacaa ggtgaaaagt caaatgaaac agtacaattc ttgatgagtg aggtgtcatc   4351

ttccaaccac acagaggacg ttttggctat gatcatctga tggcaagtga aggagaaatg   4411

agtgataggg ctttgcgttt tcatccagat gctgtggccc tgtgtttcac agcattaaga   4471

gccataattt ccaacctgca cagatcctga acaacaaatg aataacgatg aatgtctttt   4531

tggttgtaat ttaacaagtc aaataaataa tcattgctga gcacaatcac caaaaaaaaa   4591

aaaaaaaaaa aaaaaaaaaa aaaaaaaaaa aaaaaaaaaa aaagaaaaaa aaaaaaaaaa   4651

aca                                                                 4654
```

<210> SEQ ID NO 10
<211> LENGTH: 427
<212> TYPE: PRT
<213> ORGANISM: Homo sapiens

<400> SEQUENCE: 10

```
Met Val Asp Leu Cys Asn Ser Thr Lys Gly Ile Cys Leu Thr Gly Pro
  1               5                  10                  15

Ser Gly Pro Pro Gly Pro Pro Gly Ala Gly Gly Leu Pro Gly His Asn
             20                  25                  30

Gly Leu Asp Gly Gln Pro Gly Pro Gln Gly Pro Lys Gly Glu Lys Gly
         35                  40                  45

Ala Asn Gly Lys Arg Gly Lys Met Gly Ile Pro Gly Ala Ala Gly Asn
     50                  55                  60

Pro Gly Glu Arg Gly Glu Lys Gly Asp His Gly Glu Leu Gly Leu Gln
```

-continued

```
 65                  70                  75                  80

Gly Asn Glu Gly Pro Pro Gly Gln Lys Gly Glu Lys Gly Asp Lys Gly
                 85                  90                  95

Asp Val Ser Asn Asp Val Leu Leu Ala Gly Ala Lys Gly Asp Gln Gly
            100                 105                 110

Pro Pro Gly Pro Pro Gly Pro Pro Gly Pro Pro Gly Pro Pro Gly Pro
        115                 120                 125

Pro Gly Ser Arg Arg Ala Lys Gly Pro Arg Gln Pro Ser Met Phe Asn
    130                 135                 140

Gly Gln Cys Pro Gly Glu Thr Cys Ala Ile Pro Asn Asp Asp Thr Leu
145                 150                 155                 160

Val Gly Lys Ala Asp Glu Lys Ala Ser Glu His His Ser Pro Gln Ala
                165                 170                 175

Glu Ser Met Ile Thr Ser Ile Gly Asn Pro Val Gln Val Leu Lys Val
            180                 185                 190

Thr Glu Thr Phe Gly Thr Trp Ile Arg Glu Ser Ala Asn Lys Ser Asp
        195                 200                 205

Asp Arg Ile Trp Val Thr Glu His Phe Ser Gly Ile Met Val Lys Glu
    210                 215                 220

Phe Lys Asp Gln Pro Ser Leu Leu Asn Gly Ser Tyr Thr Phe Ile His
225                 230                 235                 240

Leu Pro Tyr Tyr Phe His Gly Cys Gly His Val Ala Tyr Asn Asn Ser
                245                 250                 255

Leu Tyr Tyr His Lys Gly Gly Ser Asn Thr Leu Val Arg Phe Glu Phe
            260                 265                 270

Gly Gln Glu Thr Ser Gln Thr Leu Lys Leu Glu Asn Ala Leu Tyr Phe
        275                 280                 285

Asp Arg Lys Tyr Leu Phe Ala Asn Ser Lys Thr Tyr Phe Asn Leu Ala
    290                 295                 300

Val Asp Glu Lys Gly Leu Trp Ile Ile Tyr Ala Ser Ser Val Asp Gly
305                 310                 315                 320

Ser Ser Ile Leu Val Ala Gln Leu Asp Glu Arg Thr Phe Ser Val Val
                325                 330                 335

Gln His Val Asn Thr Thr Tyr Pro Lys Ser Lys Ala Gly Asn Ala Phe
            340                 345                 350

Ile Ala Arg Gly Ile Leu Tyr Val Thr Asp Thr Lys Asp Met Arg Val
        355                 360                 365

Thr Phe Ala Phe Asp Leu Leu Gly Gly Lys Gln Ile Asn Ala Asn Phe
    370                 375                 380

Asp Leu Arg Thr Ser Gln Ser Val Leu Ala Met Leu Ala Tyr Asn Met
385                 390                 395                 400

Arg Asp Gln His Leu Tyr Ser Trp Glu Asp Gly His Leu Met Leu Tyr
                405                 410                 415

Pro Val Gln Phe Leu Ser Thr Thr Leu Asn Gln
            420                 425
```

<210> SEQ ID NO 11
<211> LENGTH: 4976
<212> TYPE: DNA
<213> ORGANISM: Homo sapiens
<220> FEATURE:
<221> NAME/KEY: CDS
<222> LOCATION: (1)..(1653)

<400> SEQUENCE: 11

-continued

```
atg gcc cga ggc gct gag gga ggc cgt ggg gac gcg ggt tgg ggc ctg        48
Met Ala Arg Gly Ala Glu Gly Gly Arg Gly Asp Ala Gly Trp Gly Leu
  1               5                  10                  15

cgt ggc gcc ctg gcg gcc gtg gcg ctg ctc tcg gcg ctc aac gct gcg        96
Arg Gly Ala Leu Ala Ala Val Ala Leu Leu Ser Ala Leu Asn Ala Ala
             20                  25                  30

ggc acg gtg ttc gcg ctg tgc cag tgg cgc ggg ctg agc tcg gcg ctg       144
Gly Thr Val Phe Ala Leu Cys Gln Trp Arg Gly Leu Ser Ser Ala Leu
         35                  40                  45

cgg gct ttg gag gcg cag cgg ggc cgg gag cag cgc gag gac agt gcc       192
Arg Ala Leu Glu Ala Gln Arg Gly Arg Glu Gln Arg Glu Asp Ser Ala
     50                  55                  60

ctg cgc tcc ttc ctg gcc gag ttg agc cgc gcg ccg cgc ggg gcg tcc       240
Leu Arg Ser Phe Leu Ala Glu Leu Ser Arg Ala Pro Arg Gly Ala Ser
 65                  70                  75                  80

gca cca ccc caa gac ccg gcc agc tca gct cgc aac aag cgc agc cac       288
Ala Pro Pro Gln Asp Pro Ala Ser Ser Ala Arg Asn Lys Arg Ser His
                 85                  90                  95

agc ggc gag ccc gcg ccg cat atc cgc gcc gag agc cat gac atg ctg       336
Ser Gly Glu Pro Ala Pro His Ile Arg Ala Glu Ser His Asp Met Leu
            100                 105                 110

atg atg atg acc tac tcc atg gtg ccg atc cga gtg atg gtg gac ctg       384
Met Met Met Thr Tyr Ser Met Val Pro Ile Arg Val Met Val Asp Leu
        115                 120                 125

tgc aac agc acc aag ggc atc tgc ctc aca gga cct tct gga cca cca       432
Cys Asn Ser Thr Lys Gly Ile Cys Leu Thr Gly Pro Ser Gly Pro Pro
    130                 135                 140

gga cct ccg gga gcc ggc ggg ttg cca gga cac aac gga ttg gat gga       480
Gly Pro Pro Gly Ala Gly Gly Leu Pro Gly His Asn Gly Leu Asp Gly
145                 150                 155                 160

cag cct ggt cct cag ggc cca aaa gga gaa aaa gga gca aat gga aaa       528
Gln Pro Gly Pro Gln Gly Pro Lys Gly Glu Lys Gly Ala Asn Gly Lys
                165                 170                 175

aga gga aaa atg ggg ata cct gga gct gca gga aat cca ggg gaa agg       576
Arg Gly Lys Met Gly Ile Pro Gly Ala Ala Gly Asn Pro Gly Glu Arg
            180                 185                 190

gga gaa aag gga gac cat ggt gaa ctg ggc ctg cag gga aat gag ggc       624
Gly Glu Lys Gly Asp His Gly Glu Leu Gly Leu Gln Gly Asn Glu Gly
        195                 200                 205

cca cca ggg cag aag gga gaa aag ggt gac aaa gga gat gtg tcc aac       672
Pro Pro Gly Gln Lys Gly Glu Lys Gly Asp Lys Gly Asp Val Ser Asn
    210                 215                 220

gac gtg ctc ctg gca ggt gcc aaa ggt gac caa ggc cca ccc ggt cca       720
Asp Val Leu Leu Ala Gly Ala Lys Gly Asp Gln Gly Pro Pro Gly Pro
225                 230                 235                 240

cct ggg ccc cca ggc cct cca ggt cct cca ggg ccc cct gga agc aga       768
Pro Gly Pro Pro Gly Pro Pro Gly Pro Pro Gly Pro Pro Gly Ser Arg
                245                 250                 255

aga gcc aaa ggc cct cgg cag cca agc atg ttc aac ggc cag tgc cca       816
Arg Ala Lys Gly Pro Arg Gln Pro Ser Met Phe Asn Gly Gln Cys Pro
            260                 265                 270

ggt gag act tgt gcc ata cca aat gat gat acc ttg gtt gga aaa gct       864
Gly Glu Thr Cys Ala Ile Pro Asn Asp Asp Thr Leu Val Gly Lys Ala
        275                 280                 285

gat gag aaa gcc agt gaa cac cat tcc cca caa gca gaa tcc atg atc       912
Asp Glu Lys Ala Ser Glu His His Ser Pro Gln Ala Glu Ser Met Ile
    290                 295                 300

act tcc att gga aac cca gtg caa gta ctg aaa gtg aca gag aca ttt       960
Thr Ser Ile Gly Asn Pro Val Gln Val Leu Lys Val Thr Glu Thr Phe
305                 310                 315                 320
```

-continued

```
ggg act tgg ata aga gag tct gct aac aag agt gat gac cgg att tgg      1008
Gly Thr Trp Ile Arg Glu Ser Ala Asn Lys Ser Asp Asp Arg Ile Trp
                325                 330                 335

gtg aca gag cat ttt tca ggc atc atg gtt aag gaa ttc aag gat cag      1056
Val Thr Glu His Phe Ser Gly Ile Met Val Lys Glu Phe Lys Asp Gln
            340                 345                 350

ccc tca ctt ctg aat ggc agt tac acg ttc atc cac ctt cca tac tat      1104
Pro Ser Leu Leu Asn Gly Ser Tyr Thr Phe Ile His Leu Pro Tyr Tyr
        355                 360                 365

ttc cat ggc tgt ggg cac gtt gct tac aac aac tct ctc tac tac cac      1152
Phe His Gly Cys Gly His Val Ala Tyr Asn Asn Ser Leu Tyr Tyr His
    370                 375                 380

aaa ggg ggt tct aat acc cta gtg aga ttt gaa ttt ggc cag gaa aca      1200
Lys Gly Gly Ser Asn Thr Leu Val Arg Phe Glu Phe Gly Gln Glu Thr
385                 390                 395                 400

tcc caa act ctg aag ctt gaa aat gcc ttg tat ttt gat cga aaa tac      1248
Ser Gln Thr Leu Lys Leu Glu Asn Ala Leu Tyr Phe Asp Arg Lys Tyr
                405                 410                 415

ctt ttt gca aat tcc aaa act tac ttc aat cta gct gta gat gaa aag      1296
Leu Phe Ala Asn Ser Lys Thr Tyr Phe Asn Leu Ala Val Asp Glu Lys
            420                 425                 430

ggc ctt tgg att atc tat gcg tca agt gtg gac ggc tcg agc att ctt      1344
Gly Leu Trp Ile Ile Tyr Ala Ser Ser Val Asp Gly Ser Ser Ile Leu
        435                 440                 445

gta gca caa ctg gat gag agg aca ttc tca gtg gtg caa cac gtc aat      1392
Val Ala Gln Leu Asp Glu Arg Thr Phe Ser Val Val Gln His Val Asn
    450                 455                 460

acc acg tac cct aaa tcc aag gct ggc aac gcc ttc att gcc cga gga      1440
Thr Thr Tyr Pro Lys Ser Lys Ala Gly Asn Ala Phe Ile Ala Arg Gly
465                 470                 475                 480

atc ctc tat gtc aca gac acc aaa gat atg agg gtc aca ttt gcc ttt      1488
Ile Leu Tyr Val Thr Asp Thr Lys Asp Met Arg Val Thr Phe Ala Phe
                485                 490                 495

gat ttg tta gga ggg aaa cag atc aat gca aac ttt gat tta aga act      1536
Asp Leu Leu Gly Gly Lys Gln Ile Asn Ala Asn Phe Asp Leu Arg Thr
            500                 505                 510

tcc cag tct gtt ctt gcc atg tta gca tac aac atg aga gat cag cat      1584
Ser Gln Ser Val Leu Ala Met Leu Ala Tyr Asn Met Arg Asp Gln His
        515                 520                 525

tta tat tca tgg gaa gat ggc cat tta atg ctt tat cct gtg cag ttt      1632
Leu Tyr Ser Trp Glu Asp Gly His Leu Met Leu Tyr Pro Val Gln Phe
    530                 535                 540

ttg tca act acc tta aat cag tgatgtgctg cattcggctc ccttcagcaa         1683
Leu Ser Thr Thr Leu Asn Gln
545                 550

atttcagggg ttttctggga ccagttctcc cccaacagga aacttgtttt tttaacgtca   1743

gccagatatt tagaaaataa cctcaaaagt gtttatatgg tcagtgagcc ccgcttagtg   1803

aaatagcaac agattggaag ttgaaatggc tgagatttgg tgatctcccc acagctggct   1863

ctgcaagtta cctctttctc cttgggcctt agtttcccca ttggtaatct gaattggcta   1923

agatgattgg ggagattttc tgtacctgta ggtaatttgg tgattcttgg tggctgctct   1983

tctcacaact tttatgtatc tgcttctgtc gtttagcttt tttagccaca tgctgaccaa   2043

atttaccttt gagttgataa gtccagtggc ttgagtagtg aatccctcag tgctgactta   2103

tatcttgttc tttgaaaaaa tgcattgact ctttaagaca tctaaagtat cacattatcc   2163

ataatttatt gcttttcttt gcatctgcac ctgccaccac agaataacca ttaccctcag   2223
```

-continued

```
ctgctgattg ggcagctctg agattagcaa aagccaggga cagctacatg ttcaggtttt   2283
tttttttttt tttttcaata ggctattttt tttcttttct tattttaaat agagagagag   2343
tcttgctatg tttcccaggc tggtcttgaa ctcctggggc tcaagtgatc ctcctgcctt   2403
ggcctcccaa aatgctggat tacaggcatg tgtgcctggc ccaggtttct taataaaaca   2463
gaatcatgat cttccaggtt ccccccagtt tctgatcatg ttgatttgta gctgtggatc   2523
atgaacactg aatccccaga tcactctgac ttcttatgct tctcctgtgg atccactatc   2583
aaagtactaa atgctgtgta agtagacgtt aatctggctg gaaccatggg aagcactttg   2643
cagtgttcag aagagaggct ccatttgtgg ctattatgta gaactgggcc agagccagtc   2703
cattgcctgt ttttttaaat aaggttttac tgagcacagc cacactcatt tgtttatgca   2763
gtacggcctg acattgcttt tgctctgcaa cagcagagtc gagtcattgc aacaaagagc   2823
atatggcccc acagtgccta aaatattgac cagctacccc tttatggaaa aagattgctg   2883
actcctgata aagaatataa agtgagcctg attcttgaaa aaatcagaac cagagcctgt   2943
tttgttttgt tctaaactaa gaagccgcat aggatgtgac ttgcgttttg agtagagggg   3003
aaggctgata acggcgtaag atgaagtggc cctccacaaa ggctggttag ggacagttc    3063
tttctctaac atagttttaa aggatgtgat ctggtcccct tggatgccag gagagaatcc   3123
agttgaactt gctcctaaat gctcttaaat atgcatattt tctgccaact cacttcttta   3183
aacatctttc agcccagcgc tgcggccccg ggaagggcca ctgcgaatag agaggaagct   3243
ggaaaagttc ctggggctct gcagccagga aggggaacca gggcaaatct tatgtaaaga   3303
tttttcagca acttgtccca atttgtgtgt attctgaaac tttctctttg ggaccaaatt   3363
cattctcaat ggccctgagt tcaatatatt attaacagca gtattttaaa acttagggtt   3423
gaactgggca tggtggcaca taactgcaat cccagctact ttggaggcag ggatgggagg   3483
atcacttgag gccaggatct caggaccagc ctagagagat cccatctcta aaaaataaaa   3543
tataagaaaa taaaacttag gggatataca gatttaaata ttcaaatctc cctgctcccc   3603
tgaaagtccc caggcagctg ttaatgactt gtttgttgtg ttctcaatat gatggctatt   3663
tgaaacttca cctacttttc attagattgg ttgtaccatg tcaccttagc ttttaaaaat   3723
actcttttca gattcacgtt ctctaacaaa gagtctcatg ttcaagatca atatgtctaa   3783
taagcgctgg tgtcctttta aagtatttaa atatatatgt tgctgttgct gaatacagga   3843
gaccaggtta ggaatatagt ttcataataa tagtacatac aatactaatt gtatataagg   3903
tagcaaccaa aagaggttgt taattagcac atattccttt tagaaaaatg tttcagaaac   3963
ctcagtcttg atatctgagc tatctgggct cccttacttg tgagtaaggg atcatgctca   4023
ccactggaga agcttacacc gggacttttt ttctttttc tttttttttt gctatgacag    4083
agtaatgcta acgtaaggac aactgagttt gatcagtgtt taatcgcagt gggtaatctt   4143
atctgattgt ctttaaaagt gaaaaggatt aagattttat tctttcttgt aaacattact   4203
tgatttttta aagaagtttt gggctcactg ctaaaataga gtatacaact gaatgttttt   4263
aagtcaagat actgttttag gagtttaccc tctcatttat aaccaaagtt gctctaaaac   4323
actttccaaa tatctgcact tctgatgtca gaatcaaacc agataattct ctaattcttc   4383
tttaatctaa agtagatagc ttcccactgg aaagtaaaca aaaccatccc tcccaacctc   4443
aaagctaggc cacactctat ttcaaggcat tttctttcag ctgataaggt gtcctcctga   4503
agccaagtag gtggttctgg tctccaagta tcgttaagca caggtgctat gacagaaaaa   4563
gttctggggt ggaagtttta agatgaggag ttctgatctt aggcatctta acagtcacaa   4623
```

-continued

```
ggtgaaaagt caaatgaaac agtacaattc ttgatgagtg aggtgtcatc ttccaaccac   4683

acagaggacg ttttggctat gatcatctga tggcaagtga aggagaaatg agtgataggg   4743

ctttgcgttt tcatccagat gctgtggccc tgtgtttcac agcattaaga gccataattt   4803

ccaacctgca cagatcctga acaacaaatg aataacgatg aatgtctttt tggttgtaat   4863

ttaacaagtc aaataaataa tcattgctga gcacaatcac caaaaaaaaa aaaaaaaaaa   4923

aaaaaaaaaa aaaaaaaaaa aaaaaaaaaa aaagaaaaaa aaaaaaaaaa aca          4976


<210> SEQ ID NO 12
<211> LENGTH: 551
<212> TYPE: PRT
<213> ORGANISM: Homo sapiens

<400> SEQUENCE: 12

Met Ala Arg Gly Ala Glu Gly Gly Arg Gly Asp Ala Gly Trp Gly Leu
  1               5                  10                  15

Arg Gly Ala Leu Ala Ala Val Ala Leu Leu Ser Ala Leu Asn Ala Ala
             20                  25                  30

Gly Thr Val Phe Ala Leu Cys Gln Trp Arg Gly Leu Ser Ser Ala Leu
         35                  40                  45

Arg Ala Leu Glu Ala Gln Arg Gly Arg Glu Gln Arg Glu Asp Ser Ala
     50                  55                  60

Leu Arg Ser Phe Leu Ala Glu Leu Ser Arg Ala Pro Arg Gly Ala Ser
 65                  70                  75                  80

Ala Pro Pro Gln Asp Pro Ala Ser Ser Ala Arg Asn Lys Arg Ser His
                 85                  90                  95

Ser Gly Glu Pro Ala Pro His Ile Arg Ala Glu Ser His Asp Met Leu
            100                 105                 110

Met Met Met Thr Tyr Ser Met Val Pro Ile Arg Val Met Val Asp Leu
        115                 120                 125

Cys Asn Ser Thr Lys Gly Ile Cys Leu Thr Gly Pro Ser Gly Pro Pro
    130                 135                 140

Gly Pro Pro Gly Ala Gly Gly Leu Pro Gly His Asn Gly Leu Asp Gly
145                 150                 155                 160

Gln Pro Gly Pro Gln Gly Pro Lys Gly Glu Lys Gly Ala Asn Gly Lys
                165                 170                 175

Arg Gly Lys Met Gly Ile Pro Gly Ala Ala Gly Asn Pro Gly Glu Arg
            180                 185                 190

Gly Glu Lys Gly Asp His Gly Glu Leu Gly Leu Gln Gly Asn Glu Gly
        195                 200                 205

Pro Pro Gly Gln Lys Gly Glu Lys Gly Asp Lys Gly Asp Val Ser Asn
    210                 215                 220

Asp Val Leu Leu Ala Gly Ala Lys Gly Asp Gln Gly Pro Pro Gly Pro
225                 230                 235                 240

Pro Gly Pro Pro Gly Pro Pro Gly Pro Pro Gly Pro Pro Gly Ser Arg
                245                 250                 255

Arg Ala Lys Gly Pro Arg Gln Pro Ser Met Phe Asn Gly Gln Cys Pro
            260                 265                 270

Gly Glu Thr Cys Ala Ile Pro Asn Asp Asp Thr Leu Val Gly Lys Ala
        275                 280                 285

Asp Glu Lys Ala Ser Glu His His Ser Pro Gln Ala Glu Ser Met Ile
    290                 295                 300

Thr Ser Ile Gly Asn Pro Val Gln Val Leu Lys Val Thr Glu Thr Phe
```

-continued

```
305                 310                 315                 320

Gly Thr Trp Ile Arg Glu Ser Ala Asn Lys Ser Asp Asp Arg Ile Trp
                325                 330                 335

Val Thr Glu His Phe Ser Gly Ile Met Val Lys Glu Phe Lys Asp Gln
            340                 345                 350

Pro Ser Leu Leu Asn Gly Ser Tyr Thr Phe Ile His Leu Pro Tyr Tyr
        355                 360                 365

Phe His Gly Cys Gly His Val Ala Tyr Asn Asn Ser Leu Tyr Tyr His
    370                 375                 380

Lys Gly Gly Ser Asn Thr Leu Val Arg Phe Glu Phe Gly Gln Glu Thr
385                 390                 395                 400

Ser Gln Thr Leu Lys Leu Glu Asn Ala Leu Tyr Phe Asp Arg Lys Tyr
                405                 410                 415

Leu Phe Ala Asn Ser Lys Thr Tyr Phe Asn Leu Ala Val Asp Glu Lys
            420                 425                 430

Gly Leu Trp Ile Ile Tyr Ala Ser Ser Val Asp Gly Ser Ser Ile Leu
        435                 440                 445

Val Ala Gln Leu Asp Glu Arg Thr Phe Ser Val Val Gln His Val Asn
    450                 455                 460

Thr Thr Tyr Pro Lys Ser Lys Ala Gly Asn Ala Phe Ile Ala Arg Gly
465                 470                 475                 480

Ile Leu Tyr Val Thr Asp Thr Lys Asp Met Arg Val Thr Phe Ala Phe
                485                 490                 495

Asp Leu Leu Gly Gly Lys Gln Ile Asn Ala Asn Phe Asp Leu Arg Thr
            500                 505                 510

Ser Gln Ser Val Leu Ala Met Leu Ala Tyr Asn Met Arg Asp Gln His
        515                 520                 525

Leu Tyr Ser Trp Glu Asp Gly His Leu Met Leu Tyr Pro Val Gln Phe
    530                 535                 540

Leu Ser Thr Thr Leu Asn Gln
545                 550
```

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cccagttcac cagcatctcc cttctctc 28

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gtctatcatc acccggatcg gcaccat 27

<210> SEQ ID NO 15
<211> LENGTH: 21
<212> TYPE: DNA
<213> ORGANISM: Rattus sp.

-continued

<400> SEQUENCE: 15
aattaagtcg tgcgccagcc c 21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 16
uuaagucgug cgccagccct t 21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 17
gggcuggcgc acgacuuaat t 21

<210> SEQ ID NO 18
<211> LENGTH: 21
<212> TYPE: DNA
<213> ORGANISM: Rattus sp.

<400> SEQUENCE: 18
aatgatgata ccttggtggg g 21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 19
ugaugauacc uuggugggt t 21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 20
ccccaccaag guaucaucat t 21

-continued

<210> SEQ ID NO 21
<211> LENGTH: 21
<212> TYPE: DNA
<213> ORGANISM: Rattus sp.

<400> SEQUENCE: 21
aatgagcgcc attctccaca a 21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide

<400> SEQUENCE: 22
ugagcgccau ucuccacaat t 21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide

<400> SEQUENCE: 23
uuguggagaa uggcgcucat t 21

<210> SEQ ID NO 24
<211> LENGTH: 21
<212> TYPE: DNA
<213> ORGANISM: Rattus sp.

<400> SEQUENCE: 24
aacccatgat cacgtccatt g 21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide

<400> SEQUENCE: 25
cccaugauca cguccauugt t 21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide -continued

<400> SEQUENCE: 26
caauggacgu gaucaugggt t 21

<210> SEQ ID NO 27
<211> LENGTH: 22
<212> TYPE: PRT
<213> ORGANISM: Rattus sp.

<400> SEQUENCE: 27

Pro Asn Asp Asp Thr Leu Val Gly Arg Ala Asp Glu Lys Val Asn Glu
1 5 10 15

Arg His Ser Pro Gln Thr
20

<210> SEQ ID NO 28
<211> LENGTH: 1650
<212> TYPE: DNA
<213> ORGANISM: Rattus sp.

<400> SEQUENCE: 28
atgacccgag ccgcagagcg aggccaaggg gctacaggct ggggactgcg aggcgccctg 60
atggccgtgg cgctgctgtc agtgctgaac gccgtgggca ccgtgttcgt gctgtaccag 120
tggcgcgagc tgagcgcggc gctgcgggca ctggaggcgc aacacggcca ggagcagcgc 180
gaggacagcg ccctacgcgc ctttctagct gaattaagtc gtgcgccagc ccgagtcccc 240
gaaccacccc aggaccccat gagtgcagcg cgcaataagc gcagccacgg cggcgagcct 300
gcgtcacaca tccgcgcgga gagccaggac atgatgatga tgatgaccta cagcatggtg 360
ccgatccggg tgatgataga cctgtgcaac agcacccagg gcatctgcct tacaggacca 420
ccgggcccac caggacctcc aggagctggt gggttaccag gccacaatgg atcagatgga 480
cagcctggtc tccagggccc aaaaggagaa aaaggagcag ttgggaagag aggaaaaatg 540
gggttacccg gagccacagg aaatccaggg gaaaagggag agaagggaga tgctggtgaa 600
ctgggcctac ctggaaatga gggaccacca ggacagaaag gagacaaagg agacaaagga 660
gatgtgtcca atgacgtgct tttgacaggt gccaaaggtg accaagggcc ccctggccca 720
cctggacccc cagggcctcc aggcccttct ggaagcagaa gagccaaagg ccctcggcag 780
ccaaattcgt tcaccaacca gtgtccaggg gagacgtgtg tcatacccaa tgatgatacc 840
ttggtgggga gagctgatga gaaagtcaat gagcgccatt ctccacaaac agaacccatg 900
atcacgtcca ttggtaaccc ggcccaagtc ctcaaagtga aagagacttt tgggacctgg 960
ctaagagagt ctgctaacag gagtgatgac cgcatttggg tgactgaaca tttttcaggc 1020
atcatggtga aggagtttga agacctgccc gccctcctga atagcagctt caccctcctc 1080
cacctcccac attacttcca tggctgcggg cacgctgttt acaacaactc tctctactac 1140
cacaaaggag gctccaacac catagtgaga tttgaatttg ggaaagagac acctcaaact 1200
ctgaagcttg aagatgcttt gtattttgat cgaaaatacc tctttgcgaa ttccaagact 1260
tacttcaaca tagcagtgga tgagaagggc ctctggatta tctacgcctc gagtgtggat 1320
ggctcaagca tccttgtggc acagctggac gagaggacat tctctgtgct gcagcacatc 1380
aataccacat accccaagtc caaggctggc aatgccttca tagctcaagg gatcctctat 1440
gtcacggaca caaaagatac aagggtcacg tttgcctttg atttgttacg agggaagcag 1500
atcaatgcaa acttcggtct cagaatgtca cagtctgttc ttgccatgtt gtcgtacaat 1560
atgagagacc agcatttgta ctcgtgggaa gacggccacc tgatgctcta tcctgtgcac 1620

-continued ttttcgtcaa cagcacccag ccagcgatag 1650

<210> SEQ ID NO 29
<211> LENGTH: 1650
<212> TYPE: DNA
<213> ORGANISM: Rattus sp.

<400> SEQUENCE: 29
atgacccgag ccgcagagcg aggccaaggg gctacaggct ggggactgcg aggcgccctg 60
atggccgtgg cgctgctgtc agtgctgaac gccgtgggca ccgtgttcgt gctgtaccag 120
tggcgcgagc tgagcgcggc gctgcgggca ctggaggcgc aacacggcca ggagcagcgc 180
gaggacagcg ccctacgcgc ctttctagct gaattaagtc gtgcgccagc ccgagtcccc 240
gaaccacccc aggaccccat gagtgcagcg cgcaataagc gcagccacgg cggcgagcct 300
gcgtcacaca tccgcgcgga gagccaggac atgatgatga tgatgaccta cagcatggtg 360
ccgatccggg tgatgataga cctgtgcaac agcacccagg gcatctgcct tacaggacca 420
ccgggcccac caggacctcc aggagctggt gggttaccag gccacaatgg atcagatgga 480
cagcctggtc tccagggccc aaaaggagaa aaaggagcag ttgggaagag aggaaaaatg 540
gggttacccg gagccacagg aaatccaggg gaaaagggag agaagggaga tgctggtgaa 600
ctgggcctac ctggaaatga gggaccacca ggacagaaag gagacaaagg agacaaagga 660
gatgtgtcca atgacgtgct tttgacaggt gccaaaggtg accaagggcc ccctggccca 720
cctggacccc cagggcctcc aggccctcct ggaagcagaa gagccaaagg ccctcggcag 780
ccaaattcgt tcaccaacca gtgtccaggg gagacgtgtg tcatacccaa tgatgatacc 840
ttggtgggga gagctgatga gaaagtcaat gagcgccatt ctccacaaac agaacccatg 900
atcacgtcca ttggtaaccc ggcccaagtc ctcaaggtga aagagacttt tgggacctgg 960
ctaagagagt ctgctaacag gagtgacgac cgcatttggg tgactgaaca tttttcaggc 1020
atcatggtga aggagtttga agacctgccc gccctcctga atagcagctt caccctcctc 1080
cacctcccac attacttcca tggctgcggg cacgctgttt acaacaactc tctctactac 1140
cacaaaggag gctccaacac catagtgaga tttgaatttg ggaaagagac acctcaaact 1200
ctgaagcttg aagatgcttt gtattttgat cgaaaatacc tctttgcgaa ttccaagact 1260
tacttcaaca tagcagtgga tgagaagggc ctctggatta tctacgcctc gagtgtggat 1320
ggctcaagca tccttgtggc acagctggac gagaggacat tctctgtgct gcggcacatc 1380
aataccacat accccaagtc caaggctggc aatgccttca tagctcaagg gatcctctat 1440
gtcacggaca ccaaagatac aagggtcacg tttgcctttg atttgttacg agggaagcag 1500
atcaatgcaa acttcggtct cagaatgtca cagtctgttc ttgccatgtt gtcgtacaat 1560
atgagagacc agcatttgta ctcgtgggaa gacggccacc tgatgctcta tcctgtgcac 1620
ttttcgtcaa cagcacccag ccagcgatag 1650

<210> SEQ ID NO 30
<211> LENGTH: 1656
<212> TYPE: DNA
<213> ORGANISM: Homo sapiens

<400> SEQUENCE: 30
atggcccgag gcgctgaggg aggccgtggg gacgcgggtt ggggcctgcg tggcgccctg 60
gcggccgtgg cgctgctctc ggcgctcaac gctgcgggca cggtgttcgc gctgtgccag 120

-continued

```
tggcgcgggc tgagctcggc gctgcgggct ttggaggcgc agcggggccg ggagcagcgc    180
gaggacagtg ccctgcgctc cttcctggcc gagttgagcc gcgcgccgcg cggggcgtcc    240
gcaccacccc aagacccggc cagctcagct cgcaacaagc gcagccacag cggcgagccc    300
gcgccgcata tccgcgccga gagccatgac atgctgatga tgatgaccta ctccatggtg    360
ccgatccgag tgatggtgga cctgtgcaac agcaccaagg gcatctgcct cacaggacct    420
tctggaccac caggacctcc gggagccggc gggttgccag gacacaacgg attggatgga    480
cagcctggtc ctcagggccc aaaaggagaa aaaggagcaa atggaaaaag aggaaaaatg    540
gggatacctg gagctgcagg aaatccaggg gaaaggggag aaaagggaga ccatggtgaa    600
ctgggcctgc agggaaatga gggcccacca gggcagaagg gagaaaaggg tgacaaagga    660
gatgtgtcca acgacgtgct cctggcaggt gccaaaggtg accaaggccc acccggtcca    720
cctgggcccc caggccctcc aggtcctcca gggcccccctg gaagcagaag agccaaaggc    780
cctcggcagc caagcatgtt caacggccag tgcccaggtg agacttgtgc cataccaaat    840
gatgatacct tggttggaaa agctgatgag aaagccagtg aacaccattc cccacaagca    900
gaatccatga tcacttccat tggaaaccca gtgcaagtac tgaaagtgac agagacattt    960
gggacttgga taagagagtc tgctaacaag agtgatgacc ggatttgggt gacagagcat   1020
ttttcaggca tcatggttaa ggaattcaag gatcagccct cacttctgaa tggcagttac   1080
acgttcatcc accttccata ctatttccat ggctgtgggc acgttgctta caacaactct   1140
ctctactacc acaaaggggg ttctaatacc ctagtgagat ttgaatttgg ccaggaaaca   1200
tcccaaactc tgaagcttga aaatgccttg tattttgatc gaaaatacct tttgcaaat   1260
tccaaaactt acttcaatct agctgtagat gaaaagggcc tttggattat ctatgcgtca   1320
agtgtggacg gctcgagcat tcttgtagca caactggatg agaggacatt ctcagtggtg   1380
caacacgtca ataccacgta ccctaaatcc aaggctggca acgccttcat tgcccgagga   1440
atcctctatg tcacagacac caaagatatg agggtcacat ttgcctttga tttgttagga   1500
gggaaacaga tcaatgcaaa ctttgattta agaacttccc agtctgttct tgccatgtta   1560
gcatacaaca tgagagatca gcatttatat tcatgggaag atggccattt aatgctttat   620
cctgtgcagt tttgtcaac taccttaaat cagtga                              1656
```

<210> SEQ ID NO 31
<211> LENGTH: 1284
<212> TYPE: DNA
<213> ORGANISM: Homo sapiens

<400> SEQUENCE: 31

```
atggtggacc tgtgcaacag caccaagggc atctgcctca caggaccttc tggaccacca     60
ggacctccgg gagccggcgg gttgccagga cacaacggat tggatggaca gcctggtcct    120
cagggcccaa aaggagaaaa aggagcaaat ggaaaaagag gaaaaatggg gatacctgga    180
gctgcaggaa atccagggga aaggggagaa aagggagacc atggtgaact gggcctgcag    240
ggaaatgagg gcccaccagg gcagaaggga gaaaagggtg acaaaggaga tgtgtccaac    300
gacgtgctcc tggcaggtgc caaaggtgac caaggcccac ccggtccacc tgggccccca    360
ggccctccag gtcctccagg gcccccctgga agcagaagag ccaaaggccc tcggcagcca    420
agcatgttca acggccagtg cccaggtgag acttgtgcca taccaaatga tgataccttg    480
gttggaaaag ctgatgagaa agccagtgaa caccattccc cacaagcaga atccatgatc    540
```

-continued

```
acttccattg gaaacccagt gcaagtactg aaagtgacag agacatttgg gacttggata    600

agagagtctg ctaacaagag tgatgaccgg atttgggtga cagagcattt ttcaggcatc    660

atggttaagg aattcaagga tcagccctca cttctgaatg gcagttacac gttcatccac    720

cttccatact atttccatgg ctgtgggcac gttgcttaca acaactctct ctactaccac    780

aaagggggtt ctaataccct agtgagattt gaatttggcc aggaaacatc ccaaactctg    840

aagcttgaaa atgccttgta ttttgatcga aaataccttt ttgcaaattc caaaacttac    900

ttcaatctag ctgtagatga aaagggcctt tggattatct atgcgtcaag tgtggacggc    960

tcgagcattc ttgtagcaca actggatgag aggacattct cagtggtgca acacgtcaat   1020

accacgtacc ctaaatccaa ggctggcaac gccttcattg cccgaggaat cctctatgtc   1080

acagacacca aagatatgag ggtcacattt gcctttgatt tgttaggagg gaaacagatc   1140

aatgcaaact ttgatttaag aacttcccag tctgttcttg ccatgttagc atacaacatg   1200

agagatcagc atttatattc atgggaagat ggccatttaa tgctttatcc tgtgcagttt   1260

ttgtcaacta ccttaaatca gtga                                          1284
```

<210> SEQ ID NO 32
<211> LENGTH: 1596
<212> TYPE: DNA
<213> ORGANISM: Rattus sp.

<400> SEQUENCE: 32

```
atgacccgag ccgcagagcg aggccaaggg gctacaggct ggggactgcg aggcgccctg     60

atggccgtgg cgctgctgtc agtgctgaac gccgtgggca ccgtgttcgt gctgtaccag    120

cagcgcgagg acagcgccct acgcgccttt ctagctgaat taagtcgtgc gccagcccga    180

gtccccgaac caccccagga ccccatgagt gcagcgcgca ataagcgcag ccacggcggc    240

gagcctgcgt cacacatccg cgcggagagc caggacatga tgatgatgat gacctacagc    300

atggtgccga tccgggtgat gatagacctg tgcaacagca cccagggcat ctgccttaca    360

ggaccaccgg gcccaccagg acctccagga gctggtgggt taccaggcca caatggatca    420

gatggacagc ctggtctcca gggcccaaaa ggagaaaaag gagcagttgg gaagagagga    480

aaaatggggt tacccggagc cacaggaaat ccaggggaaa agggagagaa gggagatgct    540

ggtgaactgg gcctacctgg aaatgaggga ccaccaggac agaaaggaga caaaggagac    600

aaaggagatg tgtccaatga cgtgcttttg acaggtgcca aaggtgacca agggcccccct   660

ggcccacctg gacccccagg gcctccaggc ccttctggaa gcagaagagc caaaggccct    720

cggcagccaa attcgttcac caaccagtgt ccaggggaga cgtgtgtcat acccaatgat    780

gataccttgg tggggagagc tgatgagaaa gtcaatgagc gccattctcc acaaacagaa    840

cccatgatca cgtccattgg taacccggcc caagtcctca aagtgaaaga gacttttggg    900

acctggctaa gagagtctgc taacaggagt gatgaccgca tttgggtgac tgaacatttt    960

tcaggcatca tggtgaagga gtttgaagac ctgcccgccc tcctgaatag cagcttcacc   1020

ctcctccacc tcccacatta cttccatggc tgcgggcacg ctgtttacaa caactctctc   1080

tactaccaca aaggaggctc caacaccata gtgagatttg aatttgggaa agagacacct   1140

caaactctga agcttgaaga tgctttgtat tttgatcgaa aatacctctt tgcgaattcc   1200

aagacttact tcaacatagc agtggatgag aagggcctct ggattatcta cgcctcgagt   1260

gtggatggct caagcatcct tgtggcacag ctggacgaga ggacattctc tgtgctgcag   1320

cacatcaata ccacataccc caagtccaag gctggcaatg ccttcatagc tcaagggatc   1380
```

-continued

```
ctctatgtca cggacacaaa agatacaagg gtcacgtttg cctttgattt gttacgaggg   1440

aagcagatca atgcaaactt cggtctcaga atgtcacagt ctgttcttgc catgttgtcg   1500

tacaatatga gagaccagca tttgtactcg tgggaagacg gccacctgat gctctatcct   1560

gtgcactttt cgtcaacagc acccagccag cgatag                             1596
```

<210> SEQ ID NO 33
<211> LENGTH: 1650
<212> TYPE: DNA
<213> ORGANISM: Mus sp.

<400> SEQUENCE: 33

```
atgacccgag ccgcagagcg aggccaaggg gctacaggct gggggctgcg cggcgccctg     60

gtggccatag cgctgctgtc cgcactgaac gccgcgggca ccgtgttcgt gctgtgccag    120

tggcgggggt taagcgcggc gctacgggcg ctggaggctc aacgcggccg agagcagcgc    180

gaggacagcg ccctacgcgc ctttctggcc gaattgagtc gtgcgccggg ccgggtcccc    240

gaaccatccc aggaccccat gagcgcagcg cgcaacaagc gcagccacaa cggcgagcct    300

gcgtcacaca tccgtgcgga gagccaggac atgatgatga tgatgaccta ctccatggtg    360

ccgattcgag tgatgataga cctgtgcaac agtacccagg gcatctgcct cacaggacca    420

ccgggcccac caggacctcc aggagccggc gggttaccag gccacaatgg atcagatgga    480

cagcctggtc tccagggccc aaaaggagaa aaaggagcaa ttggcaagag aggaaaaatg    540

gggttacctg gagccaccgg aaatccaggg gaaaagggag aaaagggaga tgctggtgaa    600

ctgggtctac ctggaaatga gggcccacca gggcagaaag gtgacaaggg agacaaagga    660

gacgtgtcca atgacgtgct tttgacaggt gccaaaggtg accaaggtcc ccctggcccc    720

cctggacctc cagggcctcc aggccctcct ggaagcagaa gatccaaagg ccctcggcca    780

ccaaacgtgt tcaacagcca gtgtccaggg gagacgtgtg tcatacccaa tgatgatacc    840

ttggtgggaa gagctgatga gaaagcaaat gaacgccatt caccacaaac agaatctatg    900

atcacttcca ttggcaaccc agcccaagtc ctaaaagtga gagagacttt tgggacttgg    960

atgagagagt ctgctaacaa aagtgacgac cgcatttggg tgactgaaca tttttcaggc   1020

atcatggtga aggagttcaa agacctgccg gcgctcctca atagcagctt cacactcctc   1080

cacctcccac attatttcca cggctgtggg cacgctgttt acaacaactc tctctactac   1140

cacaaaggag gctccaacac catagtgaga tttgaatttg ggaaagagac acctcagact   1200

ctgaagctgg aaaatgcttt gtattttgat cgaaaatacc tctttgcaaa ttccaagact   1260

tacttcaaca tagcagtgga tgagaagggc atctggatta tctacgcttc aagtgtggat   1320

ggctcaagca tccttgtagc acagctggat gagaggacat tctccgtgac acagcacatc   1380

aacaccacat accccaaatc caaggctggc aatgccttca tagcccgagg gatcctctat   1440

gtcacagaca ccaaagatac gagggtcacg tttgcctttg atttgttagg aggaaagcaa   1500

atcaatgcaa actttgattt cagaatgtcc cagtctgttc ttgccatgct gtcatacaac   1560

atgagagatc agcatttata ctcgtgggaa gatggccatc tgatgctcta tcctgtgcag   1620

tttctgtcag cggcatcaag tcagcggtag                                   1650
```

<210> SEQ ID NO 34
<211> LENGTH: 117
<212> TYPE: PRT
<213> ORGANISM: Rattus sp.

-continued

<400> SEQUENCE: 34

Cys Leu Thr Gly Pro Pro Gly Pro Pro Gly Pro Pro Gly Ala Gly Gly
1 5 10 15

Leu Pro Gly His Asn Gly Ser Asp Gly Gln Pro Gly Leu Gln Gly Pro
20 25 30

Lys Gly Glu Lys Gly Ala Val Gly Lys Arg Gly Lys Met Gly Leu Pro
35 40 45

Gly Ala Thr Gly Asn Pro Gly Glu Lys Gly Glu Lys Gly Asp Ala Gly
50 55 60

Glu Leu Gly Leu Pro Gly Asn Glu Gly Pro Pro Gly Gln Lys Gly Asp
65 70 75 80

Lys Gly Asp Lys Gly Asp Val Ser Asn Asp Val Leu Leu Thr Gly Ala
85 90 95

Lys Gly Asp Gln Gly Pro Pro Gly Pro Pro Gly Pro Pro Gly Pro Pro
100 105 110

Gly Pro Pro Gly Ser
115

<210> SEQ ID NO 35
<211> LENGTH: 120
<212> TYPE: PRT
<213> ORGANISM: Homo sapiens

<400> SEQUENCE: 35

Cys Leu Thr Gly Pro Ser Gly Pro Pro Gly Pro Pro Gly Ala Gly Gly
1 5 10 15

Leu Pro Gly His Asn Gly Leu Asp Gly Gln Pro Gly Pro Gln Gly Pro
20 25 30

Lys Gly Glu Lys Gly Ala Asn Gly Lys Arg Gly Lys Met Gly Ile Pro
35 40 45

Gly Ala Ala Gly Asn Pro Gly Glu Arg Gly Glu Lys Gly Asp His Gly
50 55 60

Glu Leu Gly Leu Gln Gly Asn Glu Gly Pro Pro Gly Gln Lys Gly Glu
65 70 75 80

Lys Gly Asp Lys Gly Asp Val Ser Asn Asp Val Leu Leu Ala Gly Ala
85 90 95

Lys Gly Asp Gln Gly Pro Pro Gly Pro Pro Gly Pro Pro Gly Pro Pro
100 105 110

Gly Pro Pro Gly Pro Pro Gly Ser
115 120

<210> SEQ ID NO 36
<211> LENGTH: 291
<212> TYPE: PRT
<213> ORGANISM: Rattus sp.

<400> SEQUENCE: 36

Arg Arg Ala Lys Gly Pro Arg Gln Pro Asn Ser Phe Thr Asn Gln Cys
1 5 10 15

Pro Gly Glu Thr Cys Val Ile Pro Asn Asp Asp Thr Leu Val Gly Arg
20 25 30

Ala Asp Glu Lys Val Asn Glu Arg His Ser Pro Gln Thr Glu Pro Met
35 40 45

Ile Thr Ser Ile Gly Asn Pro Ala Gln Val Leu Lys Val Lys Glu Thr
50 55 60

Phe Gly Thr Trp Leu Arg Glu Ser Ala Asn Arg Ser Asp Asp Arg Ile

-continued

```
 65                  70                  75                  80

Trp Val Thr Glu His Phe Ser Gly Ile Met Val Lys Glu Phe Glu Asp
                85                  90                  95

Leu Pro Ala Leu Leu Asn Ser Ser Phe Thr Leu Leu His Leu Pro His
            100                 105                 110

Tyr Phe His Gly Cys Gly His Ala Val Tyr Asn Asn Ser Leu Tyr Tyr
        115                 120                 125

His Lys Gly Gly Ser Asn Thr Ile Val Arg Phe Glu Phe Gly Lys Glu
    130                 135                 140

Thr Pro Gln Thr Leu Lys Leu Glu Asp Ala Leu Tyr Phe Asp Arg Lys
145                 150                 155                 160

Tyr Leu Phe Ala Asn Ser Lys Thr Tyr Phe Asn Ile Ala Val Asp Glu
                165                 170                 175

Lys Gly Leu Trp Ile Ile Tyr Ala Ser Ser Val Asp Gly Ser Ser Ile
            180                 185                 190

Leu Val Ala Gln Leu Asp Glu Arg Thr Phe Ser Val Leu Gln His Ile
        195                 200                 205

Asn Thr Thr Tyr Pro Lys Ser Lys Ala Gly Asn Ala Phe Ile Ala Gln
    210                 215                 220

Gly Ile Leu Tyr Val Thr Asp Thr Lys Asp Thr Arg Val Thr Phe Ala
225                 230                 235                 240

Phe Asp Leu Leu Arg Gly Lys Gln Ile Asn Ala Asn Phe Gly Leu Arg
                245                 250                 255

Met Ser Gln Ser Val Leu Ala Met Leu Ser Tyr Asn Met Arg Asp Gln
            260                 265                 270

His Leu Tyr Ser Trp Glu Asp Gly His Leu Met Leu Tyr Pro Val His
        275                 280                 285

Phe Ser Ser
    290


<210> SEQ ID NO 37
<211> LENGTH: 291
<212> TYPE: PRT
<213> ORGANISM: Homo sapiens

<400> SEQUENCE: 37

Arg Arg Ala Lys Gly Pro Arg Gln Pro Ser Met Phe Asn Gly Gln Cys
  1               5                  10                  15

Pro Gly Glu Thr Cys Ala Ile Pro Asn Asp Asp Thr Leu Val Gly Lys
             20                  25                  30

Ala Asp Glu Lys Ala Ser Glu His His Ser Pro Gln Ala Glu Ser Met
         35                  40                  45

Ile Thr Ser Ile Gly Asn Pro Val Gln Val Leu Lys Val Thr Glu Thr
     50                  55                  60

Phe Gly Thr Trp Ile Arg Glu Ser Ala Asn Lys Ser Asp Asp Arg Ile
 65                  70                  75                  80

Trp Val Thr Glu His Phe Ser Gly Ile Met Val Lys Glu Phe Lys Asp
                85                  90                  95

Gln Pro Ser Leu Leu Asn Gly Ser Tyr Thr Phe Ile His Leu Pro Tyr
            100                 105                 110

Tyr Phe His Gly Cys Gly His Val Ala Tyr Asn Asn Ser Leu Tyr Tyr
        115                 120                 125

His Lys Gly Gly Ser Asn Thr Leu Val Arg Phe Glu Phe Gly Gln Glu
    130                 135                 140
```

-continued

```
Thr Ser Gln Thr Leu Lys Leu Glu Asn Ala Leu Tyr Phe Asp Arg Lys
145                 150                 155                 160

Tyr Leu Phe Ala Asn Ser Lys Thr Tyr Phe Asn Leu Ala Val Asp Glu
                165                 170                 175

Lys Gly Leu Trp Ile Ile Tyr Ala Ser Ser Val Asp Gly Ser Ser Ile
            180                 185                 190

Leu Val Ala Gln Leu Asp Glu Arg Thr Phe Ser Val Val Gln His Val
        195                 200                 205

Asn Thr Thr Tyr Pro Lys Ser Lys Ala Gly Asn Ala Phe Ile Ala Arg
    210                 215                 220

Gly Ile Leu Tyr Val Thr Asp Thr Lys Asp Met Arg Val Thr Phe Ala
225                 230                 235                 240

Phe Asp Leu Leu Gly Gly Lys Gln Ile Asn Ala Asn Phe Asp Leu Arg
                245                 250                 255

Thr Ser Gln Ser Val Leu Ala Met Leu Ala Tyr Asn Met Arg Asp Gln
            260                 265                 270

His Leu Tyr Ser Trp Glu Asp Gly His Leu Met Leu Tyr Pro Val Gln
        275                 280                 285

Phe Leu Ser
    290


<210> SEQ ID NO 38
<211> LENGTH: 255
<212> TYPE: PRT
<213> ORGANISM: Unknown Organism
<220> FEATURE:
<223> OTHER INFORMATION: Description of Unknown Organism: Amino acid
      sequence of the olfactomedin-like domain

<400> SEQUENCE: 38

Gly Ile Leu Ala Gly Val Gly Ile Pro Val Leu Leu Ala Glu Ser Gln
  1               5                  10                  15

Tyr Gly Lys Ser Gly Ala Trp Met Arg Asp Pro Leu Pro Asn Ser Met
             20                  25                  30

Lys Ala Lys Arg Arg Trp Val Met Asp Gly Phe Ala Asp Val Ser Arg
         35                  40                  45

Val Leu Arg Glu Tyr Ser Ser Met Ser Asp Phe Leu Asp Gly Val Asn
     50                  55                  60

Lys Ile Lys Tyr Tyr Leu Pro His Ala Ala Ser Gly Thr Gly Asn Val
 65                  70                  75                  80

Val Tyr Asn Gly Ser Leu Tyr Phe Asn Lys Phe Gly Ser His Ser Ile
                 85                  90                  95

Val Arg Tyr Glu Leu Glu Thr Gly Val Gln Val Lys Glu Glu Leu Leu
            100                 105                 110

Pro Glu Ala Gly Tyr Asn Asp Cys Phe Pro Tyr Ala Trp Gly Gly His
        115                 120                 125

Ser Asp Ile Asp Leu Ala Val Asp Glu Asn Gly Leu Trp Val Ile Tyr
    130                 135                 140

Ala Thr Glu Gln Asn Ala Gly Lys Ile Val Ile Ser Lys Leu Asn Pro
145                 150                 155                 160

Ala Thr Leu Phe Val Glu Asn Thr Trp Asn Thr Glu Tyr Asn Lys Arg
                165                 170                 175

Ser Ala Ala Asn Ala Phe Met Ile Cys Gly Val Leu Tyr Val Thr Lys
            180                 185                 190

Ser Ala Asn Ser Leu Gly Thr Lys Ile Thr Tyr Ala Tyr Asp Thr Asn
        195                 200                 205
```

-continued

```
Thr Gly Lys Thr Ile Pro Leu Asp Ile Pro Phe Tyr Asn Pro Tyr Gln
    210                 215                 220

Tyr Ile Ser Met Leu Asp Tyr Asn Pro Leu Asp Arg Lys Leu Tyr Ala
225                 230                 235                 240

Trp Asp Asn Gly His Leu Leu Ser Tyr Asp Ile Arg Leu Glu Glu
                245                 250                 255
```

COMPOSITIONS FOR CONTROLLING HAIR GROWTH

CROSS REFERENCE TO RELATED APPLICATIONS

This application claims the benefit of U.S. application Ser. No. 11/096,070 entitled "Compositions for Controlling Hair Growth," filed Mar. 31, 2005, now U.S. Pat. No. 7,223,562 which in turn claims priority to U.S. Provisional Application No. 60/558,341, filed Mar. 31, 2004, now abandoned, the contents of which are hereby incorporated by reference in its entirety.

BACKGROUND OF THE INVENTION (a) Field of the Invention

The present invention relates to the field of dermatology. More specifically, the present invention relates to compositions and methods for modulating hair growth.

(b) Background

Although hair growth disorders are not life threatening, their impact on social interactions and on an individual's psychological well being is undeniable. Thus, effective methods of treating hair growth disorders are greatly desired.

One of the most common hair disorders is alopecia, where humans begin losing scalp hair at the temples and on the crown of their head as they age. Although this type of hair loss is predominantly found in males, it is also present in a certain proportion of women. Alopecia can also be induced by chemical agents or physical agents (e.g., during anti-cancer chemotherapy), and the condition also results from specific disease states.

Another type of hair growth disorder results from abnormally accentuated hair growth. For example, hirsutism is manifested as excessive androgen-dependent hair growth in women, whereas hypertrichosis is an increase in androgen-independent hair growth (Bertolino et al., "Disorders of epidermal appendages and related disorders," in *Dermatology in General Medicine,* 4th ed., pp. 671-695, Fitzpatrick et al., eds. (McGraw-Hill, 1993)).

A traditional treatment for alopecia is hair transplantation. This typically involves transplanting plugs of natural hair from areas of the scalp where hair is growing to bald or thinning areas of the scalp. This procedure is costly, time-consuming, painful, and does not provide a sufficient remedy in all cases. Electrical stimulus has been suggested as an alternative way to promote hair growth (see, e.g., U.S. Pat. No. 5,800,477 and references cited therein); however, such methods are of questionable efficacy.

Other methods for stimulating hair growth comprise the use of various chemicals or drugs, mud preparations, and plant extracts (see, e.g., U.S. Pat. Nos. 5,798,341, 5,767,152, 5,753,713, 5,750,107, 5,741,816, 5,739,111, 5,723,149, 5,679,378, 5,674,497, 5,663,160, 5,656,300, 5,643,898, 4,139,619, and references cited therein). There are two compounds currently in clinical use to treat alopecia: finasteride, sold as PROPECIA®, and minoxidil, marketed as ROGAINE®. A drawback of finasteride is that it can only be used by men. Furthermore, its use can result in sexual side effects such as a decreased desire for sex, difficulty in achieving erection, and a decrease in the amount of semen. Minoxidil is a vasodilatory drug which can have side effects in some patients. Similarly, mud preparations and plant extracts can produce unwelcome side effects in various patients and are of questionable efficacy. Moreover such treatments require a normal scalp with no local abrasions, dermatitis, or sunburn, rendering such methods unavailable to many individuals.

In addition to these hair growth disorders, individuals may also desire to increase, decrease, or prevent hair growth purely for cosmetic reasons. As a result, there is immense interest in the development of effective cosmetic and clinical treatments. Yet, most, if not all, of the known methods to control hair growth have several drawbacks.

For example, various procedures have been used to remove unwanted hair from the groin area, legs and face including shaving, electrolysis, use of depilatory creams, waxing, plucking and therapeutic anti-androgens, see, e.g., U.S. Pat. No. 6,093,748. However, these traditional methods have various drawbacks associated with them. For example, shaving can cause nicks, cuts and undesirable stubble. Although electrolysis keeps a treated area free of hair for prolonged periods of time, it can be expensive, painful, and may leave scarring in some cases. Depilatory creams have a high potential to irritate the skin. Waxing and plucking can cause pain, discomfort and poor removal of short hair. Finally, anti-androgens can have undesirable side effects.

Thus, alternative methods for controlling hair growth are needed.

SUMMARY OF THE INVENTION

The follicular papilla, a cluster of mesenchymal cells at the base of the hair follicle, plays an essential role in hair growth. It has been discovered that various genes are selectively expressed in follicular papilla compared to the neighboring dermal fibroblasts cells. For example, it has been discovered that follicular papilla-1 (FP-1) is selectively expressed in follicular papilla compared to dermal fibroblasts cells. This discovery has been exploited to develop the present invention, which relates to nucleic acids and proteins that control hair growth; compositions that control hair growth; compositions for isolating follicular papilla cells; methods for controlling hair growth; methods for repairing hair follicles; methods for screening for, or identifying, agents that control hair growth; methods for diagnosing hair disorders; and methods of diagnosing cancers.

In one aspect, the invention provides an isolated polynucleotide comprising the DNA sequence of rat FP-1. In some embodiments, the sequence of the rat FP-1 comprises SEQ ID NO:1 or SEQ ID NO:3. In additional embodiments, the invention provides an isolated polynucleotide that is the complement of the polynucleotide comprising SEQ ID NO:1 or SEQ ID NO:3.

In another embodiment, the invention provides a recombinant vector comprising any of the polynucleotides of this aspect of the invention. In a further embodiment, the invention provides a host cell comprising a recombinant vector of this aspect.

In a still further embodiment, the invention provides a method of preparing a substantially purified polypeptide encoded by a recombinant vector of this aspect. In this method, host cells transformed or transfected with a recombinant vector according to the invention are cultured under conditions conducive to the synthesis of the polypeptide. The polypeptide, in substantially purified form, is then isolated from the host cells. In another embodiment, the invention provides an isolated polypeptide comprising the amino acid sequence encoded by a polynucleotide having the DNA sequence of rat FP-1 (SEQ ID NO:1 or SEQ ID NO:3). In some embodiments, this polypeptide comprises SEQ ID NO:2 or SEQ ID NO:4.

In a still further embodiment, an antibody that specifically binds rat FP-1 (SEQ ID NO:2 or SEQ ID NO:4), is provided. In yet another embodiment, an antibody that binds both a polypeptide comprising SEQ ID NO: 2 and a polypeptide comprising SEQ ID NO: 12, is provided. In another embodiment, the invention provides an antibody that binds both a polypeptide comprising SEQ ID NO: 4 and a polypeptide comprising SEQ ID NO:12.

In another aspect of the invention, an isolated polynucleotide consisting of SEQ ID NO:1 or SEQ ID NO:3 is provided. In one embodiment, the isolated polynucleotide is the complement of any of the polynucleotides of this aspect. In another embodiment, a recombinant vector comprising any of the polynucleotides of this aspect is provided. In a further embodiment, a host cell comprising a recombinant vector of this aspect is provided.

In another embodiment, the invention provides a method of preparing a substantially purified polypeptide encoded by a recombinant vector comprising the polynucleotide consisting of SEQ ID NO:1 or SEQ ID NO:3. In this method, host cells transformed or transfected with the recombinant vector are cultured under conditions conducive to the synthesis of the polypeptide. The polypeptide is then recovered in substantially purified form from the host cells.

In yet a further embodiment of this aspect of the invention, an isolated polypeptide (SEQ ID NO:2) comprising the amino acid sequence encoded by the polynucleotide consisting of the DNA sequence of rat FP-1 (SEQ ID NO:1) is provided. In a further embodiment of this aspect, the invention provides an isolated polypeptide (SEQ ID NO:4) comprising the amino acid sequence encoded by the polynucleotide consisting of the DNA sequence of rat FP-1 (SEQ ID NO:3).

The invention also provides an isolated polynucleotide comprising the DNA sequence of human FP-1. In one embodiment, the sequence of the human FP-1 comprises SEQ ID NO:11. In an additional embodiment, the invention provides an isolated polynucleotide that is the complement of the polynucleotide comprising SEQ ID NO:11. In another embodiment, the invention provides a recombinant vector comprising any of the polynucleotides of this aspect of the invention. In a further embodiment, the invention provides a host cell comprising the recombinant vector of this aspect.

In a still further embodiment, the invention provides a method of preparing a substantially purified polypeptide encoded by the recombinant vector of this aspect. In this method, host cells transformed or transfected with the recombinant vector according to the invention are cultured under conditions conducive to the synthesis of the polypeptide. The polypeptide, in substantially purified form, is then isolated from the host cells.

In another embodiment, the invention provides an isolated polypeptide comprising the amino acid sequence encoded by the polynucleotide having the DNA sequence of human FP-1 (SEQ ID NO:11). In one embodiment, this polypeptide comprises SEQ ID NO:12. In a still further embodiment, an antibody that specifically binds human FP-1 (SEQ ID NO:12), is provided. In yet another embodiment, an antibody that binds both a polypeptide comprising SEQ ID NO: 2 and a polypeptide comprising SEQ ID NO: 12 is provided.

In still another embodiment, the invention provides an antibody that binds both a polypeptide comprising SEQ ID NO: 4 and a polypeptide comprising SEQ ID NO:12.

The invention also provides an isolated polynucleotide comprising a nucleic acid sequence that encodes a polypeptide comprising the amino acid sequence of rat FP-1 (SEQ ID NO:2 or SEQ ID NO:4). In one embodiment, the polynucleotide comprises a nucleic acid sequence that encodes a polypeptide comprising amino acids 34 to 549 of SEQ ID NO:2 or amino acids 34 to 531 of SEQ ID NO:4. In another embodiment, the isolated polynucleotide is the complement of any of the polynucleotides of this aspect. In another embodiment, a recombinant vector is provided which comprises any of the polynucleotide of this aspect. In a further embodiment, a host cell comprising a recombinant vector comprising any of the polynucleotides of this aspect is provided. In a still further embodiment, the invention provides a method of preparing a substantially purified polypeptide encoded by a recombinant vector comprising any of the polynucleotides of this aspect. In this method, cells transformed or transfected with the recombinant vector according to the invention are cultured under conditions conducive to the synthesis of the polypeptide. The polypeptide is then recovered in substantially purified form from the cells.

The invention also provides an isolated polynucleotide comprising a nucleic acid sequence that encodes a polypeptide comprising the amino acid sequence of human FP-1 (SEQ ID NO:12). In one embodiment, the polynucleotide comprises a nucleic acid sequence that encodes a polypeptide comprising amino acid 34 to 551 of SEQ ID NO:12. In another embodiment, the isolated polynucleotide is the complement of any of the polynucleotides of this aspect. In another embodiment, a recombinant vector is provided which comprises any of the polynucleotide of this aspect. In a further embodiment, a cell comprising a recombinant vector comprising any of the polynucleotides of this aspect is provided.

In a still further embodiment, the invention provides a method of preparing a substantially purified polypeptide encoded by a recombinant vector comprising the polynucleotide of this aspect. In this method, cells transformed or transfected with the recombinant vector according to the invention are cultured under conditions conducive to the synthesis of the polypeptide. The polypeptide is then recovered in substantially purified form from the cells.

In yet another aspect, the invention provides an isolated polynucleotide comprising a nucleic acid sequence that is homologous to SEQ ID NO:1 or SEQ ID NO:3, wherein the isolated polynucleotide molecule encodes a protein that controls hair growth. In some embodiments, the isolated polynucleotide of this aspect has about 80%, about 85%, about 90%, or about 95% identity to SEQ ID NO:1 or SEQ ID NO:3. In another embodiment, the isolated polynucleotide is the complement of any of the polynucleotides of this aspect of the invention. In another embodiment, a recombinant vector comprising a polynucleotide of this aspect is provided. The invention also provides a cell comprising the recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment of this invention, an isolated polypeptide of this aspect, is provided. In a still further embodiment of the invention, an antibody that specifically binds an isolated polypeptide comprising the amino acid sequence encoded by the polynucleotide of the invention is provided.

In yet another aspect, the invention provides an isolated polynucleotide comprising a nucleic acid sequence that is homologous to SEQ ID NO:11, wherein the isolated polynucleotide molecule encodes a protein that controls hair growth. In some embodiments, the isolated polynucleotide of this aspect is about has about 80%, about 85%, about 90%, or about 95% identity to SEQ ID NO:11. In another embodiment, the isolated polynucleotide is the complement of any of the polynucleotides of this aspect of the invention. In another embodiment, a recombinant vector comprising any of the polynucleotides of this aspect is provided. The invention also provides a cell comprising a recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment, the isolated polypeptide of this aspect of the invention is provided. In a still further embodiment of the invention, an antibody that specifically binds an isolated polypeptide comprising the amino acid sequence encoded by the polynucleotide of this aspect is provided.

In another aspect, the invention provides an isolated polynucleotide comprising a nucleic acid sequence that is homologous to a nucleic acid sequence that encodes a polypeptide comprising SEQ ID NO:2 or SEQ ID NO:4, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:2 or SEQ ID NO:4. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In yet another embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In a still further embodiment, the invention provides an antibody that specifically binds an isolated polypeptide of this aspect of the invention.

In another aspect, the invention provides an isolated polynucleotide comprising a nucleic acid sequence that is homologous to a nucleic acid sequence that encodes a polypeptide comprising SEQ ID NO:12, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:12. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In a still further embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In yet another embodiment, the invention provides an antibody that specifically binds an isolated polypeptide of this aspect of the invention.

In an additional aspect of the invention, an isolated polynucleotide that specifically hybridizes under highly stringent conditions to a complement of a polynucleotide sequence comprising SEQ ID NO:1 or SEQ ID NO:3, wherein the polynucleotide sequence encodes a protein that controls hair growth is provided. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided. In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided. In a still further embodiment, the invention provides an antibody that specifically binds an isolated polypeptide comprising the amino acid sequence encoded by a polynucleotide according to this aspect.

The invention also provides an isolated polynucleotide that specifically hybridizes under highly stringent conditions to a complement of a polynucleotide sequence comprising SEQ ID NO:11, wherein the polynucleotide sequence encodes a protein that controls hair growth. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided.

In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided.

In a still further embodiment, the invention provides an antibody that specifically binds an isolated polypeptide comprising the amino acid sequence encoded by a polynucleotide according to this aspect.

The present invention also encompases an isolated polynucleotide molecule that specifically hybridizes under highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that controls hair growth. In one embodiment, the present invention provides an isolated polynucleotide that is the complement of any of the polynucleotides of this aspect. In another embodiment, a recombinant vector comprising a polynucleotide molecule of this aspect is provided. In a further embodiment, the invention provides a host cell comprising a recombinant vector comprising any of the polynucleotides of this aspect.

In a still further embodiment, the invention provides a method of preparing a substantially purified polypeptide encoded by a recombinant vector comprising a polynucleotide molecule according to this aspect. In this method, host cells transformed or transfected with the recombinant vector are cultured under conditions conducive to the synthesis of the polypeptide according to the invention. The polypeptide is then recovered in substantially purified form from the host cells. In yet a further embodiment of this invention, an isolated polypeptide comprising the amino acid sequence encoded by the polynucleotide sequence comprising an isolated polynucleotide molecule of this aspect is provided.

In a still further embodiment, the invention provides an antibody that specifically binds an isolated polypeptide comprising the amino acid sequence encoded by any of the polynucleotides of this aspect.

The invention also provides a process for isolating a polynucleotide, comprising hybridizing a polynucleotide selected from the group consisting of polynucleotides having SEQ ID NO:1, SEQ ID NO:3, and SEQ ID NO:11 to genomic DNA under highly stringent conditions and isolating the DNA that hybridizes to the polynucleotide selected from the group consisting of polynucleotides having SEQ ID NO:1, SEQ ID NO:3, and SEQ ID NO:11. In one embodiment of this aspect of the invention, an isolated polynucleotide is prepared according to the process of this aspect of the invention. In another embodiment, an isolated polynucleotide that is the complement of the polynucleotide molecule of this aspect of the invention is provided. In another embodiment, a recombinant vector comprising the polynucleotide molecule of this aspect of the invention is provided. In a further embodiment, a host cell comprising the recombinant vector comprising the polynucleotide molecule of this aspect of the invention is provided.

In a still further embodiment, a method of preparing a substantially purified polypeptide encoded by the recombinant vector of this aspect of the invention, comprising culturing host cells transformed or transfected with the recombinant vector under conditions conducive to the synthesis of the polypeptide, and recovering a substantially purified polypeptide from the host cells, is provided. In yet a further embodiment of this invention, an isolated polypeptide comprising the amino acid sequence encoded by the polynucleotide sequence of this aspect of the invention is provided.

In a still further embodiment, an antibody that specifically binds the isolated polypeptide of this aspect of the invention is provided.

In another aspect, the invention provides a method for increasing or decreasing hair growth, or changing the texture/structure (i.e., rough, smooth, fragile, curly, etc.) of the hair shaft of a subject. In this method, an effective amount of a composition comprising at least any one of the polynucleotides according to the invention is administered to a subject in need thereof.

In one embodiment, the method comprises administering a polynucleotide encoding the human homolog of FP-1 (SEQ ID NO:11) to a subject in need thereof. In another embodiment, the method comprises administering to a subject in need thereof a polynucleotide having SEQ ID NO:11; and a second agent. The second agent is any substance that can control hair growth or can assist the polypeptide encoded by a polynucleotide of the invention to control hair growth. In an another embodiment, the method comprises administering a polynucleotide characterized by the nucleic acid sequence of SEQ ID NO:1 with or without a second agent.

In a further aspect, the invention provides another method for increasing or decreasing hair growth, or changing the texture/structure (i.e., rough, smooth, fragile, curly, etc.) of the hair shaft of a subject. In this method, a formulation comprising a polypeptide encoded by any of the polynucleotides according to the invention is administered to the subject in an amount effective to control hair growth. In one embodiment, the method comprises administering to the subject, a polypeptide encoded by a polynucleotide comprising the human homolog of FP-1 (SEQ ID NO:12). In another embodiment, the method comprises administering to a subject, a polypeptide comprising amino acids 34 to 551 of SEQ ID NO:12. In a further embodiment, the subject is administered a polypeptide encoded by any of the nucleic acid molecules according to the invention; and a second agent. The second agent is any substance that can control hair growth or any substance that can assist the polypeptide of the invention to control hair growth.

In yet another aspect, the invention provides a method for controlling hair growth, comprising contacting the skin of a subject with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, and any combination thereof. In one embodiment of this aspect of the invention, the hair follicle of a subject is contacted with the composition of this aspect. In another embodiment of this aspect, the follicular papilla of the subject is contacted with the composition according to the invention. In a further embodiment, the skin of a subject is contacted with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12; and a second agent. The second agent is any substance that can control hair growth or any substance that can assist the polypeptides selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, to control hair growth.

In a further aspect of the invention, the invention provides a method of treating a subject with a hair growth disorder. In this method, a pharmaceutical composition comprising a pharmaceutically acceptable carrier, and a hair growth-promoting amount of any of the polynucleotides of the invention is administered to the subject. In one embodiment, the method comprises administering a polynucleotide encoding the human homolog of FP-1 (SEQ ID NO:11), and a pharmaceutically acceptable carrier to a subject in need thereof. In a different method, a pharmaceutical composition comprising a pharmaceutically acceptable carrier, and a hair growth-promoting amount of any of the polypeptides of the invention is administered to the subject. In one embodiment the polypeptide comprises an amino acid sequence selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12.

In yet another aspect of the invention, a method of identifying an agent that modulates hair growth is provided. In one embodiment, skin, isolated follicular papilla cells, or an isolated hair follicle is contacted with a test agent. The expression of FP-1 in follicular papilla is then measured. If the test agent increases the expression of FP-1 in the isolated follicular papilla cells, or the follicular papilla of the isolated hair follicle or of the skin compared to those not contacted with the test agent, the agent is determined to stimulate hair growth. If on the other hand, the test agent decreases the expression of FP-1 in the isolated follicular papilla cells, or the follicular papilla of the isolated hair follicle or of the skin compared to those not contacted with the test agent, the agent is determined to inhibit hair growth.

The invention also provides methods for screening or identifying agents that modulate the ability of FP-1 to control hair growth. The method includes contacting FP-1 with a test agent. In this aspect, a test agent is a substance that is thought to be effective in modulating the activity of FP-1. The method includes determining if the test agent modulates the activity of FP-1. Accordingly, the agent is tested in in vitro hair growth assays to determine its ability to modulate hair growth by FP-1. The test agent is classified as an agent that stimulates hair growth if it increases the ability of FP-1 to promote hair growth, whereas the test agent is determined to be an inhibitor of hair growth if it decreases the activity of FP-1.

The invention also provides a method for stimulating hair growth in a subject, comprising contacting the skin of the subject with an amount of an agent that increases the expression of FP-1 in the follicular papilla. In some embodiments of this aspect, the hair follicle or the follicular papilla of the subject is contacted with the agent. In a further embodiment, the invention provides a method for stimulating hair growth in a subject, comprising contacting the skin of the subject with an amount of an agent that increases the expression of FP-1 in the follicular papilla; and a second agent. The second agent is any substance that controls hair growth or any substance that can assist the polypeptide of the invention to increase hair growth.

The present invention also provides a method for treating alopecia. The method comprises administering to a subject in need thereof an effective amount of FP-1, or an agent that increases the expression of FP-1 in follicular papilla of the subject. In one embodiment, the subject's skin is contacted with FP-1, or an agent that increases the expression of FP-1 in the follicular papilla of the subject. In a particular embodiment, contact with FP-1 or the agent alters the duration of the anagen in the subject. In another specific embodiment, contact with FP-1 or the agent converts telogen follicles into anagen follicles. In yet another embodiment, contact with FP-1 or the agent reverses miniaturization. In a still further embodiment, contact with FP-1 or the agent generates new hair follicles. In an additional embodiment, the method comprises administering to a subject in need thereof an effective amount of FP-1, or an agent that increases the expression of FP-1 in follicular papilla; and a second agent.

In another aspect, the present invention provides methods of diagnosing hair disorders in a subject. The method comprises collecting a blood or tissue sample from the subject and detecting the level of FP-1 expression in the sample. If the FP-1 expression is lower or higher than in blood or tissue samples from a control subject who does not have a hair disorder, the subject is determined to have a hair disorder.

The present invention also provides a method for transplanting hair in a subject. In this method, hair follicles or grafts are contacted with a polynucleotide selected from the group consisting of polynucleotides having SEQ ID NO:1, SEQ ID NO:3, SEQ ID NO:5, SEQ ID NO:7, SEQ ID NO:9, and SEQ ID NO:11, or contacted with a polypeptide selected from the group consisting of polypeptides comprising SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, and amino acids 34 to 551 of SEQ ID NO:12. The contacted hair grafts or follicles are then transplanted to a predetermined bald or thinning area of the subject. The method of this aspect of the invention may further comprise contacting the hair follicles or grafts with additional substance(s) that control hair growth.

In yet another aspect, the invention provides a method for inhibiting hair growth of a subject, comprising contacting a hair follicle with an effective amount of an agent that decreases the expression of FP-1 in follicular papilla or inhibits the activity of FP-1. In some embodiments, the hair follicle is contacted by contacting the skin or the follicular papilla of a subject. In further embodiments, the agent that decreases the expression of FP-1 in follicular papilla or inhibits the activity of FP-1 is an antibody, a mutant form of FP-1, a ribozyme, an siRNA, an antisense molecule, or a small molecule inhibitor. In a further embodiment, the method of this aspect comprises contacting a hair follicle with an effective amount of an agent that decreases the expression of FP-1 in follicular papilla or inhibits the activity of FP-1; and an inhibitor of hair growth.

The invention also provides compositions comprising an antibody that binds FP-1 attached to a surface. In one embodiment, the surface is a solid phase surface. In another embodiment, the surface is a cell surface. In yet another embodiment the solid phase surface is a bead. In a still further embodiment the bead is selected from the group consisting of biodegradable beads, magnetic beads and latex beads.

In a further aspect, the present invention provides a method of identifying and isolating follicular papilla cells. In this method, a mixture of cells from the skin or hair follicles is contacted with an antibody that specifically binds to FP-1. In one embodiment, the antibody that binds FP-1 is coupled to a surface. These FP-1 antibody-bound cells are isolated from the unbound cells. The cells that bind an antibody that specifically binds to FP-1 are determined to be follicular papilla cells.

In another aspect, the invention provides a method for screening or validation of drugs for hair growth disorders. The method comprises contacting isolated follicular papilla cells, isolated hair follicles, or skin, and treating any of these with a test drug (e.g., chemical, compound, peptide, protein, DNA, etc.) and determining whether the test drug changes the expression level of FP-1 (RNA or protein) in the isolated follicular papilla cells, isolated hair follicles, or skin. The change in the expression levels of FP-1 is an indicator of the utility of the test drug for use in increasing or decreasing hair growth, or in regulating the texture/structure of the hair of a subject. If the test drug increases FP-1 expression it indicates that the test drug is effective in promoting hair growth. If, on the other hand, the test drug decreases FP-1 expression, the test agent is effective in inhibiting hair growth.

In an additional aspect, the present invention provides methods of diagnosing cancers. The method comprises isolating blood from a subject and measuring the level of FP-1. If the level of FP-1 is higher than that in the normal population, the subject is determined to be at a risk of developing or having developed a cancer. In another embodiment, the method comprises obtaining a tissue biopsy from a subject. The tissue is then tested for expression of FP-1. If the level of FP-1 is higher than in normal tissues, the subject is determined to be at a risk of developing or having developed a cancer. In one embodiment, the tissue is obtained from the skin. In another embodiment, the tissue is from the hair follicle. In yet another embodiment, the tissue is from the liver. In a further embodiment, the tissue is from the brain. In an even further embodiment, the tissue is from the testes. In an additional embodiment, the tissue is from the muscle (e.g., skeletal muscle). In a further embodiment, the tissue is from the placenta.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 2 is a schematic representation of the nucleic acid (SEQ ID NO:1) and corresponding amino acid sequence of rat FP-1 (SEQ ID NO:2).

FIG. 3 is a schematic representation of the nucleic acid (SEQ ID NO:3) and corresponding amino acid sequence of an alternatively spliced rat FP-1 (SEQ ID NO:4).

FIG. 4 is a schematic representation of the nucleic acid (SEQ ID NO:5) and corresponding amino acid sequence (SEQ ID NO:6) of rat gliomedin.

FIG. 5 is a schematic representation of the nucleic acid (SEQ ID NO:7) and corresponding amino acid sequence (SEQ ID NO:8) of mouse cancer related gene-liver 2 (mCrg-L2).

FIG. 6 is a schematic representation of the nucleic acid (SEQ ID NO:9) and corresponding amino acid sequence (SEQ ID NO:10) of a human homolog of cancer related gene-liver 2 (hCrg-L2).

FIG. 7 is a schematic representation of a nucleic acid encoding human FP-1 (SEQ ID NO:11) and the corresponding amino acid sequence (SEQ ID NO:12).

FIG. 8 is a schematic representation of an alignment of the amino acid sequences of the rat FP-1 sequences of the present invention (SEQ ID NOS: 2 (FP-1a) and 4 (FP-1b)), rat gliomedin (SEQ ID NO: 6), mouse cancer related gene-liver 2 (SEQ ID NO: 8), the human homolog of the mouse cancer related gene-liver 2 (SEQ ID NO: 10), and the human homolog of FP-1 (SEQ ID NO: 12).

FIG. 9 is a schematic representation of an alignment of the coding regions of the nucleic acid sequences of the rat FP-1 sequences of the present invention (SEQ ID NOS: 28 (FP-1a) and 32 (FP-1b)), rat gliomedin (SEQ ID NO: 29), mouse cancer related gene-liver 2 (SEQ ID NO: 33), the human homolog of the mouse cancer related gene-liver 2 (SEQ ID NO: 31), and the human homolog of FP-1 (SEQ ID NO: 30).

FIG. 10C is a schematic representation of an amino acid sequence alignment of the olfactomedin domains of rat FP-1a and b (SEQ ID NOS: 36), human FP-1 (SEQ ID NO: 37) and the olfactomedin-like domain (SEQ ID NO: 38) (OLF: NCBI Conserved Domain Database, gnl/CDD/8214, pfam02191). The seven regions of conservation in olfactomedin-related proteins (Regions 1, 3, and 5-9) as defined by Klein and Green (*Mol. Cell. Prot.,* 1.5:394-403, 2002) are underlined.

FIG. 11A is a photographic representation of a Southern Blot analysis performed using follicular papilla-specific cDNAs (FP-) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA.

FIG. 15 is a schematic representation of the cDNA (SEQ ID NO:1) and peptide sequence (SEQ ID NO:2) of the most full-length rat FP-1. The full-length FP-1 cDNA is 2332 bp, with a 1647 bp coding region that encodes a protein having 549 amino acids. Five peptide regions used to generate antisera are underlined and labeled epitopes 1 to 5. The N-terminal 33 amino acid residues of SEQ ID NO:2, which serve as a putative signal peptide, are indicated in bold and underlined. Amino acids 139-222 and 230-251 of SEQ ID NO:2 are homologous to collagen triple helix repeats. A region comprising amino acids 253-543 of SEQ ID NO:2 is homologous to an olfactomedin-related domain. Putative N-glycosylation sites are outlined in bold and underlined.

DETAILED DESCRIPTION OF THE INVENTION

The patents and scientific literature cited herein establishes the knowledge that is available to those with skill in the art. The issued U.S. patents, published and allowed applications, and references cited herein are hereby incorporated by reference in their entirety. Unless otherwise defined, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The present invention relates to compositions and methods for modulating hair growth. Specifically, the present invention is based on the discovery of a protein, follicular papilla-1

(FP-1), which exhibits highly selective expression in the follicular papilla of the hair follicle. Significantly, the mouse FP-1 gene has been localized to a region of the mouse chromosome that has been implicated in a number of hair-related disorders. These discoveries have been exploited to develop the present invention, which relates to proteins and polynucleotides that control hair growth; compositions that control hair growth; compositions and methods for identifying and isolating follicular papilla cells; methods of controlling hair growth; methods for screening for agents that control hair growth; methods of diagnosing hair disorders; and methods of diagnosing cancers.

Figure 1A:
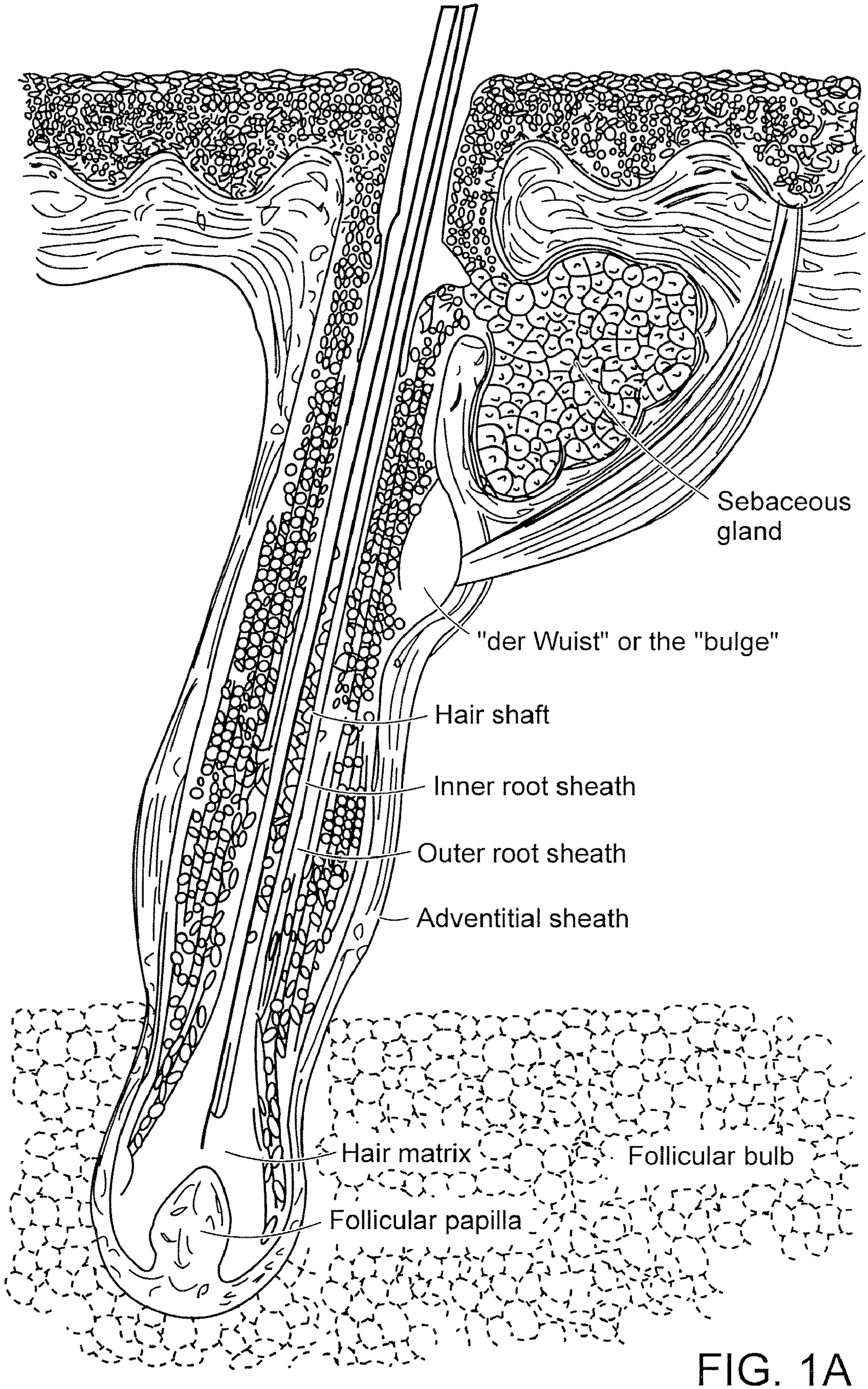
FIG. 1A is a diagrammatic representation of a human hair follicle in anagen.
Figure 1B:
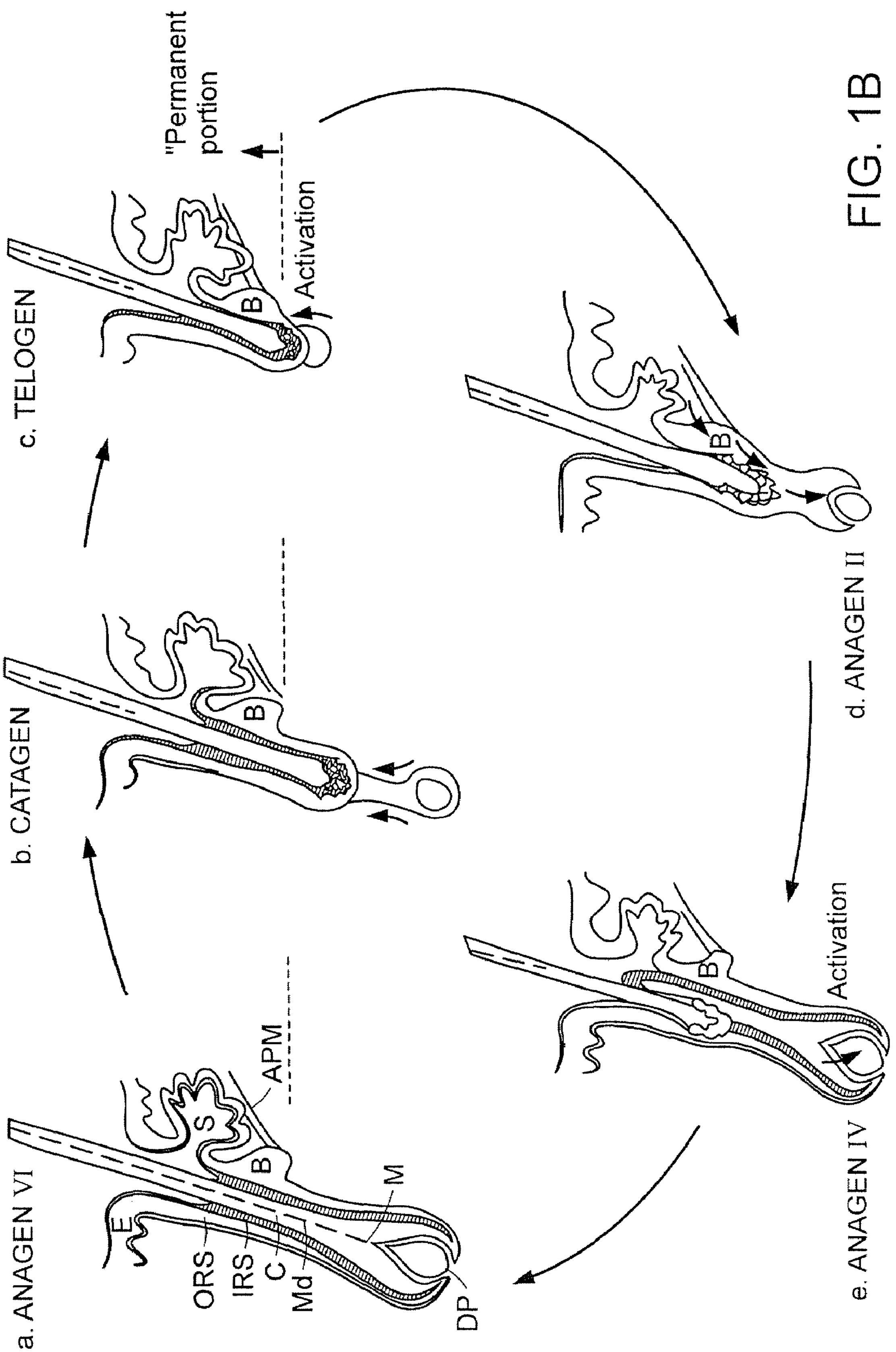
FIG. 1B is a diagrammatic representation of the different stages of a hair follicle cycle.

The outer surface of the hand, limb and body is covered by the epidermis, which is elaborated into a number of specialized appendages. One of the most prominent of these appendages is the hair follicle (FIG. 1A) which produces the hairs that fulfill a number of functions including thermoregulation, collecting sensory information, protection against environmental trauma, social communication, and mimicry (Stenn et al., *Physiol. Rev.* 81:449-494, 2001). Hair follicles have prolific growth characteristics and exhibit a complexity of differentiation (see, FIG. 1B). After initial embryonic morphogenesis, the hair follicle undergoes repeated cycles of regression and regeneration throughout the lifetime of an organism (Porter, *J. Anat.,* 202:125-131, 2003).

Hair follicle morphogenesis is governed by a series of inductive signals between epidermal keratinocytes committed to hair follicle specific differentiation and the mesenchymal cells that form the follicular papilla (Hardy, *Trends Genet.,* 8:55-61, 1992). Hair follicle precursors are first seen as thickenings or placodes in an otherwise uniform surface epithelium. These placodes send signals to the underlying dermis, causing the clustering of a group of cells—the dermal condensate—that will eventually form the follicular papilla. A second dermal signal from the dermal condensate to the follicular epithelium directs the proliferation and downgrowth of follicular epithelial cells into the dermis. These interactions eventually result in the morphogenesis of the hair bulb, in which keratinocytes rapidly proliferate and differentiate into six distinct cell populations, forming the medulla, cortex, and cuticle of the hair shaft, as well as the cuticle, Huxle and Henle layers of the inner root sheath (Bertolino et al., "Differentiation of the hair shaft," in *Differentiation of the Hair Shaft*, pp. 21-37, Olsen E A (ed.), McGraw Hill, Inc. New York, 1994). The inner root sheath separates the hair shaft from the outer root sheath, which forms the external concentric layer of epithelial cells in the hair follicle (Botchkarev et al., *J. Exp. Zool. Mol. Dev. Evol.,* 298(1):164-180, 2003).

In humans, the formation of hair follicles takes place during embryogenesis, and no new hair follicles form after birth. However, the hair follicle is a highly dynamic structure, which undergoes remodeling throughout the life of a mammal, in a cycle of growth (anagen), regression (catagen), rest (telogen), and shedding (exogen) (Muller-Rover et al., *J. Invest. Dermatol.,* 117:3-15, 2001; Cotsarelis et al., Trends Mol. Med., 7(7):293-301, 2001). During catagen, much of the follicle undergoes programmed cell death. The hair bulb shrinks and pulls away from the mesenchymal cluster of follicular papilla cells, which it previously enveloped. The whole hair follicle then retracts upwards toward the epidermal surface. During this retraction, it undergoes a carefully controlled remodeling to form a shortened structure that significantly, maintains its close association with the follicular papilla. After a period of rest in this shortened form, a signal that is thought to be from the follicular papilla initiates the next anagen phase (Porter, *J. Anat.,* 202:125-131, 2003). Follicular regeneration requires the activation of rarely cycling epithelial stem cells located in the permanent, bulge region of the follicle (Cotsarelis et al., *Cell,* 61:1329-1337, 1990). Stem cell progeny form a new follicle matrix during early anagen, and the hair shaft and inner root sheath are derived from these relatively undifferentiated matrix cells (Oshima et al., *Cell,* 104:233-245, 2001).

It has been well established that follicular papilla cells of the hair follicle play a key role in controlling hair growth. First, the diameter and length of the hair fiber appears to be directly proportional to the size of the follicular papilla (Elliott et al., *J. Invest. Dermatol.,* 113:873-877, 1999). Second, the surgical removal of the lower half of the rat vibrissa follicle results in follicular degeneration which can be prevented if one implants a follicular papilla, or a pellet of cultured follicular papilla cells, at the bottom of the damaged follicle. Implantation of dermal fibroblasts, which are embryologically closely related to the follicular papilla cells, fail to support hair growth thus establishing the importance of follicular papilla cells in maintaining the viability of the upper follicle (Oliver, *J. Embryol. Exp. Morphol.,* 15:331-347, 1966); Jahoda et al., *Nature,* 311:560-562, 1984). Like the vibrissa, the human follicle has also been shown to regenerate an active hair bulb after follicular amputation (Kim et al., *Dermatol. Surg.,* 21(4):312-313, 1995). Third, follicular papilla cells implanted under the interfollicular epidermis can induce the formation of new hair follicles; the structure of the induced follicle resembles the original follicle of the follicular papilla (Jahoda, C. A., *Development,* 115:1103-1109, 1992); Reynolds, A. J. et al., *Nature,* 402:33-34, 1999). Fourth, when cultured keratinocytes were combined with follicular papilla cells and grafted onto a nude (athymic) mouse, hair follicles were generated; however, no hair grew when cultured keratinocytes that were mixed with dermal fibroblasts were grafted onto nude mice (Kamimura et al., *J. Invest. Dermatol.,* 109(4):534-40, 1997). Fifth, Jahoda et al. recently showed trans-species hair induction by human scalp follicular papilla cells, but not dermal fibroblasts (Jahoda et al., *Exp. Dermatol.,* 10(4):229-37, 2001). Sixth, minoxidil has been shown to upregulate the synthesis and secretion of VEGF by cultured follicular papilla cells thus providing a possible explanation of the minoxidil stimulation of hair growth (Lachgar et al., *Br. J. Dermatol.,* 138:407-411, 1998). Finally, recent data indicate that hair follicular epithelial stem cells reside in the bulge, and that the interaction between follicular papilla and bulge during telogen may play a role in activating the stem cells allowing the follicle to enter into a new anagen (Cotsarelis et al., *Cell,* 61:1329-1337, 1990; Taylor et al., *Cell,* 102:451-461, 2000). Taken together, these results clearly indicate that follicular papilla cells, unlike their closely related dermal fibroblasts, are endowed with a unique capacity to maintain and to support the growth of the hair follicle.

Given the important role of the follicular papilla in regulating the morphogenesis of the hair follicle, it is of interest to define the molecular basis for why the follicular papilla cells, but not their closely related dermal fibroblasts, support hair growth. Accordingly, a rat follicular papilla-specific subtractive cDNA library was constructed to identify polynucleotides that were selectively expressed in the follicular papilla. The most abundant cDNA that was isolated from this library was named follicular papilla-1 (FP-1). This cDNA was then used to identify the full length rat cDNA.

The rat FP-1 polynucleotide (FIG. 2, SEQ ID NO:1) encodes a protein of 549 amino acids (FIG. 2, SEQ ID NO:2). A second cDNA (FIG. 3, SEQ ID NO:3), which likely corresponds to an alternatively spliced product of the rat FP-1 gene, encodes a protein of 531 amino acids (FIG. 3, SEQ ID NO:4). A search of the GENBANK® database for other FP-1 related proteins led to the discovery of rat gliomedin (FIG. 4, Accession Number AAP22419; SEQ ID NO:6), a mouse protein named cancer related gene-liver 2 (Crg-L2) (FIG. 5, Graveel et al., *Oncogene,* 22:1730-1736, 2003; Accession Number NP_796324; SEQ ID NO: 8), and a human protein named likely ortholog of mouse cancer related gene-liver 2 (FIG. 6, Accession Number NP_861454; SEQ ID NO: 10). An alignment of the rat, mouse, and human sequence (FIG. 8) indicated a high level of homology between these proteins. Interestingly, the human sequence listed in GENBANK® lacks the N-terminal region that is conserved between the mouse and the rat. Thus, it is likely that the human sequence listed in GENBANK® is an incomplete amino acid sequence. Accordingly, the present invention provides the amino acid sequence corresponding to a full-length human FP-1 protein (FIG. 7, SEQ ID NO:12). These rat (SEQ ID NOS: 2, 4, 6), mouse (SEQ ID NO: 8) and human (SEQ ID NOS:10 and 12) proteins, and any portions, derivatives, or variants thereof, are collectively referred to herein as "FP-1 proteins." The rat, mouse, and human FP-1 proteins have an N-terminal signal peptide sequence (FIG. 15) of about 33 amino acids (see for example, amino acids 1 to 33 of SEQ ID NO:2).

Figures 10A, 10B:
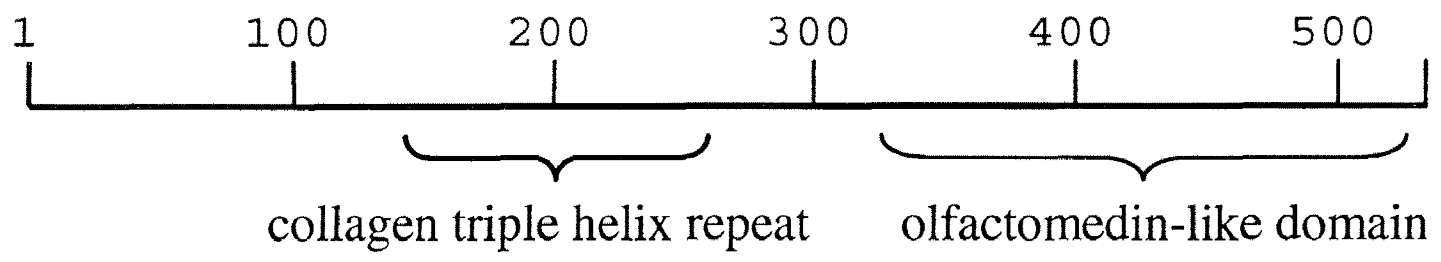
FIG. 10A is a diagrammatic representation of the location of the collagen triple helix repeat and olfactomedin-related domains of FP-1.
FIG. 10B is a schematic representation of an amino acid sequence alignment of the two regions (underlined) of rat FP-1a and b (SEQ ID NO: 34) and human FP-1 (SEQ ID NO: 35) that are homologous to the collagen triple helix repeat.

All the FP-1 proteins also possess amino acid sequences (see, e.g., amino acid 139-222 and 230-251 of SEQ ID NO:2) that are homologous to collagen triple helix repeat (20 copies) and several collagen family members such as collagen types IV, XIII and XV (FIG. 10B). Collagens are generally extracellular structural proteins involved in the formation of connective tissue structure. Collagen triple helix repeats contain 20 copies of the G-X-Y repeat (wherein G is glycine; X is any amino acid residue, but is frequently proline; and Y is any amino acid residue, but is frequently hydroxyproline) that forms a triple helix. Collagens are post-translationally modified by proline hydroxylase to form the hydroxyproline residues.

The FP-1 proteins are further characterized by the presence of an olfactomedin-related domain (see, e.g., amino acids 253-543 of SEQ ID NO:2). This domain was first identified in olfactomedin, which is an extracellular matrix glycoprotein specifically expressed in olfactory neuroepithelium (Snyder et al., *Biochem.,* 30(38):9143-153, 1991). Olfactomedin forms homopolymers through disulfide bonds and carbohydrate interactions (Bal et al., *Biochemistry,* 32(4):1047-53, 1993) and has been suggested to influence the growth and differentiation of chemosensory olfactory cilia (Yokoe et al., *Proc. Natl. Acad. Sci. USA* 90:4655-4659, 1993). In addition to olfactomedin, this domain is also found in a wide variety of proteins such as amassin, noelin, myocilin, and tiarin. Interestingly, the olfactomedin domain is primarily found in extracellular proteins. Olfactomedin domain-containing proteins have been reported to possess at least seven amino acid segments of conservation (regions 1, 3, and 5 through 9) (Green et al., *Mol. Cell. Prot.,* 1.5:394-403, 2002). These seven segments are also conserved in FP-1 proteins (see, FIG. 10C).

FP-1 proteins also have six potential glycosylation sites (FIG. 15, amino acids 130, 156, 252, 326, 354 and 461 of SEQ ID NO:2). When cell extracts having FP-1 are treated with endoglycosidase H, the molecular weight of rat FP-1 decreased from 72 kDa to roughly 60 kDa. Thus, FP-1 is a glycoprotein.

A survey of various rat tissues using Northern blot analysis indicated that FP-1 is expressed at an extremely high level in cultured rat vibrissa follicular papilla cells, and can be detected at low levels in the stomach and ovary. However, FP-1 was not detectable in the diaphragm, esophagus, stomach, brain, lung, heart, liver, spleen, kidney, bladder, intestine, colon, uterus, prostate, testis, and skeletal muscle (see, FIG. 14).

FP-1 is an extracellular matrix protein. The extracellular matrix of the follicular papilla undergoes cyclic changes such that it is completely degraded and removed during catagen, and then resynthesized and deposited in early to late anagen. These changes are important for the hair follicle cycle and thus hair growth. Thus, at least in part, FP-1 regulates hair growth by modulating the extracellular matrix of the hair follicle. Cross-species fluorescent in situ hybridization (FISH) on mouse chromosomes using rat FP-1 cDNA indicated that FP-1 is located on mouse chromosome 9 in the B-C region. This was confirmed by a BLAST search performed using rat FP-1 cDNA against the mouse genomic database after the completion of the Mouse Genome Program. Importantly, this region has three hair-related mutants, including rough fur (ruf), rough coat (rc) and fur deficient (fd).

The present invention provides isolated polynucleotides encoding FP-1. The polynucleotides of the invention can be DNA or RNA molecules that are single-stranded or double-stranded. The polynucleotides can include, but are not limited to, RNA, cDNA, genomic DNA, semisynthetic DNA or RNA, and chemically synthesized DNA or RNA sequences.

The polynucleotides comprise the sequences set forth as SEQ ID NO:1, SEQ ID NO:3 or SEQ ID NO:11. The invention also provides a nucleic acid sequence that encodes a polypeptide comprising SEQ ID NO:2, SEQ ID NO:4, or SEQ ID NO:12.

Alternatively, the isolated polynucleotides of the invention comprise a nucleic acid sequence that is homologous to any one of SEQ ID NO:1, SEQ ID NO:3 or SEQ ID NO: 11. By "homologous" is meant a polynucleotide that has at least about 70%, at least about 80%, at least about 90%, at least about 95%, or at least about 98% nucleotide sequence identity to a given nucleotide sequence, which can be determined by any standard nucleotide sequence identity algorithms such as, but not limited to, the GCG program (Devereux et al., *Nucl. Acids Res.,* 12(1): 387, 1984), BLASTN (GENBANK®), and FASTA (Altschul et al., *J. Mol. Biol.,* 215:403, 1990). For example, the invention provides an isolated polynucleotide comprising a nucleic acid sequence that has about 90%, or about 95% nucleic acid sequence identity to SEQ ID NO:1, SEQ ID NO:3, or SEQ ID NO: 11, wherein the isolated polynucleotide molecule encodes a protein that controls hair growth. By "controls hair growth" is meant to increase or decrease hair growth, or change the texture/structure of the hair shaft (e.g., rough, smooth, fragile, curly, etc.), relative to hair growth or hair texture in skin, hair follicles or follicular papilla not contacted with a polynucleotide, polypeptide, agent or composition of the invention. Some useful methods for determining whether FP-1 increases or decreases hair growth are described in the Examples below as well as in Philpott et al., Whole Hair Follicle Culture, in *Dermatologic Clinics* (Whiting D., ed.) 14(4): 595-607 (1966) and the references cited therein; and Wilson et al., *Differentiation* 55:127-136 (1994). Hair texture and structure can be assessed by direct visual study or by microscopy.

The polynucleotides of the invention alternatively comprise a nucleic acid sequence that is homologous to a nucleic acid sequence that encodes a polypeptide comprising SEQ ID NO:2, SEQ ID NO:4 or SEQ ID NO:12. For example, the polynucleotide may comprise a nucleic acid sequence that has about 90%, or about 95% nucleic acid sequence identity to a nucleic acid sequence that encodes a polypeptide comprising SEQ ID NO:2, SEQ ID NO:4 or SEQ ID NO:12, wherein the isolated polynucleotide molecule encodes a protein that increases or decreases hair growth, or changes hair texture.

The isolated polynucleotide of the invention specifically hybridize under moderately stringent or highly stringent conditions to a complement of a polynucleotide sequence comprising SEQ ID NO:1, SEQ ID NO:3 or SEQ ID NO:11, wherein the polynucleotide sequence encodes a protein that controls hair growth. As used herein, the phrase "specifically hybridizing" means the ability of a nucleic acid molecule to recognize another nucleic acid sequence by forming base pairs with it through hydrogen bonding, under moderately or highly stringent hybridization conditions. By "moderately stringent conditions" is meant hybridization to filter-bound DNA in 0.5 M NaHPO4, 7% sodium dodecyl sulfate (SDS), 1 mM EDTA at 65° C., and washing in 0.2×SSC/0.1% SDS at 42° C. (see, Ausubel et al. (eds.), *Current Protocols in Molecular Biology, Vol.* 1, 1989, Green Publishing Associates, Inc., and John Wiley & Sons, Inc., New York at p. 2.10.3). By "highly stringent conditions" is meant hybridization to filter-bound DNA in 0.5 M NaHPO4, 7% sodium dodecyl sulfate (SDS), 1 mM EDTA at 65° C., and washing in 0.1×SSC/0.11% SDS at 68° C. (Ausubel et al., supra). The polynucleotides of the invention specifically hybridize under moderately stringent or highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that increases or decreases hair growth, or changes hair texture.

Additionally, the invention provides an isolated polynucleotide that is the complement of the polynucleotide comprising any of the polynucleotides of the previous aspects.

The polynucleotides of the invention may be produced by hybridizing the polynucleotide having SEQ ID NO:1, SEQ ID NO:3 or SEQ ID NO:11 to genomic DNA under moderately stringent or highly stringent hybridization conditions and isolating the DNA polynucleotide hybridized to the polynucleotide having SEQ ID NO:1, SEQ ID NO:3 or SEQ ID NO:11. The genomic DNA can be from any eukaryotic organism including mammals, especially humans. Methods of hybridizing a polynucleotide to genomic DNA are well known in the art (Sambrook et al., *Molecular Cloning: A Laboratory Manual*, Third Edition, Cold Spring Harbor Laboratory Press).

The polynucleotides of the invention can be modified by the addition of flanking sequences such as, but not limited to, restriction enzyme recognition sequences, adaptors, nucleic acid sequences encoding epitopes recognized by antibodies (e.g., His, Flag, Myc, HA, MBP, GST) and nucleic acid sequences encoding proteins that permit detection of the fusion protein (e.g., GFP). Methods of adding or ligating desired DNA sequences to a DNA sequence of interest are well known in the art (Sambrook et al., ibid.).

The polynucleotides of the invention can also be mutated to generate polynucleotides that encode mutant FP-1 proteins. A polynucleotide sequence can be mutated by, for example, introducing one or more point mutations (e.g., a missense or nonsense mutation) or by inserting or deleting one or more bases. Any technique for mutagenesis known in the art can be used, including but not limited to, chemical mutagenesis, in vitro site-directed mutagenesis, PCR-based overlap extension, and PCR-based megaprimer mutagenesis. Methods of generating mutations in a DNA sequence are well within the skill of one of ordinary skill in the art (see, Sambrook et al., supra, Hutchinson et al., *J. Biol. Chem.,* 253:6551, 1978; Ho et al., *Gene,* 77:51-59, 1989; Sarkar et al., *Biotechniques,* 8:404-407, 1990; and Stratagene's QuikChange® Kit).

The invention provides oligonucleotides that hybridize to any of the aforementioned polynucleotides of the present invention, or that hybridize to a polynucleotide molecule having a nucleotide sequence that is the complement of any of the aforementioned polynucleotides of the invention. Such oligonucleotide molecules are at least about 10 nucleotides in length, at least about 20 nucleotides in length, at least about 30 nucleotides in length or at least about 40 nucleotides in length, and hybridize to one or more of the aforementioned polynucleotide molecules under moderately or highly stringent hybridization conditions. For shorter oligonucleotide molecules, an example of highly stringent conditions includes washing in 6×SSC/0.5% sodium pyrophosphate at about 37° C. for about 14-base oligonucleotides, at approximately 48° C. for about 17 bp oligonucleotides, at approximately 55° C. for about 20 bp oligonucleotides and at approximately 60° C. for about 23-40 base oligonucleotides. Hybridization conditions can of course be appropriately adjusted as known in the art, depending upon the particular oligonucleotide molecules utilized.

The oligonucleotides of the present invention are useful in a variety of purposes, including as primers in amplifying a FP-1 encoding polynucleotide, or as antisense molecules useful in regulating expression of FP-1 genes and gene products. A "gene product" means a product encoded by a gene, including the transcribed RNA message (including exons and introns), the spliced messenger RNA (mRNA), and the translated protein product encoded by the respective mRNA. Amplification of FP-1 polynucleotides can be carried out using suitably designed oligonucleotide molecules in conjunction with standard techniques, such as the polymerase chain reaction (PCR).

The present invention also provides recombinant cloning and expression vectors comprising any of the polynucleotide molecules of the invention. The choice of the vector and/or expression control sequences to which any of the polynucleotides of the present invention is operably linked depends directly, as well known in the art, on the functional properties desired, e.g., protein expression, and the host cell to be transformed. The regulatory sequences that are used for modulating the expression of an operably linked, protein-encoding sequence are known in the art and include, but are not limited to, inducible promoters, constitutive promoters, enhancers, and other regulatory elements known in the art that serve to drive and/or regulate expression of the polynucleotide coding sequences. The inducible promoter may be readily controlled, such as being responsive to a nutrient in the host cell's medium.

The vectors of the invention containing a polynucleotide according to the invention can include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as drug resistance. Typical bacterial drug resistance genes are those that confer resistance to ampicillin, chloramphenicol, kanamycin or tetracycline. Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase, and permits transcription to occur. Promoter sequences compatible with bacterial hosts are typically provided in plasmid vectors containing convenient restriction sites for insertion of a polynucleotide or any fragment thereof of the present invention. Typical non-limiting prokaryotic vector plasmids include pUC8, pUC9, pBR322, pBR329 (BioRad Laboratories), pKK223-2 (Clontech), pSE280, pSE380, pSE420, pTrx-Fus, pRSET, pBAD/HisABC, pTrcHis (Invitrogen), pET-3, pET-11, pCAL-n-EK, pCAL-n (Stratagene), pFLAG-1, pFLAG-ATS, pFLAG-CTS, pFLAGShift(12) (Kodak), pET-14b, pET-15b, pET-30LIC, pET-32LIC (Novagen), pMC1871, pRIT2T and pKK223-3 (Pharmacia).

Suitable yeast vectors for use in the present invention are described in U.S. Pat. No. 6,291,212, and include YRp7 (Struhl et al., *Proc. Natl. Acad. Sci. USA,* 76: 1035-1039, 1978), YEp13 (Broach et al., *Gene,* 8:121-133, 1979), pJDB249 and pJDB219 (Beggs, *Nature,* 275:104-108, 1978). Such vectors generally include a selectable marker, which may be one of any number of genes that exhibit a dominant phenotype for which a phenotypic assay exists to enable transformants to be selected. Non-limiting examples of selectable markers include those that complement host cell auxotrophy, provide antibiotic resistance or enable a cell to utilize specific carbon sources, and include LEU2 (Broach et al. ibid.), URA3 (Botstein et al., *Gene,* 8:17, 1979), HIS3 (Struhl et al., ibid.) or POT1 (Kawasaki and Bell, EP 171142). Other suitable selectable markers include the CAT gene, which confers chloramphenicol resistance on yeast cells. Examples of promoters for use in yeast include promoters from yeast glycolytic genes (Hitzeman et al., *J. Biol. Chem.,* 225:12073-12080, 1980; Alber and Kawasaki, *J. Mol. Appl. Genet.,* 1:419-434, 1982; Kawasaki, U.S. Pat. No. 4,599,311) or alcohol dehydrogenase genes (Young et al., in *Genetic Engineering of Microorganisms for Chemicals*, Hollander et al., (eds.), p. 355, Plenum, N.Y., 1982; Ammerer, *Meth. Enzymol.* 101: 192-201, 1983). Non-limiting examples of yeast promoters include the TPI1 promoter and the ADH promoter. The yeast expression vector may further comprise a transcriptional terminator such as the TPI1 terminator (Alber and Kawasaki, ibid.).

In addition to yeast polynucleotides of the present invention can be expressed in filamentous fungi, for example, strains of the fungi *Aspergillus*. Examples of useful promoters include those derived from *Aspergillus nidulans* glycolytic genes, such as the ADH3 promoter (McKnight et al., *EMBO J.,* 4:2093-2099, 1985) and the tpiA promoter. An example of a suitable terminator is the ADH3 terminator (McKnight et al., ibid.). The expression units utilizing such components may be cloned into vectors that are capable of insertion into the chromosomal DNA of *Aspergillus.*

Expression vectors compatible with mammalian cells can also be used to express the polynucleotides of the present invention. Eukaryotic cell expression vectors are well known in the art and are available from several commercial sources. Typically, such vectors are provided containing convenient restriction sites for insertion of the desired polynucleotide or any fragment thereof. Such vectors may further include a selectable marker that is effective in a eukaryotic cell, preferably a drug resistance selection marker. A useful drug resistance marker is the gene whose expression results in neomycin resistance, i.e., the neomycin phosphotransferase (neo) gene (Southern et al., *J. of Mol. and Appl. Genet.,* 1 (4):327-341, 1982). Alternatively, the selectable marker can be present on a separate plasmid, and the two vectors are introduced by co-transfection of the host cell, and selected by culturing in the appropriate drug for the selectable marker.

Mammalian expression vectors for use in carrying out the present invention will include a promoter capable of directing the transcription of a cloned gene or cDNA. Such promoters include viral promoters (e.g., the major late promoter from adenovirus 2 (Kaufman and Sharp, *Mol. Cell. Biol.,* 2:1304-1319, 1982) and the SV40 promoter (Subramani et al., *Mol. Cell. Biol.,* 1: 854-864, 1981) and cellular promoters (e.g., mouse metallothionein 1 promoter (Palmiter et al., *Science,* 222:809-814, 1983)). These expression vectors may further comprise enhancers. In addition, these expression vectors may also contain a set of RNA splice sites located downstream from the promoter and upstream from the polynucleotide encoding the protein. RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.,* 9:3719-3730, 1981). The expression vectors may include a noncoding viral leader sequence, such as the adenovirus 2 tripartite leader, located between the promoter and the RNA splice sites. Non-limiting examples of eukaryotic expression vectors include pACT, pCI, pCI-neo, pCMVTNT™(Promega), pTet-On™, pTet-Off™, pMAM neo, IRES Bicistronic, pRetro-Off™, pRetro-On™ (Clontech), pWE1, pWE2, pWE3, pWE4 (ATCC®), pIND(SP1), pCDM8, pcCDNA1.1, pcDNA3.1, pZeoSV2, pRcCMV2, pRcRSV, pTracer (Invitrogen Corp.), pSVL, pMSG (Pharmacia), pBPV-1/pML2d (International Biotechnologies, Inc.), pCMVScript™, pBK-CMV, and pBK-RSV (Stratagene).

Methods for constructing recombinant vectors are well known in the art, and any of these can be used to construct the vectors of the present invention. These methods include in vitro recombinant techniques, synthetic techniques, and in vivo genetic recombination (see e.g., Sambrook et al., supra, Ausubel et al., supra).

The present invention further provides host cells comprising a polynucleotide molecule or recombinant vector of the invention. Host cells useful in the practice of the invention include prokaryotic and eukaryotic cells such as mammalian, insect, fungal, plant, bacterial, viral and baculoviral cells. Appropriate host cells can be chosen that modify and process the gene product in the specific fashion desired. Different host cells have characteristic mechanisms for the translational and post-translational processing and modification (e.g., glycosylation, phosphorylation) of proteins. For example, expression in a bacterial system can be used to produce an unglycosylated protein product. Expression in mammalian cells can be used to ensure "native" processing of a protein product. Further, different vector/host expression systems can affect processing reactions to different degrees. Non-limiting examples of prokaryotic host cells include the *E. coli* strains HB101, JM101, DH5α, LE392, RR1, XL1-Blue and KW251. Non-limiting examples of eukaryotic host cells include, COS, 293, 293T, CHO, CV-1, Hela, NIH3T3, BHK, C33A, U20S, and primary follicular papilla cells.

The recombinant vector of the invention is transformed or transfected into one or more host cells of a substantially homogenous culture of cells. Methods of transforming and/or transfecting cells are well known in the art. The expression vector is generally introduced into host cells in accordance with known techniques such as e.g., by protoplast transformation, calcium phosphate precipitation, calcium chloride treatment, microinjection, electroporation, transfection by contact with recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance associated with the recombinant vector, as described above. Once the expression vector is introduced into the host cell, the integration and maintenance of the polynucleotides of the invention, either episomally or in the host cell chromosome can be confirmed by standard techniques, e.g., by Southern hybridization analysis, restriction enzyme analysis, PCR analysis, RT-PCR, or by immunological assays to detect the expected gene product. Host cells containing and/or expressing the recombinant polynucleotide of the invention can be identified by any approach known in the art, including: (i) DNA-DNA, DNA-RNA, or RNA-antisense RNA hybridization; (ii) detecting the presence of "marker" gene functions; (iii) assessing the level of transcription as measured by the expression of the mRNAs produced by the recombinant polynucleotide in the host cell; and (iv) detecting the presence of a mature polypeptide product as measured by, for example, an immunoassay.

Once a polynucleotide of the invention has been introduced into an appropriate host cell, the transformed host cell is cultured under conditions conducive to the maximum production of the polypeptide encoded by the recombinant polynucleotide. Such conditions typically include, e.g., growing cells to high density. Where the expression vector comprises an inducible promoter, appropriate induction conditions such as temperature shift, exhaustion of nutrients, and addition of gratuitous inducers (e.g., zinc chloride, analogs of carbohydrates such as IPTG, etc.) are employed as needed to induce expression. Where the expressed polypeptide is retained inside the host cells, the cells are harvested and lysed, and the polypeptide is isolated and purified from the lysate under extraction conditions known in the art to minimize protein degradation such as, e.g., at 4° C. and/or in the presence of protease inhibitors. Where the expressed polypeptide is secreted from the host cells, the nutrient medium can simply be collected and the polypeptide isolated therefrom.

The polypeptide can be isolated or substantially purified from cell lysates or culture medium, as appropriate, using standard methods including, but not limited to, any combination of the following methods: ammonium sulfate precipitation, gel filtration chromatography, ion exchange chromatography, HPLC, density centrifugation, affinity chromatography and immuno-affinity chromatography. If the polypeptide exhibits any measurable biological activity, increasing purity of the polypeptide preparation can be monitored at each step of the purification procedure by use of an appropriate assay. Whether or not the polypeptide exhibits biological activity, it can be detected at each step of the purification based on size or reactivity with an antibody raised to the polypeptide or by detection with an antibody that binds a fusion tag attached to the protein.

The present invention thus provides a substantially purified or isolated polypeptide encoded by a polynucleotide molecule of the present invention. As used herein, a polypeptide is "substantially purified" where the polypeptide constitutes the majority (i.e., at least about 50%) by weight of the material in a particular preparation.

The polypeptides useful in the method of the invention include rat FP-1 gene products comprising, consisting essentially of, or consisting of, the amino acid sequence of SEQ ID NO:2 or SEQ ID NO:4. In one embodiment, the polypeptide is a rat FP-1 gene product comprising, consisting essentially of, or consisting of amino acids 34 to 549 of SEQ ID NO:2. The polypeptide, alternatively, is a rat FP-1 gene product comprising, consisting essentially of, or consisting of amino acids 34 to 531 of SEQ ID NO:4. Any of the amino acid sequences lacking the signal peptide can further comprise an initiating methionine residue.

The present invention also provides an isolated polypeptide comprising the amino acid sequence encoded by any one of the polynucleotides of the invention. For example, the polypeptide is a human FP-1 gene product comprising, consisting essentially of, or consisting of SEQ ID NO: 12. Alternatively, the polypeptide is a human FP-1 gene product comprising, consisting essentially of, or consisting of amino acid 34 to 551 of SEQ ID NO: 12.

The substantially purified or isolated polypeptides of the present invention are useful for a variety of purposes, such as increasing or decreasing hair growth, changing hair texture, regulating the length of the anagen phase of the hair follicle cycle, screening for proteins or compounds that interact with FP-1 and alter its ability to control hair growth, and for raising antibodies directed to the polypeptide. Such compounds and antibodies can be used in therapeutic methods to treat or prevent hair disorders.

Also within the scope of the present invention are FP-1 proteins or FP-1 fusion proteins comprising one or more amino acid substitutions, insertions or deletions occur in the FP-1 proteins. Such proteins may function as dominant-negative forms of FP-1. The mutant FP-1 proteins or the polynucleotides coding them can be administered to a subject to inhibit or decrease hair growth. Mutant FP-1 encompassed by the invention include, but are not limited to, FP-1 proteins with a deletion or substitution of one or more amino acids in the collagen triple helix repeats, and FP-1 proteins with a deletion or substitution of one or more amino acids in the olfactomedin-related domain.

Non-limiting examples of mutations in the collagen triple helix repeats of FP-1 include, (i) deletion of amino acids 139-222 of SEQ ID NO:2 (or the corresponding region in SEQ ID NOS: 4, 6, 8, 10 and 12); (ii) deletion of amino acids 230-250 of SEQ ID NO:2 (or the corresponding region in SEQ ID NOS: 4, 6, 8, 10 and 12); (iii) deletion of amino acids 139-165 (or the corresponding t region in SEQ ID NOS: 4, 6, 8, 10 and 12); (iv) deletion of amino acids 166-195 (or the corresponding region in SEQ ID NOS: 4, 6, 8, 10 and 12); (v) deletion of amino acids 196-222 (or the corresponding region in SEQ ID NOS: 4, 6, 8, 10 and 12); (vi) mutations of one or more glycines in the region encompassing amino acids 139-222 of SEQ ID NO:2 (or the corresponding region in SEQ ID NOS: 4, 6, 8, 10 and 12) to any other amino acid; and (vii) mutations of one or more glycines in the region encompassing amino acids 230-250 of SEQ ID NO:2 (or the corresponding region in SEQ ID NOS: 4, 6, 8, 10 and 12) to any other amino acid. In one embodiment, the FP-1 proteins with mutations in the collagen triple helix repeat region have decreased or no binding to collagen. Methods of determining binding between mutant FP-1 proteins and collagen can be performed using methods well known in the art. For example, the binding of FP-1 and its mutants to collagen type 1 or other types may be studied using well established methods including gel electrophoresis and affinity chromatography (Keller et al., *Biochim. Biophys. Acta,* 882(1):1-5, 1986). The binding constant can be assessed using affinity co-electrophoresis as described by San Antonio et al. (*J. Cell Biol.,* 125(5): 1178-1188). This method can be used to compare the binding of FP-1 to procollagen or collagen fibrils in order to determine whether the binding is collagen assembly-dependent. Finally, the collagen domain that is responsible for the binding of FP-1 can be mapped using synthetic peptides or paryial collagen fragments made as recombinant proteins (Knight et al., *J. Biol. Chem.,* 273(50):33287-33294, 1998).

Non-limiting examples of mutations in the olfactomedin-related domain of FP-1 include, (i) deletion of amino acids 315-325 of SEQ ID NO:2 (or the corresponding region in SEQ ID NOS: 4, 6, 8, 10 and 12); (ii) deletion of amino acids 366-382 of SEQ ID NO:2 (or the corresponding region in SEQ ID NOS: 4, 6, 8, 10 and 12); (iii) deletion of amino acids 408-437 of SEQ ID NO:2 (or the corresponding region in SEQ ID NOS: 4, 6, 8, 10 and 12); (iv) deletion of amino acids 441-466 of SEQ ID NO:2 (or the corresponding region in SEQ ID NOS: 4, 6, 8, 10 and 12); (v) deletion of amino acids 468-484 of SEQ ID NO:2 (or the corresponding region in SEQ ID NOS: 4, 6, 8, 10 and 12); (vi) deletion of amino acids 487-494 of SEQ ID NO:2 (or the corresponding region in SEQ ID NOS: 4, 6, 8, 10 and 12); (vii) deletion of amino acids 519-539 of SEQ ID NO:2 (or the corresponding region in SEQ ID NOS: 4, 6, 8, 10 and 12); (viii) deletion of any combination of the amino acids listed above; (ix) mutation of one or more of G318, W320, R322, E323, G368, G370, A372, V373, Y374, N375, S377, L378, Y379, Y380, K382, F409, Y413, I424, A425, V426, D427, E428, G430, L431, W432, I433, I434, Y435, A436, I444, L445, V446, L449, T453, V456, N461, T462, Y464, K466, A469, N471, A472, F473, A475, G477, I478, L479, Y480, V481, T482, T484, T490, F491, A492, F493, D494, Y519, N520, D523, L526, Y527, W529, E530, D531, G532, H533, L534, Y537 and V539 of SEQ ID NO:2 (or the corresponding amino acid in SEQ ID NOS: 4, 6, 8, 10 and 12) to any other amino acid; (ix) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagine; (x) FP-1 comprising a mutation at A469 of SEQ ID NO:2 (or the corresponding amino acid in SEQ ID NOS: 4, 6, 8, 10 and 12) to any amino acid, for example, but not limited to, phenylalanine, tyrosine and aspartic acid; (xi) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagines; and (xii) FP-1 comprising a mutation at N519 of SEQ ID NO:2 (or the corresponding amino acid in SEQ ID NOS: 4, 6, 8, 10 and 12) to any amino acid, for example, but not limited to, lysine and arginine.

In addition, the invention encompasses FP-1 proteins with mutations at one or more of the glycosylation sites of FP-1 that prevent its glycosylation. In one embodiment, N130, N156, S252, N326, N354 and N461 are mutated to a different amino acid residue such as, but not limited to, glycine. Glycosylation of FP-1 and mutant FP-1 proteins can be assessed by comparing SDS-PAGE mobilities of the unmutated and mutated FP-1 proteins. N-glycosylation of each potential glycosylation site will increase the apparent SDS gel molecular weight by approximately 2 kD. Thus, the mutation of one such N-glycosylation site in FP-1 will decrease the molecular weight of FP-1 by 2 kD.

In addition, the invention encompasses FP-1 proteins, or any hair growth-controlling portion thereof, that are fusion proteins. A protein or peptide may be fused either at the N- or C-terminus of FP-1 proteins. In one embodiment, an FP-1 protein is fused to an epitope tag selected from the group consisting of H is, Flag, Myc, HA, MBP and GST.

The present invention further provides polyclonal and monoclonal antibodies, or portions thereof, that bind to the polypeptides or peptide fragments of the invention, or to a homologous polypeptide or peptide fragment of the invention. The term "antibody" as used herein refers to immunoglobulin molecules and immunologically active portions of immunoglobulin molecules, i.e., molecules that contain an antigen binding site which specifically binds (immunoreacts with) an antigen, such as FP-1. Antigen-binding fragments are also intended to be designated by the term "antibody." Examples of binding fragments encompassed within the term antibody include Fab, Fd, Fv, dAb, $F(ab')_2$, and single chain Fv (scFv). For example, antibody fragments for use in the present invention are those which are capable of crosslinking their target antigen, e.g., bivalent fragments such as $F(ab')_2$ fragments. In another embodiment, an antibody fragment which does not itself crosslink its target antigen (e.g., a Fab fragment) can be used in conjunction with a secondary antibody which serves to crosslink the antibody fragment, thereby crosslinking the target antigen. An antibody of the invention is further intended to include bispecific and chimeric molecules having a desired binding portion (e.g., FP-1).

An antibody of the present invention is used to detect the polypeptides of the invention; as affinity reagents with which to purify the polypeptides of the invention; as reagents to isolate follicular papilla cells; or to control the activity of the polypeptide of the invention. In this context, "controls hair growth" is meant to increase or decrease hair growth relative to hair growth in skin, hair follicles or follicular papilla not contacted with an antibody of the invention. For example, an antibody that binds FP-1 controls the activity of FP-1 by increasing or decreasing its ability to control hair growth. Methods of determining whether FP-1 increases or decreases hair growth can be assayed using any of the methods described or used in the Examples.

Polyclonal antibodies can be obtained from immunized animals and tested for specificity using standard techniques (Harlow et al., *Antibodies: A Laboratory Manual*, Cold Spring Harbor Laboratory Press, 1988). Alternatively, monoclonal antibodies to any of the polypeptides of the invention can be prepared using any technique that provides for the production of antibody molecules by continuous cell lines in culture. These include, but are not limited to, the hybridoma technique originally described by Kohler and Milstein (*Nature,* 256:495-497, 1975); the human B-cell hybridoma technique (Kosbor et al., *Immunol. Today,* 4:72, 1983; Cote et al., *Proc. Natl. Acad. Sci. USA,* 80:2026-2030, 1983); and the EBV-hybridoma technique (Cole et al., *Monoclonal Antibodies and Cancer Therary*, Alan R. Liss, Inc., pp. 77-96) and any other methods known in the art (Golding, *Monoclonal Antibodies: Princioles and Practice*, Academic Press, 1996). Alternatively, techniques described for the production of single chain antibodies (e.g., U.S. Pat. No. 4,946,778) can be adapted to produce single chain antibodies to the polypeptides of the present invention.

An anti-FP-1 antibody or a fragment thereof may be attached or coupled to a surface (e.g., cell surface, beads etc.). Beads that are used in the invention include, but are not limited to biodegradable beads, magnetic beads, and polymer microbeads. An antibody or fragment thereof can be immobilized directly or indirectly by, for example, by a secondary antibody, to a surface, such as a tissue culture flask or bead (see, for e.g., U.S. Pat. Nos. 6,352,694 and 6,129,916). Alternatively, antibodies can be coupled to a surface, e.g., beads by crosslinking via covalent modification, using tosyl linkage. In one method, an antibody such as anti-FP-1 is in 0.05 M borate buffer, pH 9.5 and added to tosyl activated magnetic immunobeads (Dynal Inc., Great Neck, N.Y.) according to the manufacturer's instructions. After a 24 hr incubation at 22° C., the beads are collected and washed extensively. It is not essential that immunomagnetic beads be used, as other methods are also satisfactory.

In one embodiment of the invention, an FP-1 protein, or a portion of an FP-1 protein, or a modified form of an FP-1 protein, capable of modulating hair growth is localized on the surface of a cell. This can be accomplished by transfecting a cell with a polynucleotide encoding the FP-1 protein in a form suitable for its expression on the cell surface or alternatively by coupling an FP-1 protein to the cell surface.

The FP-1 proteins may be expressed on the surface of a cell by transfection of the cell with a polynucleotide encoding the FP-1 molecule in a form suitable for expression of the molecule on the surface of the cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al., (*Molecular Cloning: A Laboratory Manual,* 2nd Edition, Cold Spring Harbor Laboratory Press, 1989) and other laboratory textbooks. The nucleic acid to be introduced may be any nucleic acid encompassing a polynucleotide encoding FP-1, sense strand RNA encoding FP-1, or a recombinant expression vector containing a cDNA encoding FP-1. Expression of FP-1 on the surface of a cell can be accomplished, for example, by including the transmembrane domain of a protein that localizes to the cell surface in the nucleic acid sequence, or by including signals which lead to modification of the protein, such as a C-terminal inositol-phosphate linkage, that allows for association of the molecule with the outer surface of the cell membrane. Expression of the FP-1 protein on the surface of the cell can be confirmed by immunofluorescence staining of the cells. For example, cells may be stained with a fluorescently labeled monoclonal antibody reactive against the FP-1 molecule.

Alternatively, FP-1 proteins can be coupled to the cell surface by any of a variety of different methods. The terms "coupled" or "coupling" refer to a chemical, enzymatic or other means (e.g., antibody) by which the FP-1 molecule is linked to a cell such that the FP-1 molecule is present on the surface of the cell. For example, the FP-1 molecule can be chemically crosslinked to the cell surface using commercially available crosslinking reagents (Pierce, Rockford Ill.). Another approach to coupling an FP-1 molecule to a cell is to use a bispecific antibody, which binds both the FP-1 molecule and a cell-surface molecule on the cell. Fragments, mutants or variants of a FP-1 molecule can also be used. The level of FP-1 expressed on or coupled to the cell surface can be determined by FACS analysis.

The present invention also encompasses methods of isolating follicular papilla cells. Since FP-1 is a secreted extracellular matrix protein at least some of the protein remains associated with the cell surface of the follicular papilla cells. Thus, antibodies to FP-1 can be used to sort the cells that bind an antibody raised to FP-1 using methods well known in the art. Alternatively, a composition comprising an anti-FP-1 antibody attached to a surface can be used to selectively isolate follicular papilla cells from a mixed population of cells from the skin or hair follicle. In this method, a composition comprising an FP-1 antibody can be used to contact a mixed population of cells from the skin or hair follicle sample from which the follicular papilla cells are to be isolated. The follicular papilla cells that bind to the FP-1 antibody can be separated from the unbound cells by any method known in the art including, but not limited to, fractionation. The isolated follicular papilla cells may be useful for (i) inducing epidermis to form new hair follicles de novo; or (ii) improving the performance of existing hair follicles that may contain defective or fewer numbers of follicular papilla cells than normal hair follicles.

Also within the scope of the present invention are oligonucleotide sequences that include antisense oligonucleotides, ribozymes, and siRNAs that function to bind to, degrade and/or inhibit the translation of the mRNA encoded by the polynucleotides of the invention. Antisense RNAs can be designed based on principles established in the art (e.g., Schiavone et al., *Curr. Pharm. Des.,* 10(7):769-784, 2004; Sczakiel, *Antisense Nucl. Acid Drug Dev.,* 7(4):439-444, 1997; Stein, *Antisense Nucl, Acid Drug Dev.,* 8(2): 129-132, 1998; and Summerton et al., *Antisense Nucl. Acid Drug Dev.,* 7(3):187-195, 1997). Methods for designing suitable siRNAs for a target gene are well known in the art (e.g., Elbashir et al., *Nature,* 411:494-498, 2001; Semizarov et al., *Proc. Natl. Acad. Sci. USA,* 100:6347-6352, 2003).

The antisense oligonucleotides, ribozymes and siRNAs of the present invention can be commercially obtained or prepared by known methods. These include techniques for chemical synthesis such as, e.g., by solid phase phosphoramidite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

Various modifications to any of the polynucleotides and oligonucleotides of the present invention can be introduced to increase intracellular stability and half-life. Possible modifications include, but are not limited to, the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The present invention also provides pharmaceutical compositions or formulations comprising the polynucleotides, polypeptides, antisense molecules, ribozymes, siRNAs or antibodies of the present invention, as an active component. For example, a pharmaceutical composition may comprise a polynucleotide selected from the group consisting of SEQ ID NO:1, SEQ ID NO:3, SEQ ID NO:5, SEQ ID NO:7, SEQ ID NO:9, SEQ ID NO:11, and any combination thereof. The pharmaceutical composition may instead comprise a polypeptide selected from the group consisting of SEQ ID NO:2, SEQ ID NO:4, SEQ ID NO:6, SEQ ID NO:8, SEQ ID NO:10, SEQ ID NO:12, and any combination thereof. The pharmaceutical composition alternatively may comprise a polypeptide such as one having amino acids 34 to 549 of SEQ ID NO:2, 34 to 531 of SEQ ID NO:4, 34 to 549 of SEQ ID NO:6, 34 to 549 of SEQ ID NO:8, 34 to 427 of SEQ ID NO:10, and/or 34 to 551 of SEQ ID NO:12. The pharmaceutical composition may instead comprise an antibody that binds to FP-1. For example, the antibody may be one that specifically binds to human FP-1, or to both the rat and human FP-1 proteins. The pharmaceutical composition may alternatively comprise an antisense molecule that inhibits or prevents translation of FP-1 mRNA, an siRNA that blocks expression of an FP-1 mRNA, or a ribozyme that cleaves an FP-1 mRNA.

In addition to the FP-1 component of the composition, the therapeutic compositions of the present invention contain suitable pharmaceutically acceptable carriers, and may also comprise excipients and auxiliaries that facilitate processing of the active compounds into preparations, which can be used pharmaceutically for delivery to the site of action. Suitable formulations for parenteral administration include aqueous solutions of the active compounds in water-soluble form, for example, water-soluble salts. In one embodiment, the pharmaceutically acceptable carrier is phosphate buffered saline. In another embodiment, the carrier is water. In addition, suspensions of the active compounds as appropriate oily injection suspensions may be administered. Suitable lipophilic solvents or vehicles include, but are not limited to, fatty oils (e.g., sesame oil), or synthetic fatty acid esters (e.g., ethyl oleate), or triglycerides. Aqueous injection suspensions may contain substances which increase the viscosity of the suspension, for example, sodium carboxymethyl cellulose, sorbitol and dextran. Optionally, the suspension may also contain stabilizers. Liposomes can also be used to encapsulate the composition for delivery into the cell (e.g., U.S. Pat. Nos. 4,828,837 and 6,224,901).

The pharmaceutical formulations of the invention may be administered to a subject in need thereof using standard administration protocols. "A subject in need thereof," is used herein, to mean a mammalian subject who is determined by a health care provider, scientist, veterinarian, animal breeder, or other qualified person to be in need of increasing or decreasing hair growth. In the case of human subjects, the health care provider may determine that the subject is in need of controlling hair growth for health or cosmetic reasons. For non-mammalian subjects, a veterinarian or animal breeder may determine that a particular subject is in need of a pharmaceutical composition of the invention to increase hair growth, e.g., in wool or fur production.

The compositions of the present invention can be administered via topical, parenteral, subcutaneous, intravenous, intramuscular, intraperitoneal, transdermal, or buccal routes. For example, a composition is administered locally to a site via microinfusion, or by topical application in a cream, gel, lotion, ointment, salve, balm, aqueous solution or patch. Alternatively, or concurrently, administration may be by the oral route. Suitable formulations for oral administration include hard or soft gelatin capsules, pills, tablets, including coated tablets, elixirs, suspensions, syrups or inhalations and controlled release forms thereof. Indeed, all types of formulations may be used simultaneously to achieve systematic administration of the active ingredient. The dosage administered is dependent upon the age, health, and weight of the recipient, kind of concurrent treatment if any, frequency of treatment, and the nature of the desired effect. The present invention further provides compositions containing one or more polypeptides of the invention. While individual needs vary, determination of optimal ranges of effective amounts of each composition of the invention is within the skill of the art. In one non-limiting example, dosages of protein for topical formulations comprise from about 0.1 ng to about 100 ng per ml of the formulation, from about 10 ng to about 50 ng, or about 30 ng.

The pharmaceutical formulations of the present invention can be provided alone, or in combination, or in sequential combination with other agents that modulate hair growth. As used herein, two agents are said to be administered in combination when the two agents are administered simultaneously or are administered independently in a way such that the agents will act at the some or almost the same time.

The use of gene therapy to administer the compositions of the invention is contemplated in one aspect of this invention. More specifically, the polynucleotides of the invention can be applied to the skin or scalp through the delivery of nucleic acid molecules. The delivery of nucleic acid molecules can be accomplished by any means known in the art. Gene delivery vehicles (GDVs) are available for delivery of polynucleotides to cells or tissue for expression. For example, a nucleic acid sequence of the invention can be administered either locally or systematically in a GDV. These constructs can utilize viral or non-viral vector approaches in vivo or ex viva. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle may be a viral vector such as, but not limited to, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector (see generally, Jolly, *Cancer Gene Therapy,* 1:51-64, 1994; Kimura, *Human Gene Therapy,* 5:845-852, 1994; Connelly, *Human Gene Therapy,* 6:185-193, 1995; and Kaplitt, *Nature Genetics,* 6:148-153, 1994). Delivery of the gene therapy constructs of this invention into cells is not limited to the above-mentioned viral vectors. Other delivery methods and media may be employed such as nucleic acid expression vectors, polycationic condensed DNA linked or unlinked to killed adenovirus alone (Curiel, *Hum. Gene Ther.,* 3:147-154, 1992), ligand linked DNA (Wu, *J. Biol. Chem.,* 264:16985-16987, 1989), eukaryotic cell delivery vehicles cells (U.S. Pat. No. 6,015,686), deposition of photopolymerized hydrogel materials, hand-held gene transfer particle gun (U.S. Pat. No. 5,149,655), ionizing radiation (U.S. Pat. No. 5,206,152 and PCT Patent Publication No. WO 92/11033), nucleic charge neutralization or fusion with cell membranes. Additional approaches are described in Phillip, *Mol. Cell. Biol.,* 14:2411-2418, 1994 and in Woffendin, *Proc. Natl. Acad. Sci. USA,* 91:1581-585, 1994. Briefly, the nucleotide sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes, that can act as gene delivery vehicles are described in U.S. Pat. No. 5,422,120, PCT Patent Publication Nos. WO 95/13796, WO 94/23697, and WO 91/144445, and EP No. 524,968.

The polynucleotide molecules of the invention may be introduced into the skin or scalp using the injectable carrier alone. Liposomal preparations are preferred for methods in which in vitro transfections of cells obtained from the skin or scalp are carried out. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide. Alternatively, an even more prolonged effect can be achieved by introducing the DNA sequence into the cell by means of a vector plasmid having the DNA sequence inserted therein. The plasmid may further comprise a replicator.

It is possible to obtain long term administration of a polypeptide to the scalp by introducing a naked DNA sequence operatively coding for the polypeptide interstitially into the skin or scalp, whereby cells of the tissue produce the polypeptide for at least one month or at least 3 months, more preferably at least 6 months. In addition, a method for obtaining transitory expression of a polypeptide in the scalp can be achieved by introducing a naked mRNA sequence operatively coding for the polypeptide interstitially into the skin or scalp, whereby cells of the tissue produce the polypeptide for less than about 20 days, usually less than about 10 days, and often less than 3 or 5 days.

The polypeptides of the invention can also be administered to a patient via depot or transdermal technology. In one embodiment, a pharmaceutical composition comprising FP-1 and a pharmaceutically acceptable carrier are delivered to a subject using one of Alza's D-TRANS® patches, Alza's E-TRANS® systems, and ALZA's Macroflux® transdermal technology. In an alternative embodiment, a pharmaceutical composition comprising FP-1 and a pharmaceutically acceptable carrier are delivered to a subject using one of Alza's DUROS® implant or AlZAMER® Depot technologies.

The pharmaceutical compositions or formulations of the present invention can be used in modulating hair growth in several contexts. By "modulate hair growth" is meant to increase or decrease hair growth. Methods of measuring or assaying hair growth are described in the Examples below, and in Philpott et al., "Whole Hair Follicle Culture" in *Dermatoloaical Clinics* 14(4): 595-607, 1996), and the references cited therein. The compositions comprising polynucleotides encoding FP-1 and FP-1 polypeptides are primarily intended for use in increasing or promoting hair growth, whereas compositions comprising mutant FP-1 polynucleotides or proteins, FP-1 ribozymes, FP-1 antisense molecules, FP-1 siRNAs, and antibodies raised to FP-1, are primarily intended for use in decreasing, or inhibiting hair growth.

Promoting hair growth or attenuating hair loss serves to combat the effects of alopecia in humans and other mammalian species. Conversely, retarding hair growth or promoting hair loss can combat the effects of hirsutism, hypertrichosis, and similar disorders of afflicted individuals. Additionally, the compositions of the invention can be employed to control hair growth in normal skin. Thus, for example, the compositions can be employed in wool or fur production (e.g., applied to alpaca, beaver, calf, chinchilla, coyote, ermine, fisher, fitch, fox, lamb, llama, lynx, marten, mink, muskrat, nutria, opossum, otter, raccoon, Russian squirrel, sable, sheep, and other fur- or wool-producing mammals), to increase hair growth thereby permitting greater net annual wool production or reducing the time needed to produce mature pelts. Alternatively, the compositions of the present invention can be employed to produce custom designs of bare skin or thin, thick, or variegated hair within pelts of treated animals.

The compositions of the present invention are utilized in the methods of the present invention, which include a method of controlling hair growth in a subject comprising administering a pharmaceutical composition of the invention to that subject. The present invention also provides a method for modulating hair growth comprising contacting the skin or hair follicle of a subject with a composition of the invention. Alternatively, the follicular papilla of a subject may be contacted with a pharmaceutical composition of the present invention. Any of these methods can further comprise administering a second agent that controls hair growth. Where it is desired to increase hair growth, the second agent is a substance that either increases hair growth or which assists the composition of the invention to increase hair growth. Where it is desired to decrease or prevent hair growth, the second agent is a substance that decreases hair growth or assists the composition of the invention to decrease hair growth. The compositions of the invention may be administered by any of the methods detailed above. For example, the composition is topically administered to the skin of a subject in an amount sufficient to achieve a dose of at least about 0.01 nmol, at least 0.1 nmol, or at least about 1 nmol per 2 cm by 4.5 cm skin surface area, up to a dose of about 100 nmol, 1,000 nmol, or 10,000 nmol or more per 2 cm×4.5 cm skin surface area.

The present invention also provides a method for transplanting hair in a subject in need thereof including the pretreatment of hair follicles or grafts to be transplanted. In a typical hair transplantation procedure, grafts of skin containing hair are removed from the back or sides of the scalp (donor area) of the individual and are transplanted to other areas, that is, the bald or thinning area (recipient area). To place the grafts onto these areas, a number of incisions are made in the scalp. The incisions are then cleaned and a graft is inserted into each incision. Hair transplantation includes a minigraft for placing only a small number of hairs into the incisions, a micrograft for placing a single hair in the incisions (also, referred to as one-haired minigraft), and a follicular unit hair transplantation.

FP-1 polynucleotides and proteins of the present invention can be used in the pretreatment of hair follicles or grafts before transplantation. Such treatment is contemplated to promote or accelerate hair implantation.

The present invention also relates to diagnostic assays such as quantitative and diagnostic assays for detecting levels of FP-1 protein in cells and tissues. FP-1 levels can be detected at the RNA or protein level. A diagnostic assay in accordance with the invention for detecting under-expression of FP-1 proteins compared to normal control tissue samples, are used to detect whether the subject is likely to develop a hair loss disorder. In one embodiment, the diagnostic assay is used for the prognosis of alopecia. Assay techniques that are used to determine levels of FP-1 proteins of the present invention, in a sample derived from a host, for example blood or scalp tissue, are well known to those of skill in the art. Such assay methods include, but are not limited to, immunoassays, radioimmunoassays, competitive-binding assays, Western Blot analysis, ELISA assays, and immunofluorescence assays. Accordingly, the present invention provides a method for diagnosing alopecia in a subject comprising collecting a blood or tissue sample from said subject and detecting FP-1 proteins in said sample.

Such diagnostic assays can also be used to diagnose cancers. Overexpression of FP-1 correlates with heightened risk for developing or having developed a cancer. In one embodiment, the invention provides a method to diagnose skin cancers (e.g., basal cell carcinoma, pilomatricoma). In other embodiments, the method permits diagnosis of liver cancers, cancers of the nervous system, stomach cancers, testicular cancer and ovarian cancer among others.

The present invention further provides methods of identifying agents that control hair growth. The method comprises contacting skin with a test agent ex vivo. A test agent may be any substance that is contemplated to potentially regulate hair growth. The method further comprises detecting or measuring the expression of FP-1 in the follicular papilla. If the test agent is found to increase expression of FP-1 in the follicular papilla it is determined to be an agent that stimulates hair growth. If, however, the test agent decreases the expression of FP-1 in the follicular papilla it is determined to be an inhibitor of hair growth.

Also contemplated are methods to identify agents that interact with FP-1 and modulate its ability to control hair growth. Methods of identifying other proteins that interact with FP-1 include, but are not limited to, immuno-precipitation and two-hybrid assays (Sambrook et al., cited supra; Fields et al., *Nature,* 340(6230):245-246, 1989; and Fields et al., *Trends Genet.,* 10(8):286-92, 1994).

The present invention also encompasses the production of transgenic non-human animals that express FP-1 protein or FP-1 fusion protein encoding construct of the instant invention. Animals, which contain exogenous DNA sequences in their genome, are referred to as transgenic animals. The successful production of transgenic, non-human animals has been described in a number of patents and publications, such as, for example U.S. Pat. Nos. 6,291,740; 6,281,408; and 6,271,436.

The most widely used method for the production of transgenic animals is the microinjection of DNA into the pronuclei of fertilized embryos (Wall et al., *J. Cell. Biochem.,* 49:113, 1992). Other methods for the production of transgenic animals include the infection of embryos with retroviruses or with retroviral vectors. Infection of both pre- and post-implantation mouse embryos with either wild-type or recombinant retroviruses has been reported (Jaenisch, *Proc. Natl. Acad. Sci. USA,* 73:1260, 1976; Jaenisch et al., *Cell,* 24:519, 1981; Stuhlmann et al., *Proc. Natl. Acad. Sci. USA,* 81:7151, 1984; Jahner et al., *Proc. Natl. Acad. Sci. USA,* 82:6927, 1985; Van der Putten et al., *Proc, Natl. Acad. Sci. USA,* 82:6148-6152, 1985; Stewart et al., *EMBO J.,* 6:383-388, 1987).

An alternative means for infecting embryos with retroviruses is the injection of virus or virus-producing cells into the blastocoele of mouse embryos (Jahner, D. et al., *Nature* 298: 623, 1982). The introduction of transgenes into the germline of mice has been reported using intrauterine retroviral infection of the midgestation mouse embryo (Jahner et al., supra, 1982). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832; and Haskell and Bowen, *Mol. Reprod. Dev.,* 40:386, 1995). PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

The ability to alter the genetic make-up of animals, such as domesticated mammals including cows, pigs, goats, horses, cattle, and sheep, allows a number of commercial applications. In the context of the present invention, FP-1 transgenic animals are useful as models to study hair growth, as well as to test drugs, compounds, etc. for use in regulating hair growth.

Without further description, a person of ordinary skill in the art can, using the preceding description and the following illustrative examples, make and utilize the present invention and practice the disclosed methods. The following working examples therefore are not to be construed as limiting in any way the remainder of the disclosure.

EXAMPLES

Example 1

Materials and Methods

I. Cell Culture (a) Follicular Papilla

Vibrissa follicles were isolated individually from the lip region of 4-6 months old male Wistar rats (Charles River). To expose follicular papilla, the lower part of the follicle was opened by a 20 gauge needle. About 35-40 follicular papillae were microdissected from each rat. The isolated follicular papillae were placed in 1 ml Chang's medium (Irvine Scientific) with 100 units/ml penicillin and 100 μg/ml streptomycin in a 35 mm petri plate, and left undisturbed in a 37° C., 5% $CO_2$ incubator for 4 days. Under these conditions most of the papillae formed outgrowths (Jahoda and Oliver, *Br. J. Dermatol.,* 105(6):623-627, 1981; Jahoda and Oliver, *J. Embryol. Exp. Morphol.,* 79:211-24, 1984; Warren et al., *J. Invest. Dermat.,* 98:693-699, 1992). The culture medium was changed every 3 days. Ten to twelve days later, the cells were treated with 0.125% trypsin and 0.01% EDTA in phosphate-buffer saline, and the dissociated single cells were then plated in Dulbecco's Modified Eagle's Medium (DMEM) containing 10% fetal bovine serum (FBS), 100 units/ml penicillin and 100 μg/ml streptomycin. Sub-confluent cells were fed every 3 days by removing old medium and adding fresh medium warmed to 37° C.

(b) Rat Dermal Fibroblasts

Rat dermal fibroblasts were cultured by explant outgrowth from small pieces (<1 $mm^3$) of interfollicular dermis from the same lip skin tissue, from which the vibrissa follicles had been removed. The primary culture and subculture conditions were the same as described above. Rat stomach, esophagus and thoracoabdominal diaphragm tissues were minced thoroughly to <1 $mm^3$ and placed in 1 ml DMEM containing 10% FBS, 100 units/ml penicillin and 100 μg/ml streptomycin in a 30 mm petri plate. After being undisturbed for a few days, fibroblasts grew out from these tissues. The subculture conditions were the same as described above. All experiments were carried out using the fourth passage of the cultured cells. One passage constituted a 1:3 dilution of subculture.

II. Subtractive cDNA Library

Total RNA of cultured cells was isolated by a system using guanidine thiocyanate and CSB (citrate/sarcosine/β-mercaptoethanol) as denaturing buffer followed by phenol extraction (The RNAgents® Total RNA Isolation System, Promega). Poly A+ RNA was separated from the total RNA using a biotinylated oligo (dT) selection with the MagneSphere® mRNA isolation system (Promega).

Cultured rat vibrissa follicular papilla-specific subtractive cDNA library was constructed using the PCR-select™ cDNA subtraction Kit (Clontech) according to the manufacturer's instructions (Diatchenko et al., *Proc. Natl. Acad. Sci. USA,* 93(12):6025-6030, 1996). For the first strand cDNA synthesis, 2 μg of cultured rat vibrissa follicular papilla cell poly A+ RNA (the "tester") and 2 μg of a mixture (1:1:1) of cultured rat stomach, esophagus and diaphragm fibroblasts poly A+ RNA were reverse-transcribed using MMLV reverse transcriptase (Gibco). The second stranded cDNA was synthesized with a 20× enzyme cocktail containing DNA polymerase 1 (6 U/μl), RNase H (0.25 U/μl), *E. coli* DNase ligase (1.2 U/μl), and T4 DNA polymerase (1.5 U/μl). The double strand cDNA obtained was phenol extracted and ethanol precipitated. After digesting with Rsa I, the tester (follicular papilla) cDNA was divided into two subpopulations, which were ligated with two different adaptors. The two subpopulations (about 15 ng each) were then hybridized with an excess amount of the driver (3 types of fibroblasts) cDNA (about 470 ng), after which they were combined. Without denaturing the DNA hybrids, the mixture of the two primary hybridization samples was hybridized again with freshly denatured driver cDNA (about 310 ng). To enrich and amplify the differentially expressed sequences, two rounds of selective PCR were performed in both subtracted and unsubtracted cDNA (tester cDNAs ligated with two different adaptors) using primers that anneal to the adaptors sequences. The PCR products were cloned into the pCRII TA cloning vector, which was then transformed into TOP10F' cells (Invitrogen).

In order to perform differential screening later, a reverse subtraction (a rat fibroblast-specific subtractive cDNA library) was also performed by the same PCR-select™ cDNA subtraction technique as described above. In the reverse subtraction, a mixture of the 3 types of fibroblast (cultured rat stomach, esophagus and diaphragm fibroblasts) served as the "tester" and follicular papilla as the "driver."

III. Differential Screening a. cDNA Array

Bacterial colonies were randomly picked from the follicular papilla-specific subtracted library and cultured overnight at 37° C. with shaking. To amplify the cDNA inserts, PCR was performed using adaptor-specific primers (Clontech). After denaturing with 0.6 N NaOH, the PCR products were transferred onto a Hybond™-XL nylon membrane (Amersham Pharmacia Biotech). Two identical blots were prepared for hybridizing with follicular papilla-specific subtracted library (FP probe) and fibroblast-specific subtracted library (F probe). The blots were neutralized with 0.5 M Tris-HCl (pH 7.5) for 2-4 min. and washed with $H_2O$. DNA was cross-linked to the membrane by UV light.

b. Colony Array

The same overnight cultures of the randomly picked bacterial clones were used to perform colony array. Each bacterial culture was transferred onto a Hybond™-XL nylon membrane (Amersham Pharmacia Biotech) placed on the LB/agar plate containing kanamycin. Two identical blots were prepared for hybridizing with the follicular papilla-specific subtracted library (FP probe) and fibroblast-specific subtracted library (F probe). After culturing overnight at 37° C., the blots were denatured with 0.5 M NaOH, 1.5 M NaCl for 4 min, neutralized with 0.5 M Tris-HCl (pH 7.5), 1.5 M NaCl for 4 min, and air dried for 30 min. The DNA was fixed to the membrane by baking at 80° C. for 2 hrs.

c. Preparation of the Subtracted cDNA Probes

The amplified PCR products of the subtracted cDNAs were purified with the NucleoTrap® PCR purification kit (Clontech), and underwent restriction enzyme digestion to remove the adaptor sequences. Three restriction enzymes were used one after another in the following order: Rsa I at 37° C. for 1 hr, Sma I at room temperature for 1 hr, and Eag I at 37° C. for 1 hr. After separation from the adaptor using the NucleoTrap® PCR purification kit (Clontech), the cDNAs were then labeled with ($\alpha$-$^{32}$P) dCTP by the Multiprime™ DNA labeling system (Amersham Pharmacia Biotech). The specific activity of the labeled probe was determined by using a scintillation counter. The total counts per probe was greater than $10^7$ cpm.

d. Hybridization with the Subtracted cDNA Probes

The blots of the cDNA array and colony array were hybridized at 60° C. over night with the labeled subtracted cDNA probes in Church solution (0.25 M $Na_2HPO_4$ (pH 7.2), 1 mM EDTA, 7% SDS, and 1% BSA). Equal amounts (about $3.5\times10^7$ cpm) of the labeled follicular papilla-specific cDNA probe (FP probe) and fibroblast-specific cDNA probe (F probe) were used in an equal amount (7.5 ml) of Church hybridization solution for every two identical colony array or cDNA array blots. Two cDNA fragments were used as hybridization negative controls: (i) a mouse testis-specific gene (GenBank® Accession No. X52128), and (ii) a human semenogelin II (GeneBank® Accession No. ANM81652), which is specific to seminal vesicles.

IV. Virtual Northern

1 µg of total RNA from cultured follicular papilla cells, fibroblasts (diaphragm, esophagus, and stomach fibroblasts in a 1:1:1 mixture), and dermal fibroblasts were separately reverse transcribed to first-strand cDNAs. Double strand cDNA (ds cDNA) was synthesized and then amplified by PCR according to the SMART™ cDNA synthesis technique (Clontech). The optimal number of PCR cycles was titrated to ensure that the ds cDNA synthesis remained in the exponential phase of amplification. The PCR-amplified ds cDNA was electrophoresed on a 1% agarose gel, and then transferred onto a Hybond™-XL nylon membrane (Amersham Pharmacia Biotech). The filter was subjected to hybridization using the procedure used for Northern blot hybridization.

V. 5' RACE (Rapid Amplification of cDNA Ends) of FP-1

5' race of FP-1 was performed according to the manufacturer's instructions (Clontech). 1 µg of poly A+ RNA from the cultured rat vibrissa follicular papilla cells was reverse transcribed into first-strand cDNA. Using the first-strand cDNA as a template, the primary PCR was performed with the Universal Primer (Clontech) and a FP-1 specific primer. The thermal cycling program was as follows: 5 cycles of 94° C., 5 sec: 72° C., 3 min.: 5 cycles of 94° C., 5 sec: 70° C., 10 sec; 72° C., 3 min.: 23 cycles of 94° C., 5 sec: 68° C., 10 sec: 72° C., 3 min. The primary PCR product was diluted to 1:50 and used as a template in the secondary PCR. The second PCR was primed with the Universal Nested Primer (Clontech) and a FP-1 specific nested primer. The thermal cycling program was as follows: 20 cycles of 94° C., 5 sec: 68° C., 10 sec; 72° C., 3 min. The nucleotide sequences of the FP-1 primer and the FP-1 nested primer were: 5' CCCAGTTCACCAGCATCTCCCTTCTCTC 3' (SEQ ID NO: 13) and 5' GTCTATCATCACCCGGATCGGCACCAT 3' (SEQ ID NO:14), respectively. The PCR product from the second PCR reaction was ligated into a TA cloning vector (Invitrogen). Individual clones were sequenced.

VI. Western Blot and Deglycosylation

Cultured cells were dissolved in lysis buffer (1% NP40, 1% deoxycholic acid, 0.1% SDS, 150 mM NaCl, 50 mM Tris-HCl (pH 7.4), 2 mM EDTA and freshly added protease inhibitor). After centrifugation at 14,000 rpm for 20 min at 4° C., the soluble proteins were quantified using a BCA kit (Pierce). 50 µg of the total proteins were resolved on a 12% polyacrylamide gel according to standard procedures (Laemmli, 1970). The separated proteins were transferred electrophoretically to an MSI-nitrocellulose membrane (Towbin et al., *Proc. Natl. Acad. Sci. USA,* 76:4350-4354, 1979; Burnette, *Anal. Biochem.,* 112:195-203, 1981). The membrane was incubated with primary antibodies and HRP-conjugated secondary antibody. Optimal concentration of the primary antibodies was determined by titration: anti-DP1 rabbit serum G320 (1:10,000), anti-β-tubulin mouse monoclonal antibody (Sigma) (1:2,000). The reaction was visualized by an enhanced chemiluminescence detection kit (Pierce) according to the manufacturer's instruction.

VII. Deglycosylation Reaction

For the deglycosylation reaction, about 250 µg total proteins was incubated with the Endo-H reaction buffer (50 mM NaAc (pH 5.5), 0.1% SDS) at room temperature for 20 min, and then digested with 10 mU Endo-H (Roche) in the same reaction buffer in the presence of freshly added 0.05% $NaN_3$ and 10 mM EDTA at 37° C. over night (Kobata, *Anal. Biochem.,* 100(1):1-14, 1979; Trimble and Maley, *Anal. Biochem.,* 141(2):515-22, 1984). Total cell lysate that went through the above procedure, but without the addition of Endo-H was used as the intact glycoprotein control. Samples were stored at −20° C. before being analyzed by Western blotting.

VIII. Endo H Digestion

Half of 100 mm plate cell lysate (about 250 µg total proteins) was incubated with Endo H reaction buffer (20 mM $Na_3PO_4$ (pH 7.5), 0.02% $NaN_3$, 0.1% SDS, 50 mM β-mercaptoethanol) at room temperature for 20 min, and then digested by 30 mU Endo H (Roche) in the same reaction buffer with freshly added 0.75% Nonidet P-40 at 37° C. over night (Tanner et al., *J. Virol.,* 62(12):4452-64, 1988). Total cell lysate that went through the above procedure, but without Endo H was used as the intact glycoprotein control. Samples were stored at −20° C. before being analyzed by Western blot.

IX. FP-1 Antibodies

Five different regions of rat FP-1 (SEQ ID NO:2), which were predicted to be hydrophilic and to be more antigenic than other regions in FP-1 according to several computer algorithms, including one that predicts hydropathy, were selected to produce antibodies to rat FP-1. These five regions of FP-1 included amino acids 87-102, 247-262, 276-297, 321-333, and 392-405 of SEQ ID NO:2.

The synthesized peptides were purified by reverse-phase high performance liquid chromatography (HPLC) and their purity was examined by mass spectrometry. A cysteine residue was placed at either the N- or C-terminus of each peptide to facilitate conjugation to the carrier protein, Keyhole Limpet Hemosyanin (KLH). For each conjugated peptide, two rabbits were immunized by subcutaneous injection of 100 μg of peptide in Freund's complete adjuvant. This primary immunization was followed by booster injections at 2-week intervals. The titer of the antisera was checked by ELISA after 3 booster injections (Genemed Synthesis).

Table I summarizes the information relating to the five polyclonal rabbit anti-rat FP-1 antibodies.

TABLE 1

| Antibody | Epitope | IB dilution | IF dilution | Mismatch/ Total aa Mouse | Mismatch/ Total aa human |
|---|---|---|---|---|---|
| G311 | 1 | 1:1,000 | n.d. | 0/16 | 3/16 |
| G312 | 2 | 1:2,000 | 1:200 | 8/22 | 1/16 |
| G320 | 3 | 1:10,000 | 1:1,000 | 0/22 | 5/22 |
| G324 | 5 | 1:500 | n.d. | 1/14 | 3/14 |
| G325 | 4 | n.d. | n.d. | 2/13 | 1/13 |

Key:
IB = immunoblot
IF = immunofluorescence
n.d. = not determined
Mismatch/Total aa = the number of amino acids that are different between the rat and mouse FP-1, or rat and human FP-1, in the peptide sequences recognized by the rat FP-1 antibodies.

X. Immunofluorescence Staining

Culture cells grown on glass cover slips (12 mm, Fisher) were fixed with cold 1:1 methanol/acetone for 20 min. and then air-dried. Fresh tissues were embedded in OCT medium (Sakura Finetek) in liquid nitrogen and sectioned into 7-8 μm according to standard procedures. The sections were fixed with cold 1:1 methanol/acetone for 10 min and air-dried.

Cover slips with cultured cells or slides with frozen sections were incubated with primary antibodies. Optimal concentration of the primary antibodies was determined by titration: anti-FP1 rabbit serum G320 (1:1,000), anti-β-COP mouse monoclonal antibody (Sigma) (1:80). After washing, the cover slips or slides with PBS for 5 min. three times, the cover slip or slide was incubated with fluorescein FITC or rhodamine conjugated secondary antibody (Molecular Probes, Eugene, Oreg.), mounted with aqueous mounting medium with anti-fading agents (Biomeda, Foster City, Calif.), and examined under a fluorescence microscope (Zeiss, Thornwood, N.Y.).

XI. Fluorescent In Situ Hybridization (FISH)

Lymphocytes were isolated from mouse spleen and cultured at 37° C. in RPMI 1640 medium supplemented with 15% fetal calf serum, 3 μg/ml concanavalin A, 10 μg/ml lipopolysaccharide and $5\times10^{-5}$ M mercaptoethanol. After 44 hr, the cultured lymphocytes were treated with 0.18 mg/ml BrdU for an additional 14 hr. The synchronized cells were washed and recultured at 37° C. for 4 hr in α-MEM with thymidine (2.5 μg/ml). Cells were harvested and chromosome slides were made by standard procedures including hypotonic treatment, fixation and air-drying (See DNA Biotech). For probe preparation, a 2.1 kb rat FP-1 cDNA fragment was amplified by PCR using the plasmid of the longest FP-1 positive clone (obtained from screening the follicular papilla cDNA library) as template and primers flanking the cDNA insert on the vector plasmid. The DNA probe was biotinylated with dATP at 15° C. for 1 hr (Gibco BRL BioNick labeling kit, Gaithersburg, Md.) (Heng et al., *Proc. Natl. Acad. Sci. USA,* 89(20):9509-13, 1992). The procedure for FISH was performed according to published methods (Heng et al., ibid; Heng and Tsui, *Chromosoma,* 102(5):325-32, 1993).

Example 2

Figures 11A, 11B, 11C, 11D, 11E:
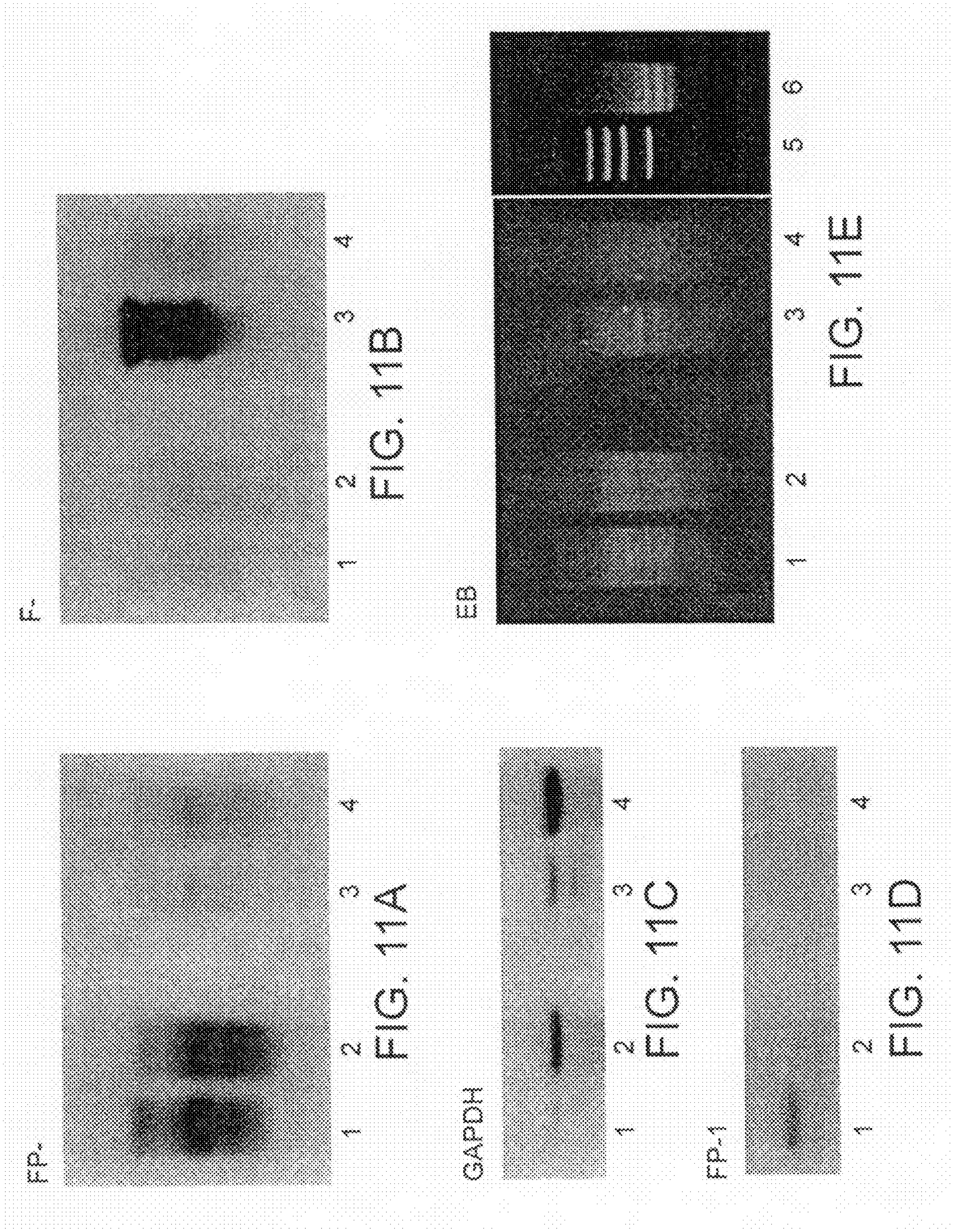
FIG. 11A is a photographic representation showing the enrichment of follicular papilla-specific cDNAs in the follicular papilla subtraction library. Specifically.
FIG. 11B is a photographic representation of a Southern Blot analysis performed using fibroblasts-specific cDNAs (F-) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA.
FIG. 11C is a photographic representation of a Southern Blot analysis performed using a GAPDH probe. Lane 1: subtracted follicular papilla cDNA; lane 2: nonsubtracted follicular papilla cDNA; lane 3: subtracted fibroblast cDNA; and lane 4: nonsubtracted fibroblast cDNA.
FIG. 11D is a photographic representation of a Southern Blot analysis performed using an FP-1 probe. Lane 1: subtracted follicular papilla cDNA; lane 2: nonsubtracted follicular papilla cDNA; lane 3: subtracted fibroblast cDNA; and lane 4: nonsubtracted fibroblast cDNA.
FIG. 11E is a photographic representation of an ethidium bromide stained gel in which the subtracted and nonsubtracted cDNAs of cultured rat follicular papilla cells, rat fibroblasts and human skeletal muscle control were separated electrophoretically. Lane 1: subtracted follicular papilla cDNA; lane 2: nonsubtracted follicular papilla cDNA; lane 3: subtracted fibroblast cDNA; lane 4: nonsubtracted fibroblast cDNA; lane 5: subtracted control (human skeletal muscle cDNA mixed with ϕX174/Hae III, and then subtracted with a human skeletal muscle cDNA); and lane 6: nonsubtracted control (human skeletal muscle cDNA).

Identification of Follicular Papilla-Specific Genes by Subtraction cDNA Library To identify genes that are expressed preferentially in follicular papilla cells, a follicular papilla-specific subtraction cDNA library was constructed. Common messages were eliminated by hybridizing the cDNAs of cultured rat vibrissa follicular papilla cells ("tester") with those of fibroblasts that had been grown under identical culture conditions ("driver"). To examine the subtraction efficiency, a series of Southern blots were performed using the following probes: (1) follicular papilla-specific cDNAs, (2) fibroblast-specific cDNAs, (3) GAPDH, a housekeeping gene, and (4) FP-1, a novel gene identified from the subtraction library. The results showed a greater than 10 fold enrichment of FP-1 in the subtracted follicular papilla library (FIG. 11D), and a greater than 20 fold reduction of GAPDH in both the subtracted follicular papilla-specific library (FIG. 11C). These data indicated that a greater than 200 fold enrichment of the differentially expressed follicular papilla messages had been achieved. Indeed, when the follicular papilla-specific cDNAs were used as the probe (FP-probe), the signals of subtracted follicular papilla cDNAs (FIG. 11A, lane 1) were much stronger than those of subtracted fibroblast cDNAs (FIG. 11A, lane 3). On the contrary, when the fibroblast-specific cDNAs were used as a probe (F-probe), the signals of subtracted fibroblast cDNAs (FIG. 11B, lane 3) were much stronger than those of subtracted follicular papilla cDNAs (FIG. 11B, lane 1). These data indicated that the follicular papilla-specific cDNAs were enriched using the subtraction technique.

Figures 12A, 12B, 12C, 12D:
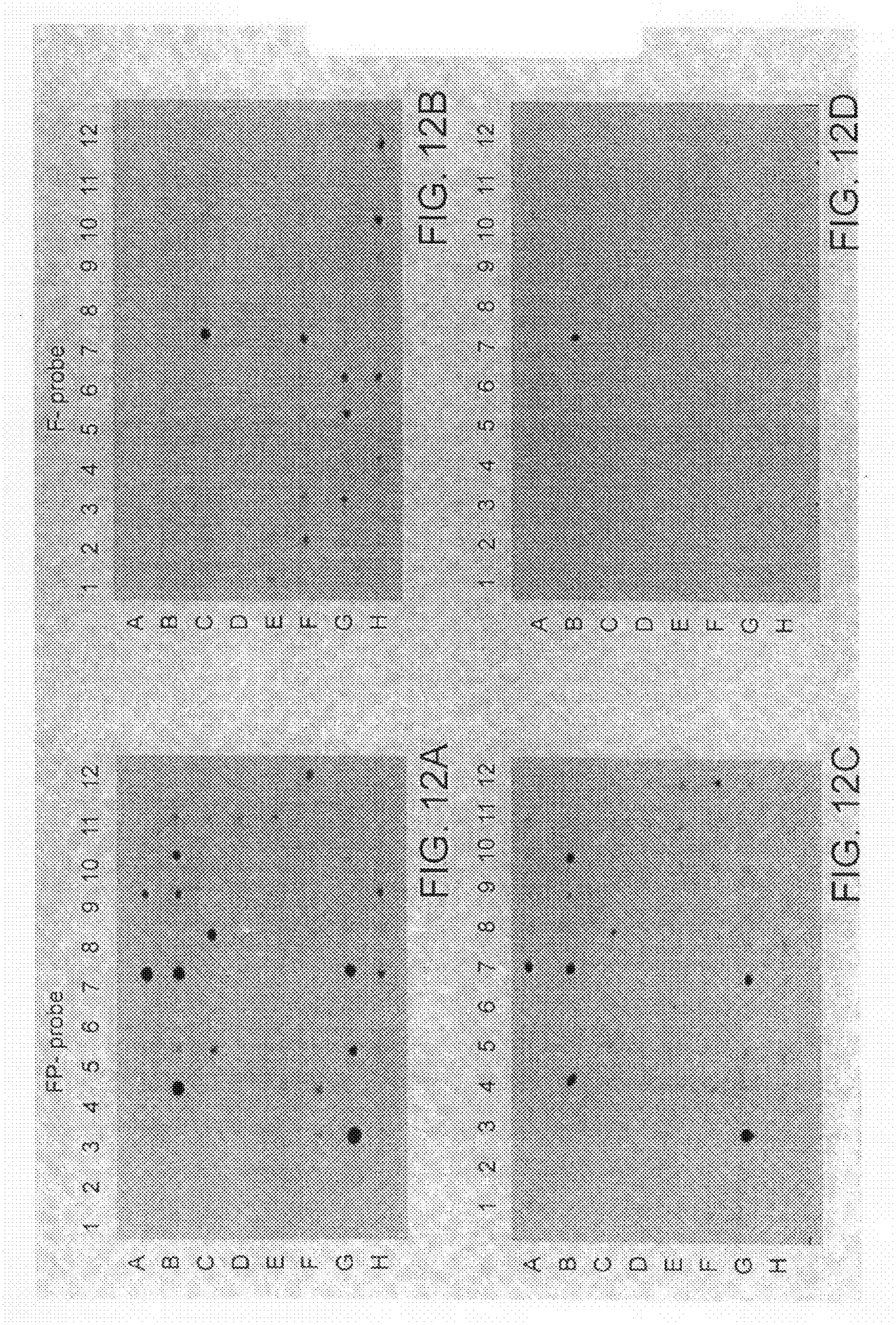
FIG. 12A is a photographic representation of a nylon membrane dotted with a cDNA array from randomly picked clones of the follicular papilla-specific subtracted library hybridized with the follicular papilla-specific cDNA (FP-probe). The following clones were used as negative controls: H1: a human homolog of a mouse testis-specific gene, and H2: human semenogelin II, which is specific to seminal vesicles.
FIG. 12B is a photographic representation of a duplicate of the cDNA array shown in FIG. 12A, but hybridized with the fibroblast-specific cDNA (F-probe).
FIG. 12C is a photographic representation of a nylon membrane dotted with a bacterial colony array from randomly picked clones of the follicular papilla-specific subtracted library hybridized with the follicular papilla-specific cDNA (FP-probe). The following clones were used as negative controls: H1: a human homolog of a mouse testis-specific gene, and H2: human semenogelin II, which is specific to seminal vesicles.
FIG. 12D is a photographic representation of a duplicate of the bacterial colony array shown in FIG. 12A, but hybridized with the fibroblast-specific cDNA (F-probe).

To identify the follicular papilla-specific clones in the subtracted library, a differential screening method was used. Randomly picked clones from the follicular papilla-specific subtracted library were hybridized with the follicular papilla-specific cDNAs (FP-probe) and fibroblast-specific cDNAs (F-probe) (FIG. 12). Clones representing differentially expressed poly A+ species in follicular papilla cells were expected to give strong signals with the FP-probe but weak or no signals with the F-probe (FIG. 12). Clones were considered as "follicular papilla-specific" only when the difference in signal intensity (FP/F) was greater than or equal to 5 fold. By screening 465 randomly picked clones from the follicular papilla-specific subtracted library, about 60 follicular papilla-specific clones representing 9 ESTs and 25 known sequences were obtained.

Figures 13A, 13B, 13C, 13D, 13E, 13F, 13G, 13H:
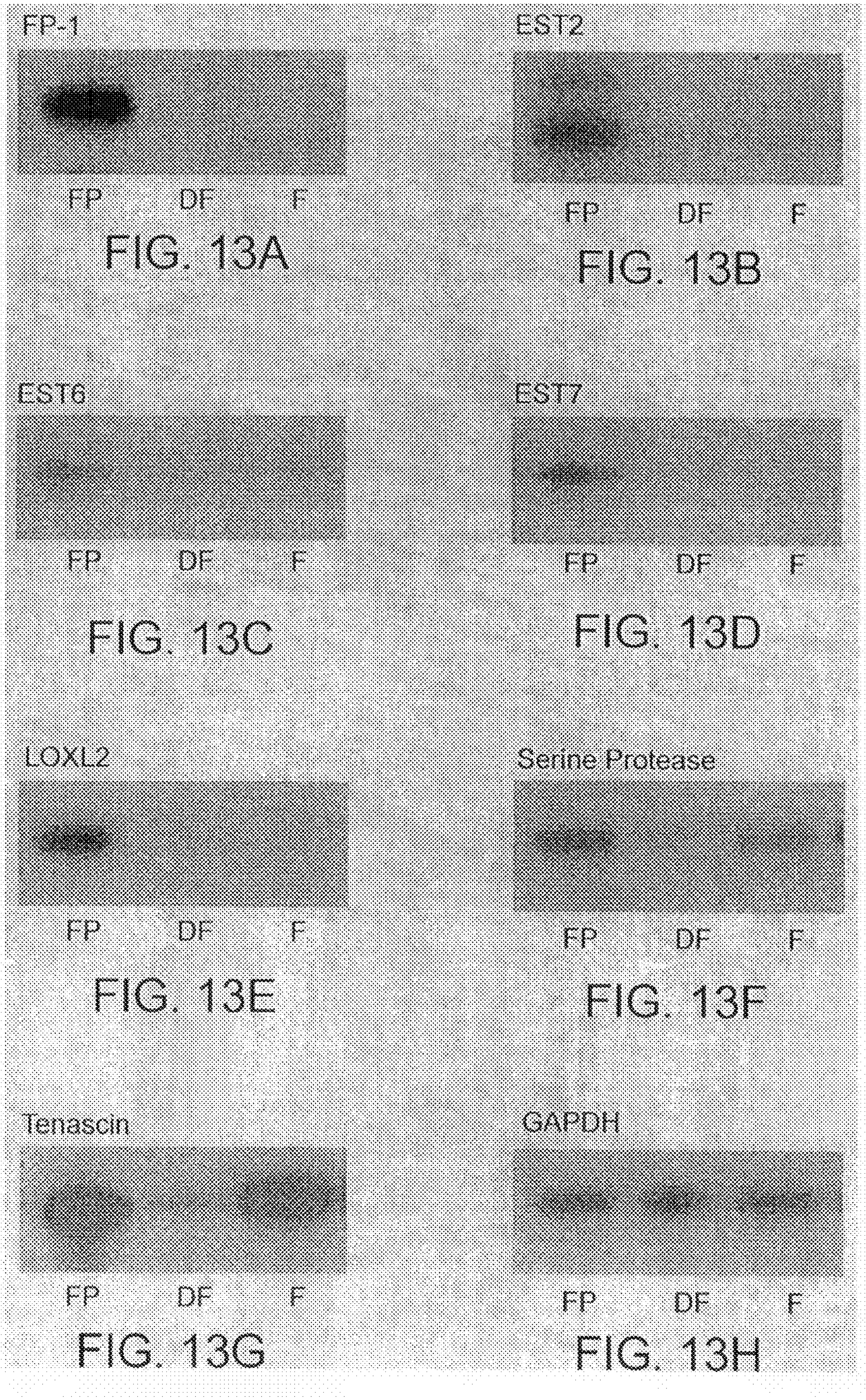
FIG. 13A is a photographic representation of a Southern blot hybridized with an FP-1 probe. FP: PCR-amplified double-stranded cDNAs of follicular papilla cells, F: PCR-amplified double-stranded cDNAs of fibroblasts (1:1:1 mixture of diaphragm, esophagus and stomach fibroblasts), and DF: PCR-amplified double-stranded cDNAs of dermal fibroblasts.
FIG. 13B is a photographic representation of the Southern blot hybridized with an EST2 probe.
FIG. 13C is a photographic representation of the Southern blot hybridized with an EST6 probe.
FIG. 13D is a photographic representation of the Southern blot hybridized with an EST7 probe.
FIG. 13E is a photographic representation of the Southern blot hybridized with a lysyl oxidase-like 2 (LOXL2) probe.
FIG. 13F is a photographic representation of the Southern blot hybridized with a serine protease probe.
FIG. 13G is a photographic representation of a Southern blot hybridized with a tenascin c probe.
FIG. 13H is a photographic representation of a Southern blot hybridized with a GAPDH probe.

To minimize the chance of eliminating follicular papilla-specific messages, a mixture of diaphragm, esophagus and stomach fibroblast cDNAs were used as the “driver” to construct the follicular papilla-specific subtraction library. To verify that the clones identified from the subtraction library were really differentially expressed in follicular papilla cells compared to dermal fibroblasts, virtual Northern blots were carried out by hybridizing PCR-amplified cDNAs from cultured cells with some of the identified clones, including EST1 (later named as FP-1), EST2, EST6, EST7, lysyl oxidase-like 2 (LOXL2), serine protease, and tenascin c. The results showed that all the cDNA clones examined by virtual Northern blots were indeed expressed at higher levels in follicular papilla cells than in the (non-dermal) fibroblast mixture (FIG. 13), again indicating the success of the subtraction. When cultured follicular papilla cells were tested against dermal fibroblasts, six out of the seven genes were found to be expressed at higher levels in follicular papilla cells than in dermal fibroblasts; only one, tenascin c, showed about equal intensity in these two cell types (FIG. 13). These data proved the follicular papilla-specificity of the genes identified from the subtraction library. From a gene expression profile point of view, the difference between follicular papilla and various types of fibroblasts was greater than the difference among the different fibroblasts.

Example 3

FP-1, a Novel Follicular Papilla Marker

Figures 14A, 14B, 14C:
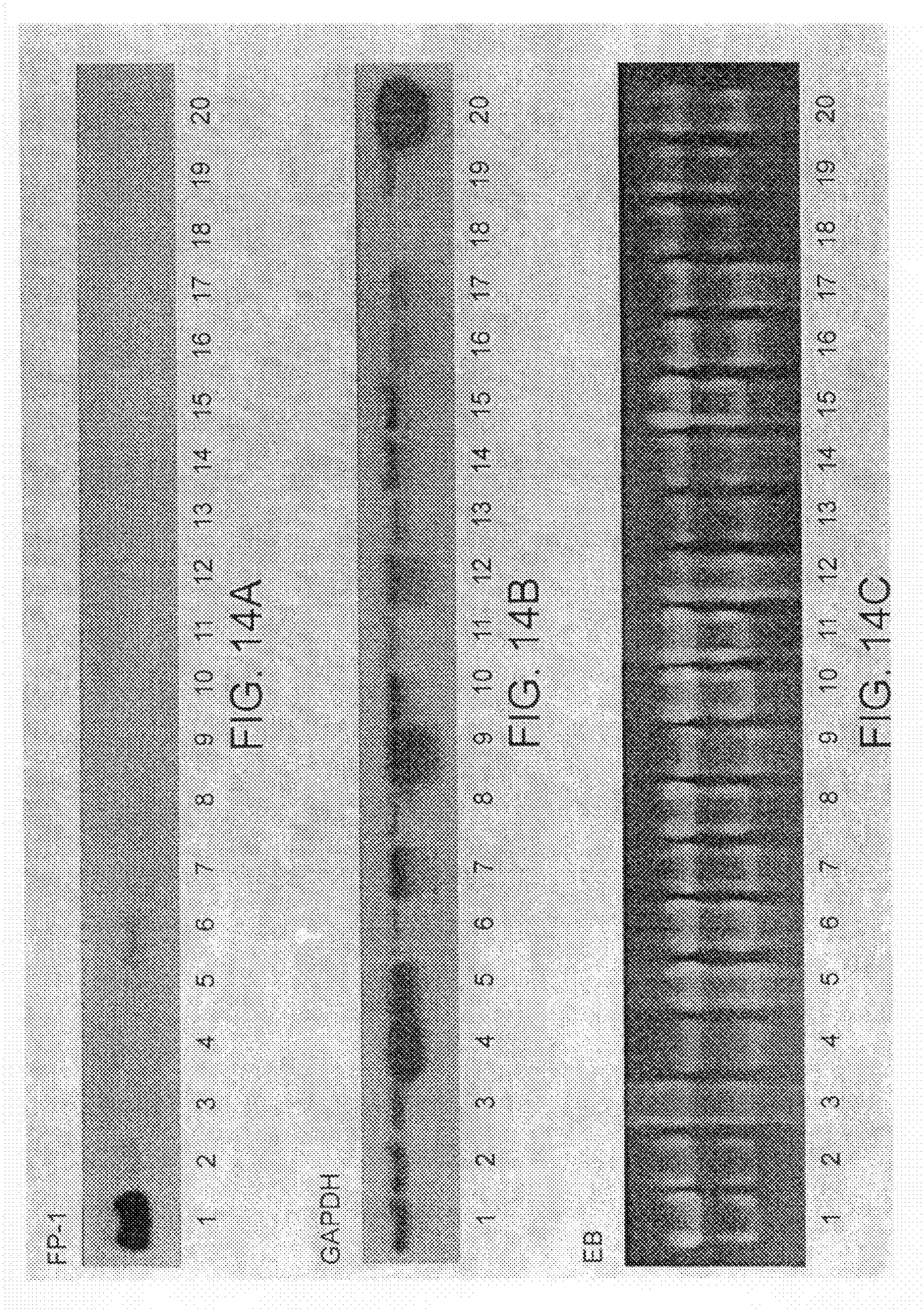
FIG. 14A is a photographic representation of a Northern blot hybridized with an FP-1 probe. Five micrograms of total RNA of cultured rat vibrissa follicular papilla cells (lane 1) and dermal fibroblasts (lane 2) and 10 μg of total RNA of 18 rat tissues (lane 3-20) were separated electrophoretically in a denaturing gel and subjected to Northern blot analysis. Lane 1: cultured follicular papilla cells; Lane 2: cultured dermal fibroblasts; Lane 3: skin; Lane 4: diaphragm; Lane 5: esophagus; Lane 6: stomach; Lane 7: brain; Lane 8: lung; Lane 9: heart; Lane 10: liver; Lane 11: spleen; Lane 12: kidney; Lane 13: bladder; Lane 14: intestine; Lane 15: colon; Lane 16: ovary; Lane 17: uterus; Lane 18: prostate; Lane 19: testis; and Lane 20: skeletal muscle.
FIG. 14B is a photographic representation of the Northern blot hybridized with a GAPDH probe.
FIG. 14C is a photographic representation of the gel stained with ethidium bromide.

Among the 25 known genes and 9 EST sequences that had been identified from the follicular papilla-specific subtraction library, EST1 (Genbank® Accession Number A1574756) was most abundant, represented by 8 independent clones. The expression level of this EST in cultured rat vibrissa follicular papilla cells was greater than 30 fold higher than that in cultured rat dermal fibroblasts (FIGS. 13 and 14). To further characterize this cDNA, its tissue distribution was examined in 18 rat tissues including skin, diaphragm, esophagus, stomach, brain, lung, heart, liver, spleen, kidney, bladder, intestine, colon, ovary, uterus, prostate testis, and skeletal muscle. This EST was only detected at relatively low levels in stomach and ovary, while the other 16 tissues were negative (FIG. 14A). Since these data indicated that this clone was preferentially expressed in follicular papilla, it was named “FP-1.”

To obtain the full-length cDNA sequence of FP-1, a cDNA phage library of cultured rat vibrissa follicular papilla cells was screened, and a 5' RACE (rapid amplification of cDNA ends) was also performed. The full-length FP-1 cDNA was 2332 bp, which had a 1647 bp coding region encoding 549 amino acids (FIG. 15). FP-1’s N- and C-terminus amino acid sequences have domains homologous to collagen triple helix repeat and an olfactomedin-like domain, respectively (FIG. 15). Computer analysis of the FP-1 protein sequence revealed that the N-terminal 31 amino acid residues of FP-1 is a signal peptide (FIG. 15), and that FP-1 has 6 potential glycosylation sites (FIG. 15).

Example 4

Immunoblotting and Immunofluorescence Studies

Figure 16A:
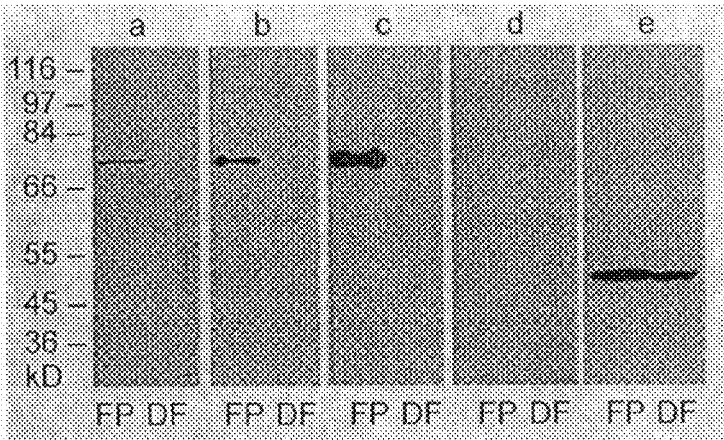
FIG. 16A is a photographic representation of a Western blot to test the antisera raised to FP-1. Total proteins of cultured rat vibrissa follicular papilla cells (FP) and dermal fibroblasts (DF) were separated electrophoretically on an SDS/polyacrylamide gel. Numbers on the left denote the positions of size markers in kilodalton (kDa). Immunoblots were performed using three separate FP-1 antisera (anti-epitopes 1, 2, and 3, panel a, b, c, respectively), pre-immune serum (panel d), and anti-β-tubulin antibody (panel e).
Figure 16B:
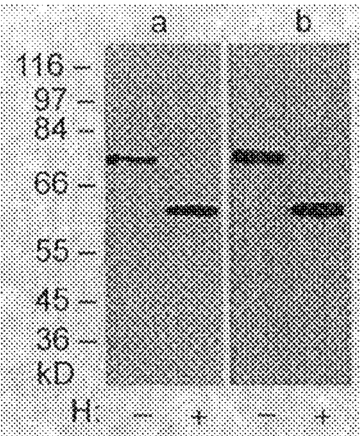
FIG. 16B is a photographic representation of a Western blot performed to test whether FP-1 was glycosylated. Total proteins of cultured rat vibrissa follicular papilla cells were digested with endoglycosidase-H (+) or left undigested (−) and the proteins were separated electrophoretically on an SDS/polyacrylamide gel. Immunoblotting was performed using two FP-1 antisera (anti-epitopes 2 and 3, panel a and b, respectively).
Figure 16C:
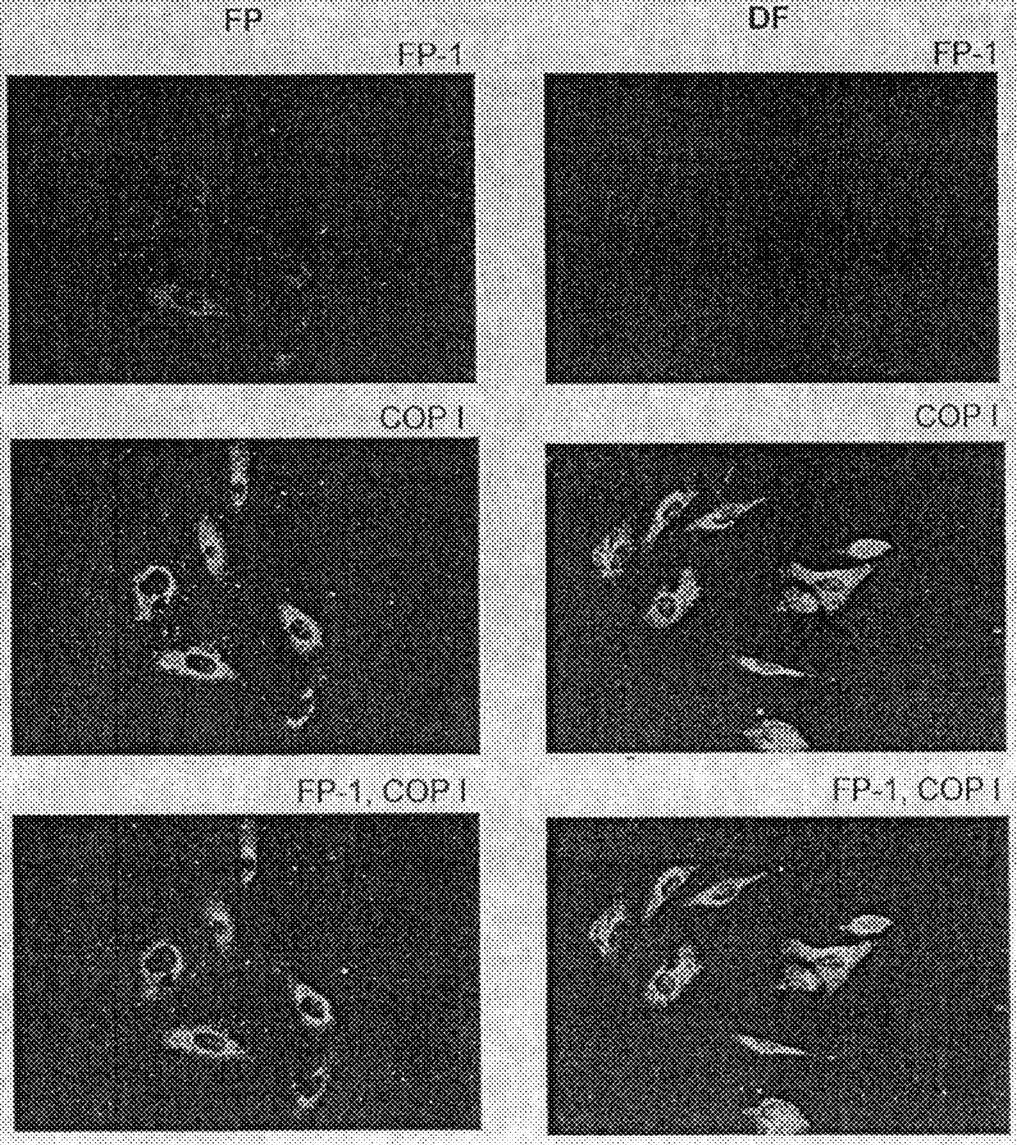
FIG. 16C is a photographic representation of immunofluorescent staining of FP-1 and COP I in cultured follicular papilla cells. Cultured rat vibrissa follicular papilla cells (FP) and fibroblasts (DF) at passage 4 were double stained with FP-1 rabbit antiserum (anti-epitope 3) and anti-COP I mouse monoclonal antibody.

To examine the protein expression pattern of FP-1, five polyclonal antibodies against FP-1 were generated (the five epitopes are indicated in FIG. 15). Immunoblot analysis showed that three of the FP-1 antisera (anti-epitopes 1, 2, and 3) recognized a single protein band of about 72 kDa in cultured rat follicular papilla cell lysate, with no detectable signals in cultured fibroblast cell lysate (FIG. 16A). Immunofluorescent staining of cultured follicular papilla cells at passage 4 using the FP-1 antisera showed very strong cytoplasmic signals in follicular papilla cells, but negative signals in fibroblasts (FIG. 16C). These data verified that FP-1 was preferentially expressed in cultured follicular papilla cells compared to fibroblasts. Staining of COP I, a Golgi complex marker, overlapped with FP-1 staining, even though FP-1 staining had a broader area (FIG. 16C).

Consistent with the presence of several potential N-glycosylation sites, FP-1 is a glycoprotein. After digestion with endoglycosidase-H, the molecular weight of FP-1 decreased to 60 kDa (FIG. 6B).

Example 5

Temporal Expression of FP-1

To analyze at what time point FP-1 expression was turned on in follicular papilla cells under cultured conditions, immunofluorescent staining was performed using primary cultures 4, 7, and 10 days after microdissection. Starting from day 4, all the cells of the whole colony derived from a follicular papilla were FP-1 positive, whereas cultured fibroblasts were always FP-1 negative (data not shown). Staining was not performed at earlier time points.

Example 6

Survey of Existing FP-1 Mouse Mutants

Since FP-1 is abundantly expressed in follicular papilla cells, which are essential for hair growth, tests were done to determine whether the gene localized to any of the loci corresponding to the 196 mouse mutants that had a hair-related phenotype in the Jackson Laboratory database (Bar Harbor, Me.).

Figures 17A, 17B, 17C, 17D:
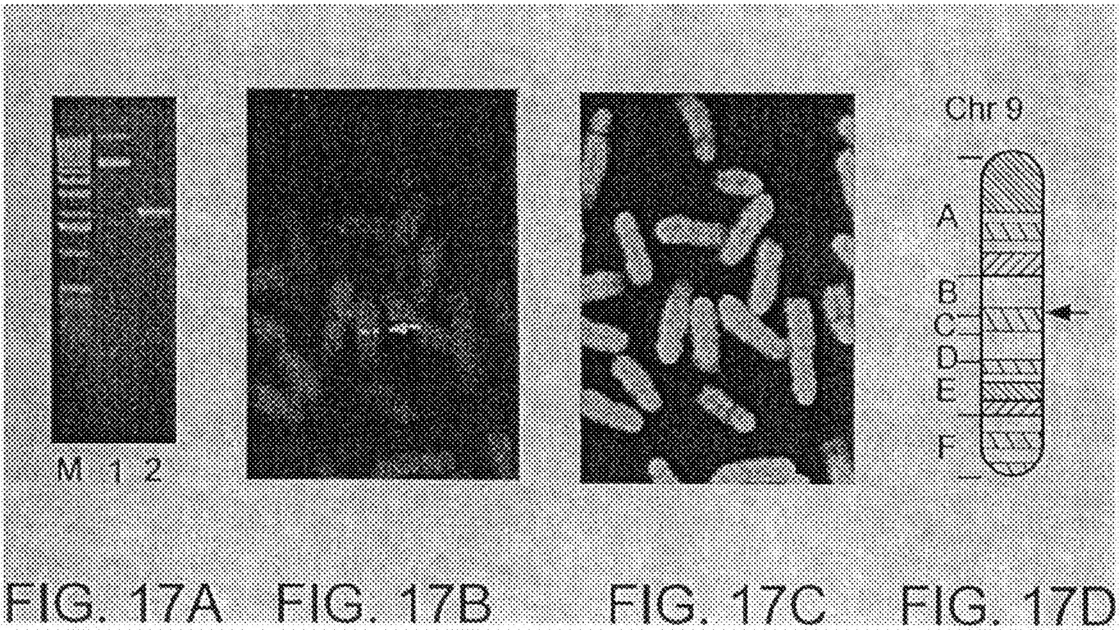
FIG. 17A is a photographic representation of an ethidium bromide-stained gel showing the probe used for fluorescent in situ hybridization (FISH). A 2.1 kb rat FP-1 cDNA fragment (lane 2) was amplified by PCR using the plasmid containing the longest FP-1 clone (lane 1) as template.
FIG. 17B is a photographic representation of a biotin-labeled rat FP-1 probe localizing specifically to a mouse chromosome (arrow).
FIG. 17C is a photographic representation of DAPI staining of mouse chromosomes confirming that mouse FP-1 gene is localized on chromosome 9.
FIG. 17D is a diagrammatic representation of mouse chromosome 9 showing the position of the FP-1 gene as the 9B-C region (arrow).

To determine whether FP-1 mapped to any of these existing mouse hair mutants, a cross-species fluorescent in situ hybridization (FISH) on mouse chromosomes using rat FP-1 cDNA as a probe was performed. The FISH analysis indicated that FP-1 was on mouse chromosome 9 B-C region (FIG. 17). Significantly, there are 3 hair-related mutants, including rough fur (ruf), rough coat (rc), and fur deficient (fd) in this region.

To examine whether there were any gross changes in the FP-1 gene in these 3 mouse mutants, a genomic Southern blot was performed. After digestion with 7 different restriction enzymes, the genomic DNA of homozygous and heterozygous mutants and their background strains (considered as wild type to the mutations) were compared. A size change greater than 1 kb due to insertion or deletion, which occurs frequently in the mouse genome, could in theory be detectable by this approach. However, no significant difference in the FP-1 sequence was found in all the 3 mutants suggesting that there was no deletion or insertion of a big DNA fragment (greater than 1 kb) within the genomic region close to FP-1 in these mutants (data not shown). Of course, it must be remembered that this finding does not rule out the possibility that there are other mutations in any of these genes, which cannot be detected by this approach.

Example 7

Immunolocalization of FP-1

To investigate FP-1 localization in hair follicles in vivo, indirect immunofluorescence staining of the depilated mouse back skin using FP-1 antiserum was performed. Back skin of C57BL/6 mice was collected on different days after depilation, snap-frozen, and cryo-sectioned. The sections were fixed with 1:1 methanol/acetone (4° C.), air-dried, and stained by indirect immunofluorescence using the tyramide signal amplification (TSA) system (Perkin Elmer). Polyclonal G320 antibody was used for staining at a dilution of 1:5,000 to 1:20,000. As a control, a preimmune serum at a comparable concentration, and an FP-1 antibody that was blocked by a peptide that bound the FP-1 antibody (the original antigen used to generate the G320 antibody) was used. Specifically, the peptide blocking experiments were performed, using the G320 antibody pre-incubated at 25° C. with the FP-1 peptide having the sequence PNDDTLVGRADEKVNERHSPQT (aa 276-297 of rat FP-1; SEQ ID NO:27). The antibody: peptide ratio for the blocking experiment was 1:4, and the antibody was incubated with the peptide for 45 minutes before the FP-1 antibody was used to stain the sections in the control experiments.

Figure 18:
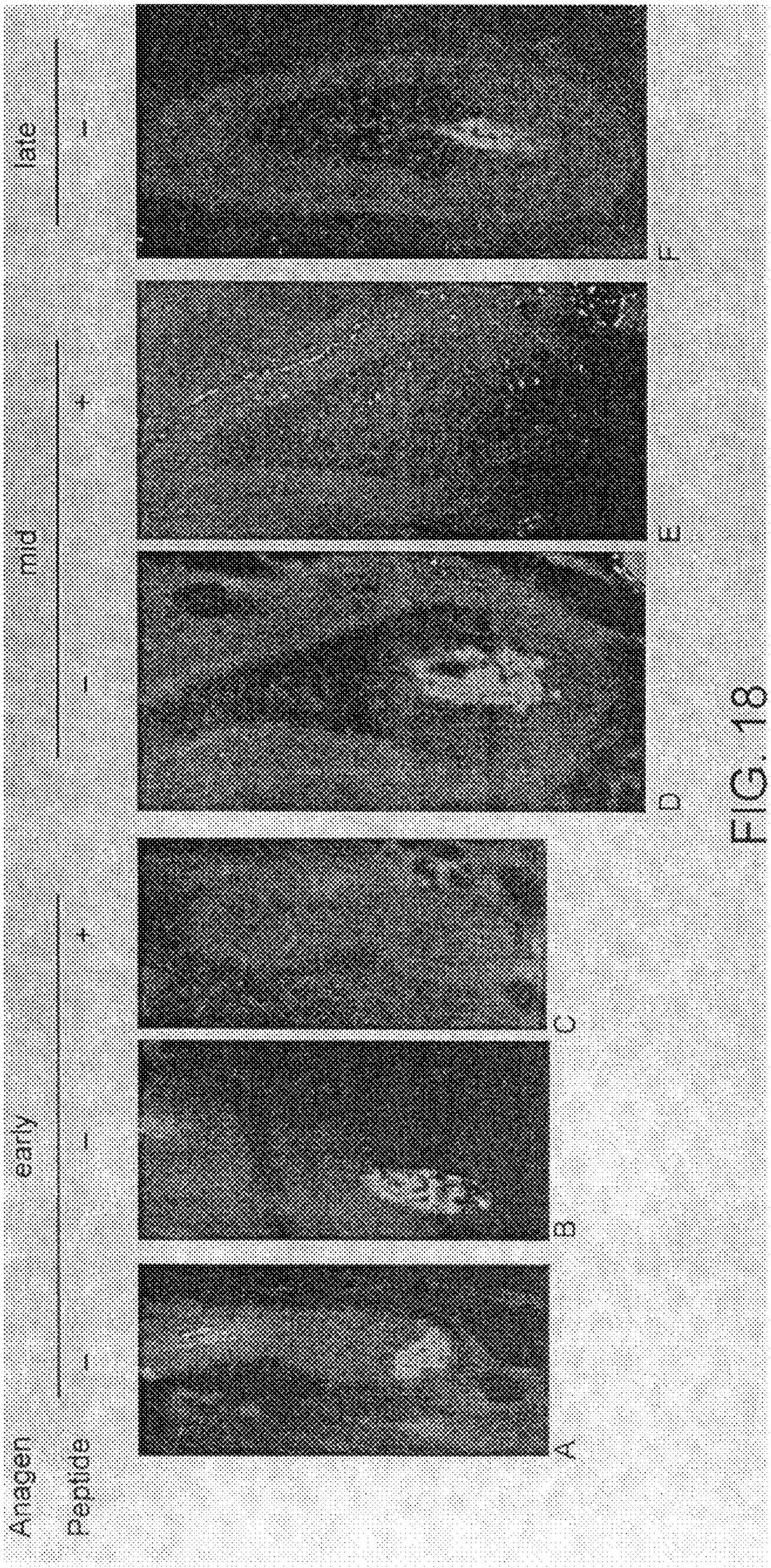
FIG. 18A is a photographic representation of immunofluorescent staining of FP-1 on C57BL/6 mouse back skin at 3 days after hair depilation.
FIG. 18B is a photographic representation of immunofluorescent staining of FP-1 on C57BL/6 mouse back skin at 5 days after hair depilation.
FIG. 18C is a photographic representation of immunofluorescent staining of FP-1 on C57BL/6 mouse back skin at 5 days after hair depilation. In this case, note that the FP-1 antiserum was pre-adsorbed with peptide antigen prior to staining.
FIG. 18D is a photographic representation of immunofluorescent staining of FP-1 on C57BL/6 mouse back skin at 8 days after hair depilation.
FIG. 18E is a photographic representation of immunofluorescent staining of FP-1 on C57BL/6 mouse back skin at 8 days after hair depilation. In this case, note that the FP-1 antiserum was pre-adsorbed with peptide antigen prior to staining.
FIG. 18F is a photographic representation of immunofluorescent staining of FP-1 on C57BL/6 mouse back skin at 12 days after hair depilation.

FP-1 was strongly expressed in the follicular papillae during the anagen phase (FIG. 18), but not in the catagen and telogen phases of the hair cycle (data not shown). This hair-cycle dependent expression pattern strongly suggested that FP-1 is involved in the control of hair growth. No staining was noted in the epidermis and other skin cells.

To analyze FP-1 expression in the follicular papilla cells under the cultured conditions, we performed immunofluorescent staining using primary cultures 4, 7 and 10 days after plating. Starting from day 4, all the cells of the whole colony derived from a follicular papilla were FP-1 positive, whereas FP-1 was barely detectable in cultured fibroblasts (FIG. 16B).

Example 8

Inhibition of FP-1 Function In Mouse Skin by Antibodies

Purified polyclonal or monoclonal antibodies that specifically bind to FP-1 are used to block FP-1 activity in the hair follicle in vivo. As a control, peptide-blocked FP-1 antibody prepared as described in Example 7, is used. For example, antibodies are purified using commercial kits, and used at several concentrations (i.e., 1 μg/ml to 1 mg/ml) and based on titration studies the concentration of antibody to be used in the experiments outlined below is determined.

Mice that are around day 35 of life are in a prolonged telogen phase. In the first experiment, mice around day 38 of life are anesthetized, and each of the mice are implanted intraperitoneally with two Alzet osmotic minipumps (Model 2001; Alza Corp., Palo Alto, Calif.). The minipumps are each loaded with 200 μl of FP-1 antibody, or peptide-blocked FP-1 in phosphate buffered saline (PBS) at the concentration determined by the titration studies. The FP-1 antibody, or preimmune antibody, or peptide-blocked FP-1 antibody, is provided systemically for approximately 14 days. The hair of the mice are plucked on day 42 (Wilson et al., *Differentiation*, 55:127-136, 1994). Mice are then sacrificed every 2 days for 17 days and the length of the hair from the dermal papilla to the skin surface is measured. The FP-1 antibody treated and control mice are compared to check whether there are differences in hair growth. Hair growth can be assessed based on the elongation rate of the hair fibers that is measured by clipping the fibers that are exposed on the skin surface. In addition, the hair cycle is analyzed by using histological methods to determine whether the follicle is in anagen, catagen, or telogen (Wilson et al., *Differentiation*, 55:127-136, 1994).

In the second experiment, 200 μl of FP-1 antibody, or the preimmune antibody, or the peptide-blocked FP-1 antibody, at the concentration identified in the titration experiments are injected subcutaneoulsly every 2 days for 15 days (Cotsarelis et al., *Cell* 61:1329-1337, 1990; Taylor et al., *Cell* 102:451-461, 2000). At the end of the subcutaneous injections, mice are sacrificed every 3 days for 15 days and the length of the hair fibers that are exposed on the skin surface is measured as mentioned above, and the length of the follicule from the dermal papilla to the skin surface is measured by histological examination. The FP-1 antibody-treated and control mice are compared to check whether there are differences in hair growth.

In both experiments described above, the FP-1 antibodies bind and neutralize FP-1 thus blocking its in vivo activity. In contrast, the preimmune antibodies and peptide-blocked FP-1 antibody do not impair the in vivo activity of FP-1.

Blocking FP-1 activity using neutralizing FP-1 antibodies results in inhibition of hair growth. However, the peptide-blocked FP-1 antibody (or pre-immune sera or control antibodies that are raised against intracellular antigens such as keratins, if used in the above experiments) show minimal, if any, effects on hair growth. Immunolocalization studies show that mouse skin of FP-1 antibody-treated mice has antibody staining in the extracellular matrix zone of the follicular papilla.

Example 9

Inhibition of FP-1 in Cultured Rat Vibrissa Follicular Papilla Cells

FP-1 expression is inhibited in cultured rat vibrissa follicular papilla cells using inhibitory agents such as antibodies to FP-1, antisense molecules, ribozymes and/or siRNA molecules directed to rat FP-1.

Prediction of suitable siRNA targets and siRNAs are possible using many different sources, (see, for example "siRNA Selection Program," Whitehead Institute for Biomedical Research, 2003; Ambion's siRNA Target Finder, etc.). Examples of siRNA target sequences and sense and antisense strand siRNAs for use in this experiment include:

(i) Target Sequence: 5' AATTAAGTCGTGCGCCAGCCC 3' (SEQ ID NO:15), (corresponding to 257-279 of SEQ ID NO.1); Sense Strand siRNA: 5' UUAAGUCGUGCGCCAGCCCtt 3' (SEQ ID NO:16); Antisense strand siRNA: 5' GGGCUGGCGCACGACUUAAtt 3' (SEQ ID NO:17); and (ii) Target Sequence: 5' AATGATGATACCTTGGTGGGG 3' (SEQ ID NO:18), (corresponding to 874-896 of SEQ ID NO:1); Sense Strand siRNA: 5' UGAUGAUACCUUGGUGGGGtt 3' (SEQ ID NO:19); Antisense strand siRNA: 5' CCCCACCAAGGUAUCAUCAtt 3' (SEQ ID NO:20); and (iii) Target Sequence: 5' AATGAGCGCCATTCTCCACCAA 3' (SEQ ID NO:21), (corresponding to 913-935 of SEQ ID NO:1); Sense Strand siRNA: 5' UGAGCGCCAUUCUCCACAAtt 3' (SEQ ID NO:22); Antisense strand siRNA: 5' UUGUGGAGAAUGGCGCUCAtt 3' (SEQ ID NO:23); and (iv) Target Sequence: 5' AACCCATGATCACGTCCATTG 3' (SEQ ID NO:24), (corresponding to 938-960 of SEQ ID NO:1); Sense Strand siRNA: 5' CCCAUGAUCACGUCCAUUGtt 3' (SEQ ID NO:24); Antisense strand siRNA: 5' CAAUGGACGUGAUCAUGGGtt 3' (SEQ ID NO:26).

Methods of using siRNA to knock down expression of a target gene are well known in the art (Kittler et al., *Semin. Cancer Biol.,* 13(4):259-65, 2003; Scherr et al., *Curr. Med. Chem.,* 10(3):245-56, 2003; and Hudson et al., *Trends Cell Biol.,* 12(6):281-7, 2002).

After treatment of cells with a FP-1 inhibitory agent that inhibits or prevents expression of FP-1, the expression of FP-1 mRNA is tested by Northern blot analysis using well-established methods (Sambrook et al., cited supra). FP-1 protein levels are tested using Western blot analysis using antibodies to FP-1.

The effect of inhibiting FP-1 on the morphological and proliferative properties of the follicular cells is also tested. Neutralizing antibodies to FP-1, FP-1 antisense molecules, FP-1 ribozymes and FP-1 siRNA molecules are expected to cause the cultured rat vibrissa cells to aggregate and suppress their growth. Immunolocalization of FP-1 antibody is expected to show it binding to both the cell surface and the extracellular matrix that is deposited on the plastic dish surface. It is also expected that preimmune sera from healthy rabbits, control antisense, ribozyme and siRNA molecules show no effects on the morphology and growth properties of the cultured vibrissa cells.

Example 10

Isolation of Follicular Papilla Cells from Skin

Rat vibrissa and mouse pelage follicular papilla are surgically isolated as described in Example 1 and dissociated into single cells by trypsinization. The rat follicular papillae are minced and treated with 0.2% trypsin in PBS at 37° C. with stirring for 30-45 minutes. The loosened tissues will be pipetted several times to suspend the cells. The single cells that are released by this procedure will be counted and mixed with an equal volume of DMEM medium containing 10% calf serum that inhibits trypsin. These cells are then treated with rabbit antibodies to FP-1 (see, Example 1), followed by fluorescein-conjugated goat anti-rabbit-IgG antibody (Jackson Laboratories). The cell-surface fluorescein-labeled, FP-1 positive cells are then isolated by fluorescein-activated cell sorting.

Alternatively, magnetic beads (4.5 μm; DYNABEADS® from DYNAL® or MACSiBead™ from Miltenyi Biotec) that are precoated with sheep anti-rabbit IgG antibody are used to adsorb rabbit anti-FP-1 antibodies, which are then used for isolating follicular papilla cells. A dissociated, single cell suspension (as obtained above) containing a mixture of follicular papilla cells and other non-follicular papilla cells (such as the dermal fibroblasts) are mixed with the FP-1 coupled magnetic beads. The FP-1 antibody-coupled magnetic beads coated with the adherent cells are then separated from the non-adherent cells by applying a magnetic field (e.g., OPTICELL@ magnetic separation, or magnetic plate, Dynal, Inc., Lake Success, N.Y.). The magnetic beads are then washed with phosphate buffered saline (PBS). Finally, the cells that have bound to the FP-1 antibodies are dissociated by a brief treatment with low pH buffer or with 0.05% trypsin in PBS, or other suitable conditions. The cells that are bound by FP-1 antibody are follicular papilla cells.

Example 11

Hair Reconstitution Experiments

The nude mouse graft model system originally described by Lichti et al. (*J. Invest. Dermatol.,* 101:124S-129S, 1993) is used for testing the role of FP-1 in regulating hair growth. In this system, a mixture of epidermal and dermal cell preparations from newborn mice are grafted onto the backs of athymic nude mouse hosts, resulting in the in vivo reconstitution of hair follicles (Lichti et al., ibid; Weinberg et al., *J. Invest. Dermatol.,* 100:229-236, 1993). Neutralizing antibodies to FP-1 (monoclonal or polyclonal antibodies), that are either perfused into the athymic nude mice system via injection of the antibody into either the left ventricle or a tail vein, or injected subcutaneously, inhibit the reconstitution of the hair follicle.

In a different approach, cultured follicular papilla cells are transfected with either FP-1 cDNA (a/b). It is expected that such FP-1 over-expressing FP cells are particularly active in supporting hair reconstitution in the athymic nude mouse hosts. In striking contrast it is expected that follicular papilla cells transfected with antisense FP-1 cDNA, or an FP-1 cDNA encoding a dominant negative FP-1 protein, or siRNA that inhibits or prevents expression of FP-1 have a diminished ability to support hair reconstitution in athymic nude mouse hosts. Hair growth can be measured using methods as described in Chamberlain et al., *Australasian J. Dermat.,* 44:10-18, 2003.

Example 12

Determination of Mitogenic Activity of Recombinant FP-1

Isolated human hair follicles are maintained in individual wells of 24-well multiwell plates containing 1 ml of KBM media (Clonetics) supplemented with 100 U/ml penicillin, 10 ng/ml hydrocortisone, 75 μg/ml bovine pituitary extract in an atmosphere of 5% $CO_2$/95% air.

The cell growth of hair follicles is measured by calorimetric MTS assays (Bunger et al., *Artif. Organs.,* 26(2):111-116, 2002; and Vorauer et al., *J. Biochem. Biophys. Methods,* 32(2):85-96, 1996). Specifically, FP-1 is added to culture media at different concentrations at different concentrations (from about 10 ng/ml, about 30 ng/ml, about 100 ng/ml, and about 1 μg/ml), and the isolated human hair follicles are incubated in these media with human FP-1 for 48 hrs before measuring by MTS assay.

A single hair follicle is then plated in a 96-well microtiter per well (see, Philpott et al., supra; Philpott et al., *J. Dermotol. Sci.* 7 *Suppl,* S55-72; and Philpott et al., J Invest Dermatol., 102:857-861); and proliferation is measured 4 hr later using a calorimetric MTS assay according to the manufacturer's suggestions (Promega). In each experiment, observations (n=8 hair follicles per group) are performed and the values are reported as mean +/−standard error (S.E.). In the proliferation assay, the negative control is evaluated using untreated hair follicle cells.

The addition of FP-1 results in dose-dependent stimulation of human hair follicle cells.

Example 13

Liposome-Mediated Delivery of FP-1 to Hair Follicles

To achieve targeted delivery of FP-1 to hair follicles, the following protocol is carried out.

Liposomes are prepared by sonication. About 20 mg of egg phosphatidycholine is rotary evaporated with a vacuum drier from a chloroform solution to form a thin film on the walls of a 5 ml round-bottomed flask for about 1 hr. The dried thin film phospholipid is suspended in about 0.5 ml phosphate buffered saline (pH 7.4) on a vortex mixer and then is sonicated with a Branson probe-type sonicator fitted with a microtip at power level 3 for about 8 min. Then 0.5 ml of a solution of mouse FP-1 protein (10 mg/ml) is entrapped with the above suspension by sonication for about an additional 4 min. Liposomes are separated from the non-entrapped FP-1 by gel-filtration on a Sepharose 4B column equilibrated with phosphate buffered saline.

Pieces of outbred white-haired mouse skin derived from 1 to 2 week-old animals (about 2×5×2 mm each) is harvested under a dissection microscope. The samples are then histocultured on collagen-gel supported sponges as described U.S. Pat. No. 6,224,901. Liposome interaction with the skin is initiated after about 24 hrs of histoculture. Mouse skin histocultures are incubated for about 12 hrs with liposomes. As a control, a solution of "free" FP-1 at the same concentration as is used in the liposome preparation is also incubated for about 12 hrs with pieces of the histocultured skin.

Example 14

Liposome-Mediated Delivery of Nucleic Acid to Hair Follicles

About 50 ng of an expression vector comprising DNA encoding mouse FP-1 is purified for liposomal delivery to cultured mouse cells.

Liposomes are prepared by freezing and thawing. About 20 mg of egg phosphatidylcholine (EPC) is rotary evaporated with a vacuum drier from a chloroform solution to form a thin film on the walls of a 5 ml round-bottomed flask for about 1 hr. The dried film phospholipid is suspended in about 0.5 ml phosphate buffered saline solution at a pH of about 7.4 in a vortex mixer and is then sonicated with a Bronson probe-type sonicator fitted with a microtip at power level 3 for about 8 min. The 0.5 ml of FP-1 DNA solution is added to the above suspension by extensive vortexing for about 1 minute and is followed by freezing and thawing. Liposomes are separated from the non-entrapped DNA by gel-filtration on a Sepharose 4B column that is equilibrated with PBS. About 50 μl calcein (about 10 mg/ml) is added into the solution in order to mark the liposomes during the separation.

Pieces of outbred white-haired-mouse skin (about 1×5×2 mm) derived from 1 to 5-week-old animals are harvested under a dissection microscope and then histocultured on collagen-gel-supported sponges as described in U.S. Pat. No. 6,224,901. Liposome interaction with the skin is initiated after about 24 hrs of histoculture. Mouse skin histocultures are then incubated for about 44 hrs with liposomes. As a control, a solution of naked DNA (lacking any inserted cDNA) at the same concentration is used in the liposome preparation and is also incubated with skin histocultures. The effects of the liposome-delivered FP-1 cDNA, or antisense RNA, or siRNA, on hair growth is assessed by measuring the length of the hair fibers exposed on the skin surface, and by measuring the length of the follicle in the skin by histology as mentioned in Example 10.

Example 15

Effect of Expressing FP-1 on Mammalian Hair Growth

An expression cassette is created, placing the entire cDNA for the murine FP-1 gene under the control of the HCMV immediate early promoter/enhancer and linked to the poladenylation sequence from SV40. This cassette is subcloned by standard methods into the deleted E1 region of an E1−/E3− adenovirus vector. Recombinant viruses are isolated, and correct insertion of the expression cassette is verified by Southern hybridization and DNA sequence analysis. The recombinant vector (termed AdFP1) is thereafter purified and grown to high titer.

Groups of 2 to 4, 7 g, 3-week-old C57 Bl/6 mice are injected intradermally with $1\times10^8$ pfu of either AdFP1, a control E1−/E3− vector lacking the FP-1 cDNA, or a sham injection of saline. After seven days, skin in the area of injection is removed from the injected animals, as well as naive animals, and is analyzed.

Northern hybridization of the excised skin patches reveals the presence of elevated levels of FP-1 mRNA in skin patches injected with AdFP1 but not in sham-injected patches, naive patches, or patches injected with the E1−/E3− control adenoviral vector. Blots of mRNA from the various skin patches are also probed for the expression of hair-specific gene expression, specifically the hair-specific keratin gene (ghHb-1), that is expressed mainly during anagen, which is the growing phase of the hair follicle. Northern blots reveals the presence of some ghHb-1 mRNA in all excised skin patches; however, the level of ghHb-1 signal is more pronounced in the skin injected with AdFP1 than in sham-injected patches, naive patches, and patches injected with the E1−/E3− control adenoviral vector. The excised skin patches above are visually examined to assess the effect of each treatment on hair growth in the area. To permit such evaluation, the mice are treated carefully during the protocol so as not to induce hair growth by the manner in which they are handled generally. Hair growth is assessed by measuring the length of the hair fibers exposed on the skin surface, and by measuring the length of the follicle in the skin by histology as mentioned in Example 10

Melanogenesis, a pigment synthesis process that occurs in association with hair growth, is evaluated using digital image analysis. Specifically, light is passed through the excised patches and the intensity of transmitted light is measured by determining the average gray scale of a digitally collected image of the transmitted light. The optical density (relative light absorbance) at the injection site is compared with the optical density of the same skin patch at a site distant from the injection site. This analysis is expected to reveal that the optical density of the excised skin patches that are injected with AdFP1 is consistently greater at the site of injection than distal from the injection or that is observed anywhere in sham-injected patches, naive patches, and patches injected with the E1−/E3− control adenoviral vector.

The growth phase of the hair follicle cycle is associated with morphologic changes in follicles including an increase in size of the follicle, which can be recognized as an increase in the area of the follicle relative to total dermal/epidermal area. To evaluate hair follicle size, digital images of cross sections of skin patches are collected and analyzed by integrating the number of pixels occupied by either hair follicles or by total dermis/epidermis. The quotient of the two measurements gives the percentage of area occupied by hair follicles. This analysis is expected to reveal that the percentage of skin represented by mature hair follicles is consistently greater in the excised skin patches that are injected with AdFP1 than that is observed in sham-injected patches; naive patches, and patches injected with the E1−/E3− control adenoviral vector.

These results indicate that transfer of a gene encoding an FP-1 protein promotes hair growth in the skin. That follicular area increases suggests the presence of larger hair follicles in anagen phase that were actively producing hair shafts. This result is important given the fact that alopecia is often correlated with increased likelihood of finding hair follicles in telogen phase, and that AdFP1 apparently induces anagen within a population of hair follicles initially in telogen.

Example 16

Identification of the FP-1 Regulatory Elements

The promoter of the mouse FP-1 gene is isolated by screening a mouse genomic library using PCR methods (Auch et al., *Nuc. Acids Res.,* 18: 6743-6744, 1990; and Garces et al., *Methods Mol. Biol.,* 161:3-8, 2001). Several overlapping clones are isolated and characterized by restriction mapping and partial sequencing. Combination of these data and the available mouse genomic sequence database allows the identification of the genomic clones having the longest 5'-upstream sequence. A segment of 3 to 6 kb 5'-upstream sequence is inserted into a suitable restriction site upstream from a lacZ reporter gene (Lin et al, Proc. Natl. Acad. Sci. USA, 92:679-683, 1995; Mercer et al., *Neuron* 7:703-716, 1991; Peschon et al., *Proc. Natl. Acad. Sci. USA,* 84:5316-5319, 1987). The fusion gene is excised by using suitable restriction enzymes, gel-purified and microinjected into fertilized mouse eggs, which are implanted into CD-1 foster mothers. The lacZ transgene is identified by Southern blot analysis of the tail DNA. Positive founder mice are back crossed with C57BL/6J×DBA2 F1 hybrids to generate hemizygous animals that are used for studying transgene expression. The promoter activities of the 5'-upstream sequence of various lengths ranging from 1 kb to 5 or 6 kb is tested to compare their expression pattern to identify the minimal sequence that achieves follicular papilla-specific expression of the lacZ reporter gene.

Example 17

Construction of FP-1 Transgenic Mice

FP-1 transgenic mice, which overexpress FP-1, or derivatives (e.g., any of the coding regions of FP-1 smaller than the full length), mutants, or variants thereof, in a follicular papilla-specific manner are constructed by operably linking a promoter that is follicular papilla-specific (for example, the promoter of the FP-1 gene, or the promoter of versican (Kishimoto, J. R. Ehama, et al., *Proc. Natl. Acad. Sci. USA,* 96 (13): 7336-41, 1999) to a FP-1 cDNA, or any portion thereof. The generation of such transgenic mice is done using standard techniques (Joyner, *Gene Targeting*, Oxford University Press, New York, 2000, (*Practical Approach Series;* 212), i-xviii).

For example, an appropriate fusion gene, comprising any follicular papilla-specific promoter operably linked to a mouse or rat FP-1 full-length cDNA, is first constructed. The fusion gene is excised from the construction vector, gel purified, and microinjected into fertilized mouse eggs (from F1 hybrids of c57BL/6J×DBA2), which can then be implanted into CDE-1 foster mothers. The transgene is identified by Southern blot analysis of tail cDNA using the mouse FP-1 cDNA as probe. Positive founder mice can be back crossed with c57BL/6J×DBA2 F1 hybrids to generate hemizygous and later homozygous mice. Over-expression of FP-1, which is normally expressed transiently during the anagen (or growing) phase of the hair cycle, prolongs the anagen phase of the hair cycle leading to longer hair fibers.

Example 18

Construction of FP-1 Knock-Out Mice

The ablation of the FP-1 gene in mice is done using standard techniques. Briefly, genomic clones of mouse FP-1 gene are isolated from a 129/Ola mouse P1 genomic library. A targeting vector can be designed to delete the third and fourth exons of the FP-1 gene; this vector can contain four portions; an approximately 3-5 kb mouse FP-1 fragment upstream of exon 2, a neomycin-resistance gene (neo) driven by the phosphoglycerate kinase (PGK) promoter in the opposite direction of exon 2 of FP-1, a 3 to 5 kb mouse FP-1 genomic fragment of exon 4 to be eliminated, and a thymidine kinase (tk) gene of herpes simplex virus driven by the PGK promoter (Joyner, *Gene Targeting*, Oxford University Press, New York, 2000 (*Practical Approach Series,* 212), i-xviii; Ramirez-Solis et al., *Methods Enzymol.,* 225:855-878, 1993). The linearized vector is electroporated into 129/SvEv embryonic stem cell line W4, and the neo-positive and tk-negative transformants are selected using G418 (240 mg/ml) and gancyclovir (2 mM). The embryonic stem (ES) cell colonies that harbor the correct homologous recombination events are detected by Southern blotting and by long-range PCR using primers. The confirmed ES cell clones are amplified and aggregated with eight cell stage embryos of Swiss Webster mice, and implanted into pseudopregnant females. Chimeric mice from two ES cell lines that are germline-transmitting are bred with SW mice to yield hybrid homozygotes, or mated with 129/SvEv mice to yield inbred 129/SvEv FP-1-knockout mice.

Example 19

Screening Tissue Sections of Cancer Patients and Cancer Cell Lines for FP-1 Expression Levels Frozen sections and paraffin sections of various normal and various abnormal tissues including tumors are prepared by standard techniques (Hu et al., *J. Cell Biol.,* 151:961-972, 2000; Deng et al., *J. Cell Biol.,* 159:685-694, 2002; and Chen et al., *Proc. Natl. Acad. Sci. USA,* 100:14012-14017, 2003) and are stained immunohistochemically using rabbit antibodies to FP-1 (G320 at 1:10,000; G311 at 1:1,000; and G312 at 1:2,000) followed by visualization using secondary goat-anti-rabbit antibodies that have been conjugated with peroxidase or fluorescein.

Cancer cell lines representing cancers of, for example, skin (e.g., basal cell carcinoma), stomach, ovary, liver, brain, etc. are used to prepare RNA. RNA is separated on a gel and is transferred to a filter for Northern analysis (Sanger et al., *Proc. Natl. Acad. Sci USA.,* 74:5463-5467, 1977). Filters with mRNAs from these cell lines are hybridized with a probe to FP-1. In those instances where the cell lines are derived from mouse cell lines, a mouse FP-1 probe is used; where rat cell lines are use, rat FP-1 probe is used; and where human cell lines are used, a human FP-1 probe is used.

FP-1 is found to be overexpressed in several cancer cell lines.

Example 20

Monoclonal Antibodies that Specifically Bind FP-1

Balb/c mice are immunized with rat or human FP-1 antigen with weekly injections of 200 to 500 μg of recombinant FP-1 protein over a period of 3 to 4 months. Mice showing high serum titers of anti-FP-1 antibodies as determined by ELISA assay against recombinant FP-1, are identified and the spleens of the mice removed. Spleen cells are fused with the mouse myeloma SP2/0 (ATCC® Accession No. CRL-8006) in accordance with the protocol described in Enfield, D. A. et al. *EMBO J.* 7:711, 1988.

Assays for FP-1 specificity are accomplished by ELISA assays against recombinant FP-1. The cell line producing an FP-1 antibody demonstrating the highest binding for recombinant FP-1 while having the least non-specific binding to an unrelated protein is selected.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polynucleotide comprising SEQ ID NO:11.

2. An isolated polynucleotide comprising a nucleic acid sequence encoding a polypeptide comprising SEQ ID NO:12 or amino acids 34 to 551 of SEQ ID NO:12.

3. The isolated polynucleotide of claim 2, comprising the nucleic acid sequence encoding the polypeptide comprising the amino acid sequence of SEQ ID NO:12.

4. The isolated polynucleotide of claim 2, comprising the nucleic acid sequence encoding the polypeptide comprising amino acids 34 to 551 of SEQ ID NO:12.

5. An isolated polynucleotide that is a full-length complement of the polynucleotide of claim 1.

6. An isolated polynucleotide that is a full-length complement of the polynucleotide of claim 3.

7. An isolated polynucleotide that is a full-length complement of the polynucleotide of claim 4.

8. A recombinant vector comprising the polynucleotide of claim 1.

9. A recombinant vector comprising the polynucleotide of claim 3.

10. A recombinant vector comprising the polynucleotide of claim 4.

11. The recombinant vector of claim 8, wherein the vector is a cloning vector or an expression vector.

12. The recombinant vector of claim 9, wherein the vector is a cloning vector or an expression vector.

13. The recombinant vector of claim 10, wherein the vector is a cloning vector or an expression vector.

14. The recombinant vector of claim 11, wherein the expression vector is a prokaryotic cell expression vector or a eukaryotic cell expression vector.

15. The recombinant vector of claim 12, wherein the expression vector is a prokaryotic cell expression vector or a eukaryotic cell expression vector.

16. The recombinant vector of claim 13, wherein the expression vector is a prokaryotic cell expression vector or a eukaryotic cell expression vector.

17. An isolated, transformed host cell comprising the recombinant vector of claim 8.

18. An isolated, transformed host cell comprising the recombinant vector of claim 9.

19. An isolated, transformed host cell comprising the recombinant vector of claim 10.

20. The isolated host cell of claim 17, wherein the cell is a prokaryotic cell or a eukaryotic cell.

21. The isolated host cell of claim 18, wherein the cell is a prokaryotic cell or a eukaryotic cell.

22. The isolated host cell of claim 19, wherein the cell is a prokaryotic cell or a eukaryotic cell.

23. A method of preparing a substantially purified polypeptide encoded by the recombinant vector of claim 8, the method comprising culturing host cells transformed with the recombinant vector under conditions conducive to the synthesis of the polypeptide, and recovering the substantially purified polypeptide from the host cells.

24. A method of preparing a substantially purified polypeptide encoded by the recombinant vector of claim 9, the method comprising culturing host cells transformed with the recombinant vector under conditions conducive to the synthesis of the polypeptide, and recovering the substantially purified polypeptide from the host cells.

25. A method of preparing a substantially purified polypeptide encoded by the recombinant vector of claim 10, the method comprising culturing host cells transformed with the recombinant vector under conditions conducive to the synthesis of the polypeptide, and recovering the substantially purified polypeptide from the host cells.

* * * * *